US012105100B2

(12) United States Patent
McQuiston et al.

(10) Patent No.: US 12,105,100 B2
(45) Date of Patent: *Oct. 1, 2024

(54) METHODS FOR AIDING IN DIAGNOSING AND EVALUATING A TRAUMATIC BRAIN INJURY IN A HUMAN SUBJECT USING A COMBINATION OF GFAP AND UCH-L1

(71) Applicant: Abbott Laboratories, Abbott Park, IL (US)

(72) Inventors: Beth McQuiston, Abbott Park, IL (US); Saul Datwyler, Abbott Park, IL (US); Raj Chandran, Abbott Park, IL (US); Jaime Marino, Abbott Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 309 days.

This patent is subject to a terminal disclaimer.

(21) Appl. No.: 17/316,257

(22) Filed: May 10, 2021

(65) Prior Publication Data

US 2021/0389334 A1 Dec. 16, 2021

Related U.S. Application Data

(63) Continuation of application No. 16/203,373, filed on Nov. 28, 2018, now Pat. No. 11,016,105.

(60) Provisional application No. 62/667,227, filed on May 4, 2018, provisional application No. 62/663,811, filed on Apr. 27, 2018, provisional application No. 62/610,805, filed on Dec. 27, 2017, provisional application No. 62/596,814, filed on Dec. 9, 2017.

(51) Int. Cl.
*G01N 33/68* (2006.01)

(52) U.S. Cl.
CPC ..... *G01N 33/6896* (2013.01); *G01N 33/6893* (2013.01); *G01N 2800/28* (2013.01); *G01N 2800/2871* (2013.01); *G01N 2800/60* (2013.01)

(58) Field of Classification Search
CPC ........... G01N 33/6896; G01N 2800/28; G01N 2800/60
See application file for complete search history.

(56) References Cited

U.S. PATENT DOCUMENTS

| | | | |
|---|---|---|---|
| 7,456,027 | B2 | 11/2008 | Wang et al. |
| 8,492,107 | B2 | 7/2013 | Wang et al. |
| 9,265,441 | B2 | 2/2016 | Pereira et al. |
| 10,849,548 | B2 * | 12/2020 | McQuiston ...... G01N 33/54366 |
| 10,877,038 | B2 * | 12/2020 | McQuiston ............ A61B 6/501 |
| 10,877,048 | B2 * | 12/2020 | McQuiston ........ G01N 33/6896 |
| 11,016,092 | B2 * | 5/2021 | McQuiston ............ A61B 6/032 |
| 11,016,105 | B2 * | 5/2021 | McQuiston ........ G01N 33/6896 |
| 11,022,617 | B2 * | 6/2021 | McQuiston ........ G01N 33/6893 |
| 2003/0199000 | A1 | 10/2003 | Valkirs et al. |
| 2007/0042425 | A1 | 2/2007 | Hochstrasser et al. |
| 2010/0261286 | A1 | 10/2010 | Kim et al. |
| 2011/0143375 | A1 | 6/2011 | Wang et al. |
| 2012/0181184 | A1 | 7/2012 | Whitesides et al. |
| 2012/0202231 | A1 | 8/2012 | Wang et al. |
| 2012/0322682 | A1 | 12/2012 | McDevitt et al. |
| 2013/0029859 | A1 | 1/2013 | Svetlov et al. |
| 2014/0273035 | A1 | 9/2014 | Dowell et al. |
| 2014/0303041 | A1 | 10/2014 | Hayes et al. |
| 2014/0342381 | A1 | 11/2014 | Hayes et al. |
| 2014/0370531 | A1 | 12/2014 | Blyth et al. |
| 2015/0224499 | A1 | 8/2015 | Wang et al. |
| 2015/0268252 | A1 | 9/2015 | Svetlov et al. |
| 2016/0178643 | A1 | 6/2016 | Everett et al. |
| 2017/0089926 | A1 | 3/2017 | Travis et al. |
| 2017/0144156 | A1 | 5/2017 | Tang et al. |
| 2017/0176460 | A1 | 6/2017 | Larner |
| 2017/0227538 | A1 | 10/2017 | Noji |
| 2018/0106800 | A1 | 4/2018 | Datwyler et al. |
| 2018/0106818 | A1 | 4/2018 | Jewell et al. |
| 2018/0120305 | A1 | 5/2018 | Harel |
| 2018/0313837 | A1 | 11/2018 | McQuiston et al. |
| 2019/0064187 | A1 | 2/2019 | Svetlov et al. |

(Continued)

FOREIGN PATENT DOCUMENTS

| | | |
|---|---|---|
| CN | 105085629 A | 11/2015 |
| EP | 105085629 A1 | 3/2005 |
| EP | 1838442 B1 | 9/2013 |

(Continued)

OTHER PUBLICATIONS

International Searching Authority, International Search Report and Written Opinion for International Application No. PCT/US2022/077128, mailed Jan. 3, 2023.

Lawrence M. Lewis et al., Utility of Serum Biomarkers in the Diagnosis and Stratification of Mild Traumatic Brain Injury, Academic Emergency Medicine, Jun. 1, 2017, vol. 24, No. 6, pp. 710-720.

International Searching Authority, International Search Report and Written Opinion for International Application No. PCT/US2022/075638, mailed Dec. 16, 2022.

(Continued)

*Primary Examiner* — Olga N Chernyshev
(74) *Attorney, Agent, or Firm* — Casimir Jones SC; Lisa Mueller

(57) ABSTRACT

Disclosed herein are methods of aiding in the diagnosis and evaluation of a subject that has sustained or may have sustained an injury to the head. For example, the present disclosure provides methods for aiding in the diagnosis and evaluation of a subject to determine whether the subject has sustained a traumatic brain injury (TBI) by detecting or measuring a combination of the levels of ubiquitin carboxy-terminal hydrolase L1 (UCH-L1) and glial fibrillary acidic protein (GFAP) in samples taken at various time points within 48 hours after the subject has sustained or may have sustained an injury to the head.

38 Claims, 11 Drawing Sheets

Specification includes a Sequence Listing.

(56) References Cited

U.S. PATENT DOCUMENTS

| | | |
|---|---|---|
| 2019/0091687 A1 | 3/2019 | Alhasnani |
| 2019/0302127 A1 | 10/2019 | Lukaszewska |

FOREIGN PATENT DOCUMENTS

| | | | |
|---|---|---|---|
| EP | | 3916387 A1 | 12/2021 |
| JP | | 2012500388 A | 1/2012 |
| JP | | 2017125853 A | 7/2017 |
| WO | WO 2005/029088 | | 3/2005 |
| WO | WO 2005/106038 | | 10/2005 |
| WO | WO 2005/113798 | | 12/2005 |
| WO | | 2007009125 A2 | 1/2007 |
| WO | WO 2009/100131 | | 8/2009 |
| WO | WO 2010/019553 A2 | | 2/2010 |
| WO | | 2010102279 A1 | 9/2010 |
| WO | | 2010148391 A2 | 12/2010 |
| WO | WO 2010/148391 | | 12/2010 |
| WO | WO 2011/011334 A2 | | 1/2011 |
| WO | WO 2011/032155 | | 3/2011 |
| WO | WO 2011/160096 A2 | | 12/2011 |
| WO | WO 2016/196522 A1 | | 12/2011 |
| WO | WO 2012/051519 | | 4/2012 |
| WO | | 2013090285 A1 | 6/2013 |
| WO | | 2014124174 A2 | 8/2014 |
| WO | WO 2014/194329 | | 12/2014 |
| WO | WO 2015/009907 | | 5/2015 |
| WO | WO 2015/066211 | | 5/2015 |
| WO | WO 2015/157300 | | 10/2015 |
| WO | WO 2016/055148 A2 | | 4/2016 |
| WO | WO 2016/166419 A1 | | 10/2016 |
| WO | WO 2018/136825 A1 | | 12/2016 |
| WO | WO 2018/067468 A1 | | 4/2018 |
| WO | WO 2018/067474 | | 4/2018 |
| WO | WO 2018/081649 A1 | | 5/2018 |
| WO | WO 2018/175942 | | 9/2018 |
| WO | WO 2018/191531 | | 10/2018 |
| WO | | 2018217792 A1 | 11/2018 |
| WO | WO 2018/200823 | | 11/2018 |
| WO | WO 2018/218169 | | 11/2018 |
| WO | WO 2018/222783 | | 12/2018 |
| WO | WO 2018/222784 | | 12/2018 |
| WO | WO 2019/112860 | | 6/2019 |
| WO | WO 2019/113525 | | 6/2019 |
| WO | WO 2019/133717 | | 7/2019 |
| WO | | 2019199869 A1 | 10/2019 |
| WO | | 2021026261 A1 | 2/2021 |

OTHER PUBLICATIONS

Andrew K. Ottens et al., "Neuroproteomics: A Biochemical Means to Discriminate the Extent and Modality of Brain Injury", Journal of Neurotrauma, Mary Ann Liebert, Inc., publishers., Oct. 1, 2010, 27(10), 1837-1852.

Agoston, Denes V. et al., "Biofluid Biomarkers of Traumatic Brain Injury" Brain Injury, 31(9):1195-1203 (Jul. 29, 2017).

Banyan BTI Brain Trauma Indicator, Publicly available Feb. 2018.

Bazarian et al., "Serum GFAP and UCH-L1 for prediction of absence of intracranial injuries on head CT (ALERT-TBI): a multicentre observational study" The Lancelot, Neurology, vol. 17, ISSUE 9, p. 782-789, Sep. 1, 2018.

Benninger et al., "Glial fibrillary acidic protein as a marker of astrocytic activation in the cerebrospinal fluid of patients with amyotrophic lateral sclerosis." Journal of Clinical Neuroscience, 26:75-78 (Nov. 2015).

Berger, et al., "Serum Concentrations of Ubiquitin C-Terminal Hydrolase-L1 and all-Spectrin Breakdown Product 145 kDa Correlate with Outcome after Pediatric TBI." Journal of Neurotrauma, Jan. 1, 2012; 29:162-167.

Blyth, Brian J. et al., "Elevated Serum Ubiquitin Carboxy-Terminal Hydrolase L1 is Associated with Abnormal Blood-Brain Barrier Function after Traumatic Brain Injury", Journal of Neurotrauma., 28(12): 2453-2462 (Dec. 1, 2011).

Bogoslovsky T. et al., "Fluid Biomarkers of Traumatic Brain Injury and Intended Context of Use." Diagnostics (Basel). Oct. 1, 20168; 6(4). pii: E37.

Brophy, M. et al., "Biokinetic analysis of ubiquitin C-terminal hydrolase-L1 (UCH-L1) in severe traumatic brain injury patient biofluids." J Neurotrauma. Jun. 2011; 28(6):861-70.

Cai et al., "The role of cardiac troponin I in prognostication of patients with isolated severe traumatic brain injury." J. Trauma Acute Care Surg., 80(3):477-483 (Mar. 2016).

Dash et al.; "Biomarkers for Diagnosis, Prognosis, and Evaluation of Treatment Efficacy for Traumatic Brain Injury." Neurotherapeutics, Jan. 2010, 7(1): 100-114.

Diaz-Arrastia, et al., "Acute biomarkers of traumatic brain injury: relationship between plasma levels of ubiquitin C-terminal hydrolase-L1 and glial fibrillary acidic protein.", Journal of Neurotrauma, 31:19-25 (Jan. 1, 2014).

Hamdi, et al., "Predictive Value of Cardiac Troponin I in Traumatic Brain Injury.", Egypt J. Neurol. Psychiat. Neurosurg, 49(4):365-373 (Oct. 2012).

Kiiski, H. et al., "Increased plasma UCH-L1 after aneurysmal subarachnoid hemorrhage is associated with unfavorable neurological outcome." J Neurol Sci. Feb. 15, 2016; 361:144-9.

Kiviniemi et al., "Serum levels of GFAP and EGFR in primary and recurrent high-grade gliomas: correlation to tumor volume molecular markers, and progression-free survival." Journal of Neuro-Oncology, 124(2):237-245 (Jun. 2015).

Kobeissy, Firas H. et al., "Novel Differential Neuroproteomics Analysis of Traumatic Brain Injury in Rats" Molecular & Cellular Proteomics, 5(10):1887-1898 (Oct. 1, 2006).

Kochanek et al., "Multi-Center Pre-clinical Consortia to Enhance Translation of Therapies and Biomarkers for Traumatic Brain Injury: Operation Brain Trauma Therapy and Beyond." Frontiers in Neurology Aug. 2018, vol. 9, 13 pages.

Korley et al., "Performance Evaluation of a Multiplex Assay for Simultaneous Detection of Four Clinically Relevant Traumatic Brain Injury Biomarkers." Journal of Neurotrauma, 2015, 35:1-6.

Kou et al., "Combining Biochemical and Imaging Markers to Improve Diagnosis and Characterization of Mild Traumatic Brain Injury in the Acute Setting: Results from a Pilot Study." PLOS ONE Nov. 2013, 8(11): e80296, 14 pages.

Lecky, "Should plasma GFAP guide the management of patients with traumatic brain injury and a negative CT scan?" Lancet Neurol 2019, 2 pages.

Lee et al., "A Role of Serum-Based Neuronal and Glial Markers as Potential Predictors for Distinguishing Severity and Related Outcomes in Traumatic Brain Injury", J. Korean Neurosurgical Society, 58(2):93-100 (Aug. 2015).

Lippi et al., "The concentration of highly-sensitive troponin I is increased in patients with brain injury after mild head trauma." International Journal of Cardiology, 168(2):1617-1618 (Sep. 2013).

Liu et al., "Ubiquitin C-terminal hydrolase-L1 as a biomarker for ischemic and traumatic brain injury in rats", Eur. J. Neurosci., 31(4):722-732 (Feb. 2010).

Luger et al., "Glial Fibrillary Acidic Protein Serum Levels Distinguish between Intracerebral Hemorrhage and Cerebral Ischemia in the Early Phase of Stroke", Clinical Chemistry, 63(1):377-385 (Nov. 23, 2016).

McMahon et al., "Measurement of the glial fibrillary acidic protein and its breakdown products GFAP-BDP biomarker for the detection of traumatic brain injury compared to computed tomography and magnetic resonance imaging." J Neurotrauma. Apr. 15, 2015; 32(8):527-33.

Metting et al., "GFAP and S100B in the acute phase of mild tramatic brain injury." Neurology, 78: 1428-1433 (2012).

Missler et al., "Measurement of Glial Fibrillary Acidic Protein in Human Blood: Analytical Method and Preliminary Clinical Results." Clinical Chemistry, 45(1):138-141 (1999).

Mondello et al., "Clinical utility of serum levels of ubiquitin cterminal hydrolase as a biomarker for severe traumatic brain injury" Neurosurgery. Mar. 2012; 70(3): 666-675.

(56) References Cited

OTHER PUBLICATIONS

Mondello et al., "Neuronal and glial markers are differently associated with computed tomography findings and outcome in patients with severe traumatic brain injury: a case control study." Care 2011, 15: R156, 10 pages.

Mondello et al., "Serum Concentrations of Ubiquitin C-Terminal Hydrolase-L1 and Glial Fibrillary Acidic Protein after Pediatric Traumatic Brain Injury." *Scientific Reports*, 6(28203): 1-6 (Jun. 2016).

Nylen et al., "Increased serum-GFAP in patients with severe traumatic brain injury is related to outcome" J. of Neurological Sciences, 240: 85-91 (2006).

Okonkwo et al., "GFAP-BDP as an acute diagnostic marker in traumatic brain injury: results from the prospective transforming research and clinical knowledge in traumatic brain injury study." J Neurotrauma. Sep. 1, 2013; 30(17):1490-7.

Papa et al., "Elevated levels of serum glial fibrillary acidic protein breakdown products in mild and moderate traumatic brain injury are associated with intracranial lesions and neurosurgical intervention." Ann Emerg Med. Jun. 2012;59(6):471-83.

Papa et al., "Serum levels of Ubiquitin C-terminal Hydrolase (UCH-L1) distinguish mild traumatic brain injury (TBI) from trauma controls and are elevated in mild and moderate TBI patients with intracranial lesions and neurosurgical intervention", *J. Trauma Acute Care Surg.*, 72(5):1335-1344 (May 2012).

Papa et al., "Time Course and Diagnostic Accuracy of Glial and Neuronal Blood Biomarkers GFAP and UCH-L1 in a Large Cohort of Trauma Patients With and Without Mild Traumatic Brain Injury." *JAMA*, 73(5) 551-560 (Mar. 28, 2016).

Papa et al., "Ubiquitin C-terminal hydrolase is a novel biomarker in humans for severe traumatic brain injury*", *Crit. Care Med.*, 38(1):138-144 (Jan. 2010).

Pelinka et al., "Glial fibrillary acidic protein in serum after traumatic brain injury and multiple trauma." J Trauma. Nov. 2004; 57(5):1006-12.

Posti et al., "Glial Fibrillary Acidic Protein and Ubiquitin C-Terminal Hydrolase-L1 Are Not Specific Biomarkers for Mild CT-Negative Traumatic Brain Injury" Journal of Neurotrauma, 34(7):1427-1438 (Apr. 1, 2017).

Prieto et al., "Proteomic analysis of traumatic brain injury: the search for biomarkers." Expert Rev Proteomics. Apr. 2008; 5(2):283-91.

Puvenna et al., "Significance of ubiquitin carboxy-terminal hydrolase L1 elevations in athletes after sub-concussive head hits.", *PLOS ONE*, 9(5):e96296 (May 2014).

Rhine et al., "Are UCH-L1 and GFAP promising biomarkers for children with mild traumatic brain injury?" Brain Injury 2016, Early Online: 1-8.

Salim et al., "Significance of Troponin Elevation After Severe Traumatic Brain Injury." The Journal of TRAUMA Injury, Infection, and Critical Care 2008, 64 (1): 46-52.

Shahjouei et al., "The diagnostic values of UCH-L1 in traumatic brain injury: A meta analysis" Brain Injury (2017)—From email on Jun. 5 at 4:14.

Song et al., "Development of Digital Elisas for Ultrasensitive Measurement of Serum Glial Fibrillary Acid Protein and Ubiquitin C-Terminal Hydrolase With Clinical Utilities in Human Traumatic Brain Injury." Alzheimer's & Dementia, 13(7):P3-240 (Jul. 2017).

Stephen et al., "The Role of Cardiac Troponin I in Prognostication of Patients with Isolated Severe Traumatic Brain Injury." J Trauma Acute Care Surg. Mar. 2016 ; 80(3):477-483.

Strathmann et al., "Blood-based biomarkers for traumatic brain injury: evaluation of research approaches, available methods and potential utility from the clinician and clinical laboratory perspectives." Clin Biochem. Jul. 2014; 47(10-11):876-88.

Streeter et al., "Diagnostic Protein Biomarkers for Severe, Moderate, and Mild Traumatic Brain Injury", Sensing Technologies for Global Health, Military Medicine, Disaster Response, and Environmental Monitoring; and Biometric Technology for Human Identification VIII, 8029(1):1-16 (May 13, 2011).

Takala et al., "Glial Fibrillary Acidic Protein and Ubiquitin C-Terminal Hydrolase-L1 as Outcome Predictors in Traumatic Brain Injury." World Neurosurg. Mar. 2016; 87:8-20.

Thelin et al., "Serial Sampling of Serum Protein Biomarkers for Monitoring Human Traumatic Brain injury Dynamics: A Systematic Review." Frontiers in Neurology Jul. 2017, vol. 8, Article 300, 23 pages.

Thermo Scientific, "Thermo Scientific Pierce Assay Development Handbook." 2006, 76 pages.

Vos et al., "Glial and neuronal proteins in serum predict outcome after severe traumatic brain injury." Neurology. Apr. 27, 2004; 62(8):1303-10.

Wang et al., "An update on diagnostic and prognostic biomarkers for traumatic brain injury." Expert Review of Molecular Diagnostics, 18(2):165-180 (Jan. 2018).

Wang et al., "Proteomic identification of biomarkers of traumatic brain injury" Expert Review of Proteomics, 2(4):603-614 (Aug. 2005).

Welch et al., "Ability of Serum Glial Fibrillary Acidic Protein, Ubiquitin C-Terminal Hydrolase-L1, and S100B To Differentiate Normal and Abnormal Head Computed Tomography Findings in Patients with Suspected Mild or Moderate Traumatic Brain Injury." *Journal of Neurotrauma*, 33:203-214 (Jan. 15, 2016).

Yamauchi et al., "Ubiquitin-mediated stress response in the spinal cord after transient ischemia." Stroke. Jun. 2008; 39(6):1883-9.

Yue et al., "Association between plasma GFAP concentrations and MRI abnormalities in patients with CT-negative traumatic brain injury in the TRACK-TBI cohort: a prospective multicentre study." Lancet Neurol 2019, 9 pages.

Zhang et al., "Biomarkers of Traumatic Brain Injury and Their Relationship to Pathology", Laskowitz D, Grant G, editors. Translational Research in Traumatic Brain Injury, Chapter 12, Taylor and Francis Group, 2016, 12 pages.

Zoltewicz et al., "Characterization of Antibodies that Detect Human GFAP after Traumatic Brain Injury." Biomarker Insights 2012; 7:71-79.

UCH-L1 Antibody (C-4): sc-271639. Datasheet [online]. Santa Cruz Biotechnology Inc., 2007, Retrieved from the Internet: <URL:https://www.scbt.com/p/uch-l1-antibody-c-4>.

UCH-L1 Antibody Goat Anti Human Protein Gene Product 9.5 (N-TERMINAL) [online]. Genwaybio, 1998, Retrieved from the Internet: <URL:https://www.genwaybio.com/protein-gene-product-9-1037>.

International Search Report & Written Opinion mailed Dec. 7, 2017 for International Application No. PCT/US2017/054787, 15 pages.

International Search Report & Written Opinion mailed Sep. 17, 2018 for International Application No. PCT/US2018/040612, 15 pages.

International Search Report & Written Opinion mailed Sep. 10, 2018 for International Application No. PCT/US2018/024112, 19 pages.

International Search Report & Written Opinion mailed Sep. 10, 2018 for International Application No. PCT/US2018/034694, 15 pages.

International Search Report & Written Opinion mailed Aug. 2, 2018 for International Application No. PCT/US2018/027353, 21 pages.

International Search Report & Written Opinion mailed Dec. 1, 2017 for International Application No. PCT/US2017/054775, 14 pages.

International Search Report & Written Opinion mailed Dec. 1, 2017 for International Application No. PCT/US2018/035232, 15 pages.

International Search Report & Written Opinion mailed Aug. 2, 2018 for International Application No. PCT/US2018/029585, 23 pages.

International Search Report & Written Opinion mailed Sep. 3, 2018 for PCT/US2018/035231, 14 pages.

International Search Report & Written Opinion mailed Apr. 2, 2019 for International Application No. PCT/US2018/062888, 18 pages.

International Search Report & Written Opinion mailed Jun. 4, 2019 for International Application No. PCT/US2018/064587, 26 pages.

International Search Report & Written Opinion mailed May 31, 2019 for International Application No. PCT/US2018/067683, 21 pages.

(56) References Cited

OTHER PUBLICATIONS

International Preliminary Report on Patentability issued Apr. 9, 2019 for International Application No. PCT/US2017/054787, 7 pages.
International Preliminary Report on Patentability issued Apr. 9, 2019 for International Application No. PCT/US2017/054775, 7 pages.
International Preliminary Report on Patentability mailed Jan. 16, 2020 for International Application No. PCT/US2018/040612, 7 pages.
International Preliminary Report on Patentability mailed Oct. 3, 2019 for International Application No. PCT/US2018/024112, 11 pages.
International Preliminary Report on Patentability mailed Oct. 3, 2019 for International Application No. PCT/US2018/027353, 13 pages.
International Preliminary Report on Patentability mailed Nov. 7, 2019 for International Application No. PCT/US2018/029585, 14 pages.
International Preliminary Report on Patentability mailed Dec. 5, 2019 for International Application No. PCT/US2018/034694, 14 pages.
International Preliminary Report on Patentability mailed Dec. 12, 2019 for International Application No. PCT/US2018/035232, 8 pages.
International Preliminary Report on Patentability mailed Dec. 12, 2019 for International Application No. PCT/US2018/035231, 8 pages.
Papa Linda et al: "Evaluating glial and neuronal blood biomarkers GFAP and UCH-L1 as gradients of brain injury in concussive, subconcussive and non-concussive trauma: a prospective cohort study", BMJ Paediatrics Open, vol. 3, No. 1, Aug. 1, 2019 (Aug. 1, 2019), p. e000473, XP055951121, DOI: 10.1136/bmjpo-2019-000473 Retrieved from the Internet: URL:https://bmjpaedsopen.bmj.com/content/b mjpo/3/1/e000473.fu11.pdf>.
Rhine Tara et al: "2443 : Investigating markers of early traumatic brain injury (iMet): An interim analysis", Journal of Clinical and Translational Science, vol. 1, No. S1, Sep. 1, 2017 (Sep. 1, 2017), pp. 78-78, XP055951100, DOI: 10.1017/cts.2017.276.
International Searching Authority, International Search Report and Written Opinion for PCT Application No. PCT/US2022/029798, mailed Aug. 31, 2022.
Metzger Ryan R. et al: "Temporal response profiles of serum ubiquitin C-terminal hydrolase-L1 and the 145-kDa alpha II-spectrin breakdown product after severe traumatic brain injury in children", Journal of Neurosurgery. Pediatrics, vo1. 22, No. 4, Oct. 1, 2018 (Oct. 1, 2018), pp. 369-374, XP055951102, us, ISSN: 1933-0707, DOI: 10.3171/2018.4.PEDS17593.
Rhine Tara et al.: "Investigating Markers of Early Traumatic Brain Injury (iMet)", Pediatrics, Aug. 1, 2019 (Aug. 1, 2019), pp. 1-4, XP055951099, Retrieved from the Internet: URL:https://publications.aap.org/pediatric s/article/144/2_MeetingAbstract/429/3499/I nvestigating-Markers-of-Early-Traumatic-Brain.
Lynne Babcock et al: "Are UCH-L1 and GFAP promising biomarkers for children with mild traumatic brain injury?", Brain Injury, vol. 30, No. 10, Aug. 23, 2016 (Aug. 23, 2016), pp. 1231-1238, XP055951118, GB, ISSN: 0269-9052, DOI: 10.1080/02699052.2016.1178396 Retrieved from the Internet: URL:https://www.ncbi.nlm.nih.gov/pmc/articles/PMC5818714/pdf/nihms831590.pdf>.
International Searching Authority, International Search Report and Written Opinion for International Application No. PCT/US2022/033337, mailed Nov. 14, 2022.
Salim, A., et al., "Significance of Troponin Elevation After Severe Traumatic Brain Injury," The Journal of Trauma Injury, Infection, and Critical Care, Jan. 1, 2008.
Lippi, G., et al., "The concentration of highly-sensitive troponin I is increased with patients with brain injury after mild head trauma," Letter To the Editor, vol. 168, issue 2, p. 1617-1618, Sep. 30, 2013, International Journal of Cardiology.
Giuseppe Lippi, et al., The concentration of highly-sensitive troponin I is increased in patients with brain injury after mild head trauma, International Journal of Cardiology, Jan. 1, 2013, vol. 168, No. 2, pp. 1617-1618.
Stephen S. Cai, et al., The Role of Cardiac Troponin I in Prognostication of Patients with Isolated Severe Traumatic Brain Injury, J Trauma Acute Care Surg., Jan. 1, 2016, vol. 80, No. 3, pp. 477-483.
Japan Patent Office, First Office Action for Japanese Patent Application No. 2019-565417, Mailing Date: Nov. 2, 2021.
Japan Patent Office, First Office Action for Japanese Patent Application No. 2019-565410 Mailing Date: Nov. 2, 2021.
Japan Patent Office, Office Action for Japanese Patent Application No. 2019-556261, Mailing Date: Oct. 26, 2021.
European Patent Office, Office Action for European Application No. 18731687 mailed Jun. 14, 2021.
Yuh Esther L. et al: "Magnetic resonance imaging improves 3-month outcome prediction in mild traumatic brain injury : MRI in MTBI", Annals of Neurology, vol. 73, No. 2, Dec. 7, 2012 (Dec. 7, 2012), pp. 224-235, XP055811737, Boston, US, ISSN: 0364-5134, DOI: 10.1002/ana.23783.
Japan Patent Office, First Office Action for Japanese Patent Application No. 2019-555751. Mailing Date: Mar. 8, 2022.
China National Intellectual Property Administration, First Office Action for Chinese Patent Application No. 201780061647.7 mailed Dec. 14, 2021.
Canadian Intellectual Property Office, Office Action for Canadian Application No. 3,036,717, mailed Jul. 9, 2021.
IP Australia, Examination report No. 1 for standard patent application for Australian Application No. 2017339858, mailed Feb. 5, 2021.
IP Australia, Examination report No. 2 for standard patent application for Australian Application No. 2017339858, mailed Jun. 3, 2021.
Japan Patent Office, First Office Action for Japanese Patent Application No. 2019-517951. Mailing Date: Aug. 3, 2021.
Japan Patent Office, First Office Action for Japanese Patent Application No. 2019-552078. Mailing Date: Mar. 8, 2022.
International Searching Authority, International Search Report and Written Opinion for International Application No. PCT/US2022/080578, mailed Mar. 24, 2023.
Korley, F. K., et al., "Comparison of GFAP and UCH-L1 Measurements from Two Prototype Assays: The Abbott i-STAT and ARCHITECT Assays," Neurotrauma Reports, vol. 2, No. 1, Apr. 7, 2021, pp. 193-199.
International Searching Authority, International Search Report and Written Opinion for International Application No. PCT/US2022/082449, mailed Mar. 24, 2023.
International Searching Authority, International Search Report and Written Opinion for International Application No. PCT/US2023/061894, mailed May 11, 2023.
Natarajan Satheesh et al: "A novel time-resolved fluorescent lateral flow immunoassay for quantitative detection of the trauma brain injury biomarker-glial fibrillary acidic protein", SENSORS & DIAGNOSTICS, vol. 1, No. 1, Jan. 20, 2022 (Jan. 20, 2022), pp. 193-197.
Evgeni Eltzov et al: "Lateral Flow Immunoassays—from Paper Strip to Smartphone Technology", Electroanalysis, VHC Publishers, Inc, US, vol. 27, No. 9, Aug. 24, 2015 (Aug. 24, 2015), pp. 2116-2130.
De Puig Helena et al: "Challenges of the Nano-Bio Interface in Lateral Flow and Dipstick Immunoassays", Trends in Biotechnology, vol. 35, No. 12, Dec. 2017 (Dec. 2017), pp. 1169-1180.
International Searching Authority, International Search Report and Written Opinion for International Application No. PCT/US2022/081763, mailed May 19, 2023.
Hauser Janosch, et al., "An Autonomous Microfluidic Device for Generating Volume-Defined Dried Plasma Spots," Analytical Chemistry, vol. 91, No. 11, May 7, 2019, pp. 7125-7130.
Hart et al., "Anger Self-Management in Chronic Traumatic Brain Injury: Protocol for a Psycho-educational Treatment With a Structurally Equivalent Control and an Evaluation of Treatment Enactment," Contemp. Clin. Trials., 40:180-192 (2015).
Gomez-de-Regil, et al., "Psychological Intervention in Traumatic Brain Injury Patients," Behavioural Neurology, pp. 1-8 (2019).

(56) References Cited

OTHER PUBLICATIONS

European Patent Office, Partial Search Report for EP Application No. 20806307.3 mailed Jun. 26, 2023.
Bazarian Jeffrey J. et al: "Persistent, Long-term Cerebral White Matter Changes after Sports-Related Repetitive Head Impacts", PLOS ONE, vol. 9, No. 4, Apr. 16, 2014 (Apr. 16, 2014), pp. 1-12, XP93054623.
Koerte Inga K. et al: "A Review of Neuroimaging Findings in Repetitive Brain Trauma: Neuroimaging Findings in Repetitive Brain Trauma", Brain Pathology. vol. 25, No. 3, Apr. 23, 2015 (Apr. 23, 2015), pp. 318-349, XP055792317.
Sengupta Mohor B et al: "Increased expression of ApoAI after neuronal injury may be beneficial for healing", Molecular and Cellular Biochemistry, Springer US, New York, vol. 424, No. 1, Oct. 13, 2016 (Oct. 13, 2016), pp. 45-55, XP036127824.
E. Mark Haacke, "Common Data Elements in Radiologic Imaging of Traumatic Brain Injury," Journal of Magnetic Resonance Imaging 32, Apr. 28, 2010, pp. 516-543.
Jennifer Middleton, "UCH-L1 and GFAP Testing (i-STAT TBI Plasma) for the Detection of Intracranial Injury Following Mild Traumatic Brain Injury," Am Fam Physician, Mar. 1, 2022;105(3):313-314.
Wheeler, S., et al. "Effectiveness of Interventions to Improve Occupational Performance for People with Psychosocial, Behavioral, and Emotional Impairments After Brain Injury: A Systematic Review," The American Journal of Occupational Therapy, 70(3):1-9 (May/Jun. 2016).
Ustinova, K.I., et al. entitled "Physical therapy for correcting postural and coordination deficits in patients with mild-to-moderate traumatic brain injury," Physiotherapy Theory and Practice, 31(1):1-7 (2015).
Zhang Z, et al. Human traumatic brain injury induces autoantibody response against glial fibrillary acidic protein and its breakdown products. PLoS One. Mar. 25, 2014;9(3):e92698. doi: 10.1371/journal.pone.0092698. Erratum in: PLoS One. 2014;9(6):e101712.
Kim, et al. Large-scale femtoliter droplet array for digital counting of single biomolecules, Lab Chip, 2012, 12, 4986-4991.
Haacke EM, et al. Imaging iron stores in the brain using magnetic resonance imaging. Magn Reson Imaging. Jan. 2005;23(1):1-25.
Ward MD, Weber A, et al., Predictive Performance of Traumatic Brain Injury Biomarkers in High-Risk Elderly Patients. J Appl Lab Med. May 1, 2020;5(3):608.
Johns Hopkins Medicine, Rehabilitation After Traumatic Brain Injury, Available at: https://www.hopkinsmedicine.org/health/treatment-tests-and-therapies/rehabilitation-after-traumatic-brain-injury Published online: Nov. 19, 2019.
Ustinova KI, et al., Physical therapy for correcting postural and coordination deficits in patients with mild-to-moderate traumatic brain injury. Physiother Theory Pract. Jan. 2015;31(1):1-7. doi: 10.3109/09593985.2014.945674. Epub Aug. 1, 2014.
Wheeler, S., et al., Effectiveness of Interventions to Improve Occupational Performance for People With Psychosocial, Behavioral, and Emotional Impairments After Brain Injury: A Systematic Review, Am J Occup Ther. May-Jun. 2016;70(3):7003180060p1-9. doi: 10.5014/ajot.115.020677.
Neselius Sanna et al: "CSF-Biomarkers in Olympic Boxing: Diagnosis and Effects of Repetitive Head Trauma", PLOS ONE, vol. 7, No. 4, Apr. 4, 2012 (Apr. 4, 2012), p. e33606, XP093111333.
Biberthaler Peter et al: "Evaluation of Acute Glial Fibrillary Acidic Protein and Ubiquitin C-Terminal Hydrolase-L1 Plasma Levels in Traumatic Brain Injury Patients with and without Intracranial Lesions", Neurotrauma Reports, vol. 2, No. 1, Dec. 1, 2021 (Dec. 1, 2021), pp. 617-625, XP093043101.
Czeiter Endre et al: "Brain Injury Biomarkers May Improve the Predictive Power of the IMPACT Outcome Calculator", Journal of Neurotrauma., vol. 29, No. 9, Jun. 10, 2012 (Jun. 10, 2012), pp. 1770-1778, XP093111467.
International Searching Authority, International Search Report and Written Opinion for International Application No. PCT/2023/074185 mailed Jan. 5, 2024.
European Patent Office, Communication Pursuant to Article 94(3) EPC for European Application No. 18731687.2 mailed Feb. 2, 2024.
European Patent Office, Communication Pursuant to Article 94(3) EPC for European Application No. 18830037 mailed Dec. 12, 2023.
European Patent Office, Extended European Search Report for European Application No. 20806307.3 mailed Dec. 15, 2023.
Petzold A,, et, "An ELISA for glial fibrillary acidic protein", J Immunol Methods, (2004/04), vol. 287, No. 1-2, pp. 169-177, DOI: 10.1016/j.jim.2004.01.015, Apr. 2004 (accepted Jan. 27, 2004).

\* cited by examiner

METHODS FOR AIDING IN DIAGNOSING AND EVALUATING A TRAUMATIC BRAIN INJURY IN A HUMAN SUBJECT USING A COMBINATION OF GFAP AND UCH-L1

RELATED APPLICATION INFORMATION

This application is a continuation of U.S. application Ser. No. 16/203,373, filed on Nov. 28, 2018, which claims priority to U.S. Application No. 62/596,814, filed on Dec. 9, 2017, U.S. Application No. 62/610,805 filed on Dec. 27, 2017, U.S. Application No. 62/663,811, filed on Apr. 27, 2018, and U.S. Application No. 62/667,227, filed on May 4, 2018, the contents of each of which are herein incorporated by reference.

SEQUENCE LISTING

The instant application contains a Sequence Listing which has been submitted in ASCII format via EFS-Web and is hereby incorporated by reference in its entirety. Said ASCII copy, created on May 10, 2021, is named 36108-306_ST25.txt and is 6,684 bytes in size.

TECHNICAL FIELD

The present disclosure relates to methods of aiding in the diagnosis and evaluation of a subject that has sustained or may have sustained an injury to the head. For example, the present disclosure provides methods for aiding in the diagnosis and evaluation of a subject to determine whether the subject has sustained a traumatic brain injury (TBI) by detecting or measuring a combination of the levels of ubiquitin carboxy-terminal hydrolase L1 (UCH-L1) and glial fibrillary acidic protein (GFAP) in samples taken at various time points within 48 hours after the subject has sustained or may have sustained an injury to the head.

BACKGROUND

More than 5 million mild traumatic brain injuries (TBIs) occur each year in the United States alone. Currently, there is no simple, objective, accurate measurement available to help in patient assessment. In fact, much of TBI evaluation and diagnosis is based on subjective data. Unfortunately, objective measurements such as head CT and Glasgow Coma Score (GCS) are not very comprehensive or sensitive in evaluating mild TBI. Moreover, head CT is unrevealing for the vast majority of the time for mild TBI, is expensive, and exposes the patient to unnecessary radiation. Additionally, a negative head CT does not mean the patient has been cleared from having a concussion; rather it just means certain interventions, such as surgery, are not warranted. Patients who have sustained a traumatic injury, such as an orthopedic injury, may also have a TBI. Clinicians and patients need objective, reliable information to accurately evaluate this condition to promote appropriate triage and recovery. To date, limited data have been available for the use of UCH-L1 and GFAP in the acute care setting to aid in patient evaluation and management.

Mild TBI or concussion is hard to objectively detect and presents an everyday challenge in emergency care units globally. Concussion frequently causes no gross pathology, such as hemorrhage, and no abnormalities on conventional computed tomography scans of the brain, but rather rapid-onset neuronal dysfunction that resolves in a spontaneous manner over a few days to a few weeks. Approximately 15% of mild TBI patients suffer persistent cognitive dysfunction. There is an unmet need for orthopedic patients and mild TBI victims to be evaluated for their TBI status on scene, in emergency rooms and clinics, in the hospital, in the sports area and in military activity (e.g., combat).

SUMMARY

In one aspect, the present disclosure relates to a method of aiding in the diagnosis of or determining whether a subject that has sustained or may have sustained an injury to the head has suffered a moderate, severe, or moderate to severe traumatic brain injury (TBI). The method comprises the steps of:

performing an assay on a sample obtained from a subject within about 48 hours after the actual or suspected injury to measure or detect a combination of a level of glial fibrillary acidic protein (GFAP) and a level of ubiquitin carboxy-terminal hydrolase L1 (UCH-L1) in the sample; and (a) determining that the subject has not sustained a moderate, severe, or a moderate to severe TBI when the level of GFAP in the sample is less than a reference level of GFAP of about 105 pg/mL, and the level of UCH-L1 in the sample is less than a reference level of UCH-L1 of about 110 pg/mL; or (b) determining that the subject has not sustained a moderate, severe, or a moderate to severe TBI when the level of GFAP in the sample is equal to a reference level of GFAP of from about 105 pg/mL to about 890 pg/mL and the level of UCH-L1 in the sample is equal to a reference level of UCH-L1 of from about 110 pg/mL to about 2000 pg/mL; or (c) determining that the subject more likely than not has sustained a moderate, severe, or a moderate to severe TBI when the level of GFAP in the sample is greater than a reference level of GFAP of about 890 pg/mL, and the level of UCH-L1 in the sample is greater than a reference level of about 2000 pg/mL.

In one embodiment of the above-described method, the subject may have received a Glasgow Coma Scale (GCS) score before or after the assay is performed. In another embodiment, a subject having received such GCS score is suspected as having a moderate TBI based on the determined GCS score. In another embodiment, a subject having receiving such GCS score is suspected as having a severe TBI. In another embodiment, a subject having received such GCS score is suspected as having moderate to severe TBI based on the determined GCS score. In yet another embodiment, in the above-described method, the reference level of GFAP and the reference level of UCH-L1 correlate with or correspond to a Glasgow Coma Scale score of 3-8 (a severe TBI). In yet other aspects, the reference level of GFAP and the reference level of UCH-L1 correlate with a Glasgow Coma Scale score of 9-12 (a moderate TBI). In other aspects, the reference level of GFAP and the reference level of UCH-L1 correlate with or correspond to a Glasgow Coma Scale score of 3-12 (a moderate to severe TBI).

In the above-described method, in one embodiment, the assay is performed on a sample obtained from a subject within about 0 to about 4 hours after the actual injury or suspected injury. In another embodiment, the assay is performed on a sample obtained from a subject within about 4 hours to about 8 hours after the actual injury or suspected injury. In yet another embodiment, the assay is performed on a sample obtained from a subject within about 8 hours to about 12 hours after the actual injury or suspected injury. In still yet a further embodiment, the assay is performed on a sample obtained from a subject within about 12 hours to about 16 hours after the actual injury or suspected injury. In still yet another embodiment, the assay is performed on a sample obtained from a subject within about 16 hours to about 20 hours after the actual injury or suspected injury. In still yet another embodiment, the assay is performed on a sample obtained from a subject within about 20 hours to about 24 hours after the actual injury or suspected injury. In still yet another embodiment, the assay is performed on a sample obtained from a subject within about 24 hours to about 28 hours after the actual injury or suspected injury. In still a further embodiment, the assay is performed on a sample obtained from a subject within about 24 hours to about 48 hours after an injury or suspected injury. In still yet a further embodiment, the assay is performed on a sample obtained from a subject within about 28 hours to about 32 hours after the actual injury or suspected injury. In still yet a further embodiment, the assay is performed on a sample obtained from a subject within about 32 hours to about 36 hours after the actual injury or suspected injury. In still yet a further embodiment, the assay is performed on a sample obtained from a subject within about 36 hours to about 40 hours after the actual injury or suspected injury. In still yet a further embodiment, the assay is performed on a sample obtained from a subject within about 40 hours to about 44 hours after the actual injury or suspected injury. In yet still another embodiment, the assay is performed on a sample obtained from a subject within about 44 to about 48 hours after the actual injury or suspected injury.

In another embodiment of the above-described method, the reference level of GFAP and the reference level of UCH-L1 are determined by an assay having a sensitivity equal to or greater than about 79% and a specificity equal to or greater than about 33%.

In yet another embodiment of the above-described method, the sample is obtained from the subject within about 8 hours to about 16 hours after the actual or suspected injury.

In still yet another embodiment of the above-described method, the assay has at least a 2% higher sensitivity and at least a 3% higher specificity compared to an assay measuring or detecting GFAP or UCH-L1 individually.

In yet still another embodiment of the above-described method:
a. the sample is obtained from the subject within about 8 hours to about 12 hours after the actual or suspected injury; wherein the reference level of GFAP is about 240 pg/mL and the reference level of UCH-L1 is about 860 pg/mL; and wherein the assay has a sensitivity equal to or greater than 97% and a specificity equal to or greater than 51%; or
b. the sample is obtained from the subject within about 12 hours to about 16 hours after the actual or suspected injury; wherein the reference level of GFAP is about 105 pg/mL and the reference level of UCH-L1 is about 840 pg/mL; and wherein the assay has a sensitivity equal to or greater than 97.5% and a specificity equal to or greater than 36%; or
c. the sample is obtained from the subject within about 8 hours to about 12 hours after the actual or suspected injury and the reference level of GFAP is about 890 pg/mL and the reference level of UCH-L1 is about 920 pg/mL; and the assay has a sensitivity equal to or greater than 90% and a specificity equal to or greater than 79%; or
d. The sample is obtained from the subject within about 12 hours to about 16 hours after the actual or suspected injury; wherein the reference level of GFAP is about 505 pg/mL and the reference level of UCH-L1 is about 1580 pg/mL; and wherein the assay has a sensitivity equal to or greater than 90% and a specificity equal to or greater than 66%.

In yet another embodiment of the above-described method, the measurement of the level of GFAP comprises:
(a) contacting the sample, either simultaneously or sequentially, in any order with:
  (1) at least one GFAP-capture antibody, which binds to an epitope on GFAP or GFAP fragment to form an at least one GFAP-capture antibody-GFAP antigen complex, and
  (2) at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and
(b) measuring the amount or concentration of GFAP in the sample based on the signal generated by the detectable label in the at least one GFAP-capture antibody-GFAP antigen—at least one GFAP-detection antibody complex.

In yet another embodiment, the measurement of UCH-L1 in the above-identified method comprises:
(a) contacting the sample, either simultaneously or sequentially, in any order with:
  (1) at least one UCH-L1-capture antibody, which binds to an epitope on UCH-L1 or UCH-L1 fragment to form an at least one UCH-L1-capture antibody-UCH-L1 antigen complex, and
  (2) at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and
(b) measuring the amount or concentration of UCH-L1 in the sample based on the signal generated by the detectable label in the at least one UCH-L1-capture antibody-UCH-L1 antigen—at least one UCH-L1-detection antibody complex.

In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a moderate, severe, or a moderate to severe TBI with a treatment for TBI (e.g., a surgical treatment, a therapeutic treatment, or combinations thereof). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is serum. In yet other embodiments, the assay is a clinical chemistry assay and the sample is serum. In still further embodiments, the assay is a single molecule detection assay and the sample is serum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

In yet another aspect, the present disclosure relates to a method of aiding in the determination of or determining whether to perform a head computerized tomography (CT) scan on a human subject that has sustained or may have sustained an injury to the head. The method comprises the steps of:

performing an assay on a sample obtained from the subject within about 48 hours after the actual or suspected injury to measure or detect a combination of a level of glial fibrillary acidic protein (GFAP) and a level of ubiquitin carboxy-terminal hydrolase L1 (UCH-L1) in the sample; and (a) determining that the subject does not need a CT scan when the level of GFAP in the sample is less than a reference level of GFAP of about 50 pg/mL, and the level of UCH-L1 in the sample is less than a reference level of UCH-L1 of about 90 pg/mL; or (b) determining that the subject does not need a CT scan when the level of GFAP in the sample is equal to a reference level of GFAP of from about 50 pg/mL to about 975 pg/mL, and the level of UCH-L1 in the sample is equal to a reference level of UCH-L1 of from about 90 pg/mL to about 2000 pg/mL; or (c) determining that the subject more likely than not does need a CT scan when the level of GFAP in the sample is greater than a reference level of GFAP of about 975 pg/mL, and the level of UCH-L1 in the sample is greater than a reference level of UCH-L1 of about 2000 pg/mL.

In one embodiment of the above-described method, the subject has received a CT scan before or after the assay is performed, and wherein the subject is suspected as having a TBI based on the CT scan result. In another embodiment, the reference level of GFAP and the reference level of UCH-L1 correlate with a negative CT scan result.

More specifically, in the above-described methods for determining or evaluating whether to perform a head CT, the subject may be suspected of having a traumatic brain injury based on a CT scan that has been or already was performed (meaning, prior to the assay being performed). For example, depending upon a subject's medical condition (such as, if the patient is unconscious), a CT scan may be conducted shortly after the subject arrives at an emergency room, trauma center, or other site in order to assess and/or evaluate whether the subject has a TBI. Such a CT scan may be performed prior to the assay being performed to confirm and determine whether or not the subject has a mild or moderate to severe TBI. After the assay is performed, one or more subsequent CT scans can be performed based on the results of the assay as part of the physician's (or other medical personnel's) management of the TBI (such as, for example, to determine whether surgical and/or pharmacological intervention may be required).

In certain aspects of the above methods, the subject may be suspected of having a traumatic brain injury based on a CT scan. For example, a subject may be suspected of having a mild TBI based on a CT scan. Alternatively, a subject may be suspected of having a moderate TBI based on a CT scan. Alternatively, a subject may be suspected of having a severe TBI based on a CT scan. Alternatively, a subject may be suspected of having a moderate to severe TBI based on a CT scan. Still further, a subject may be suspected of not having a TBI based on a CT scan.

In certain aspects of the above methods, the reference level used is correlated or corresponds to a positive head computed tomography. For example, the reference level can correlate or correspond (such as through an increase or decrease in the reference level) to subjects having a positive head computed tomography. Alternatively, the reference level can correlate or correspond (such as through an increase or decrease in the reference level) to subjects having negative head computed tomography. Still further alternatively, the reference level can correlate or correspond (such as through an increase or decrease in the reference level) to subjects experiencing a brain bleed or a brain bleed that is improving or getting worse. In other aspects of the above method, the reference level is correlated or corresponds to control subjects which have not suffered any TBI.

In the above-described method, in one embodiment, the assay is performed on a sample obtained from a subject within about 0 to about 4 hours after the actual injury or suspected injury. In another embodiment, the assay is performed on a sample obtained from a subject within about 4 hours to about 8 hours after the actual injury or suspected injury. In yet still another embodiment, the assay is performed on a sample obtained from a subject within about 8 hours to about 12 hours after the actual injury or suspected injury. In still yet a further embodiment, the assay is performed on a sample obtained from a subject within about 12 hours to about 16 hours after the actual injury or suspected injury. In still yet another embodiment, the assay is performed on a sample obtained from a subject within about 16 hours to about 20 hours after the actual injury or suspected injury. In still yet another embodiment, the assay is performed on a sample obtained from a subject within about 20 hours to about 24 hours after the actual injury or suspected injury. In still yet another embodiment, the assay is performed on a sample obtained from a subject within about 24 hours to about 28 hours after the actual injury or suspected injury. In still a further embodiment, the assay is performed on a sample obtained from a subject within about 24 hours to about 48 hours after an injury or suspected injury. In still yet a further embodiment, the assay is performed on a sample obtained from a subject within about 28 hours to about 32 hours after the actual injury or suspected injury. In still yet a further embodiment, the assay is performed on a sample obtained from a subject within about 32 hours to about 36 hours after the actual injury or suspected injury. In still yet a further embodiment, the assay is performed on a sample obtained from a subject within about 36 hours to about 40 hours after the actual injury or suspected injury. In still yet a further embodiment, the assay is performed on a sample obtained from a subject within about 40 hours to about 44 hours after the actual injury or suspected injury. In yet still another embodiment, the assay is performed on a sample obtained from a subject within about 44 to about 48 hours after the actual injury or suspected injury.

In yet another embodiment of the above-described method, the reference level of GFAP and the reference level of UCH-L1 are determined by an assay having a sensitivity equal to or greater than about 54% and a specificity equal to or greater than about 32%.

In still yet another embodiment of the above-described method, the sample is obtained from the subject within about 4 hours to about 16 hours after the actual or suspected injury.

In yet another embodiment of the above-described method, the assay has at least a 2% higher sensitivity and at least a 4% higher specificity compared to an assay measuring or detecting GFAP or UCH-L1 individually.

In still yet another embodiment of the above-described method:
  a. the sample is obtained from the subject within about 4 hours to about 8 hours after the actual or suspected injury; wherein the reference level of GFAP is about 110 pg/mL and the reference level of UCH-L1 is about 2000 pg/mL; and wherein the assay has a sensitivity equal to or greater than 95% and a specificity equal to or greater than 62%;
  b. the sample is obtained from the subject within about 8 hours to about 12 hours after the actual or suspected injury; wherein the reference level of GFAP is about 240 pg/mL and the reference level of UCH-L1 is about 300 pg/mL; and wherein the assay has a sensitivity equal to or greater than 91.5% and a specificity equal to or greater than 52%; or
  c. the sample is obtained from the subject within about 12 hours to about 16 hours after the actual or suspected injury; wherein the reference level of GFAP is about 190 pg/mL and the reference level of UCH-L1 is about 90 pg/mL; and wherein the assay has a sensitivity equal to or greater than 99% and a specificity equal to or greater than 36%.

In yet another embodiment of the above-described method, the measurement of the level of GFAP comprises:
  (a) contacting the sample, either simultaneously or sequentially, in any order with:
    (1) at least one GFAP-capture antibody, which binds to an epitope on GFAP or GFAP fragment to form an at least one GFAP-capture antibody-GFAP antigen complex, and
    (2) at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and
  (b) measuring the amount or concentration of GFAP in the sample based on the signal generated by the detectable label in the at least one GFAP-capture antibody-GFAP antigen—at least one GFAP-detection antibody complex.

In yet another embodiment, the measurement of UCH-L1 in the above-identified method comprises:
  (a) contacting the sample, either simultaneously or sequentially, in any order with:
    (1) at least one UCH-L1-capture antibody, which binds to an epitope on UCH-L1 or UCH-L1 fragment to form an at least one UCH-L1-capture antibody-UCH-L1 antigen complex, and
    (2) at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and
  (b) measuring the amount or concentration of UCH-L1 in the sample based on the signal generated by the detectable label in the at least one UCH-L1-capture antibody-UCH-L1 antigen—at least one UCH-L1-detection antibody complex.

In one aspect, using the above-described methods, the subject is assessed or evaluated as having a mild TBI. In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a TBI (e.g., such as a mild moderate, severe, or a moderate to severe TBI with a treatment for TBI (e.g., a surgical treatment, a therapeutic treatment, or combinations thereof)). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is serum. In yet other embodiments, the assay is a clinical chemistry assay and the sample is serum. In still further embodiments, the assay is a single molecule detection assay and the sample is serum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

In yet another aspect, the present disclosure relates to a method of aiding in the determination of or determining whether a human subject that has sustained an injury to the head has sustained a traumatic brain injury (TBI). The method comprises the steps of: performing an assay on a sample obtained from the subject within about 48 hours after an injury to measure or detect a combination of a level of glial fibrillary acidic protein (GFAP) and a level of ubiquitin carboxy-terminal hydrolase L1 (UCH-L1) in the sample; and (a) determining that the subject has not sustained a TBI when the level of GFAP in the sample is less than a reference level of GFAP of about 15 pg/mL, and the level of UCH-L1 in the sample is less than a reference level of UCH-L1 of about 70 pg/mL; or (b) determining that the subject more likely than not has sustained a TBI when the level of GFAP in the sample is equal to a reference level of GFAP of from about 15 pg/mL to about 40 pg/mL, and the level of UCH-L1 in the sample is equal to a reference level of UCH-L1 of from about 70 pg/mL, to about 150 pg/mL; or (c) determining that the subject more likely than not has sustained a TBI when the level of GFAP in the sample is greater than a reference level of GFAP of about 40 pg/mL, and the level of UCH-L1 in the sample is greater than a reference level of UCH-L1 of about 150 pg/mL.

In the above-described method, in one embodiment, the assay is performed on a sample obtained from a subject within about 0 to about 4 hours after the injury. In another embodiment, the assay is performed on a sample obtained from a subject within about 4 hours to about 8 hours after the injury. In yet still another embodiment, the assay is performed on a sample obtained from a subject within about 8 hours to about 12 hours after the injury. In still yet a further embodiment, the assay is performed on a sample obtained from a subject within about 12 hours to about 16 hours after the injury. In still yet another embodiment, the assay is performed on a sample obtained from a subject within about 16 hours to about 20 hours after the injury. In still yet another embodiment, the assay is performed on a sample obtained from a subject within about 20 hours to about 24 hours after the injury. In still yet another embodiment, the assay is performed on a sample obtained from a subject within about 24 hours to about 28 hours after the injury. In still a further embodiment, the assay is performed on a sample obtained from a subject within about 24 hours to about 48 hours after an injury or suspected injury. In still yet a further embodiment, the assay is performed on a sample obtained from a subject within about 28 hours to about 32 hours after the injury. In still yet a further embodiment, the assay is performed on a sample obtained from a subject within about 32 hours to about 36 hours after the injury. In still yet a further embodiment, the assay is performed on a sample obtained from a subject within about 36 hours to about 40 hours after the injury. In still yet a further embodiment, the assay is performed on a sample obtained from a subject within about 40 hours to about 44 hours after the injury. In yet still another embodiment, the assay is performed on a sample obtained from a subject within about 44 to about 48 hours after the injury.

In another embodiment of the above-described method, the reference level of GFAP and the reference level of UCH-L1 are determined by an assay having a sensitivity equal to or greater than about 90% and a specificity equal to or greater than about 35%.

In yet another embodiment of the above-described method, the sample can be obtained from the subject within about 4 hours to about 16 hours after the injury.

In still yet another embodiment, the assay in the above-described method has at least a 3% higher sensitivity and at least a 17% higher specificity compared to an assay measuring or detecting GFAP or UCH-L1 individually.

In still yet another embodiment of the above-described method:

the sample is obtained from the subject within about 8 hours to about 12 hours after the injury; wherein the reference level of GFAP is about 30 pg/mL and the reference level of UCH-L1 is about 110 pg/mL; and wherein the assay has a sensitivity equal to or greater than 92% and a specificity equal to or greater than 99%; or the sample is obtained from the subject within about 12 hours to about 16 hours after the injury; wherein the reference level of GFAP is about 30 pg/mL and the reference level of UCH-L1 is about 110 pg/mL; and wherein the assay has a sensitivity equal to or greater than 90% and a specificity equal to or greater than 99%; or the sample is obtained from the subject within about 4 hours to about 8 hours after the injury; wherein the reference level of GFAP is about 40 pg/mL and the reference level of UCH-L1 is about 100 pg/mL; and wherein the method has a sensitivity equal to or greater than 90% and a specificity equal to or greater than 94%; or the sample is obtained from the subject within about 8 hours to about 12 hours after the injury; wherein the reference level of GFAP is about 15 pg/mL and the reference level of UCH-L1 is about 150 pg/mL; and wherein the assay has a sensitivity equal to or greater than 95% and a specificity equal to or greater than 82%; or the sample is obtained from the subject within about 12 hours to about 16 hours after the injury; wherein the reference level of GFAP is about 20 pg/mL and the reference level of UCH-L1 is about 60 pg/mL; and wherein the assay has a sensitivity equal to or greater than 95% and a specificity equal to or greater than 65%.

In the above-described method, the levels of GFAP and UCH-L1 can be measured or detected using an immunoassay or clinical chemistry assay. Alternatively, in the above-described method, the levels of GFAP and UCH-L1 can be measured or detected using a single molecule detection assay.

In yet another embodiment of the above-described method, the measurement of the level of GFAP comprises:

(a) contacting the sample, either simultaneously or sequentially, in any order with:
(1) at least one GFAP-capture antibody, which binds to an epitope on GFAP or GFAP fragment to form an at least one GFAP-capture antibody-GFAP antigen complex, and
(2) at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and
(b) measuring the amount or concentration of GFAP in the sample based on the signal generated by the detectable label in the at least one GFAP-capture antibody-GFAP antigen—at least one GFAP-detection antibody complex.

In yet another embodiment, the measurement of UCH-L1 in the above-identified method comprises:

(a) contacting the sample, either simultaneously or sequentially, in any order with:
(1) at least one UCH-L1-capture antibody, which binds to an epitope on UCH-L1 or UCH-L1 fragment to form an at least one UCH-L1-capture antibody-UCH-L1 antigen complex, and
(2) at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and
(c) measuring the amount or concentration of UCH-L1 in the sample based on the signal generated by the detectable label in the at least one UCH-L1-capture antibody-UCH-L1 antigen—at least one UCH-L1-detection antibody complex.

In one aspect, using the above-described methods, the subject is assessed or evaluated as having a mild TBI. In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a TBI (e.g., such as a mild moderate, severe, or a moderate to severe TBI with a treatment for TBI (e.g., a surgical treatment, a therapeutic treatment, or combinations thereof)). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is scrum. In yet other embodiments, the assay is a clinical chemistry assay and the sample is serum. In still further embodiments, the assay is a single molecule detection assay and the sample is serum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

In yet another aspect, the present disclosure relates to a method of aiding in the determination of or determining whether to perform a head magnetic resonance imaging (MRI) procedure on a human subject that has sustained or may have sustained an injury to the head. The method comprises the steps of:

performing an assay on a sample obtained from the subject within about 48 hours after the actual or suspected injury to measure or detect a combination of a level of glial fibrillary acidic protein (GFAP) and a level of ubiquitin carboxy-terminal hydrolase L1 (UCH-L1) in the sample; and (a) determining that the subject does not need an MRI procedure when the level of GFAP in the sample is less than a reference level of GFAP of about 15 pg/mL, and the level of UCH-L1 in the sample is less than a reference level of UCH-L1 of about 50 pg/mL; or (b) determining that the subject more likely than not does need an MRI procedure when the level of GFAP in the sample is equal to a reference level of GFAP of from about 15 pg/mL to about 1000 pg/mL, and the level of UCH-L1 in the sample is equal to a reference level of UCH-L1 of from about 50 pg/mL to about 2000 pg/mL; or (c) determining that the subject more likely than not does need an MRI procedure when the level of GFAP in the sample is greater than a reference level of GFAP of about 1000 pg/mL, and the level of UCH-L1 in the sample is greater than a reference level of UCH-L1 of about 2000 pg/mL.

In the above-described method, the subject may have received an MRI after the assay is performed, and wherein the subject is suspected as having a TBI based on the MRI result. In yet another embodiment, the reference level of GFAP and the reference level of UCH-L1 correlate with a negative MRI result.

In the above-described method, in one embodiment, the assay is performed on a sample obtained from a subject within about 0 to about 4 hours after the actual injury or suspected injury. In another embodiment, the assay is performed on a sample obtained from a subject within about 4 hours to about 8 hours after the actual injury or suspected injury. In yet still another embodiment, the assay is performed on a sample obtained from a subject within about 8 hours to about 12 hours after the actual injury or suspected injury. In still yet a further embodiment, the assay is performed on a sample obtained from a subject within about 12 hours to about 16 hours after the actual injury or suspected injury. In still yet another embodiment, the assay is performed on a sample obtained from a subject within about 16 hours to about 20 hours after the actual injury or suspected injury. In still yet another embodiment, the assay is performed on a sample obtained from a subject within about 20 hours to about 24 hours after the actual injury or suspected injury. In still yet another embodiment, the assay is performed on a sample obtained from a subject within about 24 hours to about 28 hours after the actual injury or suspected injury. In still a further embodiment, the assay is performed on a sample obtained from a subject within about 24 hours to about 48 hours after an injury or suspected injury. In still yet a further embodiment, the assay is performed on a sample obtained from a subject within about 28 hours to about 32 hours after the actual injury or suspected injury. In still yet a further embodiment, the assay is performed on a sample obtained from a subject within about 32 hours to about 36 hours after the actual injury or suspected injury. In still yet a further embodiment, the assay is performed on a sample obtained from a subject within about 36 hours to about 40 hours after the actual injury or suspected injury. In still yet a further embodiment, the assay is performed on a sample obtained from a subject within about 40 hours to about 44 hours after the actual injury or suspected injury. In yet still another embodiment, the assay is performed on a sample obtained from a subject within about 44 to about 48 hours after the actual injury or suspected injury.

In the above-described methods for determining or evaluating whether to perform a MRI, the subject may be suspected of having a traumatic brain injury based on a MRI or CT scan that has been or already was performed (meaning, prior to the assay being performed). For example, depending upon a subject's medical condition (such as, if the patient is unconscious), a MRI or CT scan may be conducted shortly after the subject arrives at an emergency room, trauma center, or other site in order to assess and/or evaluate whether the subject has a TBI. Such a MRI or CT scan may be performed prior to the assay being performed to confirm and determine whether or not the subject has a mild, moderate, severe, or moderate to severe TBI. After the assay is performed, one or more subsequent MRIs (or CT scans) can be performed based on the results of the assay as part of the physician's (or other medical personnel's) management of the TBI (such as, for example, to determine whether surgical and/or pharmacological intervention may be required).

In certain aspects of the above methods, the subject may be suspected of having a traumatic brain injury based on a MRI. For example, a subject may be suspected of having a mild TBI based on a MRI. Alternatively, a subject may be suspected of having a moderate TBI based on a MRI.

Alternatively, a subject may be suspected of having a severe TBI based on a MRI. Alternatively, a subject may be suspected of having a moderate to severe TBI based on a MRI. Still further, a subject may be suspected of not having a TBI based on a MRI.

In still yet another embodiment of the above-described method, the reference level of GFAP and the reference level of UCH-L1 are determined by an assay having a sensitivity of about 80% to about 98% and a specificity of about 30% to about 85%.

In a further embodiment of the above-described method, the subject may have received a negative CT scan result before the assay is performed.

In one aspect, using the above-described methods, the subject is assessed or evaluated as having a mild TBI. In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a TBI (e.g., such as a mild moderate, severe, or a moderate to severe TBI with a treatment for TBI (e.g., a surgical treatment, a therapeutic treatment, or combinations thereof)). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is serum. In yet other embodiments, the assay is a clinical chemistry assay and the sample is serum. In still further embodiments, the assay is a single molecule detection assay and the sample is serum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

In yet another aspect, the present disclosure relates to a method of aiding in the determination of or determining whether to perform a head magnetic resonance imaging (MRI) procedure on a human subject that has sustained or may have sustained an injury to the head. The method comprises the steps of:

performing an assay on a sample obtained from the subject within about 48 hours after the actual or suspected injury to measure or detect a combination of a level of glial fibrillary acidic protein (GFAP) or a level of ubiquitin carboxy-terminal hydrolase L1 (UCH-L1) in the sample; and (a) determining that the subject does not need an MRI procedure when the level of GFAP in the sample is equal to a reference level of GFAP of from about 0 pg/mL to about 68 pg/mL, or the level of UCH-L1 in the sample is equal to a reference level of UCH-L1 of from about 0 pg/mL to about 99 pg/mL; or (b) determining that the subject more likely than not does need an MRI procedure when the level of GFAP in the sample is greater than a reference level of GFAP of about 68 pg/mL, and the level of UCH-L1 in the sample is greater than a reference level of UCH-L1 of about 99 pg/mL.

In the above-described method, in one embodiment, the assay is performed on a sample obtained from a subject within about 0 to about 4 hours after the actual injury or suspected injury. In another embodiment, the assay is performed on a sample obtained from a subject within about 4 hours to about 8 hours after the actual injury or suspected injury. In yet still another embodiment, the assay is performed on a sample obtained from a subject within about 8 hours to about 12 hours after the actual injury or suspected injury. In still yet a further embodiment, the assay is performed on a sample obtained from a subject within about 12 hours to about 16 hours after the actual injury or suspected injury. In still yet another embodiment, the assay is performed on a sample obtained from a subject within about 16 hours to about 20 hours after the actual injury or suspected injury. In still yet another embodiment, the assay is performed on a sample obtained from a subject within about 20 hours to about 24 hours after the actual injury or suspected injury. In still yet another embodiment, the assay is performed on a sample obtained from a subject within about 24 hours to about 28 hours after the actual injury or suspected injury. In still a further embodiment, the assay is performed on a sample obtained from a subject within about 24 hours to about 48 hours after an injury or suspected injury. In still yet a further embodiment, the assay is performed on a sample obtained from a subject within about 28 hours to about 32 hours after the actual injury or suspected injury. In still yet a further embodiment, the assay is performed on a sample obtained from a subject within about 32 hours to about 36 hours after the actual injury or suspected injury. In still yet a further embodiment, the assay is performed on a sample obtained from a subject within about 36 hours to about 40 hours after the actual injury or suspected injury. In still yet a further embodiment, the assay is performed on a sample obtained from a subject within about 40 hours to about 44 hours after the actual injury or suspected injury. In yet still another embodiment, the assay is performed on a sample obtained from a subject within about 44 to about 48 hours after the actual injury or suspected injury.

In the above-described method, the subject may have received an MRI after the assay is performed, and wherein the subject is suspected as having a TBI based on the MRI result. In yet another embodiment, the reference level of GFAP or the reference level of UCH-L1 correlate with a negative MRI result.

In the above-described methods for determining or evaluating whether to perform a MRI, the subject may be suspected of having a traumatic brain injury based on a MRI or CT scan that has been or already was performed (meaning, prior to the assay being performed). For example, depending upon a subject's medical condition (such as, if the patient is unconscious), a MRI or CT scan may be conducted shortly after the subject arrives at an emergency room, trauma center, or other site in order to assess and/or evaluate whether the subject has a TBI. Such a MRI or CT scan may be performed prior to the assay being performed to confirm and determine whether or not the subject has a mild or moderate to severe TBI. After the assay is performed, one or more subsequent MRIs (or CT scans) can be performed based on the results of the assay as part of the physician's (or other medical personnel's) management of the TBI (such as, for example, to determine whether surgical and/or pharmacological intervention may be required).

In certain aspects of the above methods, the subject may be suspected of having a traumatic brain injury based on a MRI. For example, a subject may be suspected of having a mild TBI based on a MRI. Alternatively, a subject may be suspected of having a moderate TBI based on a MRI. Alternatively, a subject may be suspected of having a severe TBI based on a MRI. Alternatively, a subject may be suspected of having a moderate to severe TBI based on a MRI. Still further, a subject may be suspected of not having a TBI based on a MRI.

In certain aspects of the above methods, the reference level used is correlated or corresponds to a positive head computed tomography. For example, the reference level can correlate or correspond (such as through an increase or decrease in the reference level) to subjects having a positive head computed tomography. Alternatively, the reference level can correlate or correspond (such as through an increase or decrease in the reference level) to subjects having negative head computed tomography. Still further alternatively, the reference level can correlate or correspond (such as through an increase or decrease in the reference level) to subjects experiencing a brain bleed or a brain bleed that is improving or getting worse. In other aspects of the above method, the reference level is correlated or corresponds to control subjects which have not suffered any TBI.

In still yet another embodiment of the above-described method, the reference level of GFAP is determined by an assay having a sensitivity of about 90% to about 95% and a specificity of about 31% to about 46%. In still yet another embodiment of the above-described method, the reference level of UCH-L1 are determined by an assay having a sensitivity of about 81% to about 84% and a specificity of about 31% to about 46%.

In a further embodiment of the above-described method, the subject may have received a negative CT scan result before the assay is performed.

In one aspect, using the above-described methods, the subject is assessed or evaluated as having a mild TBI. In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a TBI (e.g., such as a mild moderate, severe, or a moderate to severe TBI with a treatment for TBI (e.g., a surgical treatment, a therapeutic treatment, or combinations thereof)). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is serum. In yet other embodiments, the assay is a clinical chemistry assay and the sample is serum. In still further embodiments, the assay is a single molecule detection assay and the sample is serum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

In yet another aspect, the present disclosure relates to a method for aiding in predicting or predicting the outcome of a human subject that has sustained or may have sustained a head injury. The method comprises the steps of:

performing an assay on a sample obtained from the subject within about 48 hours after the actual or suspected injury to measure or detect a combination of a level of glial fibrillary acidic protein (GFAP) and a level of ubiquitin carboxy-terminal hydrolase L1 (UCH-L1) in the sample; and (a) predicting for the subject a favorable outcome when the level of GFAP in the sample is less than a reference level of GFAP of about 80 pg/mL, and the level of UCH-L1 in the sample is less than a reference level of UCH-L1 of about 130 pg/mL; or (b) predicting for the subject more likely than not an unfavorable outcome when the level of GFAP in the sample is equal to a reference level of GFAP of from about 80 pg/mL to about 2000 pg/mL, and the level of UCH-L1 in the sample is equal to a reference level of UCH-L1 of from about 130 pg/mL to about 2000 pg/mL; or (c) predicting for the subject more likely than not an unfavorable outcome when the level of GFAP in the sample is greater than a reference level of GFAP of about 2000 pg/mL, and the level of UCH-L1 in the sample is greater than a reference level of UCH-L1 of about 2000 pg/mL.

In another embodiment of the above-described method, the subject may have received an Extended Glasgow Outcome Scale (GOSE) score after the method is performed, and wherein the subject is suspected as having a poor outcome based on the GOSE score. In yet another embodiment, the reference level of GFAP and the reference level of UCH-L1 correlate with subjects having a poor outcome based on a GOSE score of 1.

In the above-described method, in one embodiment, the assay is performed on a sample obtained from a subject within about 0 to about 4 hours after the actual injury or suspected injury. In another embodiment, the assay is performed on a sample obtained from a subject within about 4 hours to about 8 hours after the actual injury or suspected injury. In yet still another embodiment, the assay is performed on a sample obtained from a subject within about 8 hours to about 12 hours after the actual injury or suspected injury. In still yet a further embodiment, the assay is performed on a sample obtained from a subject within about 12 hours to about 16 hours after the actual injury or suspected injury. In still yet another embodiment, the assay is performed on a sample obtained from a subject within about 16 hours to about 20 hours after the actual injury or suspected injury. In still yet another embodiment, the assay is performed on a sample obtained from a subject within about 20 hours to about 24 hours after the actual injury or suspected injury. In still yet another embodiment, the assay is performed on a sample obtained from a subject within about 24 hours to about 28 hours after the actual injury or suspected injury. In still a further embodiment, the assay is performed on a sample obtained from a subject within about 24 hours to about 48 hours after an injury or suspected injury. In still yet a further embodiment, the assay is performed on a sample obtained from a subject within about 28 hours to about 32 hours after the actual injury or suspected injury. In still yet a further embodiment, the assay is performed on a sample obtained from a subject within about 32 hours to about 36 hours after the actual injury or suspected injury. In still yet a further embodiment, the assay is performed on a sample obtained from a subject within about 36 hours to about 40 hours after the actual injury or suspected injury. In still yet a further embodiment, the assay is performed on a sample obtained from a subject within about 40 hours to about 44 hours after the actual injury or suspected injury. In yet still another embodiment, the assay is performed on a sample obtained from a subject within about 44 to about 48 hours after the actual injury or suspected injury.

In still yet another embodiment of the above-described method, the reference level of GFAP and the reference level of UCH-L1 are determined by an assay having a sensitivity of about 80% to about 97% and a specificity of about 30% to about 95%.

In the above-described method, the levels of GFAP and UCH-L1 are measured or detected using an immunoassay or clinical chemistry assay. Alternatively, in the above-described method, the levels of GFAP and UCH-L1 are measured or detected using a single molecule detection assay.

In yet another embodiment of the above-described method, the measurement of the level of GFAP comprises:

(a) contacting the sample, either simultaneously or sequentially, in any order with:

(1) at least one GFAP-capture antibody, which binds to an epitope on GFAP or GFAP fragment to form an at least one GFAP-capture antibody-GFAP antigen complex, and (2) at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and (b) measuring the amount or concentration of GFAP in the sample based on the signal generated by the detectable label in the at least one GFAP-capture antibody-GFAP antigen—at least one GFAP-detection antibody complex.

In yet another embodiment, the measurement of UCH-L1 in the above-identified method comprises:
(a) contacting the sample, either simultaneously or sequentially, in any order with:
(1) at least one UCH-L1-capture antibody, which binds to an epitope on UCH-L1 or UCH-L1 fragment to form an at least one UCH-L1-capture antibody-UCH-L1 antigen complex, and
(2) at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and
(b) measuring the amount or concentration of UCH-L1 in the sample based on the signal generated by the detectable label in the at least one UCH-L1-capture antibody-UCH-L1 antigen—at least one UCH-L1-detection antibody complex.

In one aspect, using the above-described methods, the subject is assessed or evaluated as having a mild TBI. In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a TBI (e.g., such as a mild moderate, severe, or a moderate to severe TBI with a treatment for TBI (e.g., a surgical treatment, a therapeutic treatment, or combinations thereof)). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is serum. In yet other embodiments, the assay is a clinical chemistry assay and the sample is serum. In still further embodiments, the assay is a single molecule detection assay and the sample is serum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

In yet another aspect, the present disclosure relates to a method of aiding in the diagnosis of or determining whether a subject that has sustained or may have sustained an injury to the head has suffered a moderate, severe, or moderate to severe traumatic brain injury (TBI). The method comprises the step of:
performing an assay on a sample obtained from a subject within about 48 hours after an actual or suspected injury to measure or detect a combination of a level of glial fibrillary acidic protein (GFAP) and a level of ubiquitin carboxy-terminal hydrolase L1 (UCH-L1) in the sample; and
determining that the subject has not sustained a moderate, severe, or a moderate to severe TBI when the level of GFAP in the sample is equal to a reference level of GFAP of from about 105 pg/mL to about 890 pg/mL and the level of UCH-L1 in the sample is equal to a reference level of UCH-L1 of from about 110 pg/mL to about 2000 pg/mL.

In the above-described method, in one embodiment, the assay is performed on a sample obtained from a subject within about 0 to about 4 hours after the actual injury or suspected injury. In another embodiment, the assay is performed on a sample obtained from a subject within about 4 hours to about 8 hours after the actual injury or suspected injury. In yet still another embodiment, the assay is performed on a sample obtained from a subject within about 8 hours to about 12 hours after the actual injury or suspected injury. In still yet a further embodiment, the assay is performed on a sample obtained from a subject within about 12 hours to about 16 hours after the actual injury or suspected injury. In still yet another embodiment, the assay is performed on a sample obtained from a subject within about 16 hours to about 20 hours after the actual injury or suspected injury. In still yet another embodiment, the assay is performed on a sample obtained from a subject within about 20 hours to about 24 hours after the actual injury or suspected injury. In still yet another embodiment, the assay is performed on a sample obtained from a subject within about 24 hours to about 28 hours after the actual injury or suspected injury. In still a further embodiment, the assay is performed on a sample obtained from a subject within about 24 hours to about 48 hours after an injury or suspected injury. In still yet a further embodiment, the assay is performed on a sample obtained from a subject within about 28 hours to about 32 hours after the actual injury or suspected injury. In still yet a further embodiment, the assay is performed on a sample obtained from a subject within about 32 hours to about 36 hours after the actual injury or suspected injury. In still yet a further embodiment, the assay is performed on a sample obtained from a subject within about 36 hours to about 40 hours after the actual injury or suspected injury. In still yet a further embodiment, the assay is performed on a sample obtained from a subject within about 40 hours to about 44 hours after the actual injury or suspected injury. In yet still another embodiment, the assay is performed on a sample obtained from a subject within about 44 to about 48 hours after the actual injury or suspected injury.

In one embodiment of the above-described method, the subject may have received a Glasgow Coma Scale (GCS) score before or after the assay is performed. In another embodiment, a subject having received such GCS score is suspected as having a moderate TBI based on the determined GCS score. In another embodiment, a subject having receiving such GCS score is suspected as having a severe TBI. In another embodiment, a subject having received such GCS score is suspected as having moderate to severe TBI based on the determined GCS score. In yet another embodiment, in the above-described method, the reference level of GFAP and the reference level of UCH-L1 correlate with or correspond to a Glasgow Coma Scale score of 3-8 (a severe TBI). In yet other aspects, the reference level of GFAP and the reference level of UCH-L1 correlate with a Glasgow Coma Scale score of 9-12 (a moderate TBI). In other aspects, the reference level of GFAP and the reference level of UCH-L1 correlate with or correspond to a Glasgow Coma Scale score of 3-12 (a moderate to severe TBI).

In another embodiment of the above-described method: (a) the reference level of GFAP is about 105 pg/mL and the reference level of UCH-L1 is about 840 pg/mL; (b) the reference level of GFAP is about 150 pg/mL and the reference level of UCH-L1 is about 2000 pg/mL; (c) the reference level of GFAP is about 240 pg/mL and the reference level of UCH-L1 is about 860 pg/mL; (d) the reference level of GFAP is about 265 pg/mL and the reference level of UCH-L1 is about 860 pg/mL; (e) the reference level of GFAP is about 370 pg/mL and the reference level of UCH-L1 is about 110 pg/mL; (f) the reference level of GFAP is about 505 pg/mL and the reference level of UCH-L1 is about 1580 pg/mL; (g) the reference level of GFAP is about 695 pg/mL and the reference level of UCH-L1 is about 1570 pg/mL; or (h) the reference level of GFAP is about 890 pg/mL and the reference level of UCH-L1 is about 920 pg/mL.

In yet another embodiment of the above-described method, the sample is obtained from the subject within: (a) about 8 hours to about 12 hours after the actual or suspected injury and the level of GFAP is about 240 pg/mL and the level of UCH-L1 is about 860 pg/mL; (b) about 8 hours to about 12 hours after the actual or suspected injury and the level of GFAP is about 265 pg/mL and the level of UCH-L1 is about 860 pg/mL; (c) about 8 hours to about 12 hours after the actual or suspected injury and the level of GFAP is about 890 pg/mL and the level of UCH-L1 is about 920 pg/ml; (d) about 12 hours to about 16 hours after the actual or suspected injury and the level of GFAP is about 105 pg/mL and the level of UCH-L1 is about 840 pg/mL; (e) about 12 hours to about 16 hours after the actual or suspected injury and the level of GFAP is about 370 pg/mL and the level of UCH-L1 is about 110 pg/mL; (f) about 12 hours to about 16 hours after the actual or suspected injury and the level of GFAP is about 370 pg/mL and the level of UCH-L1 is about 110 pg/mL; (g) about 12 hours to about 16 hours after the actual or suspected injury and the level of GFAP is about 505 pg/mL and the level of UCH-L1 is about 1590 pg/mL; (h) about 12 hours to about 16 hours after the actual or suspected injury and the level of GFAP is about 695 pg/mL and the level of UCH-L1 is about 1570 pg/mL; or (i) about 12 hours to about 16 hours after the actual or suspected injury and the level of GFAP is about 150 pg/mL and the level of UCH-L1 is about 2000 pg/mL.

In another embodiment of the above-described method, the reference level of GFAP and the reference level of UCH-L1 are determined by an assay having a sensitivity equal to or greater than about 79% and a specificity equal to or greater than about 33%.

In yet another embodiment of the above-described method, the sample is obtained from the subject within about 8 hours to about 16 hours after the actual or suspected injury.

In still yet another embodiment of the above-described method, the assay has at least a 2% higher sensitivity and at least a 3% higher specificity compared to an assay measuring or detecting GFAP or UCH-L1 individually.

In yet still another embodiment of the above-described method:
  c. the sample is obtained from the subject within about 8 hours to about 12 hours after the actual or suspected injury; wherein the reference level of GFAP is about 240 pg/mL and the reference level of UCH-L1 is about 860 pg/mL; and wherein the assay has a sensitivity equal to or greater than 97% and a specificity equal to or greater than 51%; or
  f. the sample is obtained from the subject within about 12 hours to about 16 hours after the actual or suspected injury; wherein the reference level of GFAP is about 105 pg/mL and the reference level of UCH-L1 is about 840 pg/mL; and wherein the assay has a sensitivity equal to or greater than 97.5% and a specificity equal to or greater than 36%; or
  g. the sample is obtained from the subject within about 8 hours to about 12 hours after the actual or suspected injury and the reference level of GFAP is about 890 pg/mL and the reference level of UCH-L1 is about 920 pg/mL; and the assay has a sensitivity equal to or greater than 90% and a specificity equal to or greater than 79%; or
  h. The sample is obtained from the subject within about 12 hours to about 16 hours after the actual or suspected injury; wherein the reference level of GFAP is about 505 pg/mL and the reference level of UCH-L1 is about 1580 pg/mL; and wherein the assay has a sensitivity equal to or greater than 90% and a specificity equal to or greater than 66%.

In yet another embodiment of the above-described method, the measurement of the level of GFAP comprises:

(a) contacting the sample, either simultaneously or sequentially, in any order with:
 (1) at least one GFAP-capture antibody, which binds to an epitope on GFAP or GFAP fragment to form an at least one GFAP-capture antibody-GFAP antigen complex, and
 (2) at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and
(b) measuring the amount or concentration of GFAP in the sample based on the signal generated by the detectable label in the at least one GFAP-capture antibody-GFAP antigen—at least one GFAP-detection antibody complex.

In yet another embodiment, the measurement of UCH-L1 in the above-identified method comprises:
(a) contacting the sample, either simultaneously or sequentially, in any order with:
 (1) at least one UCH-L1-capture antibody, which binds to an epitope on UCH-L1 or UCH-L1 fragment to form an at least one UCH-L1-capture antibody-UCH-L1 antigen complex, and
 (2) at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and
(b) measuring the amount or concentration of UCH-L1 in the sample based on the signal generated by the detectable label in the at least one UCH-L1-capture antibody-UCH-L1 antigen—at least one UCH-L1-detection antibody complex.

In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a moderate, severe, or a moderate to severe TBI with a treatment for TBI (e.g., a surgical treatment, a therapeutic treatment, or combinations thereof). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is serum. In yet other embodiments, the assay is a clinical chemistry assay and the sample is serum. In still further embodiments, the assay is a single molecule detection assay and the sample is serum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

In yet another aspect, the present disclosure relates to a method of aiding in the determination of or determining whether to perform a head computerized tomography (CT) scan on a human subject that has sustained or may have sustained an injury to the head. The method comprises the steps of:
 performing an assay on a sample obtained from a subject within about 48 hours after an actual or suspected injury to measure or detect a combination of a level of glial fibrillary acidic protein (GFAP) and a level of ubiquitin carboxy-terminal hydrolase L1 (UCH-L1) in the sample; and
 determining that the subject does not need a CT scan when the level of GFAP in the sample is equal to a reference level of GFAP of from about 50 pg/mL to about 975 pg/mL, and the level of UCH-L1 in the sample is equal to a reference level of UCH-L1 of from about 90 pg/mL to about 2000 pg/mL.

In one embodiment of the above-described method, the subject has received a CT scan before or after the assay is performed, and wherein the subject is suspected as having a TBI based on the CT scan result. In another embodiment, the reference level of GFAP and the reference level of UCH-L1 correlate with a negative CT scan result.

More specifically, in the above-described methods for determining or evaluating whether to perform a head CT, the subject may be suspected of having a traumatic brain injury based on a CT scan that has been or already was performed (meaning, prior to the assay being performed). For example, depending upon a subject's medical condition (such as, if the patient is unconscious), a CT scan may be conducted shortly after the subject arrives at an emergency room, trauma center, or other site in order to assess and/or evaluate whether the subject has a TBI. Such a CT scan may be performed prior to the assay being performed to confirm and determine whether or not the subject has a mild or moderate to severe TBI. After the assay is performed, one or more subsequent CT scans can be performed based on the results of the assay as part of the physician's (or other medical personnel's) management of the TBI (such as, for example, to determine whether surgical and/or pharmacological intervention may be required).

In certain aspects of the above methods, the subject may be suspected of having a traumatic brain injury based on a CT scan. For example, a subject may be suspected of having a mild TBI based on a CT scan. Alternatively, a subject may be suspected of having a moderate TBI based on a CT scan. Alternatively, a subject may be suspected of having a severe TBI based on a CT scan. Alternatively, a subject may be suspected of having a moderate to severe TBI based on a CT scan. Still further, a subject may be suspected of not having a TBI based on a CT scan.

In certain aspects of the above methods, the reference level used is correlated or corresponds to a positive head computed tomography. For example, the reference level can correlate or correspond (such as through an increase or decrease in the reference level) to subjects having a positive head computed tomography. Alternatively, the reference level can correlate or correspond (such as through an increase or decrease in the reference level) to subjects having negative head computed tomography. Still further alternatively, the reference level can correlate or correspond (such as through an increase or decrease in the reference level) to subjects experiencing a brain bleed or a brain bleed that is improving or getting worse. In other aspects of the above method, the reference level is correlated or corresponds to control subjects which have not suffered any TBI.

In the above-described method, in one embodiment, the assay is performed on a sample obtained from a subject within about 0 to about 4 hours after the actual injury or suspected injury. In another embodiment, the assay is performed on a sample obtained from a subject within about 4 hours to about 8 hours after the actual injury or suspected injury. In yet still another embodiment, the assay is performed on a sample obtained from a subject within about 8 hours to about 12 hours after the actual injury or suspected injury. In still yet a further embodiment, the assay is performed on a sample obtained from a subject within about 12 hours to about 16 hours after the actual injury or suspected injury. In still yet another embodiment, the assay is performed on a sample obtained from a subject within about 16 hours to about 20 hours after the actual injury or suspected injury. In still yet another embodiment, the assay is performed on a sample obtained from a subject within about 20 hours to about 24 hours after the actual injury or suspected injury. In still yet another embodiment, the assay is performed on a sample obtained from a subject within about 24 hours to about 28 hours after the actual injury or suspected injury. In still a further embodiment, the assay is performed on a sample obtained from a subject within about 24 hours to about 48 hours after an injury or suspected injury. In still yet a further embodiment, the assay is performed on a sample obtained from a subject within about 28 hours to about 32 hours after the actual injury or suspected injury. In still yet a further embodiment, the assay is performed on a sample obtained from a subject within about 32 hours to about 36 hours after the actual injury or suspected injury. In still yet a further embodiment, the assay is performed on a sample obtained from a subject within about 36 hours to about 40 hours after the actual injury or suspected injury. In still yet a further embodiment, the assay is performed on a sample obtained from a subject within about 40 hours to about 44 hours after the actual injury or suspected injury. In yet still another embodiment, the assay is performed on a sample obtained from a subject within about 44 to about 48 hours after the actual injury or suspected injury.

In yet another embodiment of the above method, the (a) reference level of GFAP is about 50 pg/mL and the reference level of UCH-L1 is about 2000 pg/mL; (b) the reference level of GFAP is about 95 pg/mL and the reference level of UCH-L1 is about 2000 pg/mL; (c) the reference level of GFAP is about 110 pg/mL and the reference level of UCH-L1 is about 2000 pg/mL; (d) the reference level of GFAP is about 115 pg/mL and the reference level of UCH-L1 is about 110 pg/mL; (e) the reference level of GFAP is about 140 pg/mL and the reference level of UCH-L1 is about 2000 pg/mL; (f) the reference level of GFAP is about 150 pg/mL and the reference level of UCH-L1 is about 190 pg/mL; (g) the reference level of GFAP is about 190 pg/mL and the reference level of UCH-L1 is about 90 pg/mL; (h) the reference level of GFAP is about 240 pg/mL and the reference level of UCH-L1 is about 300 pg/mL; (i) the reference level of GFAP is about 285 pg/mL and the reference level of UCH-L1 is about 190 pg/mL; (j) the reference level of GFAP is about 500 pg/mL and the reference level of UCH-L1 is about 1450 pg/mL; (k) the reference level of GFAP is about 555 pg/mL and the reference level of UCH-L1 is about 810 pg/mL; (l) the reference level of GFAP is about 800 pg/mL and the reference level of UCH-L1 is about 900 pg/mL; (m) the reference level of GFAP is about 840 pg/mL and the reference level of UCH-L1 is about 2000 pg/mL; (n) the reference level of GFAP is about 880 pg/mL and the reference level of UCH-L1 is about 810 pg/mL; or (0) the reference level of GFAP is about 975 pg/mL and the reference level of UCH-L1 is about 1580 pg/mL.

In yet another embodiment of the above method, the sample obtained from the subject (a) about 4 hours to about 8 hours after the actual or suspected injury and the level of GFAP is about 50 pg/mL and the level of UCH-L1 is about 2000 pg/mL; (b) about 4 hours to about 8 hours after the actual or suspected injury and the level of GFAP is about 110 pg/mL and the level of UCH-L1 is about 2000 pg/mL; (c) about 4 hours to about 8 hours after the actual or suspected injury and the level of GFAP is about 140 pg/mL and the level of UCH-L1 is about 2000 pg/mL; (d) about 4 hours to about 8 hours after the actual or suspected injury and the level of GFAP is about 500 pg/mL and the level of UCH-L1 is about 1450 pg/mL; (e) about 4 hours to about 8 hours after the actual or suspected injury and the level of GFAP is about 890 pg/mL and the level of UCH-L1 is about 920 pg/mL; (f) about 12 hours to about 16 hours after the actual or suspected injury and the level of GFAP is about 105 pg/mL and the level of UCH-L1 is about 840 pg/mL; (g) about 12 hours to about 16 hours after the actual or suspected injury and the level of GFAP is about 370 pg/mL and the level of UCH-L1 is about 110 pg/mL; (h) about 12 hours to about 16 hours after the actual or suspected injury and the level of GFAP is about 505 pg/mL and the level of UCH-L1 is about 1580 pg/mL; (i) about 12 hours to about 16 hours after the actual or suspected injury and the level of GFAP is about 695 pg/mL and the level of UCH-L1 is about 1570 pg/mL; or (j) about 12 hours to about 16 hours after the actual or suspected injury and the level of GFAP is about 150 pg/mL and the level of UCH-L1 is about 2000 pg/mL.

In yet another embodiment of the above-described method, the reference level of GFAP and the reference level of UCH-L1 are determined by an assay having a sensitivity equal to or greater than about 54% and a specificity equal to or greater than about 32%.

In still yet another embodiment of the above-described method, the sample is obtained from the subject within about 4 hours to about 16 hours after the actual or suspected injury.

In yet another embodiment of the above-described method, the assay has at least a 2% higher sensitivity and at least a 4% higher specificity compared to an assay measuring or detecting GFAP or UCH-L1 individually.

In still yet another embodiment of the above-described method:
d. the sample is obtained from the subject within about 4 hours to about 8 hours after the actual or suspected injury; wherein the reference level of GFAP is about 110 pg/mL and the reference level of UCH-L1 is about 2000 pg/mL; and wherein the assay has a sensitivity equal to or greater than 95% and a specificity equal to or greater than 62%;
e. the sample is obtained from the subject within about 8 hours to about 12 hours after the actual or suspected injury; wherein the reference level of GFAP is about 240 pg/mL and the reference level of UCH-L1 is about 300 pg/mL; and wherein the assay has a sensitivity equal to or greater than 91.5% and a specificity equal to or greater than 52%; or
f. the sample is obtained from the subject within about 12 hours to about 16 hours after the actual or suspected injury; wherein the reference level of GFAP is about 190 pg/mL and the reference level of UCH-L1 is about 90 pg/mL; and wherein the assay has a sensitivity equal to or greater than 99% and a specificity equal to or greater than 36%.

In yet another embodiment of the above-described method, the measurement of the level of GFAP comprises:
(a) contacting the sample, either simultaneously or sequentially, in any order with:
(1) at least one GFAP-capture antibody, which binds to an epitope on GFAP or GFAP fragment to form an at least one GFAP-capture antibody-GFAP antigen complex, and
(2) at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and
(b) measuring the amount or concentration of GFAP in the sample based on the signal generated by the detectable label in the at least one GFAP-capture antibody-GFAP antigen—at least one GFAP-detection antibody complex.

In yet another embodiment, the measurement of UCH-L1 in the above-identified method comprises:
(a) contacting the sample, either simultaneously or sequentially, in any order with:
(1) at least one UCH-L1-capture antibody, which binds to an epitope on UCH-L1 or UCH-L1 fragment to form an at least one UCH-L1-capture antibody-UCH-L1 antigen complex, and
(2) at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and
(b) measuring the amount or concentration of UCH-L1 in the sample based on the signal generated by the detectable label in the at least one UCH-L1-capture antibody-UCH-L1 antigen—at least one UCH-L1-detection antibody complex.

In one aspect, using the above-described methods, the subject is assessed or evaluated as having a mild TBI. In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a TBI (e.g., such as a mild moderate, severe, or a moderate to severe TBI with a treatment for TBI (e.g., a surgical treatment, a therapeutic treatment, or combinations thereof)). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is serum. In yet other embodiments, the assay is a clinical chemistry assay and the sample is serum. In still further embodiments, the assay is a single molecule detection assay and the sample is serum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

In yet another aspect, the present disclosure relates to a method of aiding in the determination of or determining whether a human subject that has sustained an injury to the head has sustained a traumatic brain injury (TBI). The method comprises the steps of:
performing an assay within about 48 hours after an actual or suspected injury on a sample obtained from the subject to measure or detect a combination of a level of glial fibrillary acidic protein (GFAP) and a level of ubiquitin carboxy-terminal hydrolase L1 (UCH-L1) in the sample; and
determining that the subject more likely than not has sustained a TBI when the level of GFAP in the sample is equal to a reference level of GFAP of from about 15 pg/mL to about 40 pg/mL, and the level of UCH-L1 in the sample is equal to a reference level of UCH-L1 of from about 70 pg/mL to about 150 pg/mL.

In the above-described method, in one embodiment, the assay is performed on a sample obtained from a subject within about 0 to about 4 hours after the injury. In another embodiment, the assay is performed on a sample obtained from a subject within about 4 hours to about 8 hours after the injury. In yet still another embodiment, the assay is performed on a sample obtained from a subject within about 8 hours to about 12 hours after the injury. In still yet a further embodiment, the assay is performed on a sample obtained from a subject within about 12 hours to about 16 hours after the injury. In still yet another embodiment, the assay is performed on a sample obtained from a subject within about 16 hours to about 20 hours after the injury. In still yet another embodiment, the assay is performed on a sample obtained from a subject within about 20 hours to about 24 hours after the injury. In still yet another embodiment, the assay is performed on a sample obtained from a subject within about 24 hours to about 28 hours after the injury. In still a further embodiment, the assay is performed on a sample obtained from a subject within about 24 hours to about 48 hours after the injury. In still yet a further embodiment, the assay is performed on a sample obtained from a subject within about 28 hours to about 32 hours after the injury. In still yet a further embodiment, the assay is performed on a sample obtained from a subject within about 32 hours to about 36 hours after the injury. In still yet a further embodiment, the assay is performed on a sample obtained from a subject within about 36 hours to about 40 hours after the injury. In still yet a further embodiment, the assay is performed on a sample obtained from a subject within about 40 hours to about 44 hours after the injury. In yet still another embodiment, the assay is performed on a sample obtained from a subject within about 44 to about 48 hours after the injury.

In yet another embodiment of the above-described method, the (a) the reference level of GFAP is about 10 pg/mL and the reference level of UCH-L1 is about 60 pg/mL; (b) the reference level of GFAP is about 15 pg/mL and the reference level of UCH-L1 is about 70 pg/mL; (c) the reference level of GFAP is about 15 pg/mL and the reference level of UCH-L1 is about 90 pg/mL; (d) the reference level of GFAP is about 15 pg/mL and the reference level of UCH-L1 is about 150 pg/mL; (e) the reference level of GFAP is about 20 pg/mL and the reference level of UCH-L1 is about 60 pg/mL; (f) the reference level of GFAP is about 30 pg/mL and the reference level of UCH-L1 is about 70 pg/mL; or (g) the reference level of GFAP is about 30 pg/mL and the reference level of UCH-L1 is about 110 pg/mL.

In still yet another embodiment of the above-described method, the sample is obtained from the subject within: (a) about 4 hours to about 8 hours after the injury and the level of GFAP is about 15 pg/mL and the level of UCH-L1 is about 70 pg/mL; (b) about 4 hours to about 8 hours after the injury and the level of GFAP is about 30 pg/mL and the level of UCH-L1 is about 70 pg/mL; (c) about 4 hours to about 8 hours after the injury and the level of GFAP is about 40 pg/mL and the level of UCH-L1 is about 100 pg/mL; (d) about 8 hours to about 12 hours after the injury and the level of GFAP is about 15 pg/mL and the level of UCH-L1 is about 90 pg/mL; (e) about 8 hours to about 12 hours after the injury and the level of GFAP is about 15 pg/mL and the level of UCH-L1 is about 150 pg/mL; (f) about 8 hours to about 12 hours after the injury and the level of GFAP is about 30 pg/mL and the level of UCH-L1 is about 110 pg/mL; (g) about 12 hours to about 16 hours after the injury and the level of GFAP is about 10 pg/mL and the level of UCH-L1 is about 60 pg/mL; (h) about 12 hours to about 16 hours after the injury and the level of GFAP is about 20 pg/mL and the level of UCH-L1 is about 60 pg/mL; or (i) about 12 hours to about 16 hours after the injury and the level of GFAP is about 30 pg/mL and the level of UCH-L1 is about 110 pg/mL.

In another embodiment of the above-described method, the reference level of GFAP and the reference level of UCH-L1 are determined by an assay having a sensitivity equal to or greater than about 90% and a specificity equal to or greater than about 35%.

In yet another embodiment of the above-described method, the sample can be obtained from the subject within about 4 hours to about 16 hours after the injury.

In still yet another embodiment, the assay in the above-described method has at least a 3% higher sensitivity and at least a 17% higher specificity compared to an assay measuring or detecting GFAP or UCH-L1 individually.

In still yet another embodiment of the above-described method:

the sample is obtained from the subject within about 8 hours to about 12 hours after the injury; wherein the reference level of GFAP is about 30 pg/mL and the reference level of UCH-L1 is about 110 pg/mL; and wherein the assay has a sensitivity equal to or greater than 92% and a specificity equal to or greater than 99%; or the sample is obtained from the subject within about 12 hours to about 16 hours after the injury; wherein the reference level of GFAP is about 30 pg/mL and the reference level of UCH-L1 is about 110 pg/mL; and wherein the assay has a sensitivity equal to or greater than 90% and a specificity equal to or greater than 99%; or the sample is obtained from the subject within about 4 hours to about 8 hours after the injury; wherein the reference level of GFAP is about 40 pg/mL and the reference level of UCH-L1 is about 100 pg/mL; and wherein the method has a sensitivity equal to or greater than 90% and a specificity equal to or greater than 94%; or the sample is obtained from the subject within about 8 hours to about 12 hours after the injury; wherein the reference level of GFAP is about 15 pg/mL and the reference level of UCH-L1 is about 150 pg/mL; and wherein the assay has a sensitivity equal to or greater than 95% and a specificity equal to or greater than 82%; or the sample is obtained from the subject within about 12 hours to about 16 hours after the injury; wherein the reference level of GFAP is about 20 pg/mL and the reference level of UCH-L1 is about 60 pg/mL; and wherein the assay has a sensitivity equal to or greater than 95% and a specificity equal to or greater than 65%.

In the above-described method, the levels of GFAP and UCH-L1 can be measured or detected using an immunoassay or clinical chemistry assay. Alternatively, in the above-described method, the levels of GFAP and UCH-L1 can be measured or detected using a single molecule detection assay.

In yet another embodiment of the above-described method, the measurement of the level of GFAP comprises:

(d) contacting the sample, either simultaneously or sequentially, in any order with:
(1) at least one GFAP-capture antibody, which binds to an epitope on GFAP or GFAP fragment to form an at least one GFAP-capture antibody-GFAP antigen complex, and
(2) at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and
(e) measuring the amount or concentration of GFAP in the sample based on the signal generated by the detectable label in the at least one GFAP-capture antibody-GFAP antigen—at least one GFAP-detection antibody complex.

In yet another embodiment, the measurement of UCH-L1 in the above-identified method comprises:

(a) contacting the sample, either simultaneously or sequentially, in any order with:
(1) at least one UCH-L1-capture antibody, which binds to an epitope on UCH-L1 or UCH-L1 fragment to form an at least one UCH-L1-capture antibody-UCH-L1 antigen complex, and
(2) at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and
(f) measuring the amount or concentration of UCH-L1 in the sample based on the signal generated by the detectable label in the at least one UCH-L1-capture antibody-UCH-L1 antigen—at least one UCH-L1-detection antibody complex.

In one aspect, using the above-described methods, the subject is assessed or evaluated as having a mild TBI. In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a TBI (e.g., such as a mild moderate, severe, or a moderate to severe TBI with a treatment for TBI (e.g., a surgical treatment, a therapeutic treatment, or combinations thereof)). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is serum. In yet other embodiments, the assay is a clinical chemistry assay and the sample is serum. In still further embodiments, the assay is a single molecule detection assay and the sample is scrum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

In yet another aspect, the present disclosure relates to a method of aiding in the determination of or determining whether to perform a head magnetic resonance imaging (MRI) procedure on a human subject that has sustained or may have sustained an injury to the head. The method comprises the steps of:
  performing an assay within about 48 hours after an actual or suspected injury on a sample obtained from the subject w to measure or detect a combination of a level of glial fibrillary acidic protein (GFAP) and a level of ubiquitin carboxy-terminal hydrolase L1 (UCH-L1) in the sample; and
  (a) determining that the subject does not need an MRI procedure when the level of GFAP in the sample is less than a reference level of GFAP of about 15 pg/mL, and the level of UCH-L1 in the sample is less than a reference level of UCH-L1 of about 50 pg/mL; or
  (b) determining that the subject more likely than not does need an MRI procedure when the level of GFAP in the sample is equal to a reference level of GFAP of from about 15 pg/mL to about 1000 pg/mL, and the level of UCH-L1 in the sample is equal to a reference level of UCH-L1 of from about 50 pg/mL to about 2000 pg/mL; or
  (c) determining that the subject more likely than not does need an MRI procedure when the level of GFAP in the sample is greater than a reference level of GFAP of about 1000 pg/mL, and the level of UCH-L1 in the sample is greater than a reference level of UCH-L1 of about 2000 pg/mL.

In the above-described method, the subject may have received an MRI after the assay is performed, and wherein the subject is suspected as having a TBI based on the MRI result. In yet another embodiment, the reference level of GFAP and the reference level of UCH-L1 correlate with a negative MRI result.

In the above-described method, in one embodiment, the assay is performed on a sample obtained from a subject within about 0 to about 4 hours after the actual injury or suspected injury. In another embodiment, the assay is performed on a sample obtained from a subject within about 4 hours to about 8 hours after the actual injury or suspected injury. In yet still another embodiment, the assay is performed on a sample obtained from a subject within about 8 hours to about 12 hours after the actual injury or suspected injury. In still yet a further embodiment, the assay is performed on a sample obtained from a subject within about 12 hours to about 16 hours after the actual injury or suspected injury. In still yet another embodiment, the assay is performed on a sample obtained from a subject within about 16 hours to about 20 hours after the actual injury or suspected injury. In still yet another embodiment, the assay is performed on a sample obtained from a subject within about 20 hours to about 24 hours after the actual injury or suspected injury. In still yet another embodiment, the assay is performed on a sample obtained from a subject within about 24 hours to about 28 hours after the actual injury or suspected injury. In still a further embodiment, the assay is performed on a sample obtained from a subject within about 24 hours to about 48 hours after an injury or suspected injury. In still yet a further embodiment, the assay is performed on a sample obtained from a subject within about 28 hours to about 32 hours after the actual injury or suspected injury. In still yet a further embodiment, the assay is performed on a sample obtained from a subject within about 32 hours to about 36 hours after the actual injury or suspected injury. In still yet a further embodiment, the assay is performed on a sample obtained from a subject within about 36 hours to about 40 hours after the actual injury or suspected injury. In still yet a further embodiment, the assay is performed on a sample obtained from a subject within about 40 hours to about 44 hours after the actual injury or suspected injury. In yet still another embodiment, the assay is performed on a sample obtained from a subject within about 44 to about 48 hours after the actual injury or suspected injury.

In the above-described methods for determining or evaluating whether to perform a MRI, the subject may be suspected of having a traumatic brain injury based on a MRI or CT scan that has been or already was performed (meaning, prior to the assay being performed). For example, depending upon a subject's medical condition (such as, if the patient is unconscious), a MRI or CT scan may be conducted shortly after the subject arrives at an emergency room, trauma center, or other site in order to assess and/or evaluate whether the subject has a TBI. Such a MRI or CT scan may be performed prior to the assay being performed to confirm and determine whether or not the subject has a mild, moderate, severe, or moderate to severe TBI. After the assay is performed, one or more subsequent MRIs (or CT scans) can be performed based on the results of the assay as part of the physician's (or other medical personnel's) management of the TBI (such as, for example, to determine whether surgical and/or pharmacological intervention may be required).

In certain aspects of the above methods, the subject may be suspected of having a traumatic brain injury based on a MRI. For example, a subject may be suspected of having a mild TBI based on a MRI. Alternatively, a subject may be suspected of having a moderate TBI based on a MRI. Alternatively, a subject may be suspected of having a severe TBI based on a MRI. Alternatively, a subject may be suspected of having a moderate to severe TBI based on a MRI. Still further, a subject may be suspected of not having a TBI based on a MRI.

In still yet another embodiment of the above-described method, the reference level of GFAP and the reference level of UCH-L1 are determined by an assay having a sensitivity of about 80% to about 98% and a specificity of about 30% to about 85%.

In a further embodiment of the above-described method, the subject may have received a negative CT scan result before the assay is performed.

In one aspect, using the above-described methods, the subject is assessed or evaluated as having a mild TBI. In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a TBI (e.g., such as a mild moderate, severe, or a moderate to severe TBI with a treatment for TBI (e.g., a surgical treatment, a therapeutic treatment, or combinations thereof)). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is serum. In yet other embodiments, the assay is a clinical chemistry assay and the sample is serum. In still further embodiments, the assay is a single molecule detection assay and the sample is serum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

In yet another aspect, the present disclosure relates to a method for aiding in predicting or predicting the outcome of a human subject that has sustained or may have sustained a head injury. The method comprises the steps of:
  performing an assay within about 48 hours after an actual or suspected injury on a sample obtained from the subject to measure or detect a combination of a level of glial fibrillary acidic protein (GFAP) and a level of ubiquitin carboxy-terminal hydrolase L1 (UCH-L1) in the sample; and
  predicting for the subject more likely than not an unfavorable outcome when the level of GFAP in the sample is equal to a reference level of GFAP of from about 80 pg/mL to about 2000 pg/mL, and the level of UCH-L1 in the sample is equal to a reference level of UCH-L1 of from about 130 pg/mL to about 2000 pg/mL.

In another embodiment of the above-described method, the subject may have received an Extended Glasgow Outcome Scale (GOSE) score after the method is performed, and wherein the subject is suspected as having a poor outcome based on the GOSE score. In yet another embodiment, the reference level of GFAP and the reference level of UCH-L1 correlate with subjects having a poor outcome based on a GOSE score of 1.

In the above-described method, in one embodiment, the assay is performed on a sample obtained from a subject within about 0 to about 4 hours after the actual injury or suspected injury. In another embodiment, the assay is performed on a sample obtained from a subject within about 4 hours to about 8 hours after the actual injury or suspected injury. In yet still another embodiment, the assay is performed on a sample obtained from a subject within about 8 hours to about 12 hours after the actual injury or suspected injury. In still yet a further embodiment, the assay is performed on a sample obtained from a subject within about 12 hours to about 16 hours after the actual injury or suspected injury. In still yet another embodiment, the assay is performed on a sample obtained from a subject within about 16 hours to about 20 hours after the actual injury or suspected injury. In still yet another embodiment, the assay is performed on a sample obtained from a subject within about 20 hours to about 24 hours after the actual injury or suspected injury. In still yet another embodiment, the assay is performed on a sample obtained from a subject within about 24 hours to about 28 hours after the actual injury or suspected injury. In still a further embodiment, the assay is performed on a sample obtained from a subject within about 24 hours to about 48 hours after an injury or suspected injury. In still yet a further embodiment, the assay is performed on a sample obtained from a subject within about 28 hours to about 32 hours after the actual injury or suspected injury. In still yet a further embodiment, the assay is performed on a sample obtained from a subject within about 32 hours to about 36 hours after the actual injury or suspected injury. In still yet a further embodiment, the assay is performed on a sample obtained from a subject within about 36 hours to about 40 hours after the actual injury or suspected injury. In still yet a further embodiment, the assay is performed on a sample obtained from a subject within about 40 hours to about 44 hours after the actual injury or suspected injury. In yet still another embodiment, the assay is performed on a sample obtained from a subject within about 44 to about 48 hours after the actual injury or suspected injury.

In still yet another embodiment of the above-described method, the reference level of GFAP and the reference level of UCH-L1 are determined by an assay having a sensitivity of about 80% to about 97% and a specificity of about 30% to about 95%.

In the above-described method, the levels of GFAP and UCH-L1 are measured or detected using an immunoassay or clinical chemistry assay. Alternatively, in the above-described method, the levels of GFAP and UCH-L1 are measured or detected using a single molecule detection assay.

In yet another embodiment of the above-described method, the measurement of the level of GFAP comprises:
(c) contacting the sample, either simultaneously or sequentially, in any order with:
(1) at least one GFAP-capture antibody, which binds to an epitope on GFAP or GFAP fragment to form an at least one GFAP-capture antibody-GFAP antigen complex, and
(2) at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and
(d) measuring the amount or concentration of GFAP in the sample based on the signal generated by the detectable label in the at least one GFAP-capture antibody-GFAP antigen—at least one GFAP-detection antibody complex.

In yet another embodiment, the measurement of UCH-L1 in the above-identified method comprises:
(c) contacting the sample, either simultaneously or sequentially, in any order with:
(1) at least one UCH-L1-capture antibody, which binds to an epitope on UCH-L1 or UCH-L1 fragment to form an at least one UCH-L1-capture antibody-UCH-L1 antigen complex, and
(2) at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and
(d) measuring the amount or concentration of UCH-L1 in the sample based on the signal generated by the detectable label in the at least one UCH-L1-capture antibody-UCH-L1 antigen—at least one UCH-L1-detection antibody complex.

In one aspect, using the above-described methods, the subject is assessed or evaluated as having a mild TBI. In one aspect, using the above-described methods, the subject is assessed or evaluated as having a moderate TBI. In another aspect, using the above-described methods, the subject is assessed or evaluated as having a severe TBI. In another aspect, using the above-described methods, the subject is assessed or evaluated as having a moderate to severe TBI. In yet still a further aspect, using the above-described methods, the subject is assessed or evaluated as not having a TBI.

The above-described methods can further comprise treating a human subject assessed or evaluated as having a TBI (e.g., such as a mild moderate, severe, or a moderate to severe TBI with a treatment for TBI (e.g., a surgical treatment, a therapeutic treatment, or combinations thereof)). Any such treatment known in the art and described further herein can be used. Moreover, in a further aspect, any subject being treated for TBI can also, optionally, be monitored during and after any course of treatment. Alternatively, said methods can further comprise monitoring a subject assessed as having a moderate, severe, or a moderate to severe TBI (such as those, who as of yet, may not be receiving any treatment).

In the above-described methods, the sample can be selected from the group consisting of a whole blood sample, a serum sample, a cerebrospinal fluid sample, and a plasma sample. In some embodiments, the sample is a whole blood sample. In some embodiments, the sample is a plasma sample. In yet other embodiments, the sample is a serum sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild, moderate, severe, or a moderate to severe TBI, the human subject's exhibition of low or high levels of UCH-L1, GFAP and or UCH-L1 and GFAP, and the timing of any event wherein the human subject may have sustained head injury.

In the above-described methods, the assay is an immunoassay. In some embodiments, the assay is a point-of-care assay. In yet other embodiments, the assay is a clinical chemistry assay. In yet other embodiments, the assay is a single molecule detection assay. In yet other embodiments, the assay is an immunoassay, the subject is a human and the sample is whole blood. In yet other embodiments, the assay is a point-of-care assay, the subject is a human and the sample is whole blood. In yet other embodiments, the assay is a clinical chemistry assay and the sample is whole blood. In still further embodiments, the assay is a single molecule detection assay and the sample is whole blood. In yet other embodiments, the assay is an immunoassay, the subject is a human and the sample is serum. In yet other embodiments, the assay is a point-of-care assay, the subject is a human and the sample is serum. In yet other embodiments, the assay is a clinical chemistry assay and the sample is serum. In still further embodiments, the assay is a single molecule detection assay and the sample is serum. In yet other embodiments, the assay is an immunoassay, the subject is a human and the sample is plasma. In yet other embodiments, the assay is a point-of-care assay, the subject is a human and the sample is plasma. In yet other embodiments, the assay is a clinical chemistry assay and the sample is plasma. In still further embodiments, the assay is a single molecule detection assay and the sample is plasma.

DETAILED DESCRIPTION

Figure 1A:
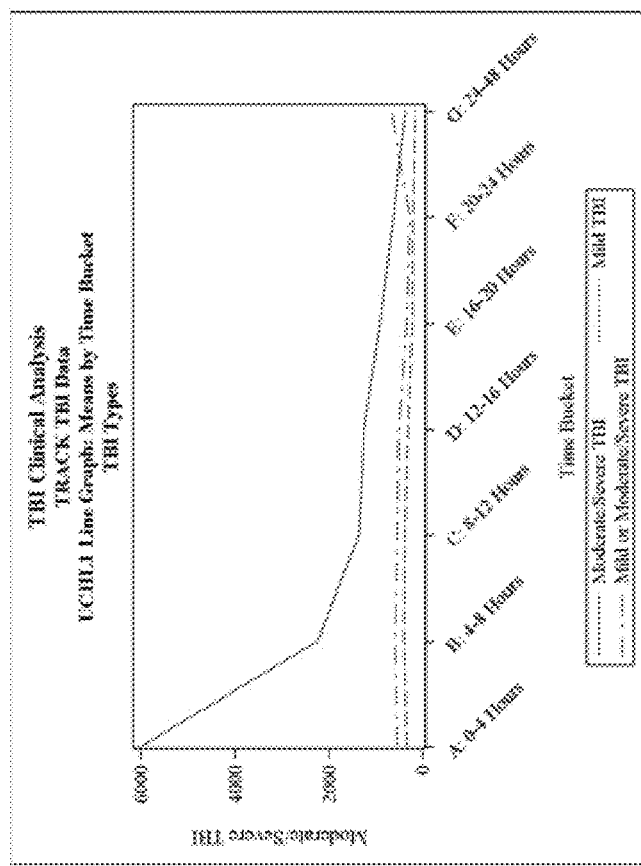
FIGS. 1A-1B include representative graphs depicting mean GFAP (FIG. 1A) and UCH-L1 (FIG. 1B) levels at various time points within 48 hours post-injury for moderate/severe TBI, mild TBI, and mild and moderate/severe TBI groups.

The present disclosure relates to methods of aiding in the diagnosis and evaluation of or diagnosing and evaluating a subject that has sustained or may have sustained an injury to the head. In particular, the present disclosure provides methods for aiding in the diagnosis and evaluation of or diagnosing and evaluating a subject to determine whether the subject has sustained a traumatic brain injury (TBI) by detecting or measuring a combination of the levels of ubiquitin carboxy-terminal hydrolase L1 (UCH-L1) and glial fibrillary acidic protein (GFAP) in samples taken at various time points within 48 hours after the subject has sustained or may have sustained an injury to the head. Embodiments of the method also include aiding in the determination of whether a human subject that has or may have sustained an injury to the head would benefit from and thus receive an imaging procedure, such as magnetic resonance imaging (MRI) or head computerized tomography (CT) scan, based on assessment of a combination of the levels of GFAP and UCH-L1. Methods can involve detecting GFAP and UCH-L1 levels in one or more samples taken from the human subject at a time point within about 48 hours, e.g., 0 to about 12 hours, of the injury to the head or suspected injury to the head. The detection of levels of GFAP and UCH-L1 that are higher than reference levels within about the first 48 hours after injury or suspected injury to the head provides an aid in the determination of whether a human subject should receive an imaging procedure (i.e., "rule in" an imaging procedure). For example, human subjects having levels of GFAP and UCH-L1 that are higher than a reference level may also be identified as likely to have a positive head CT scan or a positive MRI (e.g., an intracranial lesion present, thus indicating a potential TBI) and thus benefit from having a head CT scan or MRI. Alternatively, certain levels of GFAP and UCH-L1 can be used to "rule out" a need for further medical intervention. For example, human subjects having levels of GFAP and UCH-L1 that are lower than a reference level may be identified as likely to have a negative head CT scan or a negative MRI (i.e., an absence of an intracranial lesion, and thus a head CT scan or MRI would not be needed or performed).

The present disclosure relates to methods that involve detecting GFAP and UCH-L1 levels in one or more samples taken from the human subject at different time points within 48 hours of the injury to the head or suspected injury to the head. The detection of an increase in or elevated levels of a combination of GFAP and UCH-L1 can also aid in the diagnosis of a certain type of TBI. For example, levels of GFAP and UCH-L1 that are higher than particular reference levels can indicate that a subject has a moderate, severe or moderate to severe TBI, and concomitantly, levels of GFAP and UCH-L1 that are lower than that reference level can indicate that the subject has a mild TBI. In some cases, levels of GFAP and UCH-L1 in combination can also help to determine whether a subject that has sustained an orthopedic injury has also sustained a mild TBI, and thus requires further medical intervention to diagnose the presence or absence of a mild TBI.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Affinity matured antibody" is used herein to refer to an antibody with one or more alterations in one or more CDRs, which result in an improvement in the affinity (i.e., $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

"Antibody" and "antibodies" as used herein refers to monoclonal antibodies, monospecific antibodies (e.g., which can either be monoclonal, or may also be produced by other means than producing them from a common germ cell), multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11): 1290-1297 (2007) and PCT International Application WO 2001/058956, the contents of each of which are herein incorporated by reference), or domain antibodies (dAbs) (e.g., such as described in Holt et al. (2014) Trends in Biotechnology 21:484-490), and including single domain antibodies sdAbs that are naturally occurring, e.g., as in cartilaginous fishes and camelid, or which are synthetic, e.g., nanobodies, VHH, or other domain structure), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody" (e.g., an anti-GFAP antibody, a GFAP antibody, an anti-UCH-L1 antibody, or a UCH-L1 antibody).

"Antibody fragment" as used herein refers to a portion of an intact antibody comprising the antigen-binding site or variable region. The portion does not include the constant heavy chain domains (i.e., CH2, CH3, or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

The "area under curve" or "AUC" refers to area under a ROC curve. AUC under a ROC curve is a measure of accuracy. An AUC of 1 represents a perfect test, whereas an AUC of 0.5 represents an insignificant test. A preferred AUC may be at least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

"Bead" and "particle" are used herein interchangeably and refer to a substantially spherical solid support. One example of a bead or particle is a microparticle. Microparticles that can be used herein can be any type known in the art. For example, the bead or particle can be a magnetic bead or magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO·Fe_2O_3$). Beads can have a solid core portion that is magnetic and is surrounded by one or more non-magnetic layers. Alternately, the magnetic portion can be a layer around a non-magnetic core. The microparticles can be of any size that would work in the methods described herein, e.g., from about 0.75 to about 5 nm, or from about 1 to about 5 nm, or from about 1 to about 3 nm.

"Binding protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (see Milstein et al., Nature, 305(5934): 537-540 (1983)), by chemical conjugation of two different monoclonal antibodies (see, Staerz et al., Nature, 314(6012): 628-631 (1985)), or by knob-into-hole or similar approaches, which introduce mutations in the Fc region (see Holliger et al., Proc. Natl. Acad. Sci. USA, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

"CDR" is used herein to refer to the "complementarity determining region" within an antibody variable sequence. There are three CDRs in each of the variable regions of the heavy chain and the light chain. Proceeding from the N-terminus of a heavy or light chain, these regions are denoted "CDR1", "CDR2", and "CDR3", for each of the variable regions. The term "CDR set" as used herein refers to a group of three CDRs that occur in a single variable region that binds the antigen. An antigen-binding site, therefore, may include six CDRs, comprising the CDR set from each of a heavy and a light chain variable region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, whole blood, serum or plasma sample, in accordance with the methods described herein and other methods known in the art. Some components can be in solution or lyophilized for reconstitution for use in an assay. "Controls" as used herein generally refers to a reagent whose purpose is to evaluate the performance of a measurement system in order to assure that it continues to produce results within permissible boundaries (e.g., boundaries ranging from measures appropriate for a research use assay on one end to analytic boundaries established by quality specifications for a commercial assay on the other end). To accomplish this, a control should be indicative of patient results and optionally should somehow assess the impact of error on the measurement (e.g., error due to reagent stability, calibrator variability, instrument variability, and the like). As used herein, a "control subject" relates to a subject or subjects that have not sustained a traumatic brain injury (TBI). An "ortho control" as used herein relates to (e.g., is based on) samples or information from a subject or subjects that have sustained an orthopedic injury but have not sustained an apparent TBI. As used herein, an "ortho control subject" relates to a subject or subjects that have sustained an orthopedic injury but have not sustained an apparent TBI. In some cases, "ortho control subjects" are adult orthopedic patients who have an Abbreviated Injury Score of ≤4 (not life threatening) for their extremity and/or pelvis injury and/or rib fracture. A "healthy control" as used herein relates to (e.g., is based on) samples or information from a subject or subjects that are considered healthy and have sustained no apparent TBI or orthopedic injury. As used herein, a "healthy control subject" relates to a subject or subjects that are considered to be healthy and have sustained no apparent TBI or orthopedic injury.

"Correlated to" as used herein refers to compared to.

"CT scan" as used herein refers to a computerized tomography (CT) scan. A CT scan combines a series of X-ray images taken from different angles and uses computer processing to create cross-sectional images, or slices, of the bones, blood vessels and soft tissues inside your body. The CT scan may use X-ray CT, positron emission tomography (PET), single-photon emission computed tomography (SPECT), computed axial tomography (CAT scan), or computer aided tomography. The CT scan may be a conventional CT scan or a spiral/helical CT scan. In a conventional CT scan, the scan is taken slice by slice and after each slice the scan stops and moves down to the next slice, e.g., from the top of the abdomen down to the pelvis. The conventional CT scan requires patients to hold their breath to avoid movement artefact. The spiral/helical CT scan is a continuous scan which is taken in a spiral fashion and is a much quicker process where the scanned images are contiguous.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g., a protein domain, said protein domain being linked by covalent or non-covalent bonds. The linkage can be based on genetic fusion according to the methods known in the art. The additional domain present in the fusion protein comprising the antibody may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g., a cytokine or growth hormone), a chemical agent, a peptide, a protein, or a drug, for example.

"Determined by an assay" is used herein to refer to the determination of a reference level by any appropriate assay. The determination of a reference level may, in some embodiments, be achieved by an assay of the same type as the assay that is to be applied to the sample from the subject (for example, by an immunoassay, clinical chemistry assay, a single molecule detection assay, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS)). The determination of a reference level may, in some embodiments, be achieved by an assay of the same type and under the same assay conditions as the assay that is to be applied to the sample from the subject. As noted herein, this disclosure provides exemplary reference levels (e.g., calculated by comparing reference levels at different time points). It is well within the ordinary skill of one in the art to adapt the disclosure herein for other assays to obtain assay-specific reference levels for those other assays based on the description provided by this disclosure. For example, a set of training samples comprising samples obtained from human subjects known to have sustained an injury to the head (and more particularly, samples obtained from human subjects known to have sustained a (i) mild TBI; and/or (ii) moderate, severe, or moderate to severe TBI and samples obtained from human subjects known not to have sustained an injury to the head may be used to obtain assay-specific reference levels. It will be understood that a reference level "determined by an assay" and having a recited level of "sensitivity" and/or "specificity" is used herein to refer to a reference level which has been determined to provide a method of the recited sensitivity and/or specificity when said reference level is adopted in the methods of the disclosure. It is well within the ordinary skill of one in the art to determine the sensitivity and specificity associated with a given reference level in the methods of the disclosure, for example by repeated statistical analysis of assay data using a plurality of different possible reference levels.

Practically, when discriminating between a subject as having a traumatic brain injury or not having a traumatic brain injury or a subject as having a a mild versus a moderate, severe, or moderate to severe traumatic brain injury, the skilled person will balance the effect of raising a cutoff on sensitivity and specificity. Raising or lowering a cutoff will have a well-defined and predictable impact on sensitivity and specificity, and other standard statistical measures. It is well known that raising a cutoff will improve specificity but is likely to worsen sensitivity (proportion of those with disease who test positive). In contrast, lowering a cutoff will improve sensitivity but will worsen specificity (proportion of those without disease who test negative). The ramifications for detecting traumatic brain injury or determining a mild versus moderate, severe, or moderate to severe traumatic brain injury will be readily apparent to those skilled in the art. In discriminating whether a subject has or does not have a traumatic brain injury or a mild versus a moderate, severe, or moderate to severe traumatic brain injury, the higher the cutoff, specificity improves as more true negatives (i.e., subjects not having a traumatic brain injury, not having a mild traumatic brain injury, not have a moderate traumatic brain injury, not having a severe traumatic brain injury or not having a moderate to severe traumatic brain injury) are distinguished from those having a traumatic brain injury, a mild traumatic brain injury, a moderate traumatic brain injury, a severe traumatic brain injury or a moderate to severe traumatic brain injury. But at the same time, raising the cutoff decreases the number of cases identified as positive overall, as well as the number of true positives, so the sensitivity must decrease. Conversely, the lower the cutoff, sensitivity improves as more true positives (i.e., subjects having a traumatic brain injury, having a mild traumatic brain injury, having a moderate traumatic brain injury, having a severe traumatic brain injury or having a moderate to severe traumatic brain injury) are distinguished from those who do not have a traumatic brain injury, a mild traumatic brain injure, a moderate traumatic brain injury, a severe traumatic brain injury or a moderate to severe traumatic brain injury. But at the same time, lowering the cutoff increases the number of cases identified as positive overall, as well as the number of false positives, so the specificity must decrease.

Generally, a high sensitivity value helps one of skill rule out disease or condition (such as a traumatic brain injury, mild traumatic brain injury, moderate traumatic brain injury, severe traumatic brain injury or moderate to severe traumatic brain injury), and a high specificity value helps one of skill rule in disease or condition. Whether one of skill desires to rule out or rule in disease depends on what the consequences are for the patient for each type of error. Accordingly, one cannot know or predict the precise balancing employed to derive a test cutoff without full disclosure of the underlying information on how the value was selected. The balancing of sensitivity against specificity and other factors will differ on a case-by-case basis. This is why it is sometimes preferable to provide alternate cutoff (e.g., reference) values so a physician or practitioner can choose.

"Drugs of abuse" is used herein to refer to one or more addictive substances (such as a drug) taken for non-medical reasons (such as for, example, recreational and/or mind-altering effects). Excessive overindulgence, use or dependence of such drugs of abuse is often referred to as "substance abuse." Examples of drugs of abuse include alcohol, barbiturates, benzodiazepines, cannabis, cocaine, hallucinogens (such as ketamine, mescaline (peyote), PCP, psilocybin, DMT and/or LSD), methaqualone, opioids, amphetamines (including methamphetamines), anabolic steroids, inhalants (namely, substances which contain volatile substances that contain psychoactive properties such as, for example, nitrites, spray paints, cleaning fluids, markers, glues, etc.) and combinations thereof.

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig." Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., *Nature Biotech.*, 25: 1290-1297 (2007). A preferred example of such DVD-Ig molecules comprises a heavy chain that comprises the structural formula VD1-(X1)n-VD2-C—(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C—(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of GFAP and/or UCH-L1. Non-limiting examples of a DVD-Ig binding protein include a DVD-Ig binding protein that binds one or more epitopes of GFAP and/or UCH-L1, a DVD-Ig binding protein that binds an epitope of a human GFAP and/or UCH-L1 and an epitope of GFAP and/or UCH-L1 of another species (for example, mouse), and a DVD-Ig binding protein that binds an epitope of a human GFAP and/or UCH-L1 and an epitope of another target molecule.

"Dynamic range" as used herein refers to range over which an assay readout is proportional to the amount of target molecule or analyte in the sample being analyzed.

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"Fragment antigen-binding fragment" or "Fab fragment" as used herein refers to a fragment of an antibody that binds to antigens and that contains one antigen-binding site, one complete light chain, and part of one heavy chain. Fab is a monovalent fragment consisting of the VL, VH, CL and CH1 domains. Fab is composed of one constant and one variable domain of each of the heavy and the light chain. The variable domain contains the paratope (the antigen-binding site), comprising a set of complementarity determining regions, at the amino terminal end of the monomer. Each arm of the Y thus binds an epitope on the antigen. Fab fragments can be generated such as has been described in the art, e.g., using the enzyme papain, which can be used to cleave an immunoglobulin monomer into two Fab fragments and an Fc fragment, or can be produced by recombinant means.

"F(ab')$_2$ fragment" as used herein refers to antibodies generated by pepsin digestion of whole IgG antibodies to remove most of the Fc region while leaving intact some of the hinge region. F(ab')$_2$ fragments have two antigen-binding F(ab) portions linked together by disulfide bonds, and therefore are divalent with a molecular weight of about 110 kDa. Divalent antibody fragments (F(ab')$_2$ fragments) are smaller than whole IgG molecules and enable a better penetration into tissue thus facilitating better antigen recognition in immunohistochemistry. The use of F(ab')$_2$ fragments also avoids unspecific binding to Fc receptor on live cells or to Protein A/G. F(ab')$_2$ fragments can both bind and precipitate antigens.

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol:// vbase.mrc-cpe.cam.ac.uk/) or in the international ImMunoGeneTics® (IMGT®) information system (hypertext transfer protocol://imgt.cines.fr/texts/IMGTrepertoire/LocusGenes/).

"Functional antigen binding site" as used herein may mean a site on a binding protein (e.g., an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

"GFAP" is used herein to describe glial fibrillary acidic protein. GFAP is a protein that is encoded by the GFAP gene in humans, and which can be produced (e.g., by recombinant means, in other species).

"GFAP status" can mean either the level or amount of GFAP at a point in time (such as with a single measure of GFAP), the level or amount of GFAP associated with monitoring (such as with a repeat test on a subject to identify an increase or decrease in GFAP amount), the level or amount of GFAP associated with treatment for traumatic brain injury (whether a primary brain injury and/or a secondary brain injury) or combinations thereof.

"Glasgow Coma Scale" or "GCS" as used herein refers to a 15 point scale for estimating and categorizing the outcomes of brain injury on the basis of overall social capability or dependence on others. The test measures the motor response, verbal response and eye opening response with these values: I. Motor Response (6—Obeys commands fully; 5—Localizes to noxious stimuli; 4—Withdraws from noxious stimuli; 3—Abnormal flexion, i.e. decorticate posturing; 2—Extensor response, i.e. decerebrate posturing; and 1—No response); II. Verbal Response (5—Alert and Oriented; 4—Confused, yet coherent, speech; 3—Inappropriate words and jumbled phrases consisting of words; 2 Incomprehensible sounds; and 1—No sounds); and III. Eye Opening (4—Spontaneous eye opening; 3—Eyes open to speech; 2—Eyes open to pain; and 1—No eye opening). The final score is determined by adding the values of I+II+III. The final score can be categorized into four possible levels for survival, with a lower number indicating a more severe injury and a poorer prognosis: Mild (13-15); Moderate Disability (9-12) (Loss of consciousness greater than 30 minutes; Physical or cognitive impairments which may or may resolve; and Benefit from Rehabilitation); Severe Disability (3-8) (Coma: unconscious state. No meaningful response, no voluntary activities); and Vegetative State (Less Than 3) (Sleep wake cycles; Arousal, but no interaction with environment; No localized response to pain). Moderate brain injury is defined as a brain injury resulting in a loss of consciousness from 20 minutes to 6 hours and a Glasgow Coma Scale of 9 to 12. Severe brain injury is defined as a brain injury resulting in a loss of consciousness of greater than 6 hours and a Glasgow Coma Scale of 3 to 8.

"Glasgow Outcome Scale" as used herein refers to a global scale for functional outcome that rates patient status into one of five categories: Dead, Vegetative State, Severe Disability, Moderate Disability or Good Recovery.

"Extended Glasgow Outcome Scale" or "GOSE" as used interchangeably herein provides more detailed categorization into eight categories by subdividing the categories of severe disability, moderate disability and good recovery into a lower and upper category as shown in Table 1.

TABLE 1

| # | Category | Code | Description |
|---|---|---|---|
| 1 | Death | D | |
| 2 | Vegetative state | VX | Condition of unawareness with only reflex responses but with periods of spontaneous eye opening |
| 3 | Lower severe disability | SD− | Patient who is dependent for daily support for mental or physical disability, usually a combination of both. If the patient can be left alone for more than 8 hours at home it is upper level of SD, if not then it is low level of SD. |
| 4 | Upper severe disability | SD+ | |
| 5 | Lower moderate disability | MD− | Patients have some disability such as aphasia, hemiparesis or epilepsy and/or deficits of memory or personality but are able to look after themselves. They are independent at home but dependent outside. If they are able to return to work even with special arrangement it is upper level of MD, if not then it is low level of MD. |
| 6 | Upper moderate disability | MD+ | |
| 7 | Lower good recovery | GR− | Resumption of normal life with the capacity to work even if pre-injury status has not been achieved. Some patients have minor neurological or psychological deficits. If these deficits are not disabling then it is upper level of GR, if disabling then it is lower level of GR. |
| 8 | Upper good recovery | GR+ | |

"Humanized antibody" is used herein to describe an antibody that comprises heavy and light chain variable region sequences from a non-human species (e.g., a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98%, or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, *From Genes to Clones* (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Imaging procedure" as used herein refers to a medical test that allows the inside of a body to be seen in order to diagnose, treat, and monitor health conditions. An imaging procedure can be a non-invasive procedure that allows diagnosis of diseases and injuries without being intrusive. Examples of imaging procedures include MRI, CT scan, X-rays, positron emission tomography (PET) scan, single-photon emission computed tomography (SPECT), and diffusion tensor imaging (DTI) scan.

"Injury to the head" or "head injury" as used interchangeably herein, refers to any trauma to the scalp, skull, or brain. Such injuries may include only a minor bump on the skull or may be a serious brain injury. Such injuries include primary injuries to the brain and/or secondary injuries to the brain. Primary brain injuries occur during the initial insult and result from displacement of the physical structures of the brain. More specifically, a primary brain injury is the physical damage to parenchyma (tissue, vessels) that occurs during the traumatic event, resulting in shearing and compression of the surrounding brain tissue. Secondary brain injuries occur subsequent to the primary injury and may involve an array of cellular processes. More specifically, a secondary brain injury refers to the changes that evolve over a period of time (from hours to days) after the primary brain injury. It includes an entire cascade of cellular, chemical, tissue, or blood vessel changes in the brain that contribute to further destruction of brain tissue.

An injury to the head can be either closed or open (penetrating). A closed head injury refers to a trauma to the scalp, skull or brain where there is no penetration of the skull by a striking object. An open head injury refers a trauma to the scalp, skull or brain where there is penetration of the skull by a striking object. An injury to the head may be caused by physical shaking of a person, by blunt impact by an external mechanical or other force that results in a closed or open head trauma (e.g., vehicle accident such as with an automobile, plane, train, etc.; blow to the head such as with a baseball bat, or from a firearm), a cerebral vascular accident (e.g., stroke), one or more falls (e.g., as in sports or other activities), explosions or blasts (collectively, "blast injuries") and by other types of blunt force trauma. Alternatively, an injury to the head may be caused by the ingestion and/or exposure to a chemical, toxin or a combination of a chemical and toxin. Examples of such chemicals and/or toxins include fires, molds, asbestos, pesticides and insecticides, organic solvents, paints, glues, gases (such as carbon monoxide, hydrogen sulfide, and cyanide), organic metals (such as methyl mercury, tetraethyl lead and organic tin) and/or one or more drugs of abuse. Alternatively, an injury to the head may be caused as a result of a subject suffering from an autoimmune disease, a metabolic disorder, a brain tumor, one or more viruses, meningitis, hydrocephalus, hypoxia or any combinations thereof. In some cases, it is not possible to be certain whether any such event or injury has occurred or taken place. For example, there may be no history on a patient or subject, the subject may be unable to speak, the subject may not be aware of or have full information on what events they were exposed to, etc. Such circumstances are described herein as the subject "may have sustained an injury to the head." In certain embodiments herein, the closed head injury does not include and specifically excludes a cerebral vascular accident, such as stroke.

"Intracranial lesion" as used herein refers to an area of injury within the brain. An intracranial lesion can be an abnormality seen on a imaging procedure or brain-imaging test, such as MRI or CT scan. On CT or MRI scans, brain lesions can appear as dark or light spots that do not look like normal brain tissue.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as 3H, 14C, 32P, 33P, 35S, 90Y, 99Tc, 111In, 125I, 131I, 177Lu, 166Ho, and 153Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2nd ed., Springer Verlag, N.Y. (1997), and in Haugland, *Handbook of Fluorescent Probes and Research Chemicals* (1996), which is a combined handbook and catalogue published by Molecular Probes, Inc., Eugene, Oregon. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamezyk et al., *Bioorg. Med. Chem. Lett.* 16: 1324-1328 (2006); Adamezyk et al., *Bioorg. Med. Chem. Lett.* 4: 2313-2317 (2004); Adamezyk et al., *Biorg. Med. Chem. Lett.* 14: 3917-3921 (2004); and Adamezyk et al., *Org. Lett.* 5: 3779-3782 (2003)).

In one aspect, the acridinium compound is an acridinium-9-carboxamide. Methods for preparing acridinium 9-carboxamides are described in Mattingly, *J. Biolumin. Chemilumin.* 6: 107-114 (1991); Adamezyk et al., *J. Org. Chem.* 63: 5636-5639 (1998); Adamezyk et al., *Tetrahedron* 55: 10899-10914 (1999); Adamezyk et al., *Org. Lett.* 1: 779-781 (1999); Adamezyk et al., *Bioconjugate Chem.* 11: 714-724 (2000); Mattingly et al., *In Luminescence Biotechnology: Instruments and Applications*; Dyke, K. V. Ed.; CRC Press: Boca Raton, pp. 77-105 (2002); Adamezyk et al., *Org. Lett.* 5: 3779-3782 (2003); and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, MI). Methods for preparing acridinium 9-carboxylate aryl esters are described in McCapra et al., Photochem. Photobiol. 4: 1111-21 (1965); Razavi et al., *Luminescence* 15: 245-249 (2000); Razavi et al., *Luminescence* 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Linking sequences can be used for many purposes, including in recombinant Fabs. Exemplary linking sequences include, but are not limited to: (i) Histidine (His) tags, such as a 6×His tag, which has an amino acid sequence of HHHHHH (SEQ ID NO: 3), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO: 4) and derivatives thereof (e.g., ADDDDK (SEQ ID NO: 5), etc.); (iii) Miscellaneous sequences can be used to link or connect the light and/or heavy chain variable regions of single chain variable region fragments. Examples of other linking sequences can be found in Bird et al., *Science* 242: 423-426 (1988); Huston et al., *PNAS USA* 85: 5879-5883 (1988); and McCafferty et al., *Nature* 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological.

"Magnetic resonance imaging" or "MRI" as used interchangeably herein refers to a medical imaging technique used in radiology to form pictures of the anatomy and the physiological processes of the body in both health and disease (e.g., referred to herein interchangeably as "an MRI", "an MRI procedure" or "an MRI scan"). MRI is a form of medical imaging that measures the response of the atomic nuclei of body tissues to high-frequency radio waves when placed in a strong magnetic field, and that produces images of the internal organs. MRI scanners, which is based on the science of nuclear magnetic resonance (NMR), use strong magnetic fields, radio waves, and field gradients to generate images of the inside of the body.

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

"Negative predictive value" or "NPV" as used interchangeably herein refers to the probability that a subject has a negative outcome (i.e., the proposed result is absent) given that they have a negative test result (i.e., the subject that tested negative for the proposed result does not have the proposed result).

"Point-of-care device" refers to a device used to provide medical diagnostic testing at or near the point-of-care (namely, outside of a laboratory), at the time and place of patient care (such as in a hospital, physician's office, urgent or other medical care facility, a patient's home, a nursing home and/or a long-term care and/or hospice facility). Examples of point-of-care devices include those produced by Abbott Laboratories (Abbott Park, Ill.) (e.g., i-STAT and i-STAT Alinity, Universal Biosensors (Rowville, Australia) (see US 2006/0134713), Axis-Shield PoC AS (Oslo, Norway) and Clinical Lab Products (Los Angeles, USA).

"Positive predictive value" or "PPV" as used interchangeably herein refers to the probability that a subject has a positive outcome (i.e., the proposed result is present) given that they have a positive test result (i.e., the subject that tested positive for the proposed result has the proposed result).

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a reference level or control level (e.g., "low", "medium", or "high" levels), can be used.

Multiple calibrators (i.e., more than one calibrator or a varying amount of calibrator(s)) can be used in conjunction to comprise a "sensitivity panel."

A "receiver operating characteristic" curve or "ROC" curve refers to a graphical plot that illustrates the performance of a binary classifier system as its discrimination threshold is varied. For example, an ROC curve can be a plot of the true positive rate against the false positive rate for the different possible cutoff points of a diagnostic test. It is created by plotting the fraction of true positives out of the positives (TPR=true positive rate) vs. the fraction of false positives out of the negatives (FPR=false positive rate), at various threshold settings. TPR is also known as sensitivity, and FPR is one minus the specificity or true negative rate. The ROC curve demonstrates the tradeoff between sensitivity and specificity (any increase in sensitivity will be accompanied by a decrease in specificity); the closer the curve follows the left-hand border and then the top border of the ROC space, the more accurate the test; the closer the curve comes to the 45-degree diagonal of the ROC space, the less accurate the test; the slope of the tangent line at a cutoff point gives the likelihood ratio (LR) for that value of the test; and the area under the curve is a measure of test accuracy.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., *Nature Biotechnology*, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Reference level" as used herein refers to an assay cutoff value (or level) that is used to assess diagnostic, prognostic, or therapeutic efficacy and that has been linked or is associated herein with various clinical parameters (e.g., presence of disease, stage of disease, severity of disease, progression, non-progression, or improvement of disease, etc.). As used herein, the term "cutoff" refers to a limit (e.g., such as a number) above which there is a certain or specific clinical outcome and below which there is a different certain or specific clinical outcome.

This disclosure provides exemplary reference levels. However, it is well-known that reference levels may vary depending on the nature of the immunoassay (e.g., antibodies employed, reaction conditions, sample purity, etc.) and that assays can be compared and standardized. It further is well within the ordinary skill of one in the art to adapt the disclosure herein for other immunoassays to obtain immunoassay-specific reference levels for those other immunoassays based on the description provided by this disclosure. Whereas the precise value of the reference level may vary between assays, the findings as described herein should be generally applicable and capable of being extrapolated to other assays.

"Risk assessment," "risk classification," "risk identification," or "risk stratification" of subjects (e.g., patients) as used herein refers to the evaluation of factors including biomarkers, to predict the risk of occurrence of future events including disease onset or disease progression, so that treatment decisions regarding the subject may be made on a more informed basis.

"Sample," "test sample," "specimen," "sample from a subject," and "patient sample" as used herein may be used interchangeable and may be a sample of blood, such as whole blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

A variety of cell types, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, red blood cells, platelets, interstitial fluid, cerebral spinal fluid, etc. In some embodiments, the sample is a whole blood sample. In some embodiments, the sample is a serum sample. In yet other embodiments, the sample is a plasma sample. Cell types and tissues may also include lymph fluid, cerebrospinal fluid, a fluid collected by A tissue or cell type may be provided by removing a sample of cells from a human and a non-human animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

"Sensitivity" of an assay as used herein refers to the proportion of subjects for whom the outcome is positive that are correctly identified as positive (e.g., correctly identifying those subjects with a disease or medical condition for which they are being tested). For example, this might include correctly identifying subjects as having a TBI from those who do not have a TBI, correctly identifying subjects having a moderate, severe, or moderate to severe TBI from those having a mild TBI, correctly identifying subjects as having a mild TBI from those having a moderate, severe, or moderate to severe TBI, correctly identifying subjects as having a moderate, severe, or moderate to severe TBI from those having no TBI or correctly identifying subjects as having a mild TBI from those having no TBI, correctly identifying subjects as likely to benefit from a head CT scan or a MRI from those who are not likely to benefit from a head CT scan or MRI, etc.).

"Specificity" of an assay as used herein refers to the proportion of subjects for whom the outcome is negative that are correctly identified as negative (e.g., correctly identifying those subjects who do not have a disease or medical condition for which they are being tested). For example, this might include correctly identifying subjects having an TBI from those who do not have a TBI, correctly identifying subjects not having a moderate, severe, or moderate to severe TBI from those having a mild TBI, correctly identifying subjects as not having a mild TBI from those having a moderate, severe, or moderate to severe TBI or correctly identifying subjects as not having any TBI, or correctly identifying subjects as having a mild TBI from those having no TBI, etc.).

"Series of calibrating compositions" refers to a plurality of compositions comprising a known concentration of the analytes, such as GFAP and UCH-L1, wherein each of the compositions differs from the other compositions in the series by the concentration of the analytes, such as GFAP and UCH-L1.

As used herein the term "single molecule detection" refers to the detection and/or measurement of a single molecule of an analyte in a test sample at very low levels of concentration (such as pg/mL or femtogram/mL levels). A number of different single molecule analyzers or devices are known in the art and include nanopore and nanowell devices. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

"Solid phase" or "solid support" as used interchangeably herein, refers to any material that can be used to attach and/or attract and immobilize (1) one or more capture agents or capture specific binding partners, or (2) one or more detection agents or detection specific binding partners. The solid phase can be chosen for its intrinsic ability to attract and immobilize a capture agent. Alternatively, the solid phase can have affixed thereto a linking agent that has the ability to attract and immobilize the (1) capture agent or capture specific binding partner, or (2) detection agent or detection specific binding partner. For example, the linking agent can include a charged substance that is oppositely charged with respect to the capture agent (e.g., capture specific binding partner) or detection agent (e.g., detection specific binding partner) itself or to a charged substance conjugated to the (1) capture agent or capture specific binding partner or (2) detection agent or detection specific binding partner. In general, the linking agent can be any binding partner (preferably specific) that is immobilized on (attached to) the solid phase and that has the ability to immobilize the (1) capture agent or capture specific binding partner, or (2) detection agent or detection specific binding partner through a binding reaction. The linking agent enables the indirect binding of the capture agent to a solid phase material before the performance of the assay or during the performance of the assay. For examples, the solid phase can be plastic, derivatized plastic, magnetic, or non-magnetic metal, glass or silicon, including, for example, a test tube, microtiter well, sheet, bead, microparticle, chip, and other configurations known to those of ordinary skill in the art.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Statistically significant" as used herein refers to the likelihood that a relationship between two or more variables is caused by something other than random chance. Statistical hypothesis testing is used to determine whether the result of a data set is statistically significant. In statistical hypothesis testing, a statistical significant result is attained whenever the observed p-value of a test statistic is less than the significance level defined of the study. The p-value is the probability of obtaining results at least as extreme as those observed, given that the null hypothesis is true. Examples of statistical hypothesis analysis include Wilcoxon signed-rank test, t-test, Chi-Square or Fisher's exact test. "Significant" as used herein refers to a change that has not been determined to be statistically significant (e.g., it may not have been subject to statistical hypothesis testing).

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human). In some embodiments, the subject is a human. The subject or patient may be undergoing other forms of treatment. In some embodiments, the subject is a human that may be undergoing other forms of treatment. The subject or patient may be undergoing other forms of treatment. In some embodiments, when the subject is a human, the subject does not include any humans who have suffered a cerebrovascular accident (e.g., a stroke). In some embodiments, the subject is suspected to have sustained an injury to the head. In some embodiments, the subject is known to have sustained an injury to the head. In some embodiments, the subject is suspected to be suffering from mild, moderate, severe, or moderate to severe TBI. In some embodiments, the subject is suspected to be suffering from mild TBI. In some embodiments, the subject is suspected to be suffering from moderate TBI. In some embodiments, the subject is suspected to be suffering from severe TBI.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Traumatic Brain Injury" or "TBI" as used interchangeably herein refers to a complex injury with a broad spectrum of symptoms and disabilities. TBI is most often an acute event similar to other injuries. TBI can be classified as "mild," "moderate," or "severe." The causes of TBI are diverse and include, for example, physical shaking by a person, a car accident, injuries from firearms, cerebral vascular accidents (e.g., strokes), falls, explosions or blasts and other types of blunt force trauma. Other causes of TBI include the ingestion and/or exposure to one or more chemicals or toxins (such as fires, molds, asbestos, pesticides and insecticides, organic solvents, paints, glues, gases (such as carbon monoxide, hydrogen sulfide, and cyanide), organic metals (such as methyl mercury, tetraethyl lead and organic tin), one or more drugs of abuse or combinations thereof). Alternatively, TBI can occur in subjects suffering from an autoimmune disease, a metabolic disorder, a brain tumor, hypoxia, one or more viruses, meningitis, hydrocephalus or combinations thereof. Young adults and the elderly are the age groups at highest risk for TBI. In certain embodiments herein, traumatic brain injury or TBI does not include and specifically excludes cerebral vascular accidents such as strokes.

"Mild TBI" as used herein refers to a brain injury where loss of consciousness is brief and usually a few seconds or minutes and/or confusion and disorientation is shorter than 1 hour. Mild TBI is also referred to as a concussion, minor head trauma, minor TBI, minor brain injury, and minor head injury. While MRI and CT scans may be normal, the individual with mild TBI may have cognitive problems such as headache, difficulty thinking, memory problems, attention deficits, mood swings and frustration.

Mild TBI is the most prevalent TBI and is often missed at time of initial injury. Typically, a subject has a Glasgow Coma scale number of between 13-15 (such as 13-15 or 14-15). Fifteen percent (15%) of people with mild TBI have symptoms that last 3 months or more. Mild TBI is defined as the result of the forceful motion of the head or impact causing a brief change in mental status (confusion, disorientation or loss of memory) or loss of consciousness for less than 30 minutes. Common symptoms of mild TBI include fatigue, headaches, visual disturbances, memory loss, poor attention/concentration, sleep disturbances, dizziness/loss of balance, irritability-emotional disturbances, feelings of depression, and seizures. Other symptoms associated with mild TBI include nausea, loss of smell, sensitivity to light and sounds, mood changes, getting lost or confused, and/or slowness in thinking.

"Moderate TBI" as used herein refers to a brain injury where loss of consciousness and/or confusion and disorientation is between 1 and 24 hours and the subject has a Glasgow Coma scale number of between 9-13 (such as 9-12 or 9-13). The individual with moderate TBI have abnormal brain imaging results. "Severe TBI" as used herein refers to a brain injury where loss of consciousness is more than 24 hours and memory loss after the injury or penetrating skull injury longer than 24 hours and the subject has a Glasgow Coma scale number between 3-8. The deficits range from impairment of higher level cognitive functions to comatose states. Survivors may have limited function of arms or legs, abnormal speech or language, loss of thinking ability or emotional problems. Individuals with severe injuries can be left in long-term unresponsive states. For many people with severe TBI, long-term rehabilitation is often necessary to maximize function and independence.

"Moderate to severe" TBI as used herein refers to a spectrum of brain injury that includes moderate to severe and thus encompasses moderate TBI alone, severe TBI alone and moderate to severe TBI combined. Subjects suffering from a moderate to severe TBI can have a Glasgow Coma scale number of between 3-13 (such as 3-12 or 3-13). For example, in some clinical situations, a subject may initially be diagnosed as having a moderate TBI but who, over the course of time (minutes, hours or days), progress to having a severe TBI (such, as for example, in situations when there is a brain bleed). Such subjects would be examples of patients that could be classified as "moderate to severe". Common symptoms of moderate to severe TBI include cognitive deficits including difficulties with attention, concentration, distractibility, memory, speed of processing, confusion, perseveration, impulsiveness, language processing, and/or "executive functions", not understanding the spoken word (receptive aphasia), difficulty speaking and being understood (expressive aphasia), slurred speech, speaking very fast or very slow, problems reading, problems writing, difficulties with interpretation of touch, temperature, movement, limb position and fine discrimination, the integration or patterning of sensory impressions into psychologically meaningful data, partial or total loss of vision, weakness of eye muscles and double vision (diplopia), blurred vision, problems judging distance, involuntary eye movements (nystagmus), intolerance of light (photophobia), hearing, such as decrease or loss of hearing, ringing in the ears (tinnitus), increased sensitivity to sounds, loss or diminished sense of smell (anosmia), loss or diminished sense of taste, the convulsions associated with epilepsy that can be several types and can involve disruption in consciousness, sensory perception, or motor movements, control of bowel and bladder, sleep disorders, loss of stamina, appetite changes, regulation of body temperature, menstrual difficulties, dependent behaviors, emotional ability, lack of motivation, irritability, aggression, depression, disinhibition, or denial/lack of awareness.

"Ubiquitin carboxy-terminal hydrolase L1" or "UCH-L1" as used interchangeably herein refers to a deubiquitinating enzyme encoded by the UCH-L1 gene in humans. UCH-L1, also known as ubiquitin carboxyl-terminal esterase L1 and ubiquitin thioesterase, is a member of a gene family whose products hydrolyze small C-terminal adducts of ubiquitin to generate the ubiquitin monomer.

"UCH-L1 status" can mean either the level or amount of UCH-L1 at a point in time (such as with a single measure of UCH-L1), the level or amount of UCH-L1 associated with monitoring (such as with a repeat test on a subject to identify an increase or decrease in UCH-L1 amount), the level or amount of UCH-L1 associated with treatment for traumatic brain injury (whether a primary brain injury and/or a secondary brain injury) or combinations thereof.

"Variant" is used herein to describe a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art.

Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-analyte (such as GFAP and/or UCH-L1) antibody that differs from the corresponding fragment of anti-analyte (such as GFAP and/or UCH-L1) antibody in amino acid sequence but is still antigenically reactive and can compete with the corresponding fragment of anti-analyte (such as GFAP and/or UCH-L1) antibody for binding with the analyte (such as GFAP and/or UCH-L1). "Variant" also can be used to describe a polypeptide or a fragment thereof that has been differentially processed, such as by proteolysis, phosphorylation, or other post-translational modification, yet retains its antigen reactivity.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. METHODS OF AIDING IN THE DIAGNOSIS OF SUBJECTS WHO HAVE SUSTAINED OR ARE SUSPECTED OF HAVING SUSTAINED AN INJURY TO THE HEAD USING A COMBINATION OF GFAP AND UCH-L1 REFERENCE LEVELS

The present disclosure relates, among other methods, to a method of aiding in the diagnosis and evaluation of a subject that has sustained or may have sustained an injury to the head. In particular, the present disclosure provides methods for aiding in the diagnosis and evaluation of a subject to determine whether the subject has sustained a traumatic brain injury (TBI), such as, for example, moderate to severe traumatic brain injury, by detecting or measuring a combination of the levels of ubiquitin carboxy-terminal hydrolase L1 (UCH-L1) and glial fibrillary acidic protein (GFAP) in samples taken at various time points within 48 hours after the subject has sustained or may have sustained an injury to the head. As disclosed herein, the diagnosis and evaluation of a subject suspected of having a TBI includes a determination of whether to perform an imaging procedure, along with other medical evaluation (e.g., clinical assessments) based on the levels of GFAP and UCH-L1 in the subject, as compared to various reference levels. Such diagnosis and evaluation based on a combination of GFAP and UCH-L1 levels can help to determine whether the subject is more likely than not to have a positive MRI scan and/or a positive head CT scan (i.e., the presence of an intracranial lesion).

In some embodiments, the method can help to determine whether a subject that has sustained an injury to the head has sustained a traumatic brain injury based on levels of GFAP and UCH-L1 as compared to reference levels. In accordance with these embodiments, the method can comprise the steps of performing an assay on a sample obtained from the subject within about 48 hours after an injury to the head to measure or detect a combination of a level of GFAP and a level of UCH-L1 in the sample; and (a) determining that the subject has not sustained a TBI when the level of GFAP in the sample is less than a reference level of GFAP of about 15 pg/mL, and the level of UCH-L1 in the sample is less than a reference level of UCH-L1 of about 70 pg/mL; or (b) determining that the subject more likely than not has sustained a TBI when the level of GFAP in the sample is equal to a reference level of GFAP of from about 15 pg/mL to about 40 pg/mL, and the level of UCH-L1 in the sample is equal to a reference level of UCH-L1 of from about 70 pg/mL to about 150 pg/mL; or (c) determining that the subject more likely than not has sustained a TBI when the level of GFAP in the sample is greater than a reference level of GFAP of about 40 pg/mL, and the level of UCH-L1 in the sample is greater than a reference level of UCH-L1 of about 150 pg/mL.

In some embodiments, the method can include obtaining a sample within about 48 hours of a suspected injury to the subject and contacting the sample with an antibody for UCH-L1, and/or GFAP to allow formation of a complex of the antibody and the UCH-L1 and/or GFAP. The method also includes detecting the resulting antibody-GFAP/UCH-L1 complex. In accordance with these methods, GFAP and UCH-L1 levels can be measured or detected and then correlated to one or more clinical parameters (e.g., GCS score and/or CT scan), either before or after the method is conducted, in order to establish GFAP and UCH-L1 reference levels that can be used to determine whether the subject has a TBI.

In some embodiments, GFAP and UCH-L1 reference levels can be used as part of an assay having at least about 35% specificity and at least about 90% sensitivity, as described further herein. Additionally, in other embodiments, the method when used as an assay has at least a 3% higher sensitivity and at least a 17% higher specificity compared to a method or assay that measures or detects GFAP or UCH-L1 individually. In other embodiments, the method when used as an assay has at least a 5% higher sensitivity and at least a 20% higher specificity compared to a method or assay that measures or detects GFAP or UCH-L1 individually. In other embodiments, the method when used as an assay has at least an 8% higher sensitivity and at least a 25% higher specificity compared to a method or assay that measures or detects GFAP or UCH-L1 individually.

In some embodiments, reference levels of GFAP and UCH-L1 are determined by an assay having a sensitivity of between at least about 70% to about 100% and a specificity of between at least about 30% to about 100%. In some embodiments, the sensitivity is between at least about 70% to about 100%, between at least about 70% to at least about 99%, between at least about 70% to at least about 95%, between at least about 70% to at least about 90%, between at least about 70% to at least about 85%, between at least about 75% to about 100%, between at least about 75% to at least about 99%, between at least about 75% to at least about 95%, between at least about 75% to at least about 90%, between at least about 75% to at least about 85%, between at least about 80% to about 100%, between at least about 80% to at least about 99%, between at least about 80% to at least about 95%, between at least about 80% to at least about 90%, between at least about 80% to at least about 85%, between at least about 85% to about 100%, between at least about 85% to at least about 99%, between at least about 85% to at least about 95%, between at least about 85% to at least about 90%, between at least about 90% to about 100%, between at least about 90% to at least about 99%, between at least about 90% to at least about 95%, between at least about 95% to about 100%, or between at least about 95% to at least about 99%. In some embodiments, the sensitivity is at least about 70.0%, at least about 75.0%, at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%.

In some embodiments, the specificity is between at least about 30% to about 100%, between at least about 30% to about 99%, between at least about 30% to about 95%, between at least about 30% to about 90%, between at least about 30% to about 85%, between at least about 30% to about 80%, between at least about 30% to about 75%, between at least about 30% to about 70%, between at least about 30% to about 60%, between at least about 30% to about 50%, between at least about 40% to about 100%, between at least about 40% to about 99%, between at least about 40% to about 95%, between at least about 40% to about 90%, between at least about 40% to about 85%, between at least about 40% to about 80%, between at least about 40% to about 75%, between at least about 40% to about 70%, between at least about 40% to about 60%, between at least about 40% to about 50%, between at least about 50% to about 100%, between at least about 50% to about 99%, between at least about 50% to about 95%, between at least about 50% to about 90%, between at least about 50% to about 85%, between at least about 50% to about 80%, between at least about 50% to about 75%, between at least about 50% to about 70%, between at least about 50% to about 60%, between at least about 60% to about 100%, between at least about 60% to about 99%, between at least about 60% to about 95%, between at least about 60% to about 90%, between at least about 60% to about 85%, between at least about 60% to about 80%, between at least about 60% to about 75%, between at least about 60% to about 70%, between at least about 70% to about 100%, between at least about 70% to about 99%, between at least about 70% to about 95%, between at least about 70% to about 90%, between at least about 70% to about 85%, between at least about 70% to about 80%, between at least about 70% to about 75%, between at least about 80% to about 100%, between at least about 80% to about 99%, between at least about 80% to about 95%, between at least about 80% to about 90%, between at least about 80% to about 85%, between at least about 90% to about 100%, between at least about 90% to about 99%, between at least about 90% to about 95%, between at least about 95% to about 99%, or between at least about 95% to about 100. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, in some embodiments, the sensitivity is at least about 99% and the specificity is at least about 75%, the sensitivity is at least about 99% and the specificity is at least about 99%, or the sensitivity is at least about 100% and the specificity is at least about 100%. In some embodiments, GFAP and UCH-L1 reference levels can be used as part of an assay having at least about 35% specificity and at least about 90% sensitivity.

In some embodiments, a sample is taken from the human subject within about 48 hours of injury or suspected injury to the head, such as within about 0 to about 4 hours, within about 0 to about 8 hours, within about 0 to about 12 hours, within about 0 to about 16 hours, within about 0 to about 20 hours, within about 0 to about 24 hours, and within about 0 to about 48 hours. In some embodiments, a sample is taken from the human subject within within about 4 hours to about 8 hours, within about 8 hours to about 12 hours, within about 12 hours to about 16 hours, within about 16 hours to about 20 hours, within about 20 hours to about 24 hours, and within about 24 hours to about 48 hours. In other embodiments, the sample can be taken from the human subject within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours of injury or suspected injury to the head. In some embodiments, the onset of the presence of the combination of GFAP and UCH-L1 appears within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after injury to the head. In one aspect, the sample is obtained from the subject within about 4 hours to about 16 hours after the injury. In another aspect, the sample is obtained from the subject within about 4 to about 8 hours after the injury. In yet another aspect, the sample is obtained from the subject within about 8 to about 12 hours after the injury. In yet another aspect, the sample is obtained from the subject within about 12 to about 16 hours after the injury.

In some embodiments, the sample is obtained from the subject within about 4 hours to about 8 hours after the injury (or post injury) and the reference level of GFAP is about 40 pg/mL and the reference level of UCH-L1 is about 100 pg/mL and the assay has a sensitivity equal to or greater than 90% and a specificity equal to or greater than 94%.

In some embodiments, the sample is obtained from the subject within about 8 hours to about 12 hours after the injury (or post injury) and the reference level of GFAP is about 15 pg/mL and the reference level of UCH-L1 is about 150 pg/mL and the assay has a sensitivity equal to or greater than 95% and a specificity equal to or greater than 82%.

In some embodiments, the sample is obtained from the subject within about 12 hours to about 16 hours after the injury (or post injury) and the reference level of GFAP is about 20 pg/mL and the reference level of UCH-L1 is about 60 pg/mL and the assay has a sensitivity equal to or greater than 95% and a specificity equal to or greater than 65%.

In some embodiments, reference levels of GFAP can be between about 15 pg/mL and about 40 pg/mL, and reference levels of UCH-L1 can be between at least about 70 pg/mL to about 150 pg/mL. In other embodiments, reference levels of GFAP can be between about 20 pg/mL and about 40 pg/mL, and reference levels of UCH-L1 can be between at least about 80 pg/mL to about 150 pg/mL. In other embodiments, reference levels of GFAP can be between about 25 pg/mL and about 40 pg/mL, and reference levels of UCH-L1 can be between at least about 90 pg/mL to about 150 pg/mL. In other embodiments, reference levels of GFAP can be between about 30 pg/mL and about 40 pg/mL, and reference levels of UCH-L1 can be between at least about 100 pg/mL to about 150 pg/mL. In other embodiments, reference levels of GFAP can be between about 15 pg/mL and about 30 pg/mL, and reference levels of UCH-L1 can be between at least about 70 pg/mL to about 140 pg/mL. In other embodiments, reference levels of GFAP can be between at least about 15 pg/mL and about 25 pg/mL, and reference levels of UCH-L1 can be between at least about 70 pg/mL to about 130 pg/mL. In some embodiments, the reference level of GFAP is about 40 pg/mL, and the reference level of UCH-L1 is about 100 pg/mL. In other embodiments, the reference level of GFAP is about 15 pg/mL and the reference level of UCH-L1 is about 150 pg/mL. In still other embodiments, the reference level of GFAP is about 20 pg/mL and the reference level of UCH-L1 is about 60 pg/mL.

In some embodiments, the subject has received an imaging procedure, such as MRI or CT scan or in some instances, both, before or after the assay is performed. In some embodiments, the subject is suspected as having a traumatic brain injury based on the imaging procedure. In some embodiments, reference levels of UCH-L1 and GFAP correlate with a positive MRI scan and/or positive head CT scan (i.e., the presence of an intracranial lesion). In some embodiments, references levels of GFAP and UCH-L1 can be used to indicate whether a subject is in need of an MRI procedure, independent of performing a CT scan, and independent of a CT scan that is negative (i.e., indicates that a TBI has not been sustained). Generally, a reference level of a biomarker, such as UCH-L1 or GFAP, and a combination thereof, can be employed as a benchmark against which to assess results obtained upon assaying a test sample for GFAP and UCH-L1. In making such a comparison, for example, reference levels of GFAP and UCH-L1 can be obtained by running a particular assay a sufficient number of times and under appropriate conditions such that a linkage or association of analyte presence, amount or concentration with a particular stage or endpoint of TBI or with particular indicia can be made. Typically, reference levels of GFAP and UCH-L1 obtained by performing assays on samples of reference subjects (or populations of subjects). The GFAP and UCH-L1 measured can include fragments thereof, degradation products thereof, and/or enzymatic cleavage products thereof.

In other embodiments, the method can help to diagnose the type of TBI (such as, for example, a moderate to severe TBI) that a subject may have sustained based on levels of GFAP and UCH-L1 as compared to reference levels. In accordance with these embodiments, the method can comprise the steps of performing an assay on a sample obtained from the subject within about 48 hours after a suspected injury to the head to measure or detect a combination of a level of GFAP and a level of UCH-L1 in the sample; and (a) determining that the subject has not sustained a moderate, severe, or a moderate to severe TBI when the level of GFAP in the sample is less than a reference level of GFAP of about 105 pg/mL, and the level of UCH-L1 in the sample is less than a reference level of UCH-L1 of about 110 pg/mL; or (b) determining that the subject has not sustained a moderate, severe, or a moderate to severe TBI when the level of GFAP in the sample is equal to a reference level of GFAP of from about 105 pg/mL to about 890 pg/mL and the level of UCH-L1 in the sample is equal to a reference level of UCH-L1 of from about 110 pg/mL to about 2000 pg/mL; or (c) determining that the subject more likely than not has sustained a moderate, severe, or a moderate to severe TBI when the level of GFAP in the sample is greater than a reference level of GFAP of about 890 pg/mL, and the level of UCH-L1 in the sample is greater than a reference level of about 2000 pg/mL.

In some embodiments, the method can include obtaining a sample within about 48 hours of a suspected injury to the subject and contacting the sample with an antibody for UCH-L1, and/or GFAP to allow formation of a complex of the antibody and the UCH-L1 and/or GFAP. The method also includes detecting the resulting antibody-GFAP/UCH- L1 complex. In accordance with these methods, GFAP and UCH-L1 levels can be measured or detected and then correlated to one or more clinical parameters (e.g., GCS score and/or CT scan), either before or after the method is conducted, in order to establish GFAP and UCH-L1 reference levels that can be used to diagnose and evaluate a subject that has sustained or may have sustained a TBI. For example, in some embodiments, the subject may have received a Glasgow Coma Scale (GCS) score before or after the method is performed. If the GCS score is less than or equal to 12, the subject is likely to be suspected as having a moderate to severe TBI.

GFAP and UCH-L1 reference levels can be used as part of an assay having at least about 30% specificity and at least about 90% sensitivity, as described further below.

In some embodiments, a sample is taken from the human subject within about 48 hours of injury or suspected injury to the head, such as within about 0 to about 4 hours, within about 0 to about 8 hours, within about 0 to about 12 hours, within about 0 to about 16 hours, within about 0 to about 20 hours, within about 0 to about 24 hours, and within about 0 to about 48 hours. In some embodiments, a sample is taken from the human subject within about within about 4 hours to about 8 hours, within about 8 hours to about 12 hours, within about 12 hours to about 16 hours, within about 16 hours to about 20 hours, within about 20 hours to about 24 hours, and within about 24 hours to about 48 hours. In other embodiments, the sample can be taken from the human subject within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours of injury or suspected injury to the head. In some embodiments, the onset of the presence of the combination of GFAP and UCH-L1 appears within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after injury to the head. In one aspect, the sample is obtained from the subject within about 8 hours to about 16 hours after the actual or suspected injury. In another aspect, the sample is obtained from the subject within about 8 hours to about 12 hours after the actual or suspected injury. In yet another aspect, the sample is obtained from the subject within about 12 hours to about 16 hours after the actual or suspected injury.

In some embodiments, the subject has received an imaging procedure, such as MRI or CT scan, before or after the assay is performed. In some embodiments, the subject is suspected as having a traumatic brain injury based on the imaging procedure. In some embodiments, reference levels of UCH-L1 and GFAP correlate with a positive MRI scan and/or positive head CT scan (i.e., the presence of an intracranial lesion). In some embodiments, references levels of GFAP and UCH-L1 can be used to indicate whether a subject is in need of an MRI procedure, independent of performing a CT scan, and independent of a CT scan that is negative (i.e., indicates that a TBI has not been sustained).

Generally, a reference level of a biomarker, such as UCH-L1 or GFAP, and a combination thereof, can be employed as a benchmark against which to assess results obtained upon assaying a test sample for GFAP and UCH-L1. In making such a comparison, for example, reference levels of GFAP and UCH-L1 can be obtained by running a particular assay a sufficient number of times and under appropriate conditions such that a linkage or association of analyte presence, amount or concentration with a particular stage or endpoint of TBI or with particular indicia can be made. Typically, reference levels of GFAP and UCH-L1 obtained by performing assays on samples of reference subjects (or populations of subjects). The GFAP and UCH-L1 measured can include fragments thereof, degradation products thereof, and/or enzymatic cleavage products thereof.

In some embodiments, reference levels of GFAP and UCH-L1 are determined by an assay having a sensitivity of between at least about 70% to about 100% and a specificity of between at least about 30% to about 100%. In some embodiments, the sensitivity is between at least about 70% to about 100%, between at least about 70% to at least about 99%, between at least about 70% to at least about 95%, between at least about 70% to at least about 90%, between at least about 70% to at least about 85%, between at least about 75% to about 100%, between at least about 75% to at least about 99%, between at least about 75% to at least about 95%, between at least about 75% to at least about 90%, between at least about 75% to at least about 85%, between at least about 80% to about 100%, between at least about 80% to at least about 99%, between at least about 80% to at least about 95%, between at least about 80% to at least about 90%, between at least about 80% to at least about 85%, between at least about 85% to about 100%, between at least about 85% to at least about 99%, between at least about 85% to at least about 95%, between at least about 85% to at least about 90%, between at least about 90% to about 100%, between at least about 90% to at least about 99%, between at least about 90% to at least about 95%, between at least about 95% to about 100%, or between at least about 95% to at least about 99%. In some embodiments, the sensitivity is at least about 70.0%, at least about 75.0%, at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%.

In some embodiments, the specificity is between at least about 30% to about 100%, between at least about 30% to about 99%, between at least about 30% to about 95%, between at least about 30% to about 90%, between at least about 30% to about 85%, between at least about 30% to about 80%, between at least about 30% to about 75%, between at least about 30% to about 70%, between at least about 30% to about 60%, between at least about 30% to about 50%, between at least about 40% to about 100%, between at least about 40% to about 99%, between at least about 40% to about 95%, between at least about 40% to about 90%, between at least about 40% to about 85%, between at least about 40% to about 80%, between at least about 40% to about 75%, between at least about 40% to about 70%, between at least about 40% to about 60%, between at least about 40% to about 50%, between at least about 50% to about 100%, between at least about 50% to about 99%, between at least about 50% to about 95%, between at least about 50% to about 90%, between at least about 50% to about 85%, between at least about 50% to about 80%, between at least about 50% to about 75%, between at least about 50% to about 70%, between at least about 50% to about 60%, between at least about 60% to about 100%, between at least about 60% to about 99%, between at least about 60% to about 95%, between at least about 60% to about 90%, between at least about 60% to about 85%, between at least about 60% to about 80%, between at least about 60% to about 75%, between at least about 60% to about 70%, between at least about 70% to about 100%, between at least about 70% to about 99%, between at least about 70% to about 95%, between at least about 70% to about 90%, between at least about 70% to about 85%, between at least about 70% to about 80%, between at least about 70% to about 75%, between at least about 80% to about 100%, between at least about 80% to about 99%, between at least about 80% to about 95%, between at least about 80% to about 90%, between at least about 80% to about 85%, between at least about 90% to about 100%, between at least about 90% to about 99%, between at least about 90% to about 95%, between at least about 95% to about 99%, or between at least about 95% to about 100. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, in some embodiments, the sensitivity is at least about 99% and the specificity is at least about 75%, the sensitivity is at least about 99% and the specificity is at least about 99%, or the sensitivity is at least about 100% and the specificity is at least about 100%. By way of another example, in some embodiments, the reference level of GFAP and the reference level of UCH-L1 are determined by an assay having a sensitivity equal to or greater than about 79% and a specificity equal to or greater than about 33%. Additionally, in other embodiments, the method when used as an assay has at least a 3% higher sensitivity and at least a 17% higher specificity compared to a method or assay that measures or detects GFAP or UCH-L1 individually. In other embodiments, the method when used as an assay has at least a 5% higher sensitivity and at least a 20% higher specificity compared to a method or assay that measures or detects GFAP or UCH-L1 individually. In other embodiments, the method when used as an assay has at least a 8% higher sensitivity and at least a 25% higher specificity compared to a method or assay that measures or detects GFAP or UCH-L1 individually.

In some embodiments, reference levels of GFAP can be between about 50 pg/mL and about 2000 pg/mL, and reference levels of UCH-L1 can be between at least about 100 pg/mL to about 2000 pg/mL. In some embodiments, reference levels of GFAP or reference levels of UCH-L1 can be between at least about 10 pg/mL to about 500 pg/mL, between at least about 10 pg/mL to about 400 pg/mL, between at least about 10 pg/mL to about 300 pg/mL, between at least about 10 pg/mL to about 200 pg/mL, between at least about 10 pg/mL to about 100 pg/mL, between at least about 10 pg/mL to about 50 pg/mL, between at least about 10 pg/mL to about 40 pg/mL, between at least about 10 pg/mL to about 30 pg/mL, between at least about 20 pg/mL to about 500 pg/mL, between at least about 20 pg/mL to about 400 pg/mL, between at least about 20 pg/mL to about 300 pg/mL, between at least about 20 pg/mL to about 200 pg/mL, between at least about 20 pg/mL to about 100 pg/mL, between at least about 20 pg/mL to about 50 pg/mL, between at least about 20 pg/mL to about 40 pg/mL, between at least about 20 pg/mL to about 30 pg/mL, between at least about 30 pg/mL to about 500 pg/mL, between at least about 30 pg/mL to about 400 pg/mL, between at least about 30 pg/mL to about 300 pg/mL, between at least about 30 pg/mL to about 200 pg/mL, between at least about 30 pg/mL to about 100 pg/mL, between at least about 30 pg/mL to about 50 pg/mL, between at least about 30 pg/mL to about 40 pg/mL, between at least about 40 pg/mL to about 500 pg/mL, between at least about 40 pg/mL to about 400 pg/mL, between at least about 40 pg/mL to about 300 pg/mL, between at least about 40 pg/mL to about 200 pg/mL, between at least about 40 pg/mL to about 100 pg/mL, between at least about 40 pg/mL to about 50 pg/mL, between at least about 50 pg/mL to about 500 pg/mL, between at least about 50 pg/mL to about 400 pg/mL, between at least about 50 pg/mL to about 300 pg/mL, between at least about 50 pg/mL to about 200 pg/mL, between at least about 50 pg/mL to about 100 pg/mL, between at least about 75 pg/mL to about 500 pg/mL, between at least about 75 pg/mL to about 400 pg/mL, between at least about 75 pg/mL to about 300 pg/mL, between at least about 75 pg/mL to about 200 pg/mL, between at least about 75 pg/mL to about 100 pg/mL, between at least about 100 pg/mL to about 500 pg/mL, between at least about 100 pg/mL to about 400 pg/mL, between at least about 100 pg/mL to about 300 pg/mL, between at least about 100 pg/mL to about 200 pg/mL, between at least about 150 pg/mL to about 500 pg/mL, between at least about 150 pg/mL to about 400 pg/mL, between at least about 150 pg/mL to about 300 pg/mL, between at least about 150 pg/mL to about 200 pg/mL, between at least about 200 pg/mL to about 500 pg/mL, between at least about 200 pg/mL to about 400 pg/mL, or between at least about 200 pg/mL to about 300 pg/mL. For example, the reference level for UCH-L1 can be between at least about 80 pg/mL to about 150 pg/mL and the reference level for GFAP can be between at least about 20 pg/mL to about 200 pg/mL. By way of a further example, in other embodiments, the reference level for GFAP is from about 105 pg/mL to about 890 pg/mL and the reference level for UCH-L1 is from about 110 pg/mL to about 2000 pg/mL. In some embodiments, the reference level for GFAP is about 105 pg/mL and the reference level for UCH-L1 is about 110 pg/mL. In some embodiments, the reference level for GFAP is about 890 pg/mL and the reference level for UCH-L1 is about 920 pg/mL. In other embodiments, the reference level for GFAP is about 505 pg/mL and the reference level for UCH-L1 is about 1580 pg/mL.

In some embodiments, the sample is obtained from the subject within about 8 hours to about 12 hours after the actual or suspected injury and the reference level of GFAP is about 890 pgm/L and the reference level of UCH-L1 is about 920 pg/mL and the method has a sensitivity equal to or greater than 90% and a specificity equal to or greater than 79%. In another embodiment, the sample is obtained from the subject within about 12 hours to about 16 hours after the actual or suspected injury and the reference level of GFAP is about 505 pgm/L and the reference level of UCH-L1 is about 1580 pg/mL and the method has a sensitivity equal to or greater than 90% and a specificity equal to or greater than 66%.

In some embodiments, the method further includes treating the human subject with a traumatic brain injury treatment and/or monitoring the human subject, as described below.

The nature of the assay employed in the methods described herein is not critical and the test can be any assay known in the art such as, for example, immunoassays, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in a clinical chemistry format such as would be known by one of ordinary skill in the art. Such assays are described in further detail herein in Sections 5-9. It is known in the art that the values (e.g., reference levels, cutoffs, thresholds, specificities, sensitivities, concentrations of calibrators and/or controls etc.) used in an assay that employs specific sample type (e.g., such as an immunoassay that utilizes serum or a point-of-care device that employs whole blood) can be extrapolated to other assay formats using known techniques in the art, such as assay standardization. For example, one way in which assay standardization can be performed is by applying a factor to the calibrator employed in the assay to make the sample concentration read higher or lower to get a slope that aligns with the comparator method. Other methods of standardizing results obtained on one assay to another assay are well known and have been described in the literature (See, for example, David Wild, Immunoassay Handbook, 4th edition, chapter 3.5, pages 315-322, the contents of which are herein incorporated by reference).

3. METHODS OF AIDING IN THE DETERMINATION OF WHETHER TO PERFORM IMAGING ON A HUMAN SUBJECT WHO HAS SUSTAINED AN INJURY TO THE HEAD

The present disclosure relates, among other methods, to a method of aiding in determining whether to perform an imaging procedure, such as MRI or CT scan, on a human subject who has sustained or may have sustained an injury to the head. As used herein, "determination of whether to perform an imaging procedure, such as MRI or CT scan, on a human subject" refers to the fact that the aforementioned method can be used with other information (e.g., clinical assessment data) to determine that the subject is more likely than not to have a positive MRI scan or positive head CT scan (i.e., the presence of an intracranial lesion).

In some embodiments, the method can help to determine whether a subject that has sustained a TBI is in need of a computerized tomography (CT) scan based on levels of GFAP, UCH-L1 or GFAP and UCH-L1 as compared to reference levels. In accordance with these embodiments, the method can comprise the steps of performing an assay on a sample obtained from the subject within about 48 hours after an actual or suspected injury to measure or detect a combination of a level of GFAP and a level of UCH-L1 in the sample, and (a) determining that the subject does not need a CT scan when the level of GFAP in the sample is less than a reference level of GFAP of about 50 pg/mL, and the level of UCH-L1 in the sample is less than a reference level of UCH-L1 of about 90 pg/mL; or (b) determining that the subject does not need a CT scan when the level of GFAP in the sample is equal to a reference level of GFAP of from about 50 pg/mL to about 975 pg/mL, and the level of UCH-L1 in the sample is equal to a reference level of UCH-L1 of from about 90 pg/mL to about 2000 pg/mL; or (c) determining that the subject more likely than not does need a CT scan when the level of GFAP in the sample is greater than a reference level of GFAP of about 975 pg/mL, and the level of UCH-L1 in the sample is greater than a reference level of UCH-L1 of about 2000 pg/mL In some embodiments, reference levels of GFAP can be between about 50 pg/mL and about 975 pg/mL, and reference levels of UCH-L1 can be between at least about 90 pg/mL to about 2000 pg/mL. In some embodiments, reference levels of GFAP can be between about 100 pg/mL and about 975 pg/mL, and reference levels of UCH-L1 can be between at least about 100 pg/mL to about 2000 pg/mL. In some embodiments, reference levels of GFAP can be between about 200 pg/mL and about 975 pg/mL, and reference levels of UCH-L1 can be between at least about 200 pg/mL to about 2000 pg/mL. In some embodiments, reference levels of GFAP can be between about 300 pg/mL and about 975 pg/mL, and reference levels of UCH-L1 can be between at least about 300 pg/mL to about 2000 pg/mL. In some embodiments, reference levels of GFAP can be between about 400 pg/mL and about 975 pg/mL, and reference levels of UCH-L1 can be between at least about 400 pg/mL to about 2000 pg/mL. In some embodiments, reference levels of GFAP can be between about 500 pg/mL and about 975 pg/mL, and reference levels of UCH-L1 can be between at least about 500 pg/mL to about 2000 pg/mL. In some embodiments, the reference levels of GFAP can be between about 110 pg/mL and about 975 pg/mL, and reference levels of UCH-L1 can be between at least about 90 pg/mL to about 2000 pg/mL. In some embodiments, reference levels of GFAP can be between about 240 pg/mL and about 975 pg/mL, and reference levels of UCH-L1 can be between at least about 300 pg/mL to about 2000 pg/mL. In some embodiments, reference levels of GFAP can be between about 190 pg/mL and about 975 pg/mL, and reference levels of UCH-L1 can be between at least about 90 pg/mL to about 2000 pg/mL. In some embodiments, the reference level of GFAP is at least 110 pg/mL and the reference level of UCH-L1 is at least 2000 pg/mL. In other embodiments, the reference level of GFAP is at least 240 pg/mL and the reference level of UCH-L1 is at least 300 pg/mL. In other embodiments, the reference level of GFAP is at least 190 pg/mL and the reference level of UCH-L1 is at least 90 pg/mL.

In some embodiments, a sample is taken from the human subject within about 48 hours of injury or suspected injury to the head, such as within about 0 to about 4 hours, within about 0 to about 8 hours, within about 0 to about 12 hours, within about 0 to about 16 hours, within about 0 to about 20 hours, within about 0 to about 24 hours, and within about 0 to about 48 hours. In some embodiments, a sample is taken from the human subject within about within about 4 hours to about 8 hours, within about 8 hours to about 12 hours, within about 12 hours to about 16 hours, within about 16 hours to about 20 hours, within about 20 hours to about 24 hours, and within about 24 hours to about 48 hours. In other embodiments, the sample can be taken from the human subject within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours of injury or suspected injury to the head. In some embodiments, the onset of the presence of the combination of GFAP and UCH-L1 appears within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after injury to the head. In one aspect, the sample is obtained from the subject within about 4 hours to about 16 hours after the actual or suspected injury. In another aspect, the sample is obtained from the subject within about 4 hours to about 8 hours after the actual or suspected injury. In yet another aspect, the sample is obtained from the subject within about 8 hours to about 12 hours after the actual or suspected injury. In still yet another aspect, the sample is obtained from the subject within about 12 hours to about 16 hours after the actual or suspected injury.

In some embodiments, the reference level of GFAP and the reference level of UCH-L1 are determined by a method having a sensitivity equal to or greater than about 54% and a specificity equal to or greater than about 32% as discussed further herein.

In some embodiments, reference levels of GFAP and UCH-L1 are determined by an assay having a sensitivity of between at least about 50% to about 100% and a specificity of between at least about 30% to about 100%. In some embodiments, the sensitivity is between at least about 50% to about 100%, between at least about 50% to at least about 99%, between at least about 50% to at least about 95%, between at least about 50% to at least about 90%, between at least about 50% to at least about 85%, between at least about 55% to about 100%, between at least about 55% to at least about 99%, between at least about 55% to at least about 95%, between at least about 55% to at least about 90%, between at least about 55% to at least about 85%, between at least about 60% to about 100%, between at least about 60% to at least about 99%, between at least about 60% to at least about 95%, between at least about 60% to at least about 90%, between at least about 60% to at least about 85%, between at least about 70% to about 100%, between at least about 70% to at least about 99%, between at least about 70% to at least about 95%, between at least about 70% to at least about 90%, between at least about 70% to at least about 85%, between at least about 80% to about 100%, between at least about 80% to at least about 99%, between at least about 80% to at least about 95%, between at least about 80% to at least about 90%, between at least about 80% to at least about 85%, between at least about 85% to about 100%, between at least about 85% to at least about 99%, between at least about 85% to at least about 95%, between at least about 85% to at least about 90%, between at least about 90% to about 100%, between at least about 90% to at least about 99%, between at least about 90% to at least about 95%, between at least about 95% to about 100%, or between at least about 95% to at least about 99%. In some embodiments, the sensitivity is at least 50%, at least 51%, at least 52%, at least 53%, at least 54%, at least about 55%, at least about 60%, at least about 65%, at least about 70.0%, at least about 75.0%, at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. In some embodiments, the sensitivity of the assay is equal to or greater than 54%.

In some embodiments, the specificity is between at least about 30% to about 100%, between at least about 30% to about 99%, between at least about 30% to about 95%, between at least about 30% to about 90%, between at least about 30% to about 85%, between at least about 30% to about 80%, between at least about 30% to about 75%, between at least about 30% to about 70%, between at least about 30% to about 60%, between at least about 30% to about 50%, between at least about 40% to about 100%, between at least about 40% to about 99%, between at least about 40% to about 95%, between at least about 40% to about 90%, between at least about 40% to about 85%, between at least about 40% to about 80%, between at least about 40% to about 75%, between at least about 40% to about 70%, between at least about 40% to about 60%, between at least about 40% to about 50%, between at least about 50% to about 100%, between at least about 50% to about 99%, between at least about 50% to about 95%, between at least about 50% to about 90%, between at least about 50% to about 85%, between at least about 50% to about 80%, between at least about 50% to about 75%, between at least about 50% to about 70%, between at least about 50% to about 60%, between at least about 60% to about 100%, between at least about 60% to about 99%, between at least about 60% to about 95%, between at least about 60% to about 90%, between at least about 60% to about 85%, between at least about 60% to about 80%, between at least about 60% to about 75%, between at least about 60% to about 70%, between at least about 70% to about 100%, between at least about 70% to about 99%, between at least about 70% to about 95%, between at least about 70% to about 90%, between at least about 70% to about 85%, between at least about 70% to about 80%, between at least about 70% to about 75%, between at least about 80% to about 100%, between at least about 80% to about 99%, between at least about 80% to about 95%, between at least about 80% to about 90%, between at least about 80% to about 85%, between at least about 90% to about 100%, between at least about 90% to about 99%, between at least about 90% to about 95%, between at least about 95% to about 99%, or between at least about 95% to about 100. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, in some embodiments, the sensitivity is at least about 99% and the specificity is at least about 75%, the sensitivity is at least about 99% and the specificity is at least about 99%, or the sensitivity is at least about 100% and the specificity is at least about 100%

In other embodiments, the sample is obtained from the subject within about 4 hours to about 8 hours after the actual or suspect injury and the reference level of GFAP is about 110 pg/mL and the reference level of UCH-L1 is about 2000 pg/mL and the method has a sensitivity equal to or greater than 95% and a specificity equal to or greater than 62%. In still yet other embodiments, the sample is obtained from the subject within about 8 hours to about 12 hours after the actual or suspect injury and the reference level of GFAP is about 240 pg/mL and the reference level of UCH-L1 is about 300 pg/mL and the method has a sensitivity equal to or greater than 91.5% and a specificity equal to or greater than 52%. In still further embodiments, the sample is obtained from the subject within about 12 hours to about 16 hours after the actual or suspect injury and the reference level of GFAP is about 190 pg/mL and the reference level of UCH-L1 is about 90 pg/mL and the method has a sensitivity equal to or greater than 99% and a specificity equal to or greater than 36%.

In other embodiments, the method can help to determine whether a subject that has sustained a TBI is in need of an MRI procedure based on levels of GFAP and UCH-L1 as compared to reference levels. In accordance with these embodiments, the method can comprise the steps of performing an assay on a sample obtained from the subject within about 48 hours after an actual or suspected injury to measure or detect a combination of a level of GFAP and a level of UCH-L1 in the sample, and (a) determining that the subject does not need an MRI procedure when the level of GFAP in the sample is less than a reference level of GFAP of about 15 pg/mL, and the level of UCH-L1 in the sample is less than a reference level of UCH-L1 of about 50 pg/mL; or (b) determining that the subject more likely than not does need an MRI procedure when the level of GFAP in the sample is equal to a reference level of GFAP of from about 15 pg/mL to about 1000 pg/mL, and the level of UCH-L1 in the sample is equal to a reference level of UCH-L1 of from about 50 pg/mL to about 2000 pg/mL; or (c) determining that the subject more likely than not does need an MRI procedure when the level of GFAP in the sample is greater than a reference level of GFAP of about 1000 pg/mL, and the level of UCH-L1 in the sample is greater than a reference level of UCH-L1 of about 2000 pg/mL.

In some embodiments, reference levels of GFAP can be between about 10 pg/mL and about 1000 pg/mL, and reference levels of UCH-L1 can be between at least about 40 pg/mL to about 2000 pg/mL. In some embodiments, reference levels of GFAP can be between about 15 pg/mL and about 1000 pg/mL, and reference levels of UCH-L1 can be between at least about 50 pg/mL to about 2000 pg/mL. In some embodiments, reference levels of GFAP can be between about 25 pg/mL and about 1000 pg/mL, and reference levels of UCH-L1 can be between at least about 75 pg/mL to about 2000 pg/mL. In some embodiments, reference levels of GFAP can be between about 50 pg/mL and about 1000 pg/mL, and reference levels of UCH-L1 can be between at least about 100 pg/mL to about 2000 pg/mL. In some embodiments, reference levels of GFAP can be between about 75 pg/mL and about 1000 pg/mL, and reference levels of UCH-L1 can be between at least about 150 pg/mL to about 2000 pg/mL. In some embodiments, reference levels of GFAP can be between about 100 pg/mL and about 1000 pg/mL, and reference levels of UCH-L1 can be between at least about 200 pg/mL to about 2000 pg/mL.

In some embodiments, a sample is taken from the human subject within about 48 hours of injury or suspected injury to the head, such as within about 0 to about 4 hours, within about 0 to about 8 hours, within about 0 to about 12 hours, within about 0 to about 16 hours, within about 0 to about 20 hours, within about 0 to about 24 hours, and within about 0 to about 48 hours. In some embodiments, a sample is taken from the human subject within about within about 4 hours to about 8 hours, within about 8 hours to about 12 hours, within about 12 hours to about 16 hours, within about 16 hours to about 20 hours, within about 20 hours to about 24 hours, and within about 24 hours to about 48 hours. In other embodiments, the sample can be taken from the human subject within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours of injury or suspected injury to the head. In some embodiments, the onset of the presence of the combination of GFAP and UCH-L1 appears within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after injury to the head. In one aspect, the sample is obtained from the subject within about 4 hours to about 16 hours after the actual or suspected injury. In another aspect, the sample is obtained from the subject within about 4 hours to about 8 hours after the actual or suspected injury. In yet another aspect, the sample is obtained from the subject within about 8 hours to about 12 hours after the actual or suspected injury. In still yet another aspect, the sample is obtained from the subject within about 12 hours to about 16 hours after the actual or suspected injury.

In some embodiments, the reference level of GFAP and the reference level of UCH-L1 are determined by a method having a sensitivity of about 80% to about 98% and a specificity of about 30% to about 85% as discussed in more detail below.

In some embodiments, reference levels of GFAP and UCH-L1 are determined by an assay having a sensitivity of between at least about 70% to about 100% and a specificity of between at least about 30% to about 100%. In some embodiments, the sensitivity is between at least about 70% to about 100%, between at least about 70% to at least about 99%, between at least about 70% to at least about 95%, between at least about 70% to at least about 90%, between at least about 70% to at least about 85%, between at least about 75% to about 100%, between at least about 75% to at least about 99%, between at least about 75% to at least about 95%, between at least about 75% to at least about 90%, between at least about 75% to at least about 85%, between at least about 80% to about 100%, between at least about 80% to at least about 99%, between at least about 80% to at least about 95%, between at least about 80% to at least about 90%, between at least about 80% to at least about 85%, between at least about 85% to about 100%, between at least about 85% to at least about 99%, between at least about 85% to at least about 95%, between at least about 85% to at least about 90%, between at least about 90% to about 100%, between at least about 90% to at least about 99%, between at least about 90% to at least about 95%, between at least about 95% to about 100%, or between at least about 95% to at least about 99%. In some embodiments, the sensitivity is at least about 70.0%, at least about 75.0%, at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%.

In some embodiments, the specificity is between at least about 30% to about 100%, between at least about 30% to about 99%, between at least about 30% to about 95%, between at least about 30% to about 90%, between at least about 30% to about 85%, between at least about 30% to about 80%, between at least about 30% to about 75%, between at least about 30% to about 70%, between at least about 30% to about 60%, between at least about 30% to about 50%, between at least about 40% to about 100%, between at least about 40% to about 99%, between at least about 40% to about 95%, between at least about 40% to about 90%, between at least about 40% to about 85%, between at least about 40% to about 80%, between at least about 40% to about 75%, between at least about 40% to about 70%, between at least about 40% to about 60%, between at least about 40% to about 50%, between at least about 50% to about 100%, between at least about 50% to about 99%, between at least about 50% to about 95%, between at least about 50% to about 90%, between at least about 50% to about 85%, between at least about 50% to about 80%, between at least about 50% to about 75%, between at least about 50% to about 70%, between at least about 50% to about 60%, between at least about 60% to about 100%, between at least about 60% to about 99%, between at least about 60% to about 95%, between at least about 60% to about 90%, between at least about 60% to about 85%, between at least about 60% to about 80%, between at least about 60% to about 75%, between at least about 60% to about 70%, between at least about 70% to about 100%, between at least about 70% to about 99%, between at least about 70% to about 95%, between at least about 70% to about 90%, between at least about 70% to about 85%, between at least about 70% to about 80%, between at least about 70% to about 75%, between at least about 80% to about 100%, between at least about 80% to about 99%, between at least about 80% to about 95%, between at least about 80% to about 90%, between at least about 80% to about 85%, between at least about 90% to about 100%, between at least about 90% to about 99%, between at least about 90% to about 95%, between at least about 95% to about 99%, or between at least about 95% to about 100. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. In some embodiments, the reference level of GFAP and the reference level of UCH-L1 are determined by a method having a sensitivity of about 80% to about 98% and a specificity of about 30% to about 85%.

In some embodiments, the sample is obtained from the subject within about 24 hours to about 48 hours after the injury and the reference level of GFAP is about 35 pg/mL the assay has a sensitivity equal to or greater than 94% and a specificity equal to or greater than 30%. In yet other embodiments, the sample is obtained from the subject within about 24 hours to about 48 hours after the injury and the reference level of GFAP is about 143 pg/mL the assay has a sensitivity equal to or greater than 88% and a specificity equal to or greater than 50%. the sample is obtained from the subject within about 24 hours to about 48 hours after the injury and the reference level of GFAP is about 602 pg/mL the assay has a sensitivity equal to or greater than 57% and a specificity equal to or greater than 95%.

In some embodiments, the method is performed on a subject that has received a CT scan before or after the assay is performed, and in some cases, the CT scan indicates a TBI has not occurred (i.e., a normal CT scan). In such cases, if a subject's levels of GFAP and UCH-L1 indicate, for example, that a MRI procedure is required, the method can include determining that an MRI procedure should be performed to diagnose and evaluate the subject, and/or determine what type of TBI was sustained by the subject, independent of the CT scan result. In some embodiments, the subject has not received a CT scan prior to or after performing the assay. In such cases, if the subject's levels of GFAP and UCH-L1 indicate, for example, that a MRI procedure is required, the method can include determining that an MRI procedure should be performed to diagnose and evaluate the subject, and/or determine what type of TBI was sustained by the subject, independent of the absence of a negative CT scan. In some embodiments, reference levels of GFAP and UCH-L1 are correlated with a positive MRI scan or positive head CT scan (i.e., the presence of an intracranial lesion).

In other embodiments, the method can help to determine whether a subject that has sustained a TBI is in need of an MRI procedure based on levels of GFAP or UCH-L1 as compared to reference levels. In accordance with these embodiments, the method can comprise the steps of performing an assay on a sample obtained from the subject within about 48 hours after an actual or suspected injury to measure or detect a combination of a level of GFAP or a level of UCH-L1 in the sample, and (a) determining that the subject does not need a MRI procedure when the level of GFAP in the sample is equal to a reference level of GFAP of from about 0 pg/mL to about 68 pg/mL or the level of UCH-L1 in the sample is equal to a reference level of UCH-L1 of from about 0 pg/mL to about 99 pg/mL; or (b) determining that the subject more likely than not does not need a MRI procedure when the level of GFAP in the sample is greater than a reference level of GFAP of about 68 pg/mL or the level of UCH-L1 in the sample is greater than a reference level of UCH-L1 of about 99 pg/mL.

In some embodiments, reference levels of GFAP can be between about 1 pg/mL and about 68 pg/mL or the reference levels of UCH-L1 can be between at least about 1 pg/mL to about 99 pg/mL. In some embodiments, reference levels of GFAP can be between about 5 pg/mL and about 68 pg/mL, or reference levels of UCH-L1 can be between at least about 5 pg/mL to about 99 pg/mL. In some embodiments, reference levels of GFAP can be between about 5 pg/mL and about 65 pg/mL, or reference levels of UCH-L1 can be between at least about 5 pg/mL to about 95 pg/mL. In some embodiments, reference levels of GFAP can be between about 5 pg/mL and about 60 pg/mL, or reference levels of UCH-L1 can be between at least about 5 pg/mL to about 90 pg/mL. In some embodiments, reference levels of GFAP can be between about 5 pg/mL and about 55 pg/mL, or reference levels of UCH-L1 can be between at least about 5 pg/mL to about 85 pg/mL. In some embodiments, reference levels of GFAP can be between about 5 pg/mL and about 50 pg/mL, or reference levels of UCH-L1 can be between at least about 5 pg/mL to about 80 pg/mL.

In some embodiments, a sample is taken from the human subject within about 48 hours of injury or suspected injury to the head, such as within about 0 to about 4 hours, within about 0 to about 8 hours, within about 0 to about 12 hours, within about 0 to about 16 hours, within about 0 to about 20 hours, within about 0 to about 24 hours, and within about 0 to about 48 hours. In some embodiments, a sample is taken from the human subject within about within about 4 hours to about 8 hours, within about 8 hours to about 12 hours, within about 12 hours to about 16 hours, within about 16 hours to about 20 hours, within about 20 hours to about 24 hours, and within about 24 hours to about 48 hours. In other embodiments, the sample can be taken from the human subject within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours of injury or suspected injury to the head. In some embodiments, the onset of the presence of the combination of GFAP and UCH-L1 appears within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after injury to the head. In one aspect, the sample is obtained from the subject within about 4 hours to about 16 hours after the actual or suspected injury. In another aspect, the sample is obtained from the subject within about 4 hours to about 8 hours after the actual or suspected injury. In yet another aspect, the sample is obtained from the subject within about 8 hours to about 12 hours after the actual or suspected injury. In still yet another aspect, the sample is obtained from the subject within about 12 hours to about 16 hours after the actual or suspected injury.

In some embodiments, the reference level of GFAP are determined by a method having a sensitivity of about 90% to about 95% and a specificity of about 31% to about 46% as shown in more detail in the table below.

|  | Sensitivity | | | | | | |
|---|---|---|---|---|---|---|---|
| Specificity | 31% | 90% | 91% | 92% | 93% | 94% | 95% |
|  | 32% | 90% | 91% | 92% | 93% | 94% | 95% |
|  | 33% | 90% | 91% | 92% | 93% | 94% | 95% |
|  | 34% | 90% | 91% | 92% | 93% | 94% | 95% |
|  | 35% | 90% | 91% | 92% | 93% | 94% | 95% |
|  | 36% | 90% | 91% | 92% | 93% | 94% | 95% |
|  | 37% | 90% | 91% | 92% | 93% | 94% | 95% |
|  | 38% | 90% | 91% | 92% | 93% | 94% | 95% |
|  | 39% | 90% | 91% | 92% | 93% | 94% | 95% |
|  | 40% | 90% | 91% | 92% | 93% | 94% | 95% |
|  | 41% | 90% | 91% | 92% | 93% | 94% | 95% |
|  | 42% | 90% | 91% | 92% | 93% | 94% | 95% |
|  | 43% | 90% | 91% | 92% | 93% | 94% | 95% |
|  | 44% | 90% | 91% | 92% | 93% | 94% | 95% |
|  | 45% | 90% | 91% | 92% | 93% | 94% | 95% |
|  | 46% | 90% | 91% | 92% | 93% | 94% | 95% |

In some embodiments, the reference level of GFAP are determined by a method having a sensitivity of about 81% to about 84% and a specificity of about 31% to about 34% as shown in more detail in the table below:

|  | Sensitivity | | | | |
|---|---|---|---|---|---|
| Specificity | 31% | 81% | 82% | 83% | 84% |
|  | 32% | 81% | 82% | 83% | 84% |
|  | 33% | 81% | 82% | 83% | 84% |
|  | 34% | 81% | 82% | 83% | 84% |

In some embodiments, the method is performed on a subject that has received a CT scan before or after the assay is performed, and in some cases, the CT scan indicates a TBI has not occurred (i.e., a normal CT scan). In such cases, if a subject's levels of GFAP or UCH-L1 indicate, for example, that a MRI procedure is required, the method can include determining that an MRI procedure should be performed to diagnose and evaluate the subject, and/or determine what type of TBI was sustained by the subject, independent of the CT scan result. In some embodiments, the subject has not received a CT scan prior to or after performing the assay. In such cases, if the subject's levels of GFAP or UCH-L1 indicate, for example, that a MRI procedure is required, the method can include determining that an MRI procedure should be performed to diagnose and evaluate the subject, and/or determine what type of TBI was sustained by the subject, independent of the absence of a negative CT scan. In some embodiments, reference levels of GFAP or UCH-L1 are correlated with a positive MRI scan or positive head CT scan (i.e., the presence of an intracranial lesion).

4. METHODS OF AIDING IN PREDICTING THE OUTCOME OF A HUMAN SUBJECT THAT HAS SUSTAINED A HEAD INJURY

The present disclosure relates, among other methods, to a method of predicting the outcome of a subject that has sustained or may have sustained an injury to the head. As described herein, predicting the outcome of a subject that has sustained a head injury includes predicting a favorable or unfavorable outcome of a subject that has sustained a TBI based on levels of GFAP and UCH-L1 as compared to reference levels. In accordance with these embodiments, the method can comprise the steps of performing an assay on a sample obtained from the subject within about 48 hours after the actual or suspected injury to the head to measure or detect a combination of a level of GFAP and a level of UCH-L1 in the sample, and In some embodiments, reference levels of GFAP can be between about 70 pg/mL and about 2000 pg/mL, and reference levels of UCH-L1 can be between at least about 100 pg/mL to about 2000 pg/mL. In some embodiments, reference levels of GFAP can be between about 100 pg/mL and about 2000 pg/mL, and reference levels of UCH-L1 can be between at least about 150 pg/mL to about 2000 pg/mL. In some embodiments, reference levels of GFAP can be between about 200 pg/mL and about 2000 pg/mL, and reference levels of UCH-L1 can be between at least about 200 pg/mL to about 2000 pg/mL. In some embodiments, reference levels of GFAP can be between about 300 pg/mL and about 2000 pg/mL, and reference levels of UCH-L1 can be between at least about 300 pg/mL to about 2000 pg/mL. In some embodiments, reference levels of GFAP can be between about 80 pg/mL and about 2000 pg/mL, and reference levels of UCH-L1 can be between at least about 130 pg/mL to about 2000 pg/mL.

In some embodiments, the reference level of GFAP and the reference level of UCH-L1 are determined by a method having a sensitivity of about 80% to about 97% and a specificity of about 30% to about 95% as discussed in more detail below.

In some embodiments, a subject has received an Extended Glasgow Outcome Scale (GOSE) score after the method has been performed and is predicted to have either a favorable or unfavorable (e.g., poor) outcome based on the GOSE score. In some embodiments, the reference level of GFAP and the reference level of UCH-L1 will correlate with subjects having a poor outcome based on a GOSE score of 1.

In some embodiments, the method is performed on a subject that has not received a medical diagnosis for TBI (e.g., as where the subject has sustained or may have sustained and injury to the head, but TBI has not been diagnosed). In such cases, if a subject's levels of GFAP and UCH-L1 are above reference levels predicting, for example, an unfavorable outcome, the method can include determining that further medical intervention is required, such as performing a CT scan and/or an MRI procedure to diagnose and evaluate the subject, and/or determine what type of TBI the subject may have sustained. In some embodiments, a subject may have received a diagnosis that a TBI has been sustained. In such cases, the method can include determining if the subject's GFAP and UCH-L1 levels are above reference levels, thus confirming the diagnosis and predicting an unfavorable outcome. However, in some embodiments, a subject's GFAP and UCH-L1 levels may be below reference levels of GFAP and UCH-L1, and may thus contradict the TBI diagnosis by predicting a favorable outcome. In such cases, the method can include reevaluating whether the subject has sustained a TBI, such as with a MRI procedure or head CT scan (i.e., to detect the presence of an intracranial lesion).

In some embodiments, reference levels of GFAP and UCH-L1 are determined by an assay having a sensitivity of between at least about 70% to about 100% and a specificity of between at least about 30% to about 100%. In some embodiments, the sensitivity is between at least about 70% to about 100%, between at least about 70% to at least about 99%, between at least about 70% to at least about 95%, between at least about 70% to at least about 90%, between at least about 70% to at least about 85%, between at least about 75% to about 100%, between at least about 75% to at least about 99%, between at least about 75% to at least about 95%, between at least about 75% to at least about 90%, between at least about 75% to at least about 85%, between at least about 80% to about 100%, between at least about 80% to at least about 99%, between at least about 80% to at least about 95%, between at least about 80% to at least about 90%, between at least about 80% to at least about 85%, between at least about 85% to about 100%, between at least about 85% to at least about 99%, between at least about 85% to at least about 95%, between at least about 85% to at least about 90%, between at least about 90% to about 100%, between at least about 90% to at least about 99%, between at least about 90% to at least about 95%, between at least about 95% to about 100%, or between at least about 95% to at least about 99%. In some embodiments, the sensitivity is at least about 70.0%, at least about 75.0%, at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%.

In some embodiments, the specificity is between at least about 30% to about 100%, between at least about 30% to about 99%, between at least about 30% to about 95%, between at least about 30% to about 90%, between at least about 30% to about 85%, between at least about 30% to about 80%, between at least about 30% to about 75%, between at least about 30% to about 70%, between at least about 30% to about 60%, between at least about 30% to about 50%, between at least about 40% to about 100%, between at least about 40% to about 99%, between at least about 40% to about 95%, between at least about 40% to about 90%, between at least about 40% to about 85%, between at least about 40% to about 80%, between at least about 40% to about 75%, between at least about 40% to about 70%, between at least about 40% to about 60%, between at least about 40% to about 50%, between at least about 50% to about 100%, between at least about 50% to about 99%, between at least about 50% to about 95%, between at least about 50% to about 90%, between at least about 50% to about 85%, between at least about 50% to about 80%, between at least about 50% to about 75%, between at least about 50% to about 70%, between at least about 50% to about 60%, between at least about 60% to about 100%, between at least about 60% to about 99%, between at least about 60% to about 95%, between at least about 60% to about 90%, between at least about 60% to about 85%, between at least about 60% to about 80%, between at least about 60% to about 75%, between at least about 60% to about 70%, between at least about 70% to about 100%, between at least about 70% to about 99%, between at least about 70% to about 95%, between at least about 70% to about 90%, between at least about 70% to about 85%, between at least about 70% to about 80%, between at least about 70% to about 75%, between at least about 80% to about 100%, between at least about 80% to about 99%, between at least about 80% to about 95%, between at least about 80% to about 90%, between at least about 80% to about 85%, between at least about 90% to about 100%, between at least about 90% to about 99%, between at least about 90% to about 95%, between at least about 95% to about 99%, or between at least about 95% to about 100. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. In some embodiments, the reference level of GFAP and the reference level of UCH-L1 are determined by a method having a sensitivity of about 80% to about 97% and a specificity of about 30% to about 95%. In some embodiments, a sample is taken from the human subject within about 48 hours of injury or suspected injury to the head, such as within about 0 to about 4 hours, within about 0 to about 8 hours, within about 0 to about 12 hours, within about 0 to about 16 hours, within about 0 to about 20 hours, within about 0 to about 24 hours, and within about 0 to about 48 hours. In some embodiments, a sample is taken from the human subject within about within about 4 hours to about 8 hours, within about 8 hours to about 12 hours, within about 12 hours to about 16 hours, within about 16 hours to about 20 hours, within about 20 hours to about 24 hours, and within about 24 hours to about 48 hours. In other embodiments, the sample can be taken from the human subject within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours of injury or suspected injury to the head. In some embodiments, the onset of the presence of the combination of GFAP and UCH-L1 appears within about 0 minutes, about 30 minutes, about 60 minutes, about 90 minutes, about 120 minutes, about 3 hours, about 4 hours, about 5 hours, about 6 hours, 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after injury to the head. In one aspect, the sample is obtained from the subject within about 4 hours to about 16 hours after the actual or suspected injury. In another aspect, the sample is obtained from the subject within about 4 hours to about 8 hours after the actual or suspected injury. In yet another aspect, the sample is obtained from the subject within about 8 hours to about 12 hours after the actual or suspected injury. In still yet another aspect, the sample is obtained from the subject within about 12 hours to about 16 hours after the actual or suspected injury.

5. TREATMENT AND MONITORING OF SUBJECTS WHO HAVE SUSTAINED AN INJURY TO THE HEAD

The subject identified or assessed in the methods described above as having traumatic brain injury, such as mild traumatic brain injury or moderate to severe traumatic brain injury, may be treated or monitored. In some embodiments, the method further includes treating the human subject assessed as having traumatic brain injury with a traumatic brain injury treatment, such as any treatments known in the art. For example, treatment of traumatic brain injury can take a variety of forms depending on the severity of the injury to the head. For example, for subjects suffering from mild TBI, the treatment may include one or more of rest, abstaining from events that aggravate symptoms (such as sports), avoiding light or wearing sunglasses when out in the light, symptomatic management such as medication for relief of a headache or migraine, anti-nausea medication, etc. Treatment for patients suffering from severe TBI might include administration of one or more appropriate medications (such as, for example, diuretics, anti-convulsant medications, medications to sedate and put an individual in a drug-induced coma, or other pharmaceutical or biopharmaceutical medications (either known or developed in the future for treatment of TBI), one or more surgical procedures (such as, for example, removal of a hematoma, repairing a skull fracture, decompressive craniectomy, etc.) and one or more therapies (such as, for example one or more rehabilitation, cognitive behavioral therapy, anger management, counseling psychology, etc.). In some embodiments, the method further includes monitoring the human subject assessed as having traumatic brain injury (e.g., mild or moderate to severe traumatic brain injury). In some embodiments, a subject identified as having traumatic brain injury, such as mild traumatic brain injury or severe traumatic brain injury, may be monitored with CT scan or MRI.

6. METHODS FOR MEASURING THE LEVEL OF UCH-L1

In the methods described above, UCH-L1 levels can be measured by any means, such as antibody dependent methods, such as immunoassays, protein immunoprecipitation, immunoelectrophoresis, chemical analysis, SDS-PAGE and Western blot analysis, protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in clinical chemistry format or single molecule detection assay, such as would be known by one skilled in the art.

In some embodiments, measuring the level of UCH-L1 includes contacting the sample with a first specific binding member and second specific binding member. In some embodiments the first specific binding member is a capture antibody and the second specific binding member is a detection antibody. In some embodiments, measuring the level of UCH-L1 includes contacting the sample, either simultaneously or sequentially, in any order: (1) at least one capture antibody (e.g., UCH-L1-capture antibody), which binds to an epitope on UCH-L1 or UCH-L1 fragment to form an at least one capture antibody-UCH-L1 antigen complex (e.g., UCH-L1-capture antibody-UCH-L1 antigen complex), and (2) at least one detection antibody (e.g., UCH-L1-detection antibody), which includes a detectable label and binds to an epitope on UCH-L1 that is not bound by the capture antibody, to form a UCH-L1 antigen—at least one detection antibody complex (e.g., UCH-L1 antigen-UCH-L1-detection antibody complex), such that an at least one capture antibody-UCH-L1 antigen—at least one detection antibody complex (e.g., UCH-L1-capture antibody-UCH-L1 antigen-UCH-L1-detection antibody complex) is formed, and measuring the amount or concentration of UCH-L1 in the sample based on the signal generated by the detectable label in the capture antibody-UCH-L1 antigen-detection antibody complex.

In some embodiments, the method further comprises a third specific binding member, such as a second detection antibody which includes a detectable label and binds to an epitope on UCH-L1 that is not bound by the capture antibody and the first detection antibody.

In some embodiments, the first specific binding member is immobilized on a solid support. In some embodiments, the second specific binding member is immobilized on a solid support. In some embodiments, the first specific binding member is a UCH-L1 antibody as described below.

In some embodiments, the sample is diluted or undiluted. The sample can be from about 1 to about 25 microliters, about 1 to about 24 microliters, about 1 to about 23 microliters, about 1 to about 22 microliters, about 1 to about 21 microliters, about 1 to about 20 microliters, about 1 to about 18 microliters, about 1 to about 17 microliters, about 1 to about 16 microliters, about 15 microliters or about 1 microliter, about 2 microliters, about 3 microliters, about 4 microliters, about 5 microliters, about 6 microliters, about 7 microliters, about 8 microliters, about 9 microliters, about 10 microliters, about 11 microliters, about 12 microliters, about 13 microliters, about 14 microliters, about 15 microliters, about 16 microliters, about 17 microliters, about 18 microliters, about 19 microliters, about 20 microliters, about 21 microliters, about 22 microliters, about 23 microliters, about 24 microliters or about 25 microliters. In some embodiments, the sample is from about 1 to about 150 microliters or less or from about 1 to about 25 microliters or less.

Some instruments (such as, for example the Abbott Laboratories instrument ARCHITECT®, and other core laboratory instruments) other than a point-of-care device may be capable of measuring levels of UCH-L1 in a sample higher or greater than 25,000 pg/mL. Other methods of detection include the use of or can be adapted for use on a nanopore device or nanowell device, e.g., for single molecule detection. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety. Other devices and methods appropriate for single molecule detection also can be employed.

7. UCH-L1 ANTIBODIES

The methods described herein may use an isolated antibody that specifically binds to ubiquitin carboxy-terminal hydrolase L1 ("UCH-L1") (or fragments thereof), referred to as "UCH-L1 antibody." The UCH-L1 antibodies can be used to assess the UCH-L1 status as a measure of traumatic brain injury, detect the presence of UCH-L1 in a sample, quantify the amount of UCH-L1 present in a sample, or detect the presence of and quantify the amount of UCH-L1 in a sample.

a. Ubiquitin Carboxy-Terminal Hydrolase L1 (UCH-L1)

Ubiquitin carboxy-terminal hydrolase L1 ("UCH-L1"), which is also known as "ubiquitin C-terminal hydrolase," is a deubiquitinating enzyme. UCH-L1 is a member of a gene family whose products hydrolyze small C-terminal adducts of ubiquitin to generate the ubiquitin monomer. Expression of UCH-L1 is highly specific to neurons and to cells of the diffuse neuroendocrine system and their tumors. It is abundantly present in all neurons (accounts for 1-2% of total brain protein), expressed specifically in neurons and testis/ovary. The catalytic triad of UCH-L1 contains a cysteine at position 90, an aspartate at position 176, and a histidine at position 161 that are responsible for its hydrolase activity.

Human UCH-L1 may have the following amino acid sequence:

(SEQ ID NO: 1)
MQLKPMEINPEMLNKVLSRLGVAGQWRFVDVLGLEEESLGSVPAPACALLL

LFPLTAQHENFRKKQIEELKGQEVSPKVYFMKQTIGNSCGTIGLIHAVANN

QDKLGFEDGSVLKQFLSETEKMSPEDRAKCFEKNEAIQAAHDAVAQEGQCR

VDDKVNFHFILFNNVDGHLYELDGRMPFPVNHGASSEDTLLKDAAKVCREF

TEREQGEVRFSAVALCKAA.

The human UCH-L1 may be a fragment or variant of SEQ ID NO: 1. The fragment of UCH-L1 may be between 5 and 225 amino acids, between 10 and 225 amino acids, between 50 and 225 amino acids, between 60 and 225 amino acids, between 65 and 225 amino acids, between 100 and 225 amino acids, between 150 and 225 amino acids, between 100 and 175 amino acids, or between 175 and 225 amino acids in length. The fragment may comprise a contiguous number of amino acids from SEQ ID NO: 1.

b. UCH-L1-Recognizing Antibody

The antibody is an antibody that binds to UCH-L1, a fragment thereof, an epitope of UCH-L1, or a variant thereof. The antibody may be a fragment of the anti-UCH-L1 antibody or a variant or a derivative thereof. The antibody may be a polyclonal or monoclonal antibody. The antibody may be a chimeric antibody, a single chain antibody, an affinity matured antibody, a human antibody, a humanized antibody, a fully human antibody or an antibody fragment, such as a Fab fragment, or a mixture thereof. Antibody fragments or derivatives may comprise $F(ab')_2$, Fv or scFv fragments. The antibody derivatives can be produced by peptidomimetics. Further, techniques described for the production of single chain antibodies can be adapted to produce single chain antibodies.

The anti-UCH-L1 antibodies may be a chimeric anti-UCH-L1 or humanized anti-UCH-L1 antibody. In one embodiment, both the humanized antibody and chimeric antibody are monovalent. In one embodiment, both the humanized antibody and chimeric antibody comprise a single Fab region linked to an Fc region.

Human antibodies may be derived from phage-display technology or from transgenic mice that express human immunoglobulin genes. The human antibody may be generated as a result of a human in vivo immune response and isolated. See, for example, Funaro et al., *BMC Biotechnology*, 2008(8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-UCH-L1 antibodies. For example, libraries of naïve human single chain variable fragments (scFv) may be used to select human anti-UCH-L1 antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The antibody is distinguishable from known antibodies in that it possesses different biological function(s) than those known in the art.

(1) Epitope

The antibody may immunospecifically bind to UCH-L1 (SEQ ID NO: 1), a fragment thereof, or a variant thereof. The antibody may immunospecifically recognize and bind at least three amino acids, at least four amino acids, at least five amino acids, at least six amino acids, at least seven amino acids, at least eight amino acids, at least nine amino acids, or at least ten amino acids within an epitope region. The antibody may immunospecifically recognize and bind to an epitope that has at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids of an epitope region.

c. Exemplary Anti-UCH-L1 Antibodies

Anti-UCH-L1 antibodies may be generated using the techniques described herein as well as using routine techniques known in the art. In some embodiments, the anti-UCH-L1 antibody may be an unconjugated UCH-L1 antibody, such as UCH-L1 antibodies available from United State Biological (Catalog Number: 031320), Cell Signaling Technology (Catalog Number: 3524), Sigma-Aldrich (Catalog Number: HPA005993), Santa Cruz Biotechnology, Inc. (Catalog Numbers: sc-58593 or sc-58594), R&D Systems (Catalog Number: MAB6007), Novus Biologicals (Catalog Number: NB600-1160), Biorbyt (Catalog Number: orb33715), Enzo Life Sciences, Inc. (Catalog Number: ADI-905-520-1), Bio-Rad (Catalog Number: VMA00004), Bio Vision (Catalog Number: 6130-50), Abcam (Catalog Numbers: ab75275 or ab104938), Invitrogen Antibodies (Catalog Numbers: 480012), ThermoFisher Scientific (Catalog Numbers: MA1-46079, MA5-17235, MA1-90008, or MA1-83428), EMD Millipore (Catalog Number: MABN48), or Sino Biological Inc. (Catalog Number: 50690-R011). The anti-UCH-L1 antibody may be conjugated to a fluorophore, such as conjugated UCH-L1 antibodies available from Bio Vision (Catalog Number: 6960-25) or Aviva Systems Biology (Cat. Nos. OAAF01904-FITC). Other UCH-L1 antibodies that can be used in the methods described herein include those described in WO 2018/081649, the contents of which are herein incorporated by reference.

d. Antibody Preparation/Production

Antibodies may be prepared by any of a variety of techniques, including those well known to those skilled in the art. In general, antibodies can be produced by cell culture techniques, including the generation of monoclonal antibodies via conventional techniques, or via transfection of antibody genes, heavy chains, and/or light chains into suitable bacterial or mammalian cell hosts, to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, Proc. Natl. Acad. Sci. USA, 77: 4216-4220 (1980)), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies. In addition, bifunctional antibodies may be produced in which one heavy and one light chain are an antibody (i.e., binds human UCH-L1) and the other heavy and light chain are specific for an antigen other than human UCH-L1 by crosslinking an antibody to a second antibody by standard chemical crosslinking methods.

In a preferred system for recombinant expression of an antibody, or antigen-binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the method of synthesizing a recombinant antibody may be by culturing a host cell in a suitable culture medium until a recombinant antibody is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with UCH-L1 or a fragment and/or variant thereof. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes electrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsried/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) *Microbiol. Immunol.* 41:901-907; Sandhu et al. (1996) *Crit. Rev. Biotechnol.* 16:95-118; Eren et al. (1998) *Immunol.* 93:154-161) that are capable of producing a repertoire of human antibodies, as known in the art and/or as described herein. Such techniques, include, but are not limited to, ribosome display (Hanes et al. (1997) *Proc. Natl. Acad. Sci. USA,* 94:4937-4942; Hanes et al. (1998) *Proc. Natl. Acad. Sci. USA,* 95:14130-14135); single cell antibody producing technologies (e.g., selected lymphocyte antibody method ("SLAM") (U.S. Pat. No. 5,627,052, Wen et al. (1987) *J. Immunol.* 17:887-892; Babcook et al. (1996) *Proc. Natl. Acad. Sci. USA* 93:7843-7848); gel microdroplet and flow cytometry (Powell et al. (1990) Biotechnol. 8:333-337; One Cell Systems, (Cambridge, Mass).; Gray et al. (1995) *J. Imm. Meth.* 182:155-163; Kenny et al. (1995) Bio/Technol. 13:787-790); B-cell selection (Steenbakkers et al. (1994) *Molec. Biol. Reports* 19:125-134 (1994)).

An affinity matured antibody may be produced by any one of a number of procedures that are known in the art. For example, see Marks et al., *BioTechnology,* 10: 779-783 (1992) describes affinity maturation by VH and VL domain shuffling. Random mutagenesis of CDR and/or framework residues is described by Barbas et al., *Proc. Nat. Acad. Sci. USA,* 91: 3809-3813 (1994); Schier et al., *Gene,* 169: 147-155 (1995); Yelton et al., *J. Immunol.,* 155: 1994-2004 (1995); Jackson et al., *J. Immunol.,* 154(7): 3310-3319 (1995); Hawkins et al, *J. Mol. Biol.,* 226: 889-896 (1992). Selective mutation at selective mutagenesis positions and at contact or hypermutation positions with an activity enhancing amino acid residue is described in U.S. Pat. No. 6,914,128 B1.

Antibody variants can also be prepared using delivering a polynucleotide encoding an antibody to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide to provide transgenic plants and cultured plant cells (e.g., but not limited to tobacco, maize, and duckweed) that produce such antibodies, specified portions or variants in the plant parts or in cells cultured therefrom. For example, Cramer et al. (1999) *Curr. Top. Microbiol. Immunol.* 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., *Adv. Exp. Med. Biol.* (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) *Plant Mol. Biol.* 38:101-109 and reference cited therein. Thus, antibodies can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) *Proc. Natl. Acad. Sci. USA* 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al., (1995) *Protein Eng.* 8(10):1057-1062. Briefly, these antibodies comprise a pair of tandem Fd segments (VH—CH1-VH—CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Rc), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

Antibody production via the use of hybridoma technology, the selected lymphocyte antibody method (SLAM), transgenic animals, and recombinant antibody libraries is described in more detail below.

(1) Anti-UCH-L1 Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: *A Laboratory Manual*, second edition, (Cold Spring Harbor Laboratory Press, Cold Spring Harbor, 1988); Hammerling, et al., In *Monoclonal Antibodies and T-Cell Hybridomas*, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods of generating monoclonal antibodies as well as antibodies produced by the method may comprise culturing a hybridoma cell secreting an antibody wherein, preferably, the hybridoma is generated by fusing splenocytes isolated from an animal, e.g., a rat or a mouse, immunized with UCH-L1 with myeloma cells and then screening the hybridomas resulting from the fusion for hybridoma clones that secrete an antibody able to bind a polypeptide. Briefly, rats can be immunized with a UCH-L1 antigen. In a preferred embodiment, the UCH-L1 antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with a UCH-L1 antigen, antibodies and/or antibody-producing cells may be obtained from the animal. An anti-UCH-L1 antibody-containing serum is obtained from the animal by bleeding or sacrificing the animal. The serum may be used as it is obtained from the animal, an immunoglobulin fraction may be obtained from the serum, or the anti-UCH-L1 antibodies may be purified from the serum. Serum or immunoglobulins obtained in this manner are polyclonal, thus having a heterogeneous array of properties.

Once an immune response is detected, e.g., antibodies specific for the antigen UCH-L1 are detected in the rat serum, the rat spleen is harvested and splenocytes isolated. The splenocytes are then fused by well-known techniques to any suitable myeloma cells, for example, cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding UCH-L1. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using UCH-L1, or a portion thereof, or a cell expressing UCH-L1. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-UCH-L1 antibody-producing hybridomas are selected, cloned, and further screened for desirable characteristics, including robust hybridoma growth, high antibody production, and desirable antibody characteristics. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-UCH-L1 antibody.

Antibody fragments that recognize specific epitopes may be generated by known techniques. For example, Fab and F(ab')$_2$ fragments may be produced by proteolytic cleavage of immunoglobulin molecules, using enzymes such as papain (to produce two identical Fab fragments) or pepsin (to produce an F(ab')$_2$ fragment). A F(ab')$_2$ fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, an F(ab')$_2$ fragment is still capable of cross-linking antigen molecules like the parent IgG molecule.

(2) Anti-UCH-L1 Monoclonal Antibodies Using SLAM

In another aspect, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., *Proc. Natl. Acad. Sci. USA*, 93: 7843-7848 (1996). In this method, single cells secreting antibodies of interest, e.g., lymphocytes derived from any one of the immunized animals are screened using an antigen-specific hemolytic plaque assay, wherein the antigen UCH-L1, a subunit of UCH-L1, or a fragment thereof, is coupled to sheep red blood cells using a linker, such as biotin, and used to identify single cells that secrete antibodies with specificity for UCH-L1. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to UCH-L1. The amplified immunoglobulin sequences further can be manipulated in vitro, such as by in vitro affinity maturation method. See, for example, PCT Publication No. WO 97/29131 and PCT Publication No. WO 00/56772.

(3) Anti-UCH-L1 Monoclonal Antibodies Using Transgenic Animals

In another embodiment, antibodies are produced by immunizing a non-human animal comprising some, or all, of the human immunoglobulin locus with a UCH-L1 antigen. In an embodiment, the non-human animal is a XENOMOUSE® transgenic mouse, an engineered mouse strain that comprises large fragments of the human immunoglobulin loci and is deficient in mouse antibody production. See, e.g., Green et al., *Nature Genetics,* 7: 13-21 (1994) and U.S. Pat. Nos. 5,916,771; 5,939,598; 5,985,615; 5,998,209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., *Nature Genetics,* 15: 146-156 (1997), Green and Jakobovits, *J. Exp. Med.,* 188: 483-495 (1998), the disclosures of which are hereby incorporated by reference.

(4) Anti-UCH-L1 Monoclonal Antibodies Using Recombinant Antibody Libraries

In vitro methods also can be used to make the antibodies, wherein an antibody library is screened to identify an antibody having the desired UCH-L1-binding specificity. Methods for such screening of recombinant antibody libraries are well known in the art and include methods 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., *Bio/Technology,* 9: 1369-1372 (1991); Hay et al., *Hum. Antibod. Hybridomas,* 3: 81-85 (1992); Huse et al., *Science,* 246: 1275-1281 (1989); McCafferty et al., *Nature,* 348: 552-554 (1990); Griffiths et al., *EMBO J.,* 12: 725-734 (1993); Hawkins et al., J. Mol. Biol., 226: 889-896 (1992); Clackson et al., Nature, 352: 624-628 (1991); Gram et al., *Proc. Natl. Acad. Sci. USA,* 89: 3576-3580 (1992); Garrard et al., *Bio/Technology,* 9: 1373-1377 (1991); Hoogenboom et al., Nucl. Acids Res., 19: 4133-4137 (1991); Barbas et al., *Proc. Natl. Acad. Sci. USA,* 88: 7978-7982 (1991); U.S. Patent Application Publication No. 2003/0186374; and PCT Publication No. WO 97/29131, the contents of each of which are incorporated herein by reference.

The recombinant antibody library may be from a subject immunized with UCH-L1, or a portion of UCH-L1. Alternatively, the recombinant antibody library may be from a naive subject, i.e., one who has not been immunized with UCH-L1, such as a human antibody library from a human subject who has not been immunized with human UCH-L1. Antibodies are selected by screening the recombinant antibody library with the peptide comprising human UCH-L1 to thereby select those antibodies that recognize UCH-L1. Methods for conducting such screening and selection are well known in the art, such as described in the references in the preceding paragraph. To select antibodies having particular binding affinities for UCH-L1, such as those that dissociate from human UCH-L1 with a particular $K_{off}$ rate constant, the art-known method of surface plasmon resonance can be used to select antibodies having the desired $K_{off}$ rate constant. To select antibodies having a particular neutralizing activity for hUCH-L1, such as those with a particular $IC_{50}$, standard methods known in the art for assessing the inhibition of UCH-L1 activity may be used.

In one aspect, the disclosure pertains to an isolated antibody, or an antigen-binding portion thereof, that binds human UCH-L1. Preferably, the antibody is a neutralizing antibody. In various embodiments, the antibody is a recombinant antibody or a monoclonal antibody.

For example, antibodies can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies include those disclosed in Brinkmann et al., *J. Immunol. Methods,* 182: 41-50 (1995); Ames et al., J. Immunol. Methods, 184:177-186 (1995); Kettleborough et al., *Eur. J. Immunol.,* 24: 952-958 (1994); Persic et al., Gene, 187: 9-18 (1997); Burton et al., Advances in *Immunology,* 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT publication No. WO 92/22324; Mullinax et al., *BioTechniques,* 12(6): 864-869 (1992); Sawai et al., *Am. J. Reprod. Immunol.,* 34: 26-34 (1995); and Better et al., *Science,* 240: 1041-1043 (1988). Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., *Proc. Natl. Acad. Sci. USA,* 90: 7995-7999 (1993); and Skerra et al., Science, 240: 1038-1041 (1988).

Alternative to screening of recombinant antibody libraries by phage display, other methodologies known in the art for screening large combinatorial libraries can be applied to the identification of antibodies. One type of alternative expression system is one in which the recombinant antibody library is expressed as RNA-protein fusions, as described in PCT Publication No. WO 98/31700 (Szostak and Roberts), and in Roberts and Szostak, *Proc. Natl. Acad. Sci. USA,* 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology is PROfusion display technology.

In another approach, the antibodies can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies include those disclosed in U.S. Pat. No. 6,699,658 (Wittrup et al.) incorporated herein by reference.

e. Production of Recombinant UCH-L1 Antibodies

Antibodies may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, *Proc. Natl. Acad. Sci. USA,* 77: 4216-4220 (1980), used with a DHFR selectable marker, e.g., as described in Kaufman and Sharp, *J. Mol. Biol.,* 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies. In addition, bifunctional antibodies may be produced in which one heavy and one light chain are an antibody (i.e., binds human UCH-L1) and the other heavy and light chain are specific for an antigen other than human UCH-L1 by crosslinking an antibody to a second antibody by standard chemical crosslinking methods.

In a preferred system for recombinant expression of an antibody, or antigen-binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the disclosure provides a method of synthesizing a recombinant antibody by culturing a host cell in a suitable culture medium until a recombinant antibody is synthesized. The method can further comprise isolating the recombinant antibody from the culture medium.

(1) Humanized Antibody

The humanized antibody may be an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG 1, IgG2, IgG3, and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, *From Genes to Clones* (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816, 567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present disclosure can be performed using any known method, such as but not limited to those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The humanized antibody may retain high affinity for UCH-L1 and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for UCH-L1, is achieved. In general, the hypervariable region residues may be directly and most substantially involved in influencing antigen binding. As an alternative to humanization, human antibodies (also referred to herein as "fully human antibodies") can be generated. For example, it is possible to isolate human antibodies from libraries via PROfusion and/or yeast related technologies. It is also possible to produce transgenic animals (e.g., mice that are capable, upon immunization, of producing a full repertoire of human antibodies in the absence of endogenous immunoglobulin production. For example, the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429; 5,833,985; 5,837,243; 5,922,845; 6,017,517; 6,096,311; 6,111,166; 6,270,765; 6,303,755; 6,365,116; 6,410,690; 6,682,928; and 6,984,720, the contents each of which are herein incorporated by reference.

8. METHODS FOR MEASURING THE LEVEL OF GFAP

In the methods described above, GFAP levels can be measured by any means, such as antibody dependent methods, such as immunoassays, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in clinical chemistry format or single molecule detection assay, such as would be known by one skilled in the art.

In some embodiments, measuring the level of GFAP includes contacting the sample with a first specific binding member and second specific binding member. In some embodiments the first specific binding member is a capture antibody and the second specific binding member is a detection antibody. In some embodiments, measuring the level of GFAP includes contacting the sample, either simultaneously or sequentially, in any order: (1) at least one capture antibody (e.g., GFAP-capture antibody), which binds to an epitope on GFAP or GFAP fragment to form an at least one capture antibody-GFAP antigen complex (e.g., GFAP-capture antibody-GFAP antigen complex), and (2) at least one detection antibody (e.g., GFAP-detection antibody), which includes a detectable label and binds to an epitope on GFAP that is not bound by the capture antibody, to form a GFAP antigen—at least one detection antibody complex (e.g., GFAP antigen-GFAP-detection antibody complex), such that an at least one capture antibody-GFAP antigen—at least one detection antibody complex (e.g., GFAP-capture antibody-GFAP antigen-GFAP-detection antibody complex) is formed, and measuring the amount or concentration of GFAP in the sample based on the signal generated by the detectable label in the at least one capture antibody-GFAP antigen—at least one detection antibody complex.

In some embodiments, the first specific binding member is immobilized on a solid support. In some embodiments, the second specific binding member is immobilized on a solid support. In some embodiments, the first specific binding member is a GFAP antibody as described below.

In some embodiments, the sample is diluted or undiluted. The sample can be from about 1 to about 25 microliters, about 1 to about 24 microliters, about 1 to about 23 microliters, about 1 to about 22 microliters, about 1 to about 21 microliters, about 1 to about 20 microliters, about 1 to about 18 microliters, about 1 to about 17 microliters, about 1 to about 16 microliters, about 15 microliters or about 1 microliter, about 2 microliters, about 3 microliters, about 4 microliters, about 5 microliters, about 6 microliters, about 7 microliters, about 8 microliters, about 9 microliters, about 10 microliters, about 11 microliters, about 12 microliters, about 13 microliters, about 14 microliters, about 15 microliters, about 16 microliters, about 17 microliters, about 18 microliters, about 19 microliters, about 20 microliters, about 21 microliters, about 22 microliters, about 23 microliters, about 24 microliters or about 25 microliters. In some embodiments, the sample is from about 1 to about 150 microliters or less or from about 1 to about 25 microliters or less.

Some instruments (such as, for example the Abbott Laboratories instrument ARCHITECT®, and other core laboratory instruments) other than a point-of-care device may be capable of measuring levels of GFAP in a sample higher or greater than 50,000 pg/mL.

Other methods of detection include the use of or can be adapted for use on a nanopore device or nanowell device, e.g., for single molecule detection. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety. Other devices and methods appropriate for single molecule detection also can be employed.

9. GFAP ANTIBODIES

The methods described herein may use an isolated antibody that specifically binds to Glial fibrillary acidic protein ("GFAP") (or fragments thereof), referred to as "GFAP antibody." The GFAP antibodies can be used to assess the GFAP status as a measure of traumatic brain injury, detect the presence of GFAP in a sample, quantify the amount of GFAP present in a sample, or detect the presence of and quantify the amount of GFAP in a sample.

a. Glial Fibrillary Acidic Protein (GFAP)

Glial fibrillary acidic protein (GFAP) is a 50 kDa intracytoplasmic filamentous protein that constitutes a portion of the cytoskeleton in astrocytes, and it has proved to be the most specific marker for cells of astrocytic origin. GFAP protein is encoded by the GFAP gene in humans. GFAP is the principal intermediate filament of mature astrocytes. In the central rod domain of the molecule, GFAP shares considerable structural homology with the other intermediate filaments. GFAP is involved in astrocyte motility and shape by providing structural stability to astrocytic processes. Glial fibrillary acidic protein and its breakdown products (GFAP-BDP) are brain-specific proteins released into the blood as part of the pathophysiological response after traumatic brain injury (TBI). Following injury to the human CNS caused by trauma, genetic disorders, or chemicals, astrocytes proliferate and show extensive hypertrophy of the cell body and processes, and GFAP is markedly upregulated. In contrast, with increasing astrocyte malignancy, there is a progressive loss of GFAP production. GFAP can also be detected in Schwann cells, enteric glia cells, salivary gland neoplasms, metastasizing renal carcinomas, epiglottic cartilage, pituicytes, immature oligodendrocytes, papillary meningiomas, and myoepithelial cells of the breast.

Human GFAP may have the following amino acid sequence:

(SEQ ID NO: 2)
MERRRITSAARRSYVSSGEMMVGGLAPGRRLGPGTRLSLARMPPPLPTRVD

FSLAGALNAGFKETRASERAEMMELNDRFASYIEKVRFLEQQNKALAAELN

QLRAKEPTKLADVYQAELRELRLRLDQLTANSARLEVERDNLAQDLATVRQ

KLQDETNLRLEAENNLAAYRQEADEATLARLDLERKIESLEEEIRFLRKIH

EEEVRELQEQLARQQVHVELDVAKPDLTAALKEIRTQYEAMASSNMHEAEE

WYRSKFADLTDAAARNAELLRQAKHEANDYRRQLQSLTCDLESLRGTNESL

ERQMREQEERHVREAASYQEALARLEEEGQSLKDEMARHLQEYQDLLNVKL

ALDIEIATYRKLLEGEENRITIPVQTFSNLQIRETSLDTKSVSEGHLKRNI

VVKTVEMRDGEVIKESKQEHKDVM.

The human GFAP may be a fragment or variant of SEQ ID NO: 2. The fragment of GFAP may be between 5 and 400 amino acids, between 10 and 400 amino acids, between 50 and 400 amino acids, between 60 and 400 amino acids, between 65 and 400 amino acids, between 100 and 400 amino acids, between 150 and 400 amino acids, between 100 and 300 amino acids, or between 200 and 300 amino acids in length. The fragment may comprise a contiguous number of amino acids from SEQ ID NO: 2. The human GFAP fragment or variant of SEQ ID NO: 2 may be a GFAP breakdown product (BDP). The GFAP BDP may be 38 kDa, 42 kDa (fainter 41 kDa), 47 kDa (fainter 45 kDa); 25 kDa (fainter 23 kDa); 19 kDa, or 20 kDa.

It has been found that using at least two antibodies that bind non-overlapping epitopes within GFAP breakdown products (BDP), such as the 38 kDa BDP defined by amino acids 60-383 of the GFAP protein sequence (SEQ ID NO:2), may assist with maintaining the dynamic range and low end sensitivity of the immunoassays. In one aspect, at least two antibodies bind non-overlapping epitopes near the N-terminus of the 38 kDa BDP. In another aspect, at least two antibodies bind non-overlapping epitopes between amino acids 60-383 of SEQ ID NO:2. In another aspect, at least one first antibody (such as a capture antibody) binds to an epitope near the N-terminus of the 38 kDa BDP and at least one second antibody (such as a detection antibody) binds to an epitope near the middle of the 38 kDa BDP that does not overlap with the first antibody. In another aspect, at least one first antibody (such as a capture antibody) binds to an epitope between amino acids 60-383 of SEQ ID NO:2 and at least one second antibody binds to an epitope between amino acids 60-383 of SEQ ID NO:2 that do not overlap with the first antibody. The epitope bound by first antibody may be 10 amino acids, 11 amino acids, 12 amino acids, 13 amino acids, 14 amino acids or 15 amino acids in length. The epitope bound by the second antibody may be 10 amino acids, 11 amino acids, 12 amino acids, 13 amino acids, 14 amino acids or 15 amino acids in length. One skilled in the art could readily determine antibodies binding to non-overlapping epitopes within the 38 kDa BDP defined by amino acids 60-383 of SEQ ID NO:2 using routine techniques known in the art.

Likewise it is possible that other antibodies can be selected which similarly may assist with maintaining the dynamic range and low end sensitivity of the immunoassays. For example, it may be useful to select at least one first antibody (such as a capture antibody) that binds to an epitope near the N-terminus of the 38 kDa BDP and at least one second antibody (such as a detection antibody) that binds to an epitope near the middle of the 38 kDa BDP, e.g., near the middle of the 38 kDa BDP, and that does not overlap with the first antibody. Other variations are possible and could be readily tested by one of ordinary skill, such as by confirming antibodies bind to different epitopes by examining binding to short peptides, and then screening antibody pairs using low calibrator concentration. Moreover, selecting antibodies of differing affinity for GFAP also can assist with maintaining or increasing the dynamic range of the assay. GFAP antibodies have been described in the literature and are commercially available.

b. GFAP-Recognizing Antibody

The antibody is an antibody that binds to GFAP, a fragment thereof, an epitope of GFAP, or a variant thereof. The antibody may be a fragment of the anti-GFAP antibody or a variant or a derivative thereof. The antibody may be a polyclonal or monoclonal antibody. The antibody may be a chimeric antibody, a single chain antibody, an affinity matured antibody, a human antibody, a humanized antibody, a fully human antibody or an antibody fragment, such as a Fab fragment, or a mixture thereof. Antibody fragments or derivatives may comprise F(ab')$_2$, Fv or scFv fragments. The antibody derivatives can be produced by peptidomimetics. Further, techniques described for the production of single chain antibodies can be adapted to produce single chain antibodies.

The anti-GFAP antibodies may be a chimeric anti-GFAP or humanized anti-GFAP antibody. In one embodiment, both the humanized antibody and chimeric antibody are monovalent. In one embodiment, both the humanized antibody and chimeric antibody comprise a single Fab region linked to an Fc region.

Human antibodies may be derived from phage-display technology or from transgenic mice that express human immunoglobulin genes. The human antibody may be generated as a result of a human in vivo immune response and isolated. See, for example, Funaro et al., BMC Biotechnology, 2008(8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-GFAP antibodies. For example, libraries of naïve human single chain variable fragments (scFv) may be used to select human anti-GFAP antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The antibody is distinguishable from known antibodies in that it possesses different biological function(s) than those known in the art.

(1) Epitope

The antibody may immunospecifically bind to GFAP (SEQ ID NO: 2), a fragment thereof, or a variant thereof. The antibody may immunospecifically recognize and bind at least three amino acids, at least four amino acids, at least five amino acids, at least six amino acids, at least seven amino acids, at least eight amino acids, at least nine amino acids, or at least ten amino acids within an epitope region. The antibody may immunospecifically recognize and bind to an epitope that has at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids of an epitope region.

c. Exemplary Anti-GFAP Antibodies

Anti-GFAP antibodies may be generated using the techniques described herein as well as using routine techniques known in the art. In some embodiments, the anti-GFAP antibody may be an unconjugated GFAP antibody, such as GFAP antibodies available from Dako (Catalog Number: M0761), ThermoFisher Scientific (Catalog Numbers: MA5-12023, A-21282, 13-0300, MA1-19170, MA1-19395, MA5-15086, MA5-16367, MA1-35377, MA1-06701, or MA1-20035), AbCam (Catalog Numbers: ab10062, ab4648, ab68428, ab33922, ab207165, ab190288, ab115898, or ab21837), EMD Millipore (Catalog Numbers: FCMAB257P, MAB360, MAB3402, 04-1031, 04-1062, MAB5628), Santa Cruz (Catalog Numbers: sc-166481, sc-166458, sc-58766, sc-56395, sc-51908, sc-135921, sc-71143, sc-65343, or sc-33673), Sigma-Aldrich (Catalog Numbers: G3893 or G6171) or Sino Biological Inc. (Catalog Number: 100140-R012-50). The anti-GFAP antibody may be conjugated to a fluorophore, such as conjugated GFAP antibodies available from ThermoFisher Scientific (Catalog Numbers: A-21295 or A-21294), EMD Millipore (Catalog Numbers: MAB3402X, MAB3402B, MAB3402B, or MAB3402C3) or AbCam (Catalog Numbers: ab49874 or ab194325). Other GFAP antibodies that can be used in the methods described herein include those described in WO 2018/081649, the contents of which are herein incorporated by reference.

d. Antibody Preparation/Production

Antibodies may be prepared by any of a variety of techniques, including those well known to those skilled in the art. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, *Proc. Natl. Acad. Sci. USA,* 77: 4216-4220 (1980)), used with a DHFR selectable marker, e.g., as described in Kaufman and Sharp, *J. Mol. Biol.,* 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies. In addition, bifunctional antibodies may be produced in which one heavy and one light chain are an antibody (i.e., binds human GFAP) and the other heavy and light chain are specific for an antigen other than human GFAP by crosslinking an antibody to a second antibody by standard chemical crosslinking methods.

In a preferred system for recombinant expression of an antibody, or antigen-binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the method of synthesizing a recombinant antibody may be by culturing a host cell in a suitable culture medium until a recombinant antibody is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with GFAP or a fragment and/or variant thereof. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes electrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsried/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) *Microbiol. Immunol.* 41:901-907; Sandhu et al. (1996) *Crit. Rev. Biotechnol.* 16:95-118; Eren et al. (1998) *Immunol.* 93:154-161) that are capable of producing a repertoire of human antibodies, as known in the art and/or as described herein. Such techniques, include, but are not limited to, ribosome display (Hanes et al. (1997) *Proc. Natl. Acad. Sci. USA*, 94:4937-4942; Hanes et al. (1998) *Proc. Natl. Acad. Sci. USA*, 95:14130-14135); single cell antibody producing technologies (e.g., selected lymphocyte antibody method ("SLAM") (U.S. Pat. No. 5,627,052, Wen et al. (1987) *J. Immunol.* 17:887-892; Babcook et al. (1996) *Proc. Natl. Acad. Sci. USA* 93:7843-7848); gel microdroplet and flow cytometry (Powell et al. (1990) *Biotechnol.* 8:333-337; One Cell Systems, (Cambridge, Mass).; Gray et al. (1995) *J. Imm. Meth.* 182:155-163; Kenny et al. (1995) Bio/Technol. 13:787-790); B-cell selection (Steenbakkers et al. (1994) *Molec. Biol. Reports* 19:125-134 (1994)).

An affinity matured antibody may be produced by any one of a number of procedures that are known in the art. For example, see Marks et al., *BioTechnology*, 10: 779-783 (1992) describes affinity maturation by VH and VL domain shuffling. Random mutagenesis of CDR and/or framework residues is described by Barbas et al., *Proc. Nat. Acad. Sci. USA*, 91: 3809-3813 (1994); Schier et al., Gene, 169: 147-155 (1995); Yelton et al., *J. Immunol.*, 155: 1994-2004 (1995); Jackson et al., *J. Immunol.*, 154(7): 3310-3319 (1995); Hawkins et al, *J. Mol. Biol.*, 226: 889-896 (1992). Selective mutation at selective mutagenesis positions and at contact or hypermutation positions with an activity enhancing amino acid residue is described in U.S. Pat. No. 6,914,128 B1.

Antibody variants can also be prepared using delivering a polynucleotide encoding an antibody to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide to provide transgenic plants and cultured plant cells (e.g., but not limited to tobacco, maize, and duckweed) that produce such antibodies, specified portions or variants in the plant parts or in cells cultured therefrom. For example, Cramer et al. (1999) *Curr. Top. Microbiol. Immunol.* 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., *Adv. Exp. Med. Biol.* (1999) 464:127-147 and references cited therein. Antibody variants have also been produced in large amounts from transgenic plant seeds including antibody fragments, such as single chain antibodies (scFv's), including tobacco seeds and potato tubers. Sec, e.g., Conrad et al. (1998) *Plant Mol. Biol.* 38:101-109 and reference cited therein. Thus, antibodies can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) *Proc. Natl. Acad. Sci. USA* 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two-fold stronger than the binding affinity of the parent antibody for the antigen.

The antibody may be a linear antibody. The procedure for making a linear antibody is known in the art and described in Zapata et al. (1995) *Protein Eng.* 8(10): 1057-1062. Briefly, these antibodies comprise a pair of tandem Fd segments (VH-CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

Antibody production via the use of hybridoma technology, the selected lymphocyte antibody method (SLAM), transgenic animals, and recombinant antibody libraries is described in more detail below.

(1) Anti-GFAP Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: *A Laboratory Manual*, second edition, (Cold Spring Harbor Laboratory Press, Cold Spring Harbor, 1988); Hammerling, et al., *In Monoclonal Antibodies and T-Cell Hybridomas*, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods of generating monoclonal antibodies as well as antibodies produced by the method may comprise culturing a hybridoma cell secreting an antibody wherein, preferably, the hybridoma is generated by fusing splenocytes isolated from an animal, e.g., a rat or a mouse, immunized with GFAP with myeloma cells and then screening the hybridomas resulting from the fusion for hybridoma clones that secrete an antibody able to bind a polypeptide. Briefly, rats can be immunized with a GFAP antigen. In a preferred embodiment, the GFAP antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with a GFAP antigen, antibodies and/or antibody-producing cells may be obtained from the animal. An anti-GFAP antibody-containing serum is obtained from the animal by bleeding or sacrificing the animal. The serum may be used as it is obtained from the animal, an immunoglobulin fraction may be obtained from the serum, or the anti-GFAP antibodies may be purified from the serum. Serum or immunoglobulins obtained in this manner are polyclonal, thus having a heterogeneous array of properties.

Once an immune response is detected, e.g., antibodies specific for the antigen GFAP are detected in the rat serum, the rat spleen is harvested and splenocytes isolated. The splenocytes are then fused by well-known techniques to any suitable myeloma cells, for example, cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding GFAP. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using GFAP, or a portion thereof, or a cell expressing GFAP. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-GFAP antibody-producing hybridomas are selected, cloned, and further screened for desirable characteristics, including robust hybridoma growth, high antibody production, and desirable antibody characteristics. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-GFAP antibody.

Antibody fragments that recognize specific epitopes may be generated by known techniques. For example, Fab and F(ab')$_2$ fragments may be produced by proteolytic cleavage of immunoglobulin molecules, using enzymes such as papain (to produce two identical Fab fragments) or pepsin (to produce an F(ab')$_2$ fragment). A F(ab')$_2$ fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, an F(ab')$_2$ fragment is still capable of cross-linking antigen molecules like the parent IgG molecule.

(2) Anti-GFAP Monoclonal Antibodies Using SLAM

In another aspect, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., *Proc. Natl. Acad. Sci. USA*, 93: 7843-7848 (1996). In this method, single cells secreting antibodies of interest, e.g., lymphocytes derived from any one of the immunized animals are screened using an antigen-specific hemolytic plaque assay, wherein the antigen GFAP, a subunit of GFAP, or a fragment thereof, is coupled to sheep red blood cells using a linker, such as biotin, and used to identify single cells that secrete antibodies with specificity for GFAP. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to GFAP. The amplified immunoglobulin sequences further can be manipulated in vitro, such as by in vitro affinity maturation method. See, for example, PCT Publication No. WO 97/29131 and PCT Publication No. WO 00/56772.

(3) Anti-GFAP Monoclonal Antibodies Using Transgenic Animals

In another embodiment, antibodies are produced by immunizing a non-human animal comprising some, or all, of the human immunoglobulin locus with a GFAP antigen. In an embodiment, the non-human animal is a XENOMOUSE® transgenic mouse, an engineered mouse strain that comprises large fragments of the human immunoglobulin loci and is deficient in mouse antibody production. Sec, e.g., Green et al., *Nature Genetics*, 7: 13-21 (1994) and U.S. Pat. Nos. 5,916,771; 5,939,598; 5,985,615; 5,998,209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., *Nature Genetics*, 15: 146-156 (1997), Green and Jakobovits, *J. Exp. Med.*, 188: 483-495 (1998), the disclosures of which are hereby incorporated by reference.

(4) Anti-GFAP Monoclonal Antibodies Using Recombinant Antibody Libraries

In vitro methods also can be used to make the antibodies, wherein an antibody library is screened to identify an antibody having the desired GFAP-binding specificity. Methods for such screening of recombinant antibody libraries are well known in the art and include methods 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., Bio/Technology, 9: 1369-1372 (1991); Hay et al., *Hum. Antibod. Hybridomas*, 3: 81-85 (1992); Huse et al., *Science*, 246: 1275-1281 (1989); McCafferty et al., *Nature*, 348: 552-554 (1990); Griffiths et al., *EMBO J.*, 12: 725-734 (1993); Hawkins et al., *J. Mol. Biol.*, 226: 889-896 (1992); Clackson et al., *Nature*, 352: 624-628 (1991); Gram et al., *Proc. Natl. Acad. Sci. USA*, 89: 3576-3580 (1992); Garrard et al., *Bio/Technology*, 9: 1373-1377 (1991); Hoogenboom et al., Nucl. Acids Res., 19: 4133-4137 (1991); Barbas et al., *Proc. Natl. Acad. Sci. USA*, 88: 7978-7982 (1991); U.S. Patent Application Publication No. 2003/0186374; and PCT Publication No. WO 97/29131, the contents of each of which are incorporated herein by reference.

The recombinant antibody library may be from a subject immunized with GFAP, or a portion of GFAP. Alternatively, the recombinant antibody library may be from a naive subject, i.e., one who has not been immunized with GFAP, such as a human antibody library from a human subject who has not been immunized with human GFAP. Antibodies are selected by screening the recombinant antibody library with the peptide comprising human GFAP to thereby select those antibodies that recognize GFAP. Methods for conducting such screening and selection are well known in the art, such as described in the references in the preceding paragraph. To select antibodies having particular binding affinities for GFAP, such as those that dissociate from human GFAP with a particular $K_{off}$ rate constant, the art-known method of surface plasmon resonance can be used to select antibodies having the desired $K_{off}$ rate constant. To select antibodies having a particular neutralizing activity for hGFAP, such as those with a particular $IC_{50}$, standard methods known in the art for assessing the inhibition of GFAP activity may be used.

In one aspect, the disclosure pertains to an isolated antibody, or an antigen-binding portion thereof, that binds human GFAP. Preferably, the antibody is a neutralizing antibody. In various embodiments, the antibody is a recombinant antibody or a monoclonal antibody.

For example, antibodies can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies include those disclosed in Brinkmann et al., *J. Immunol. Methods*, 182: 41-50 (1995); Ames et al., *J. Immunol. Methods*, 184: 177-186 (1995); Kettleborough et al., *Eur. J. Immunol.*, 24: 952-958 (1994); Persic et al., Gene, 187: 9-18 (1997); Burton et al., Advances in *Immunology*, 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT publication No. WO 92/22324; Mullinax et al., *BioTechniques*, 12(6): 864-869 (1992); Sawai et al., *Am. J. Reprod. Immunol.*, 34: 26-34 (1995); and Better et al., *Science*, 240: 1041-1043 (1988). Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., *Proc. Natl. Acad. Sci. USA*, 90: 7995-7999 (1993); and Skerra et al., *Science*, 240: 1038-1041 (1988).

Alternative to screening of recombinant antibody libraries by phage display, other methodologies known in the art for screening large combinatorial libraries can be applied to the identification of antibodies. One type of alternative expression system is one in which the recombinant antibody library is expressed as RNA-protein fusions, as described in PCT Publication No. WO 98/31700 (Szostak and Roberts), and in Roberts and Szostak, Proc. Natl. Acad. Sci. USA, 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology is PROfusion display technology.

In another approach, the antibodies can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies include those disclosed in U.S. Pat. No. 6,699,658 (Wittrup et al.) incorporated herein by reference.

e. Production of Recombinant GFAP Antibodies

Antibodies may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, *Proc. Natl. Acad. Sci. USA*, 77: 4216-4220 (1980), used with a DHFR selectable marker, e.g., as described in Kaufman and Sharp, *J. Mol. Biol.*, 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies. In addition, bifunctional antibodies may be produced in which one heavy and one light chain are an antibody (i.e., binds human GFAP) and the other heavy and light chain are specific for an antigen other than human GFAP by crosslinking an antibody to a second antibody by standard chemical crosslinking methods.

In a preferred system for recombinant expression of an antibody, or antigen-binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the disclosure provides a method of synthesizing a recombinant antibody by culturing a host cell in a suitable culture medium until a recombinant antibody is synthesized. The method can further comprise isolating the recombinant antibody from the culture medium.

(1) Humanized Antibody

The humanized antibody may be an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG 1, IgG2, IgG3, and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, *From Genes to Clones* (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816, 567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present disclosure can be performed using any known method, such as but not limited to those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The humanized antibody may retain high affinity for GFAP and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for GFAP, is achieved. In general, the hypervariable region residues may be directly and most substantially involved in influencing antigen binding.

As an alternative to humanization, human antibodies (also referred to herein as "fully human antibodies") can be generated. For example, it is possible to isolate human antibodies from libraries via PROfusion and/or yeast related technologies. It is also possible to produce transgenic animals (e.g. mice that are capable, upon immunization, of producing a full repertoire of human antibodies in the absence of endogenous immunoglobulin production. For example, the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429; 5,833,985; 5,837,243; 5,922,845; 6,017,517; 6,096,311; 6,111,166; 6,270,765; 6,303,755; 6,365,116; 6,410,690; 6,682,928; and 6,984,720, the contents each of which are herein incorporated by reference.

10. VARIATIONS ON METHODS

The disclosed methods of determining the presence or amount of the analytes of interest (UCH-L1 and GFAP) present in a sample may be as described herein. The methods may also be adapted in view of other methods for analyzing analytes. Examples of well-known variations include, but are not limited to, immunoassay, such as sandwich immunoassay (e.g., monoclonal-monoclonal sandwich immunoassays, monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogenous assay, capture on the fly assay, single molecule detection assay, etc.
a. Immunoassay The analytes of interest, and peptides of fragments thereof (e.g., UCH-L1 and GFAP, and/or peptides or fragments thereof, i.e., UCH-L1 and/or GFAP fragments), may be analyzed using UCH-L1 and GFAP antibodies in an immunoassay. The presence or amount of analytes (e.g., UCH-L1 and GFAP) can be determined using antibodies and detecting specific binding to the analytes (e.g., UCH-L1 and GFAP). For example, the antibody, or antibody fragment thereof, may specifically bind to the analytes (e.g., UCH-L1 and/or GFAP). If desired, one or more of the antibodies can be used in combination with one or more commercially available monoclonal/polyclonal antibodies. Such antibodies are available from companies such as R&D Systems, Inc. (Minneapolis, MN) and Enzo Life Sciences International, Inc. (Plymouth Meeting, PA).

The presence or amount of the analytes (e.g., UCH-L1 and GFAP) present in a body sample may be readily determined using an immunoassay, such as sandwich immunoassay (e.g., monoclonal-monoclonal sandwich immunoassays, monoclonal-polyclonal sandwich immunoassays, including radioisotope detection (radioimmunoassay (RIA)) and enzyme detection (enzyme immunoassay (FIA) or enzyme-linked immunosorbent assay (ELISA) (e.g., Quantikine ELISA assays, R&D Systems, Minneapolis, MN)). An example of a point-of-care device that can be used is i-STAT® (Abbott, Laboratories, Abbott Park, Ill.). Other methods that can be used include a chemiluminescent microparticle immunoassay, in particular one employing the ARCHITECT® automated analyzer (Abbott Laboratories, Abbott Park, Ill.), as an example. Other methods include, for example, mass spectrometry, and immunohistochemistry (e.g., with sections from tissue biopsies), using anti-analyte (e.g., anti-UCH-L1 and anti-GFAP) antibodies (monoclonal, polyclonal, chimeric, humanized, human, etc.) or antibody fragments thereof against the analytes (e.g., UCH-L1 and GFAP). Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Specific immunological binding of the antibody to the analyte (e.g., UCH-L1 or GFAP) can be detected via direct labels, such as fluorescent or luminescent tags, metals and radionuclides attached to the antibody or via indirect labels, such as alkaline phosphatase or horseradish peroxidase.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

A homogeneous format may be used. For example, after the test sample is obtained from a subject, a mixture is prepared. The mixture contains the test sample being assessed for the analytes (e.g., UCH-L1 and GFAP), a first specific binding partner, and a second specific binding partner. The order in which the test sample, the first specific binding partner, and the second specific binding partner are added to form the mixture is not critical. The test sample is simultaneously contacted with the first specific binding partner and the second specific binding partner. In some embodiments, the first specific binding partner and any UCH-L1 or GFAP contained in the test sample may form a first specific binding partner-analyte (e.g., UCH-L1 or GFAP)-antigen complex and the second specific binding partner may form a first specific binding partner-analyte of interest (e.g., UCH-L1 or GFAP)-second specific binding partner complex. In some embodiments, the second specific binding partner and any UCH-L1 and/or GFAP contained in the test sample may form a second specific binding partner-analyte (e.g., UCH-L1)-antigen complex and the first specific binding partner may form a first specific binding partner-analyte of interest (e.g., UCH-L1 or GFAP)-second specific binding partner complex. The first specific binding partner may be an anti-analyte antibody (e.g., anti-UCH-L1 antibody that binds to an epitope having an amino acid sequence comprising at least three contiguous (3) amino acids of SEQ ID NO: 1 or anti-GFAP antibody that binds to an epitope having an amino acid sequence comprising at least three contiguous (3) amino acids of SEQ ID NO: 2). The second specific binding partner may be an anti-analyte antibody (e.g., anti-UCH-L1 antibody that binds to an epitope having an amino acid sequence comprising at least three contiguous (3) amino acids of SEQ ID NO: 1 or anti-GFAP antibody that binds to an epitope having an amino acid sequence comprising at least three contiguous (3) amino acids of SEQ ID NO: 2). Moreover, the second specific binding partner is labeled with or contains a detectable label as described above.

A heterogeneous format may be used. For example, after the test sample is obtained from a subject, a first mixture is prepared. The mixture contains the test sample being assessed for the analytes (e.g., UCH-L1 and GFAP) and a first specific binding partner, wherein the first specific binding partner and any UCH-L1 or GFAP contained in the test sample form a first specific binding partner-analyte (e.g., UCH-L1 or GFAP)-antigen complex. The first specific binding partner may be an anti-analyte antibody (e.g., anti-UCH-L1 antibody that binds to an epitope having an amino acid sequence comprising at least three contiguous (3) amino acids of SEQ ID NO: 1 or anti-GFAP antibody that binds to an epitope having an amino acid sequence comprising at least three contiguous (3) amino acids of SEQ ID NO: 2). The order in which the test sample and the first specific binding partner are added to form the mixture is not critical.

The first specific binding partner may be immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc, and a chip. In those embodiments where the solid phase is a bead, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFc_2O_4$, $Fe_3O_4$ (or $FeO·Fe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the mixture containing the first specific binding partner-analyte (e.g., UCH-L1 or GFAP) antigen complex is formed, any unbound analyte (e.g., UCH-L1 or GFAP) is removed from the complex using any technique known in the art. For example, the unbound analyte (e.g., UCH-L1 or GFAP) can be removed by washing. Desirably, however, the first specific binding partner is present in excess of any analyte (e.g., UCH-L1 or GFAP) present in the test sample, such that all analyte (e.g., UCH-L1 or GFAP) that is present in the test sample is bound by the first specific binding partner.

After any unbound analyte (e.g., UCH-L1 or GFAP) is removed, a second specific binding partner is added to the mixture to form a first specific binding partner-analyte of interest (e.g., UCH-L1 or GFAP)-second specific binding partner complex. The second specific binding partner may be an anti-analyte antibody (e.g., anti-UCH-L1 antibody that binds to an epitope having an amino acid sequence comprising at least three contiguous (3) amino acids of SEQ ID NO: 1 or anti-GFAP antibody that binds to an epitope having an amino acid sequence comprising at least three contiguous (3) amino acids of SEQ ID NO: 2). Moreover, the second specific binding partner is labeled with or contains a detectable label as described above.

The use of immobilized antibodies or antibody fragments thereof may be incorporated into the immunoassay. The antibodies may be immobilized onto a variety of supports, such as magnetic or chromatographic matrix particles (such as a magnetic bead), latex particles or modified surface latex particles, polymer or polymer film, plastic or plastic film, planar substrate, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

(1) Sandwich Immunoassay

A sandwich immunoassay measures the amount of antigen between two layers of antibodies (i.e., at least one capture antibody) and a detection antibody (i.e., at least one detection antibody). The capture antibody and the detection antibody bind to different epitopes on the antigen, e.g., analyte of interest such as UCH-L1 or GFAP. Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify the analyte (e.g., UCH-L1 or GFAP) in a test sample. More specifically, the at least two antibodies bind to certain epitopes of analyte (e.g., UCH-L1 or GFAP) forming an immune complex which is referred to as a "sandwich". One or more antibodies can be used to capture the analytes (e.g., UCH-L1 and GFAP) in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, the binding of an antibody to its epitope desirably is not diminished by the binding of any other antibody in the assay to its respective epitope. Antibodies are selected so that the one or more first antibodies brought into contact with a test sample suspected of containing the analytes (e.g., UCH-L1 and GFAP) do not bind to all or part of an epitope recognized by the second or subsequent antibodies, thereby interfering with the ability of the one or more second detection antibodies to bind to the analyte (e.g., UCH-L1 or GFAP).

The antibodies may be used as a first antibody in said immunoassay. The antibody immunospecifically binds to epitopes on analyte (e.g., UCH-L1 or GFAP). In addition to the antibodies of the present disclosure, said immunoassay may comprise a second antibody that immunospecifically binds to epitopes that are not recognized or bound by the first antibody.

A test sample suspected of containing the analytes (e.g., UCH-L1 and GFAP) can be contacted with at least one first capture antibody (or antibodies) and at least one second detection antibodies either simultaneously or sequentially. In the sandwich assay format, a test sample suspected of containing the analytes (e.g., UCH-L1 and GFAP) is first brought into contact with the at least one first capture antibody that specifically binds to a particular epitope under conditions which allow the formation of a first antibody-analyte (e.g., UCH-L1 or GFAP) antigen complex. If more than one capture antibody is used, a first multiple capture antibody-UCH-L1 or GFAP antigen complex is formed. In a sandwich assay, the antibodies, preferably, the at least one capture antibody, are used in molar excess amounts of the maximum amount of analyte (e.g., UCH-L1 or GFAP) expected in the test sample. For example, from about 5 μg/mL to about 1 mg/mL of antibody per ml of microparticle coating buffer may be used.

i. Anti-UCH-L1 and/or GFAP Capture Capture Antibody

Optionally, prior to contacting the test sample with the at least one first capture antibody, the at least one first capture antibody can be bound to a solid support which facilitates the separation of the first antibody-analyte (e.g., UCH-L1 and/or GFAP) complex from the test sample. Any solid support known in the art can be used, including but not limited to, solid supports made out of polymeric materials in the forms of wells, tubes, or beads (such as a microparticle). The antibody (or antibodies) can be bound to the solid support by adsorption, by covalent bonding using a chemical coupling agent or by other means known in the art, provided that such binding does not interfere with the ability of the antibody to bind analyte (e.g., UCH-L1 and/or GFAP). Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing analyte (e.g., UCH-L1 and/or GFAP) is incubated in order to allow for the formation of a first capture antibody (or multiple antibody)-analyte (e.g., UCH-L1 and/or GFAP) complex. The incubation can be carried out at a pH of from about 4.5 to about 10.0, at a temperature of from about 2° C. to about 45° C., and for a period from at least about one (1) minute to about eighteen (18) hours, from about 2-6 minutes, from about 7-12 minutes, from about 5-15 minutes, or from about 3-4 minutes.

ii. Detection Antibody

After formation of the first/multiple capture antibody-analyte (e.g., UCH-L1 and/or GFAP) complex, the complex is then contacted with at least one second detection antibody (under conditions that allow for the formation of a first/multiple antibody-analyte (e.g., UCH-L1 or GFAP) antigen-second antibody complex). In some embodiments, the test sample is contacted with the detection antibody simultaneously with the capture antibody. If the first antibody-analyte (e.g., UCH-L1 or GFAP) complex is contacted with more than one detection antibody, then a first/multiple capture antibody-analyte (e.g., UCH-L1 or GFAP)-multiple antibody detection complex is formed. As with first antibody, when the at least second (and subsequent) antibody is brought into contact with the first antibody-analyte (e.g., UCH-L1 or GFAP) complex, a period of incubation under conditions similar to those described above is required for the formation of the first/multiple antibody-analyte (e.g., UCH-L1 or GFAP)-second/multiple antibody complex. Preferably, at least one second antibody contains a detectable label. The detectable label can be bound to the at least one second antibody prior to, simultaneously with or after the formation of the first/multiple antibody-analyte (e.g., UCH-L1 or GFAP)-second/multiple antibody complex. Any detectable label known in the art can be used.

Chemiluminescent assays can be performed in accordance with the methods described in Adamezyk et al., Anal. Chim. Acta 579(1): 61-67 (2006). While any suitable assay format can be used, a microplate chemiluminometer (Mithras LB-940, Berthold Technologies U.S.A., LLC, Oak Ridge, TN) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-antigen (e.g., UCH-L1 or GFAP) complexes form. Alternatively, if a second specific binding partner is used and the second specific binding partner is detectably labeled with an acridinium compound, detectably labeled first specific binding partner-analyte (e.g., UCH-L1 or GFAP)-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of analyte (e.g., UCH-L1 or GFAP) is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample. Other labels other than chemiluminescent labels can be employed. For instance, enzymatic labels (including but not limited to alkaline phosphatase) can be employed.

The chemiluminescent signal, or other signal, that is generated can be detected using routine techniques known to those skilled in the art. Based on the intensity of the signal generated, the amount of analyte of interest (e.g., UCH-L1 and GFAP) in the sample can be quantified. Specifically, the amount of analyte (e.g., UCH-L1 and GFAP) in the sample is proportional to the intensity of the signal generated. The amount of analyte (e.g., UCH-L1 and GFAP) present can be quantified by comparing the amount of light generated to a standard curve for analyte (e.g., UCH-L1 or GFAP) or by comparison to a reference standard. The standard curve can be generated using serial dilutions or solutions of known concentrations of analyte (e.g., UCH-L1 or GFAP) by mass spectroscopy, gravimetric methods, and other techniques known in the art. Quantitation for panel assays, and for multiplex assays likewise has been described in the scientific literature and is known to those skilled in the art.

(2) Forward Competitive Inhibition Assay

In a forward competitive format, an aliquot of labeled analyte of interest (e.g., analyte (e.g., UCH-L1 and GFAP) having a fluorescent label, a tag attached with a cleavable linker, etc.) of a known concentration is used to compete with analyte of interest (e.g., UCH-L1 and GFAP) in a test sample for binding to analyte of interest antibody (e.g., UCH-L1 or GFAP antibody).

In a forward competition assay, an immobilized specific binding partner (such as an antibody) can either be sequentially or simultaneously contacted with the test sample and a labeled analyte of interest, analyte of interest fragment or analyte of interest variant thereof. The analyte of interest peptide, analyte of interest fragment or analyte of interest variant can be labeled with any detectable label, including a detectable label comprised of tag attached with a cleavable linker. In this assay, the antibody can be immobilized on to a solid support. Alternatively, the antibody can be coupled to an antibody, such as an antispecies antibody, that has been immobilized on a solid support, such as a microparticle or planar substrate.

The labeled analyte of interest, the test sample and the antibody are incubated under conditions similar to those described above in connection with the sandwich assay format. Two different species of antibody-analyte of interest complexes may then be generated. Specifically, one of the antibody-analyte of interest complexes generated contains a detectable label (e.g., a fluorescent label, etc.) while the other antibody-analyte of interest complex does not contain a detectable label. The antibody-analyte of interest complex can be, but does not have to be, separated from the remainder of the test sample prior to quantification of the detectable label. Regardless of whether the antibody-analyte of interest complex is separated from the remainder of the test sample, the amount of detectable label in the antibody-analyte of interest complex is then quantified. The concentration of analyte of interest (such as membrane-associated analyte of interest, soluble analyte of interest, fragments of soluble analyte of interest, variants of analyte of interest (membrane-associated or soluble analyte of interest) or any combinations thereof) in the test sample can then be determined, e.g., as described above.

(3) Reverse Competitive Inhibition Assay

In a reverse competition assay, an immobilized analyte of interest (e.g., UCH-L1 or GFAP) can either be sequentially or simultaneously contacted with a test sample and at least one labeled antibody.

The analyte of interest can be bound to a solid support, such as the solid supports discussed above in connection with the sandwich assay format.

The immobilized analyte of interest, test sample and at least one labeled antibody are incubated under conditions similar to those described above in connection with the sandwich assay format. Two different species analyte of interest-antibody complexes are then generated. Specifically, one of the analyte of interest-antibody complexes generated is immobilized and contains a detectable label (e.g., a fluorescent label, etc.) while the other analyte of interest-antibody complex is not immobilized and contains a detectable label. The non-immobilized analyte of interest-antibody complex and the remainder of the test sample are removed from the presence of the immobilized analyte of interest-antibody complex through techniques known in the art, such as washing. Once the non-immobilized analyte of interest antibody complex is removed, the amount of detectable label in the immobilized analyte of interest-antibody complex is then quantified following cleavage of the tag. The concentration of analyte of interest in the test sample can then be determined by comparing the quantity of detectable label as described above.

(4) One-Step Immunoassay or "Capture on the Fly" Assay

In a capture on the fly immunoassay, a solid substrate is pre-coated with an immobilization agent. The capture agent, the analyte (e.g., UCH-L1 or GFAP) and the detection agent are added to the solid substrate together, followed by a wash step prior to detection. The capture agent can bind the analyte (e.g., UCH-L1 or GFAP) and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody.

In certain other embodiments, in a one-step immunoassay or "capture on the fly", a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is streptavidin, the ligand on the first specific binding member may be biotin) and also binds to the analyte of interest (e.g., UCH-L1 or GFAP). The second specific binding member comprises a detectable label and binds to an analyte of interest (e.g., UCH-L1 or GFAP). The solid support and the first and second specific binding members may be added to a test sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the detectable label is detected. An optional wash step may be employed before the detection. In certain embodiments, in a one-step assay more than one analyte may be measured. In certain other embodiments, more than two specific binding members can be employed. In certain other embodiments, multiple detectable labels can be added. In certain other embodiments, multiple analytes of interest can be detected, or their amounts, levels or concentrations, measured, determined or assessed.

The use of a capture on the fly assay can be done in a variety of formats as described herein, and known in the art. For example, the format can be a sandwich assay such as described above, but alternately can be a competition assay, can employ a single specific binding member, or use other variations such as are known.

(5) Single Molecule Detection Assay

Single molecule detection assays and methods, such as the use of a nanopore device or nanowell device, can also be used. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety. Other devices and methods appropriate for single molecule detection can also be employed.

11. OTHER FACTORS

The methods of diagnosing, prognosticating, and/or assessing, as described above, can further include using other factors for the diagnosis, prognostication, and assessment. In some embodiments, traumatic brain injury may be diagnosed using the Glasgow Coma Scale or the outcome of the traumatic brain injury may be predicted using the Extended Glasgow Outcome Scale (GOSE). Other tests, scales or indices can also be used either alone or in combination with the Glasgow Coma Scale. An example is the Ranchos Los Amigos Scale. The Ranchos Los Amigos Scale measures the levels of awareness, cognition, behavior and interaction with the environment. The Ranchos Los Amigos Scale includes: Level I: No Response; Level II: Generalized Response; Level III: Localized Response; Level IV: Confused-agitated; Level V: Confused-inappropriate; Level VI: Confused-appropriate; Level VII: Automatic-appropriate; and Level VIII: Purposeful-appropriate.

Other classification systems based on CT scan results can be used to predict outcome in patients, such as any classification systems known in the art. An example is the Marshall classification of traumatic brain injury, which places patients into one of six categories (I to VI) of increasing severity on the basis of findings on non-contrast CT scan of the brain. Higher categories have worse prognosis and survival. The Marshall classification is primarily concerned with two features: 1) degree of swelling, as determined by midline shift and/or compression of basal cisterns, and 2) presence and size of contusions/hemorrhages referred to "high or mixed density lesions." Another example is the Rotterdam score, which incorporates additional variables (e.g. subarachnoid hemorrhage) and attempts to address some of the recognized limitations of the Marshall system, such as struggling to classifying patients who have injuries of multiple types. The Rotterdam classification includes four independently scored elements. Similar to the Marshall system, the Rotterdam classification includes 1) degree of basal cistern compression and 2) degree of midline shift. The Rotterdam does not, however, include contusions, but rather restricts mass lesions to 3) epidural hematomas, and adds 4) intraventricular and/or subarachnoid blood. Each of these is given a score, and these scores are tallied, with the addition of 1 to the total. Higher scores worse prognosis and survival.

12. SAMPLES

In some embodiments, the sample is obtained after the human subject sustained an injury to the head caused by physical shaking, blunt impact by an external mechanical or other force that results in a closed or open head trauma, one or more falls, explosions or blasts or other types of blunt force trauma. In some embodiments, the sample is obtained after the human subject has ingested or been exposed to a chemical, toxin or combination of a chemical and toxin. Examples of such chemicals and/or toxins include, fires, molds, asbestos, pesticides and insecticides, organic solvents, paints, glues, gases (such as carbon monoxide, hydrogen sulfide, and cyanide), organic metals (such as methyl mercury, tetraethyl lead and organic tin) and/or one or more drugs of abuse. In some embodiments, the sample is obtained from a human subject that suffers from an autoimmune disease, a metabolic disorder, a brain tumor, hypoxia, one or more viruses, meningitis, hydrocephalus or combinations thereof.

In yet another embodiment, the methods described herein use samples that also can be used to determine whether or not a subject has or is at risk of developing mild traumatic brain injury by determining the levels of UCH-L1 and GFAP in a subject using the anti-UCH-L1 and anti-GFAP antibodies described below, or antibody fragments thereof. Thus, in particular embodiments, the disclosure also provides a method for determining whether a subject having, or at risk for, traumatic brain injuries, discussed herein and known in the art, is a candidate for therapy or treatment. Generally, the subject is at least one who: (i) has experienced an injury to the head; (ii) ingested and/or been exposed to one or more chemicals and/or toxins; (iii) suffers from an autoimmune disease, a metabolic disorder, a brain tumor, hypoxia, one or more viruses, meningitis, hydrocephalus or suffers from any combinations thereof; or (iv) any combinations of (i)-(iii); or, who has actually been diagnosed as having, or being at risk for TBI (such as, for example, subjects suffering from an autoimmune disease, a metabolic disorder, a brain tumor, hypoxia, one or more viruses, meningitis, hydrocephalus or combinations thereof), and/or who demonstrates an unfavorable (i.e., clinically undesirable) concentration or amount of UCH-L1 or GFAP, or UCH-L1 or GFAP fragment, as described herein.

a. Test or Biological Sample

As used herein, "sample", "test sample", "biological sample" refer to fluid sample containing or suspected of containing UCH-L1 and GFAP. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing UCH-L1 and GFAP may be assayed directly. In a particular example, the source of UCH-L1 and GFAP is a human bodily substance (e.g., bodily fluid, blood such as whole blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 µL, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01

µL and about 1 mL, between about 0.01 µL and about 100 µL, or between about 0.1 µL, and about 10 µL.

In some cases, the fluid sample may be diluted prior to use in an assay. For example, in embodiments where the source of UCH-L1 and GFAP is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use. In other cases, the fluid sample is not diluted prior to use in an assay.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source of UCH-L1 and GFAP is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

b. Controls

It may be desirable to include a control (such as a positive and/or negative control, which are well known in the art). The control may be analyzed concurrently with the sample from the subject as described above. The results obtained from the subject sample can be compared to the results or information obtained from the control sample. Standard curves may be provided, with which assay results for the sample may be compared. Such standard curves present levels of marker as a function of assay units (i.e., fluorescent signal intensity, if a fluorescent label is used). Using samples taken from multiple donors, standard curves can be provided for reference levels of the UCH-L1 and GFAP in normal healthy subjects, as well as for "at-risk" levels of the UCH-L1 and GFAP in tissue taken from donors, who may have one or more of the characteristics set forth above. In some cases, controls may relate to (e.g., be based on) samples or information taken from a subject that has sustained an orthopedic injury but no apparent TBI ("ortho controls"), or samples or information taken from healthy subjects that have no apparent injury ("healthy controls"). In some embodiments, the method can be carried out on any subject without regard to factors selected from the group consisting of the subject's clinical condition, the subject's laboratory values, the subject's classification as suffering from mild, moderate, severe or moderate to severe traumatic brain injury, and the timing of any event wherein said subject may have sustained an orthopedic injury.

Thus, in view of the above, a method for determining the presence, amount, or concentration of UCH-L1 and GFAP in a test sample is provided. The method comprises assaying the test sample for UCH-L1 and GFAP by an immunoassay, for example, employing at least one capture antibody that binds to an epitope on UCH-L1 or GFAP and at least one detection antibody that binds to an epitope on UCH-L1 or GFAP which is different from the epitope for the capture antibody and optionally includes a detectable label, and comprising comparing a signal generated by the detectable label as a direct or indirect indication of the presence, amount or concentration of UCH-L1 or GFAP in the test sample to a signal generated as a direct or indirect indication of the presence, amount or concentration of UCH-L1 or GFAP in a calibrator. The calibrator is optionally, and is preferably, part of a series of calibrators in which each of the calibrators differs from the other calibrators in the series by the concentration of UCH-L1 or GFAP.

13. KIT

Provided herein is a kit, which may be used in the methods described herein for assaying or assessing a test sample for UCH-L1 and GFAP, or UCH-L1 and GFAP fragment. The kit comprises at least one component for assaying the test sample for UCH-L1 and GFAP instructions for assaying the test sample for UCH-L1 and GFAP. For example, the kit can comprise instructions for assaying the test sample for UCH-L1 and GFAP by immunoassay, e.g., chemiluminescent microparticle immunoassay. Instructions included in kits can be affixed to packaging material, can be included as a package insert, or can be viewed or downloaded from a particular website that is recited as part of the kit packaging or inserted materials. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The at least one component may include at least one composition comprising one or more isolated antibodies or antibody fragments thereof that specifically bind to UCH-L1 or GFAP. The antibody may be a UCH-L1 or GFAP capture antibody or a UCH-L1 and/or GFAP detection antibody.

Alternatively or additionally, the kit can comprise a calibrator or control, e.g., purified, and optionally lyophilized, UCH-L1 or GFAP, and/or at least one container (e.g., tube, microtiter plates or strips, which can be already coated with an anti-UCH-L1 or GFAP monoclonal antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve.

The kit may further comprise reference standards for quantifying UCH-L1 and GFAP. The reference standards may be employed to establish standard curves for interpolation and/or extrapolation of UCH-L1 and GFAP concentrations. The reference standards may include a high UCH-L1 and GFAP concentration level, for example, about 100000 pg/mL, about 125000 pg/mL, about 150000 pg/mL, about 175000 pg/mL, about 200000 pg/mL, about 225000 pg/mL, about 250000 pg/mL, about 275000 pg/mL, or about 300000 pg/mL; a medium UCH-L1 and GFAP concentration level, for example, about 25000 pg/mL, about 40000 pg/mL, about 45000 pg/mL, about 50000 pg/mL, about 55000 pg/mL, about 60000 pg/mL, about 75000 pg/mL or about 100000 pg/ml; and a low UCH-L1 and GFAP concentration level, for example, about 1 pg/mL, about 5 pg/mL, about 10 pg/mL, about 12.5 pg/mL, about 15 pg/mL, about 20 pg/mL, about 25 pg/mL, about 30 pg/mL, about 35 pg/mL, about 40 pg/mL, about 45 pg/mL, about 50 pg/mL, about 55 pg/mL, about 60 pg/mL, about 65 pg/mL, about 70 pg/mL, about 75 pg/mL, about 80 pg/mL, about 85 pg/mL, about 90 pg/mL, about 95 pg/mL, or about 100 pg/mL.

Any antibodies, which are provided in the kit, such as recombinant antibodies specific for UCH-L1 or GFAP, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes (e.g., UCH-L1 and GFAP) or reagents for detecting the analyte (e.g., UCH-L1 and GFAP). The antibodies, calibrators, and/or controls can be provided in separate containers or pre-dispensed into an appropriate assay format, for example, into microtiter plates, Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays, The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine, whole blood, plasma, or serum sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc, or chip.

If desired, the kit can further comprise one or more components, alone or in further combination with instructions, for assaying the test sample for another analyte, which can be a biomarker, such as a biomarker of traumatic brain injury or disorder.

a. Adaptation of Kit and Method

The kit (or components thereof), as well as the method for assessing or determining the concentration of UCH-L1 and GFAP in a test sample by an immunoassay as described herein, can be adapted for use in a variety of automated and semi-automated systems (including those wherein the solid phase comprises a microparticle), as described, e.g., U.S. Pat. No. 5,063,081, U.S. Patent Application Publication Nos. 2003/0170881, 2004/0018577, 2005/0054078, and 2006/0160164 and as commercially marketed e.g., by Abbott Laboratories (Abbott Park, Ill.) as Abbott Point of Care (i-STAT® or i-STAT Alinity, Abbott Laboratories) as well as those described in U.S. Pat. Nos. 5,089,424 and 5,006,309, and as commercially marketed, e.g., by Abbott Laboratories (Abbott Park, Ill.) as ARCHITECT® or the series of Abbott Alinity devices.

Some of the differences between an automated or semi-automated system as compared to a non-automated system (e.g., ELISA) include the substrate to which the first specific binding partner (e.g., analyte antibody or capture antibody) is attached (which can affect sandwich formation and analyte reactivity), and the length and timing of the capture, detection, and/or any optional wash steps. Whereas a non-automated format such as an ELISA may require a relatively longer incubation time with sample and capture reagent (e.g., about 2 hours), an automated or semi-automated format (e.g., ARCHITECT® and any successor platform, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT® and any successor platform) may have a relatively shorter incubation time (e.g., approximately 4 minutes for the ARCHITECT® and any successor platform).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits, and kit components can be employed in other formats, for example, on electrochemical or other hand-held or point-of-care assay systems. As mentioned previously, the present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Patent App. Publication Nos. 2003/0170881, 2004/0018577, 2005/0054078, and 2006/0160164, which are incorporated in their entireties by reference for their teachings regarding same.

In particular, with regard to the adaptation of an assay to the i-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an i-STAT® cartridge with a fluidics format suitable for immunoassay. On a portion of the silicon chip, there is a specific binding partner for UCH-L1 or GFAP, such as one or more UCH-L1 or GFAP antibodies (one or more monoclonal/polyclonal antibody or a fragment thereof, a variant thereof, or a fragment of a variant thereof that can bind UCH-L1 or GFAP) or one or more anti-UCH-L1 and/or GFAP DVD-Igs (or a fragment thereof, a variant thereof, or a fragment of a variant thereof that can bind UCH-L1 or GFAP), either of which can be detectably labeled. Within the fluid pouch of the cartridge is an aqueous reagent that includes p-aminophenol phosphate.

In operation, a sample from a subject suspected of suffering from TBI is added to the holding chamber of the test cartridge, and the cartridge is inserted into the i-STAT® reader. A pump element within the cartridge pushes the sample into a conduit containing the chip. The sample is brought into contact with the sensors allowing the enzyme conjugate to dissolve into the sample. The sample is oscillated across the sensors to promote formation of the sandwich of approximately 2-12 minutes. In the penultimate step of the assay, the sample is pushed into a waste chamber and wash fluid, containing a substrate for the alkaline phosphatase enzyme, is used to wash excess enzyme conjugate and sample off the sensor chip. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of UCH-L1 and GFAP in the sample by means of an embedded algorithm and factory-determined calibration curve. Adaptation of a cartridge for multiplex use, such as used for i-Stat, has been described in the patent literature, such as for example, U.S. Pat. No. 6,438,498, the contents of which are herein incorporated by reference.

The methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an i-STAT® cartridge format, using a nucleic acid sequence linked to the signal antibody as a signal amplifier.

While certain embodiments herein are advantageous when employed to assess disease, such as traumatic brain injury, the assays and kits also optionally can be employed to assess UCH-L1 and GFAP in other diseases, disorders, and conditions as appropriate.

The method of assay also can be used to identify a compound that ameliorates diseases, such as traumatic brain injury. For example, a cell that expresses UCH-L1 or GFAP can be contacted with a candidate compound. The level of expression of UCH-L1 or GFAP in the cell contacted with the compound can be compared to that in a control cell using the method of assay described herein. This application herein references U.S. Application No. 62/596,805 filed on Dec. 9, 2017, U.S. Application No. 62/611,707 filed on Dec. 29, 2017 and U.S. Application No. 62/652,734 filed on Apr. 4, 2018, having the title, "METHODS FOR AIDING IN THE DIAGNOSIS AND EVALUATION OF A SUBJECT WHO HAS SUSTAINED AN ORTHOPEDIC INJURY AND THAT HAS OR MAY HAVE SUSTAINED AN INJURY TO THE HEAD, SUCH AS MILD TRAUMATIC BRAIN INJURY (TBI), USING GLIAL FIBRILLARY ACIDIC PROTEIN (GFAP) AND/OR UBIQUITIN CARBOXY-TERMINAL HYDROLASE L1 (UCH-L1)".

The present disclosure has multiple aspects, illustrated by the following non-limiting examples.

14. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Assays Used in Examples i-STAT® UCH-L1 Assay. The i-STAT® UCH-L1 assay was used in a TBI patient population study. Monoclonal antibody pairs, such as Antibody A as a capture monoclonal antibody and Antibody B and C as a detection monoclonal antibody, were used. Antibody A is an exemplary anti-UCH-L1 antibody that was internally developed at Abbott Laboratories (Abbott Park, Ill.). Antibody B and C recognize different epitopes of UCH-L1 and enhance the detection of antigen in the sample that were developed by Banyan Biomarkers (Alachua, Florida). The combination of the antibodies provides a synergistic effect when used together and provides for an increased signal as compared to use of the antibodies not in combination. Other antibodies that were internally developed at Abbott Laboratories (Abbott Park, Ill.), or other commercially available antibodies, also show or are expected to show similar enhancement of signal when used together as capture antibodies or detection antibodies, in various combinations. The UCH-L1 assay design was evaluated against key performance attributes. The cartridge configuration was Antibody Configuration: Antibody A (Capture Antibody)/Antibody B+C (Detection Antibody); Reagent conditions: 0.8% solids, 125 µg/mL Fab Alkaline Phosphatase cluster conjugate; and Sample Inlet Print: UCH-L1 standard. The assay time was 10-15 min (with 7-12 min sample capture time).

i-STAT@ GFAP Assay. The i-STAT® GFAP assay was used in a TBI patient population study. Monoclonal antibody pairs, such as Antibody A as a capture monoclonal antibody and Antibody B as a detection monoclonal antibody, were used. Antibody A and Antibody B are exemplary anti-GFAP antibodies that were internally developed at Abbott Laboratories (Abbott Park, Ill.). Antibody A and Antibody B both bind to epitopes within the same GFAP breakdown product (BDP). The combination of the antibodies provided a synergistic effect when used together and provided for an increased signal as compared to use of the antibodies not in combination. The GFAP assay design was evaluated against key performance attributes. The cartridge configuration was Antibody Configuration: Antibody A (Capture Antibody)/ Antibody B (Detection Antibody); Reagent conditions: 0.8% solids, 250 µg/mL Fab Alkaline Phosphatase cluster conjugate; and Sample Inlet Print: GFAP specific. The assay time was 10-15 min (with 7-12 min sample capture time).

Example 2

TBI Population Study (TRACK-TBI)

The Transforming Research and Clinical Knowledge in Traumatic Brain Injury (TRACK-TBI) study is a large and complex project. Its institutional and public-private partnership is comprised of over 11 clinical sites, 7 Cores, for a total of nearly 50 collaborating institutions, corporations, and philanthropy. An earlier TRACK-TBI Pilot study, based on clinical data from three clinical sites, helped refine TBI Common Data Elements and created a prototype of the TBI Information Commons for the TRACK-TBI study.

Subject Groups: A total of 2,700 to 3000 TBI patients were enrolled evenly across 3 clinical groups, differentiated by clinical care path: 1. Patients evaluated in the Emergency Department and discharged (ED); 2. Patients admitted to the hospital, but not to ICU (ADM); and 3. Patients admitted to the ICU (ICU). An additional 100 patients per clinical group (n=300) with extracranial trauma but no TBI were enrolled as controls for a total enrollment of 3000 patients. This stratification plan facilitated comparative effectiveness research (CER) analysis and was not constrained by traditional differentiation into "Mild/Moderate/Severe" TBI. Data collection was dependent on the clinical care path (ED, ADM, ICU) and requirements of each aim. Patients in each group were stratified into 3 cohorts that define the extent of data to be collected.

The controls were adult orthopedic trauma patients ("ortho controls") who met the following criteria: 1. An Abbreviated Injury Score of ≤4 (not life threatening) for their extremity and/or pelvis injury and/or rib fracture; 2. Met the same inclusion and exclusion criteria as the TBI subjects except that the criterion of having undergone a CT or MRI in the ED for suspected head injury did not apply. TBI was ruled out for the current injury by interviewing potential controls about loss of consciousness (LOC), disturbance of consciousness, and posttraumatic amnesia (PTA)/RA; 3. Each site was provided a plan for the number of controls to target according to age and gender distributions derived from the TBI Cohort; and 4. Controls were enrolled into the CA-MRI cohort for follow-up and drop to comprehensive assessment (CA) at 2-weeks if unable to complete the MRI visit.

Subject Eligibility: Adult patients were enrolled of all ages presenting to the Emergency Department (ED) with a history of acute TBI as per American Congress of Rehabilitation Medicine (ACRM) Criteria, in which the patient had sustained a traumatically induced physiological disruption of brain function, as manifested by ≥one of the following: any period of loss of consciousness (LOC); any loss of memory for events (e.g., amnesia) immediately before or after the accident; any alteration of mental state at the time of the accident (feeling dazed, disoriented, and/or confused); and/or focal neurologic deficits that may or may not be permanent. Traumatically induced included the head being struck, the head striking an object, or the brain undergoing an acceleration/deceleration movement (e.g., whiplash) without direct external trauma to the head.

The Inclusion/Exclusion Criteria used are shown in Table 2.

TABLE 2

| | Criterion | Data Source | Comments |
|---|---|---|---|
| | Inclusion Criteria | | |
| 1. | Age 0-89 | Chart | |
| 2. | Documented/verified TBI (ACRM Criteria) | Chart, Interview | |
| 3. | Injury occurred <24 hours ago | Chart, Interview | |
| 4. | Acute brain CT for clinical care | Chart | Subject must have brain CT scan |
| 5. | Visual acuity/hearing adequate for testing | Chart, Interview | |
| 6. | Fluency in English or Spanish | Chart, Interview | Test battery or personnel availability |
| 7. | Ability to provide informed consent | Interview | |
| | Exclusion Criteria | | |
| 1. | Significant polytrauma that would interfere with follow-up and outcome assessment | Chart | Significant body trauma may confound TBI outcomes testing. |
| 2. | Prisoners or patients in custody | Chart, Interview | |
| 3. | Pregnancy in female subjects | Chart, Interview | |
| 4. | Patients on psychiatric hold | Chart | |
| 5. | Major debilitating baseline mental health disorders (e.g., schizophrenia or bipolar disorder) that would interfere with follow-up and the validity of outcome assessment | Chart, Interview | Debilitating psychiatric disorders can significantly impact the reliability of follow up and/or pose difficulties in attributing to index TBI. |
| 6. | Major debilitating neurological disease (e.g., stroke, CVA, dementia, tumor) impairing baseline awareness cognition or validity of follow-up and outcome assessment | Chart, Interview | Documented debilitating baseline cognitive impairment will confound outcome assessment in addition to not being fully consentable. |
| 7. | Significant history of pre-existing conditions that would interfere with follow-up and outcome assessment (e.g., substance abuse, alcoholism, HIV/AIDS, major transmittable diseases that may interfere with consent, end-stage cancers, learning disabilities, developmental disorders) | Chart, Interview | |
| 8. | Contraindications to MRI (for CA + MRI cohort) | MRI Screening | |
| 9. | Low likelihood of follow-up (e.g., participant or family indicating low interest, residence in another state or country, homelessness or lack of reliable contacts) | Interview | |

TABLE 2-continued

| | Criterion | Data Source | Comments |
|---|---|---|---|
| 10. | Current participant in an interventional trial (e.g., drug, device, behavioral) | Chart, Interview | Exception to co-enrollment exclusion is made for sites participating in Resuscitation Outcomes Consortium Prehospital Tranexamic Acid for TBI Study. |
| 11. | Penetrating TBI | Chart | |
| 12. | Spinal cord injury with ASIA score of C or worse | Chart | |

For each of the 3 clinical groups (i.e., ED, ADM, and ICU), the subjects were further placed into one of three different assessment cohorts: Brief Assessment (BA Cohort), Compressive Assessment (CA) Cohort, or Comprehensive Assessment+MRI (CA+MRI) Cohort. See Table 3 for Milestone plan with 80% follow up rate.

TABLE 3

| | Year 1 | | | Year 2 | | | Year 3 | | | Year 4 | Total |
|---|---|---|---|---|---|---|---|---|---|---|---|
| Group | CA + MRI | CA | N | CA + MRI | CA | N | CA | BA | N | BA | N |
| ED | 150 | 87 | 237 | 50 | 58 | 108 | 155 | 100 | 255 | 300 | 900 |
| ADM | 150 | 87 | 237 | 50 | 58 | 108 | 155 | 100 | 255 | 300 | 900 |
| ICU | 150 | 87 | 237 | 50 | 58 | 108 | 155 | 100 | 255 | 300 | 900 |
| Controls | 0 | 99 | 99 | 0 | 66 | 66 | 135 | 0 | 135 | 0 | 300 |
| Total | 450 | 360 | 810 | 150 | 240 | 390 | 600 | 300 | 900 | 900 | 3000 |

The Brief Assessment (BA) Cohort included 1200 total subjects, with 400 subjects each for ED, ADM, and ICU Groups. The following data was gathered for the BA Cohort: demographic and full clinical course data; blood draw for serum, plasma, DNA and RNA on Day 1 (<24 hours of injury); repeat blood draw for serum within 3-6 hours of the Day 1 baseline collection (optional for sites to include this component); clinical brain CT scan from Day 1 acquired as part of hospital course; and outcome data collected via structured telephone interview at 2 weeks, 3, 6, and 12 months using NIH TBI-CDEs v.2.0 Core outcome measures as published on the NINDS CDE website.

The Compressive Assessment (CA) Cohort included 1200 total subjects, with 300 subjects+100 controls each for ED, ADM, and ICU Groups. The following data was gathered for the CA Cohort: demographic and full clinical course data; high density daily clinical data for ADM and ICU Groups; blood draw for serum, plasma, RNA, and DNA on Day 1 (<24 hours of injury); repeat blood draw for serum within 3-6 hours of the Day 1 baseline collection (optional for sites to include this component); blood draw for serum, plasma and RNA of Day 3 (48-72 hours) and 5 (96-120 hours) for ADM and ICU; collection of cerebrospinal fluid on days 1 through 5 (optional for sites to include this component); all clinical brain CT scans acquired as part of hospital course; blood draw for serum, plasma and RNA at 2 weeks and 6 months; and outcome data collected via structured in-person interview at 2 weeks, 6, and 12 months and at 3 months via structured telephone interview using NIH TBI-CDEs v.2.0 Core, Basic and Supplemental outcome measures.

The Comprehensive Assessment+MRI (CA+MRI) Cohort included 600 total subjects, with 200 each for ED, ADM, and ICU Groups. The following data was gathered for the CA+MRI Cohort: demographic and full clinical course data; high density daily clinical data for ADM and ICU Groups; blood draw for serum, plasma, RNA, and DNA on Day 1 (<24 hours of injury); repeat blood draw for serum within 3-6 hours of the Day 1 baseline collection (optional for sites to include this component); blood draw for serum, plasma, and RNA on Day 3 (48-72 hours) and 5 (96-120 hours) for ADM and ICU; collection of cerebrospinal fluid on days 1 through 5 (optional for sites to include this component); all clinical head CT scans acquired as part of hospital course; blood draw for serum, plasma and RNA at 2 weeks and 6 months; 3T research MRI acquired at 2 weeks and 6 months; and outcome data collected via structured in-person interview at 2 weeks, 6, and 12 months and at 3 month via structured telephone interview using NIH TBI-CDEs v.2.0 Core, Basic, and Supplemental outcome measures.

Upon enrollment, data collection began in the hospital. For CA+MRI patients, the 2-week MRI was completed at 14 days±4 days from the date of injury. Corresponding 2-week outcomes were completed ±3 days of the 2-week MRI. For CA and BA patients, 2-week outcomes were completed ±4 days of 14 days from the date of injury. Outcomes at 3 months were completed ±7 days of 90 days from the date of injury. For CA+MRI patients, MRIs at 6 months were completed ±14 days of 180 days from the date of injury, with corresponding 6-month outcomes ±14 days of the 6-month MRI. For CA and BA patients, 6-month outcomes were completed ±14 days of 180 days from the date of injury. BTACT should be completed with ±7 days of Outcomes (but not on the same day and no greater than 201 days from injury). Outcomes at 12 months were completed ±30 days of 360 days from the date of injury.

UCH-L1 and GFAP were measured in a small sample size of 59 TRACK TBI patients in the i-STAT assay format (Table 4).

TABLE 4

Subject Characteristics by CT Scan and MRI Result

| Subject Characteristics | Total (n = 59) | CT or MRI Positive[a] (n = 46, 77.97%) | CT and MRI Negative[a] (n = 13, 22.03%) | P value |
|---|---|---|---|---|
| Age | 46.0 [24.0 to 60.0] | 45.5 [23.0 to 60.0] | 50.0 [39.0 to 57.0] | 0.7419 |
| Sex | | | | |
| Male | 50/59 (85%) | 39/46 (85%) | 11/13 (85%) | 1.0000 |
| Female | 9/59 (15%) | 7/46 (15%) | 2/13 (15%) | |
| Race/Ethnicity | | | | |
| African-American or African | 6/58 (10%) | 4/45 (9%) | 2/13 (15%) | 0.2398 |
| Caucasian | 48/58 (83%) | 39/45 (87%) | 9/13 (69%) | |
| Hispanic | 4/58 (7%) | 2/45 (4%) | 2/13 (15%) | |
| TBI History | | | | |
| Yes, with No LOC | 9/56 (16%) | 3/43 (7%) | 6/13 (46%) | 0.0037 |
| Yes, with LOC | 8/56 (14%) | 6/43 (14%) | 2/13 (15%) | |
| No Prior TBI | 39/56 (70%) | 34/43 (79%) | 5/13 (38%) | |
| ED Presentation | | | | |
| Loss of Consciousness | | | | |
| No | 6/58 (10%) | 2/45 (4%) | 4/13 (31%) | 0.0227 |
| Yes | 47/58 (81%) | 38/45 (84%) | 9/13 (69%) | |
| Unknown | 5/58 (9%) | 5/45 (11%) | | |
| Glasgow Coma Scale | 15.0 [3.0 to 15.0] | 14.0 [3.0 to 15.0] | 15.0 [15.0 to 15.0] | 0.0162 |
| Glasgow Coma Scale Classification | | | | |
| Severe (3-8) | 16/59 (27%) | 16/46 (35%) | | 0.0177 |
| Moderate (9-12) | 3/59 (5%) | 3/46 (7%) | | |
| Mild (13-15) | 40/59 (68%) | 27/46 (59%) | 13/13 (100%) | |
| Mechanism of Injury | | | | |
| Motor vehicle (driver/passenger) | 10/59 (17%) | 9/46 (20%) | 1/13 (8%) | 0.2975 |
| Motorcycle/ATV/golf cart (driver/passenger) | 5/59 (8%) | 3/46 (7%) | 2/13 (15%) | |
| Individual struck by any type of vehicle | 3/59 (5%) | 2/46 (4%) | 1/13 (8%) | |
| Fall from a moving object (bike/skateboard/horse/etc.) | 3/59 (5%) | 3/46 (7%) | | |
| Fall from stationary object (roof/ladder/etc.) | 27/59 (46%) | 20/46 (43%) | 7/13 (54%) | |
| Assault | 10/59 (17%) | 9/46 (20%) | 1/13 (8%) | |
| Struck on head by object, not assault (tree/etc.) | 1/59 (2%) | | 1/13 (8%) | |
| Alcohol Level (g/dL) | 0.1 [0.0 to 0.2] | 0.1 [0.0 to 0.2] | 0.0 [0.0 to 0.0] | 0.1588 |
| Drug Screen | | | | |
| Negative | 51/59 (86%) | 41/46 (89%) | 10/13 (77%) | 0.3567 |
| Positive | 8/59 (14%) | 5/46 (11%) | 3/13 (23%) | |
| Biomarker Results | | | | |
| Collection Time Since Injury (Minutes) | 771.0 (+/−339.8) | 779.4 (+/−296.8) | 743.0 (+/−468.7) | 0.7383 |
| GFAP (pg/mL) | 643.8 [188.6 to 2138.6] | 876.6 [519.7 to 2409.5] | 31.3 [26.3 to 166.2] | <0.0001 |
| UCH-L1 (pg/mL) | 342.5 [102.8 to 718.3] | 514.0 [167.2 to 859.8] | 62.4 [44.5 to 136.8] | <0.0001 |
| Prognostic Scores | | | | |
| Glasgow Outcome Scale (3 months) | 6.0 [5.0 to 7.0] | 5.5 [4.0 to 7.0] | 7.0 [7.0 to 7.0] | 0.0130 |
| Glasgow Outcome Scale (6 months) | 6.0 [5.0 to 7.0] | 6.0 [4.0 to 7.0] | 7.0 [5.5 to 7.5] | 0.1941 |
| Glasgow Outcome Scale (12 months) | 7.0 [5.0 to 8.0] | 6.5 [5.0 to 8.0] | 7.0 [6.0 to 8.0] | 0.4412 |
| Rivermead Questionnaire First 3 Items (6 months) | 0.0 [0.0 to 2.0] | 0.0 [0.0 to 2.5] | 0.0 [0.0 to 2.0] | 0.8378 |
| Rivermead Questionnaire Last 13 Items (6 months) | 9.0 [4.0 to 15.0] | 8.5 [4.0 to 15.0] | 13.0 [0.0 to 27.0] | 0.5449 |
| WAIS-III Processing Speed Index (6 months) | 30.0 [5.0 to 55.0] | 30.0 [5.0 to 50.0] | 43.0 [18.0 to 77.0] | 0.3235 |
| Satisfaction with Life Scale (6 months) | 21.5 (+/−6.2) | 21.7 (+/−5.7) | 20.4 (+/−8.5) | 0.6205 |
| Functional Independence Measure (6 months) | 126.0 [125.0 to 126.0] | 126.0 [124.0 to 126.0] | 126.0 [126.0 to 126.0] | 0.2958 |

[a] 24 subjects received an MRI.

Continuous variables are presented as median [25-75% Inter Quartile Range] and compared using Wilcoxon rank sum test or Mean (+/−SD) and compared using a t-test based on the distribution of the data.
Categorical variables are presented as number/total (percent) and compared using Chi-Square or Fisher's exact test.

In addition to a blood draw within 24 hours of brain injury, each patient had an extensive medical evaluation including head CT, neuropsychiatric testing, Glasgow Coma Score (GCS), and many patients also had a follow up MRI within 2 weeks of injury. Following a meticulous standardized blood draw protocol and processing, plasma samples were aliquotted for storage at −80° C., later thawed and tested. Each sample was run in duplicate with the listed results being an average of the two runs. UCH-L1 levels and GFAP levels correlated with injury throughout the first 24 hours after injury (range approximately 2-23 hours) in an exemplary subset of subjects (data not shown). Table 4 shows that ethanol (ETOH) levels did not correlate with biomarker levels (Pearson Correlation=0.023, p-value=0.89) as ETOH consumption is frequently related to TBI, in particular severe TBI.

For the various conditions present in the dataset (Table 5), GFAP and UCH-L1 levels were measured, and mean, minimum, maximum, $5^{th}$ percentile and $95^{th}$ percentile were calculated. In addition to assessing overall GFAP and UCH- L1 levels over 48 hours after injury (or suspected injury) to the head, analysis was also performed on various time segments during these 48 hours post-injury. As shown below, GFAP (Table 6) and UCH-L1 (Table 7) levels were measured, and mean, minimum, maximum, $5^{th}$ percentile and $95^{th}$ percentile were calculated from 0-4 hours, from 4-8 hours, from 8-12 hours, from 12-16 hours, from 16-20 hours, from 20-24 hours, and from 24-48 hours.

TABLE 5

Clinical Analysis of TRACK TBI Data - Subject Characteristics

| Biomarker | Condition | n | Median | Mean | Std. Dev. | Min. | Max | 5th Percentile | 95th Percentile |
|---|---|---|---|---|---|---|---|---|---|
| GFAP | Control | 17 | 11 | 11 | 6.5 | 0 | 27 | 0 | 27 |
| | Ortho Control | 38 | 14 | 22 | 29.7 | 2 | 181 | 2 | 67 |
| | Mild TBI* | 1123 | 244 | 803 | 2191.0 | 0 | 35085 | 9 | 3160 |
| | Mild or Moderate/Severe TBI | 1378 | 335 | 1828 | 6529.4 | 0 | 130418 | 9 | 6459 |
| | Moderate/Severe TBI** | 201 | 3095 | 7116 | 14607.8 | 5 | 130418 | 123 | 26717 |
| UCH-L1 | Control | 17 | 53 | 55 | 23.9 | 26 | 106 | 26 | 106 |
| | Ortho Control | 38 | 120 | 149 | 73.0 | 62 | 345 | 68 | 305 |
| | Mild TBI* | 1123 | 175 | 292 | 416.0 | 1 | 6399 | 39 | 870 |
| | Mild or Moderate/Severe TBI | 1378 | 200 | 441 | 863.9 | 1 | 11020 | 42 | 1575 |
| | Moderate/Severe TBI** | 201 | 684 | 1157 | 1636.3 | 42 | 10390 | 92 | 3385 |

*Glasgow Coma Scale >=13
**Glasgow Coma Scale <=12

TABLE 6

Clinical Analysis of TRACK TBI Data - GFAP Levels by Time Segment

| Time Bucket | Type | n | Mean | Std. Dev. | Min. | Max | 5th Percentile | 95th Percentile |
|---|---|---|---|---|---|---|---|---|
| 0-4 Hours | Mild TBI* | 86 | 162 | 243.8 | 3 | 1108 | 4 | 754 |
| | Mild or Moderate/Severe TBI | 93 | 1726 | 13566.3 | 3 | 130418 | 4 | 931 |
| | Moderate/Severe TBI** | 3 | 44204 | 74671.2 | 28 | 130418 | 28 | 130418 |
| 4-8 Hours | Mild TBI* | 182 | 427 | 707.1 | 0 | 5251 | 10 | 1503 |
| | Mild or Moderate/Severe TBI | 212 | 845 | 1744.9 | 0 | 11933 | 10 | 4192 |
| | Moderate/Severe TBI** | 20 | 4230 | 3205.9 | 753 | 11933 | 802 | 10371 |
| 8-12 Hours | Mild TBI* | 143 | 1030 | 3190.6 | 2 | 35085 | 12 | 3662 |
| | Mild or Moderate/Severe TBI | 177 | 1677 | 4474.2 | 2 | 35085 | 12 | 6356 |
| | Moderate/Severe TBI** | 30 | 4969 | 7617.8 | 10 | 33907 | 202 | 24659 |
| 12-16 Hours | Mild TBI* | 192 | 951 | 1859.9 | 0 | 16445 | 8 | 4359 |
| | Mild or Moderate/Severe TBI | 242 | 2129 | 5759.3 | 0 | 53244 | 9 | 7894 |
| | Moderate/Severe TBI** | 42 | 6296 | 10701.7 | 73 | 53244 | 109 | 19745 |
| 16-20 Hours | Mild TBI* | 208 | 869 | 1936.0 | 2 | 22515 | 9 | 3401 |
| | Mild or Moderate/Severe TBI | 252 | 1619 | 3533.2 | 2 | 31671 | 9 | 6222 |
| | Moderate/Severe TBI** | 38 | 5775 | 6529.9 | 5 | 31671 | 358 | 16294 |
| 20-24 Hours | Mild TBI* | 264 | 1030 | 2938.8 | 1 | 35004 | 11 | 3757 |
| | Mild or Moderate/Severe TBI | 335 | 2265 | 7829.2 | 1 | 101104 | 12 | 8374 |
| | Moderate/Severe TBI** | 55 | 8731 | 16907.3 | 13 | 101104 | 83 | 31220 |
| 24-48 Hours | Mild TBI* | 24 | 736 | 1270.5 | 5 | 6131 | 7 | 1634 |
| | Mild or Moderate/Severe TBI | 38 | 2966 | 7248.2 | 5 | 41781 | 7 | 17388 |
| | Moderate/Severe TBI** | 8 | 2789 | 2708.1 | 14 | 7179 | 14 | 7179 |

*Glasgow Coma Scale >=13
**Glasgow Coma Scale <=12

TABLE 7

Clinical Analysis TRACK TBI Data - UCH-L1 Levels by Time Segment

| Time Bucket | Condition | n | Mean | Std. Dev. | Min. | Max | 5th Percentile | 95th Percentile |
|---|---|---|---|---|---|---|---|---|
| 0-4 Hours | Mild TBI* | 86 | 350 | 325.0 | 22 | 2235 | 77 | 870 |
| | Mild or Moderate/Severe TBI | 93 | 555 | 1321.9 | 22 | 10390 | 77 | 1183 |
| | Moderate/Severe TBI** | 3 | 6036 | 5312.9 | 116 | 10390 | 116 | 10390 |
| 4-8 Hours | Mild TBI* | 182 | 398 | 476.1 | 6 | 3134 | 56 | 1207 |
| | Mild or Moderate/Severe TBI | 212 | 593 | 1054.3 | 6 | 9187 | 56 | 2124 |
| | Moderate/Severe TBI** | 20 | 2258 | 2537.5 | 48 | 9187 | 129 | 9182 |
| 8-12 Hours | Mild TBI* | 143 | 387 | 570.2 | 4 | 3666 | 50 | 1160 |
| | Mild or Moderate/Severe TBI | 177 | 546 | 958.3 | 4 | 8542 | 51 | 2447 |
| | Moderate/Severe TBI** | 30 | 1363 | 1771.2 | 100 | 8542 | 173 | 5816 |

TABLE 7-continued

Clinical Analysis TRACK TBI Data - UCH-L1 Levels by Time Segment

| Time Bucket | Condition | n | Mean | Std. Dev. | Min. | Max | 5th Percentile | 95th Percentile |
|---|---|---|---|---|---|---|---|---|
| 12-16 Hours | Mild TBI* | 192 | 312 | 581.4 | 6 | 6399 | 39 | 900 |
| | Mild or Moderate/Severe TBI | 242 | 503 | 945.0 | 6 | 8235 | 43 | 2216 |
| | Moderate/Severe TBI** | 42 | 1262 | 1605.9 | 62 | 8235 | 72 | 4348 |
| 16-20 Hours | Mild TBI* | 208 | 224 | 227.2 | 1 | 1424 | 34 | 686 |
| | Mild or Moderate/Severe TBI | 252 | 343 | 474.6 | 1 | 3488 | 38 | 1256 |
| | Moderate/Severe TBI** | 38 | 920 | 735.5 | 90 | 2901 | 154 | 2532 |
| 20-24 Hours | Mild TBI* | 264 | 203 | 215.1 | 9 | 1882 | 36 | 549 |
| | Mild or Moderate/Severe TBI | 335 | 272 | 327.9 | 9 | 2062 | 38 | 996 |
| | Moderate/Severe TBI** | 55 | 632 | 525.8 | 42 | 2062 | 74 | 1634 |
| 24-48 Hours | Mild TBI* | 24 | 164 | 152.0 | 20 | 717 | 27 | 444 |
| | Mild or Moderate/Severe TBI | 38 | 679 | 1895.3 | 20 | 11020 | 27 | 4481 |
| | Moderate/Severe TBI** | 8 | 370 | 299.3 | 161 | 890 | 161 | 890 |

*Glasgow Coma Scale >=13
**Glasgow Coma Scale <= 12

Figure 1B:
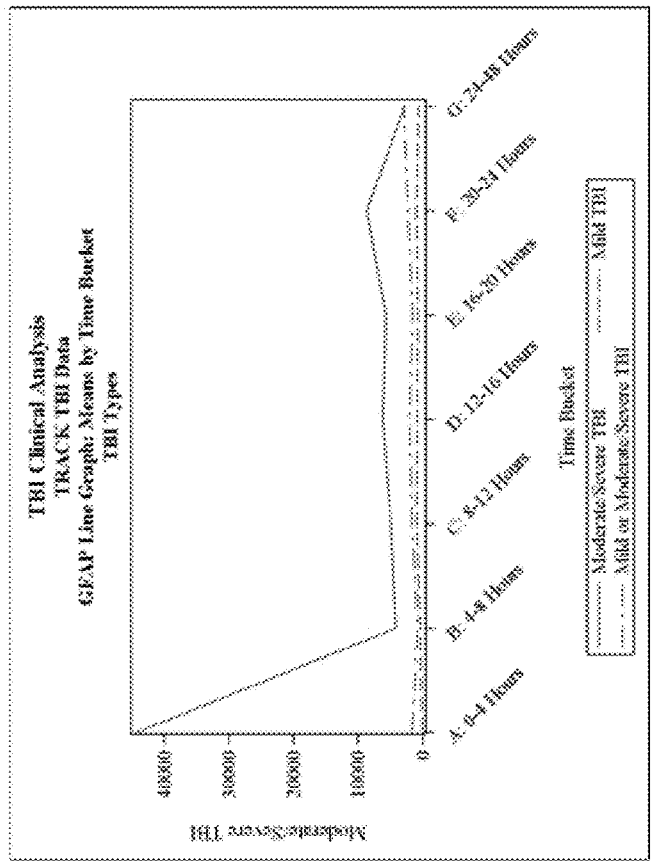

FIGS. 1A-1B include representative graphs depicting mean GFAP (FIG. 1A) and UCH-L1 (FIG. 1B) levels at various time points within 48 hours post-injury for moderate/severe TBI, mild TBI, and mild and moderate/severe TBI groups. Levels of both GFAP and UCH-L1 are highest between 0-4 hours post-injury in the moderate/severe TBI group.

Figure 2B:
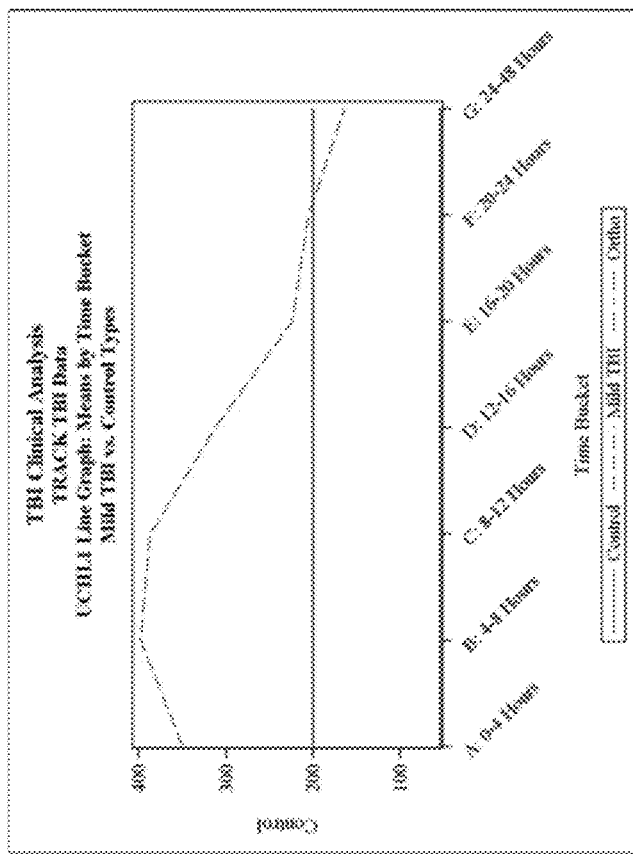
FIGS. 2A-2B include representative graphs depicting mean GFAP (FIG. 2A) and UCH-L1 (FIG. 2B) levels at various time points within 48 hours post-injury for mild TBI, healthy Control, and Ortho Control groups.
Figure 2A:
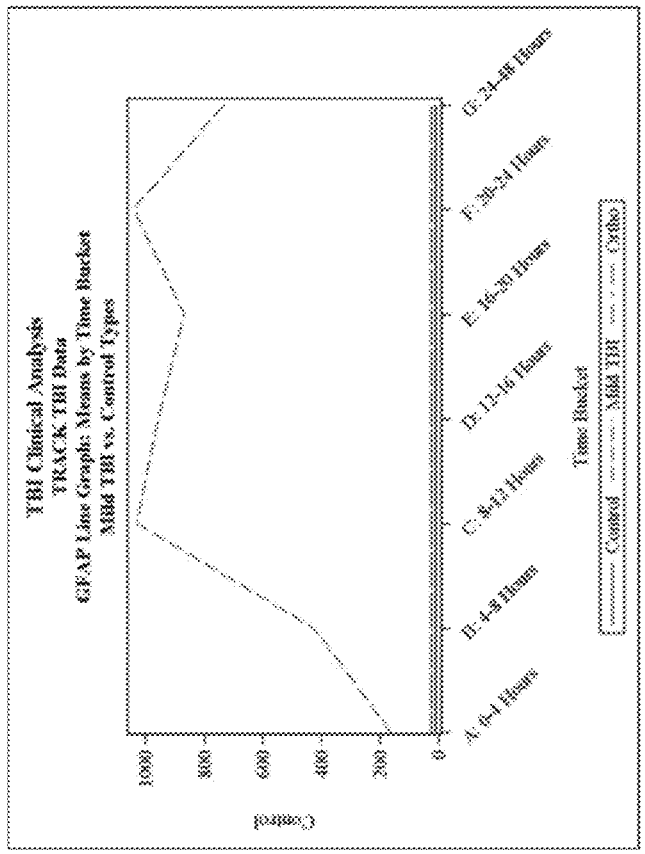
Figure 3A:
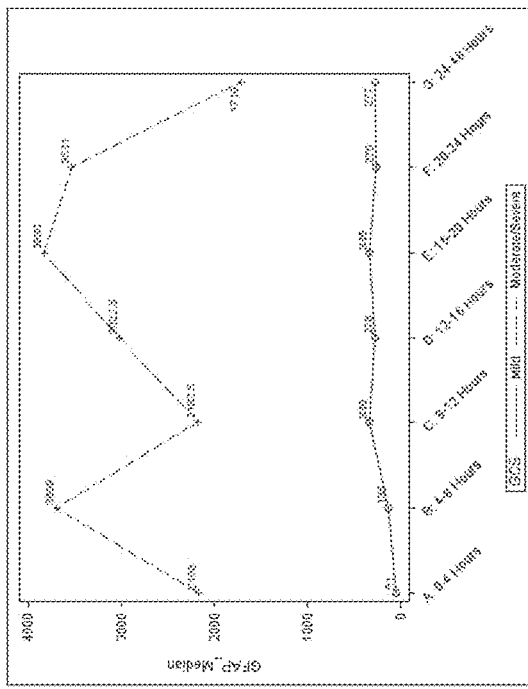
FIGS. 3A-3D include representative plots of median GFAP levels by timepoint in subjects assigned GCS scores (13-15=mild TBI; 9-12=moderate TBI; less than or equal to 8=severe TBI) (FIGS. 3A and 3B), and based on imaging results (CT scan result in FIG. 3C; MRI result in FIG. 3D).
Figure 3B:
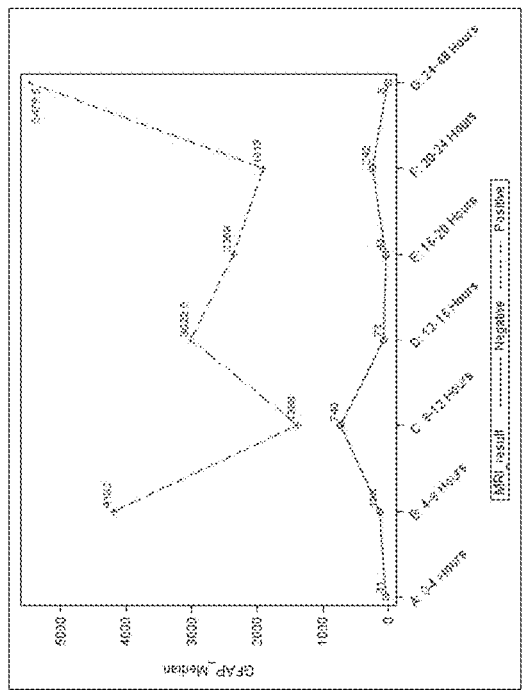
Figure 3C:
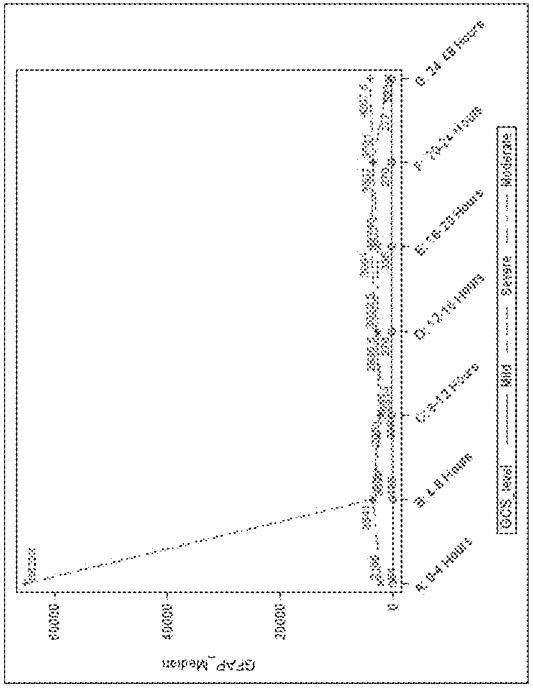
Figure 3D:
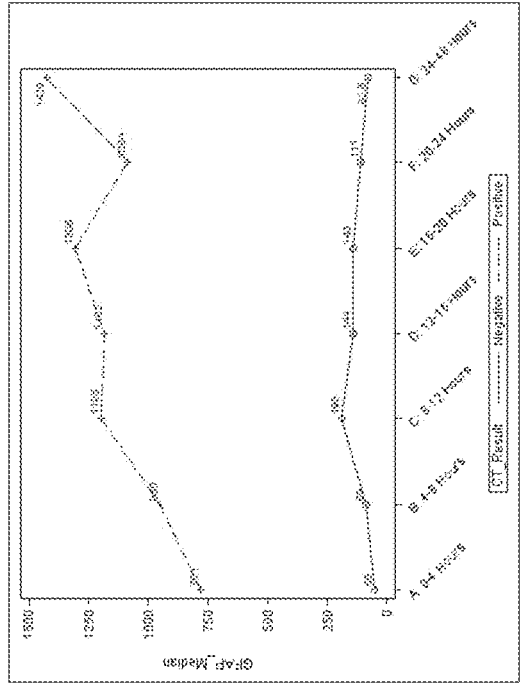
Figures 4A, 4B, 4C, 4D:
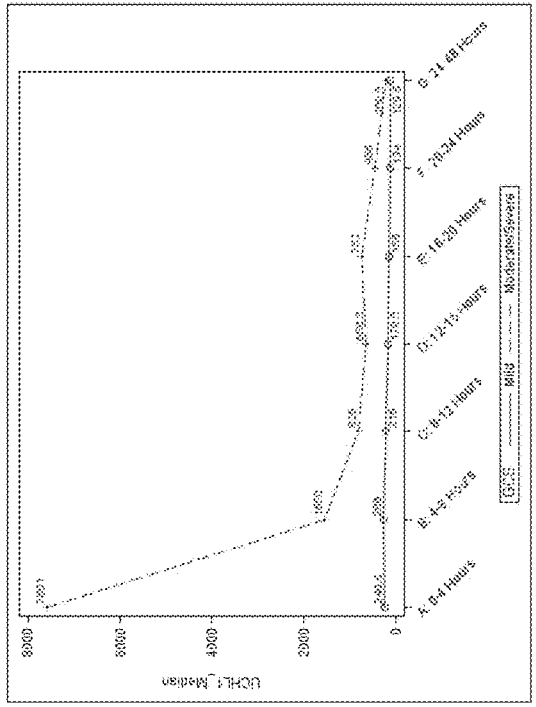
FIGS. 4A-4D include representative plots of median GFAP levels by timepoint in subjects assigned GCS scores (13-15=mild TBI; 9-12=moderate TBI; less than or equal to 8=severe TBI) (FIGS. 4A and 4B), and based on imaging results (CT scan result in FIG. 4C; MRI result in FIG. 4D).

Similar data was obtained from both healthy controls (no trauma sustained) and ortho controls (an orthopedic injury was sustained, but no TBI). FIGS. 2A-2B include representative graphs depicting mean GFAP (FIG. 2A) and UCH-L1 (FIG. 2B) levels at various time points within 48 hours post-injury for mild TBI, healthy control, and ortho control groups. Both GFAP and UCH-L1 levels are elevated in the mild TBI group as compared to both healthy controls and ortho controls from 0-48 hours post-injury. UCH-L1 levels were also elevated in the ortho control group as compared to healthy controls.

Data analysis was also performed to correlate median GFAP and UCH-L1 levels at various time points over 48 hours post-injury with a TBI diagnosis based on a clinical outcome (GCS score, CT scan result, or MRI scan result). FIGS. 3A-3D include representative plots of median GFAP levels by timepoint in subjects assigned GCS scores (13-15=mild TBI; 9-12=moderate TBI; less than or equal to 8=severe TBI) (FIGS. 3A and 3B), and based on imaging results (CT scan result in FIG. 3C; MRI result in FIG. 3D). FIGS. 4A-4D include representative plots of median GFAP levels by timepoint in subjects assigned GCS scores (13-15=mild TBI; 9-12=moderate TBI; less than or equal to 8=severe TBI) (FIGS. 4A and 4B), and based on imaging results (CT scan result in FIG. 4C; MRI result in FIG. 4D). Together, these data demonstrate that elevated GFAP and UCH-L1 levels at various time points over 48 hours post-injury correlate well with clinical outcomes indicating the presence of a TBI (e.g., "positive"), including both mild TBI and moderate/severe TBI.

Figure 5A:
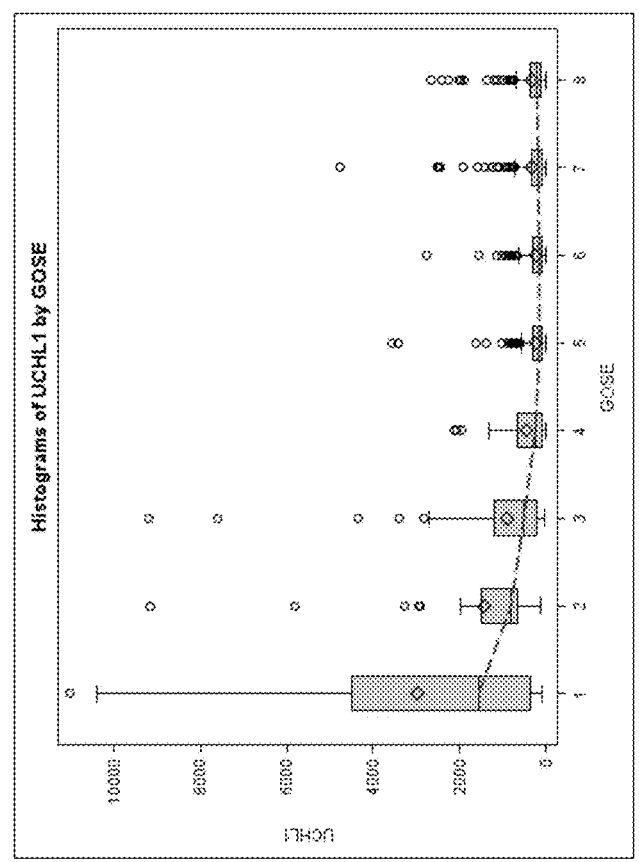
FIGS. 5A-5B include representative box plots of GFAP (FIG. 5A) and UCH-L1 (FIG. 5B) levels in subjects grouped according to GOSE scores.
Figure 5B:
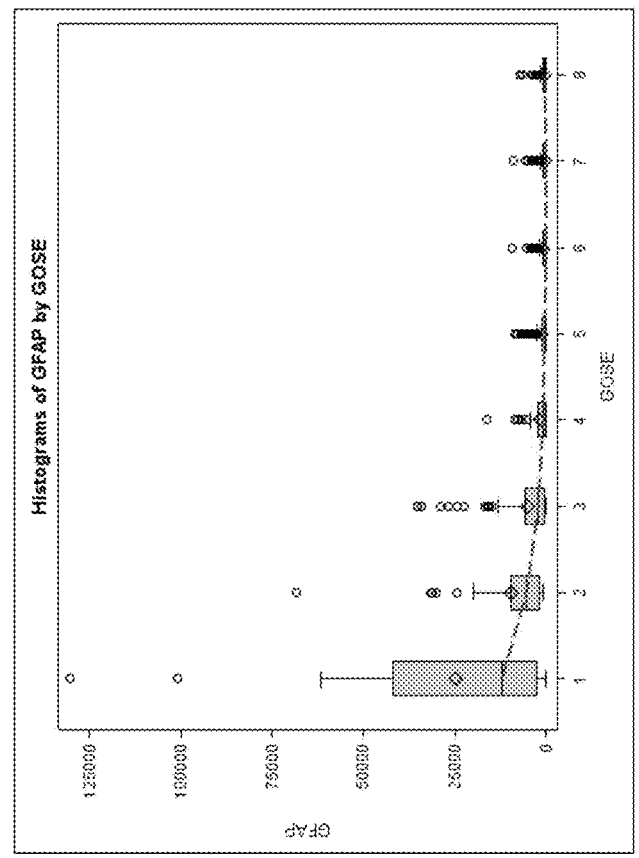

Data analysis was also performed to correlate GFAP and UCH-L1 levels with GOSE scores. FIGS. 5A-5B include representative box plots of GFAP (FIG. 5A) and UCH-L1 (FIG. 5B) levels in subjects grouped according to GOSE scores. As demonstrated, both GFAP and UCH-L1 levels are elevated in subjects with GOSE scores closer to 1 (death/TBI), as compared to subject with GOSE scores closer to 8 (recovered/healthy).

In addition to assessing correlations between GFAP and UCH-L1 levels individually with various clinical indicators of TBI, data from the present disclosure also addresses the predictive diagnostic value of a combination of GFAP and UCH-L1 reference levels in determining whether a subject has sustained a TBI. Analyses were based on the use of simultaneous reference values, or cut-offs, for both GFAP and UCH-L1. If a level of GFAP or a level of UCH-L1 measured or detected in a subject is greater than a corresponding GFAP or UCH-L1 reference value, then one or more clinical outcomes is predicted to be positive, or indicative of a TBI in that subject. If a level of GFAP and a level of UCH-L1 measured or detected in a subject are both less than corresponding GFAP or UCH-L1 reference values, then one or more clinical outcomes is predicted to be negative, or indicative of a subject that has not sustained a TBI (healthy subject).

Figure 6:
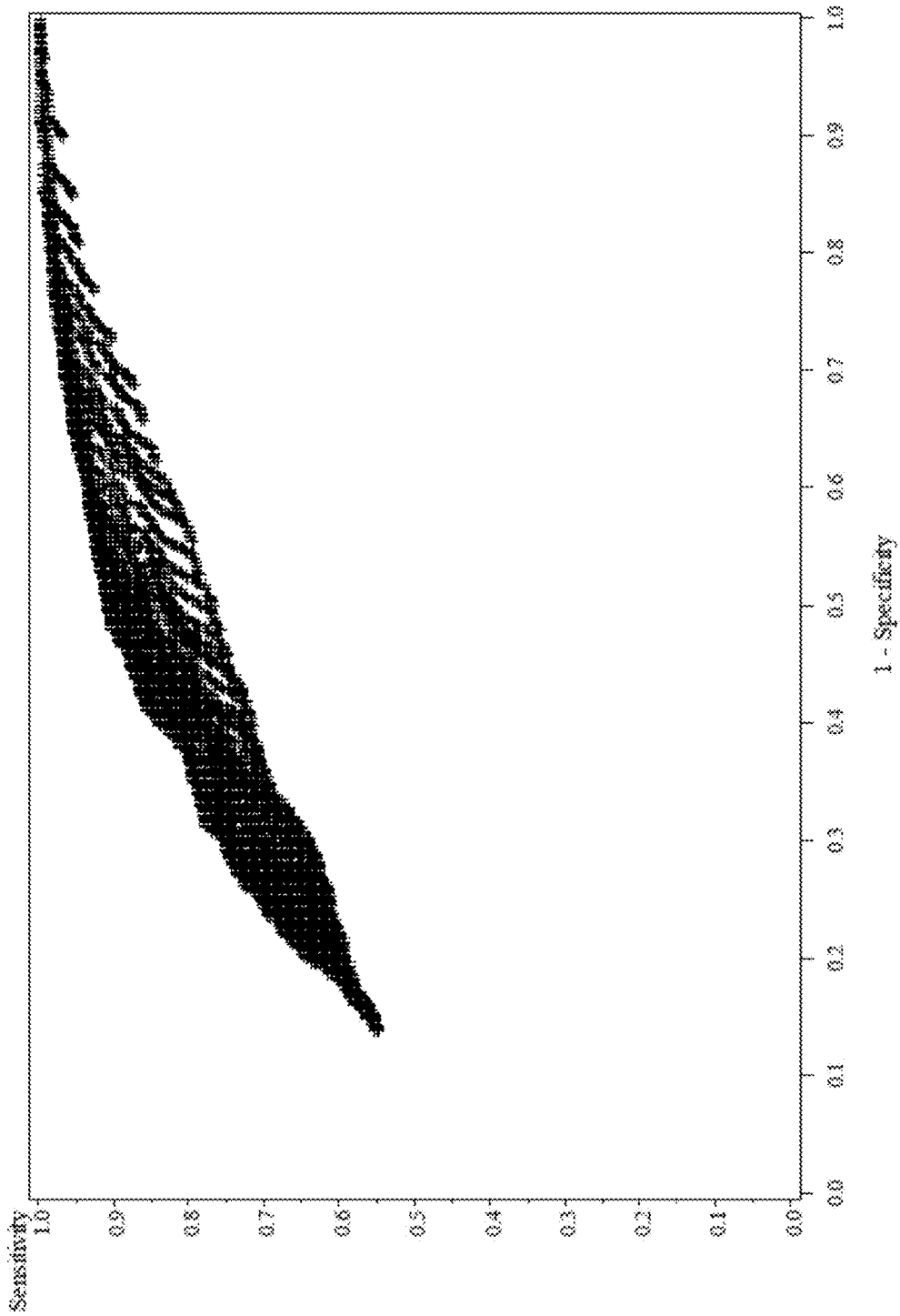
FIG. 6 is a representative graph comparing assay sensitivity and specificity for various GFAP and UCH-L1 levels in subjects diagnosed as having a TBI based on CT scan result (CT positive) and healthy control subjects (CT negative).

GFAP and UCH-L1 levels in subjects diagnosed as having a TBI based on CT scan result. FIG. 6 is a representative graph comparing assay sensitivity and specificity for various GFAP and UCH-L1 levels in subjects diagnosed as having a TBI based on CT scan result (CT positive) and healthy control subjects (CT negative). Each data point (depicted using a "+" sign) represents the sensitivity and specificity associated with a level of GFAP and a level of UCH-L1 from a subject diagnosed as having a TBI based on CT scan, or a from a healthy subject (CT negative). As shown in FIG. 6, combinations of reference levels for both GFAP and UCH-L1 can be correlated with one or more clinical outcomes, such as CT scan result, to determine whether a subject has sustained a TBI.

Table 8 below is a summary of data correlating GFAP and UCH-L1 reference levels with assay sensitivity and specificity ranges at various time points over 48 hours post-injury.

TABLE 8

Biomarker Cut-offs (Reference Levels) for GFAP/UCH-L1
Combination Based on CT Result, GCS Score, and MRI

| Suspected TBI vs Healthy | | Sensitivity Range | Specificity Range (%) | GFAP Range (pg/mL) | UCH-L1 Range (pg/mL) | NPV Range (pg/mL) | PPV Range (pg/mL) |
|---|---|---|---|---|---|---|---|
| CT | All | 90.09-96.45 | 30.03-52.04 | 40-480 | 110-2000 | 84.13-93.65 | 43.29-52.61 |
| | 0-4 hrs | Less than 70% | 90.38-97.12 | 395-1000 | 710-2000 | 96.15-97.96 | 23.08-42.86 |
| | 4-8 hrs | 91.53-98.31 | 30-62.35 | 20-1000 | 130-2000 | 94.05-98.73 | 32.39-45.83 |
| | 8-12 hrs | 91.30-98.55 | 30.40-52 | 35-670 | 90-2000 | 86.36-97.44 | 42.00-51.22 |
| | 12-16 hrs | 90.52-99.14 | 30.49-61.59 | 20-1000 | 90-2000 | 84.72-98.04 | 48.65-62.50 |
| | 16-20 hrs | 90.65-99.07 | 30.25-53.09 | 35-1000 | 80-2000 | 87.18-98.00 | 47.91-56.07 |
| | 20-24 hrs | 90.32-96.77 | 30.46-55.84 | 30-1000 | 70-2000 | 82.14-92.42 | 51.25-62.01 |
| | 24-48 hrs | 80.00-100 | 48.57-82.86 | 30-1000 | 70-2000 | 87.50-100 | 51.35-72.73 |
| GCS | All | 90.05-97.51 | 30.01-65.65 | 70-1000 | 110-2000 | 96.11-98.68 | 17.77-29.77 |
| | 0-4 hrs | Less than 70% | 90.65-97.20 | 605-1000 | 740-2000 | 98.98-99.05 | 16.67-40.00 |
| | 4-8 hrs | 90.00-100.00 | 42.58-85.65 | 280-1000 | 210-2000 | 98.88-100 | 13.67-37.50 |
| | 8-12 hrs | 90.00-96.67 | 30.49-79.27 | 80-1000 | 100-2000 | 96.70-98.82 | 20.28-44.26 |
| | 12-16 hrs | 90.48-97.62 | 30.41-64.52 | 75-1000 | 100-2000 | 94.87-98.73 | 20.53-33.04 |
| | 16-20 hrs | 92.11-97.37 | 30.30-66.23 | 60-1000 | 100-2000 | 97.87-99.19 | 18.69-30.97 |
| | 20-24 hrs | 90.91-98.18 | 30.30-61.28 | 65-1000 | 90-2000 | 95.74-98.91 | 19.77-30.30 |
| | 24-48 hrs | 100 | 61.7-65.96 | 540-1000 | 140-180 | 100 | 30.77-33.33 |
| GOSE | All | 82.61-95.65 | 30-93.33 | 80-2000 | 130-2000 | 96.92-99.05 | 12.50-57.58 |
| MRI | All | 80.60-97.01 | 30.19-84.91 | 15-1000 | 50-2000 | 77.59-94.44 | 63.73-87.69 |

For several time points, assay sensitivity and specificity improved using a combination of reference levels for GFAP and UCH-L1, as compared to assay sensitivity and specificity based on a GFAP reference level alone as shown below in Table 9.

TABLE 9

Biomarker Cut-offs (Reference Levels) for GFAP/UCH-L1 Combination
Compared to GFAP Alone (based on CT scan result)

| | Combined Biomarker Cut-offs | | | | |
|---|---|---|---|---|---|
| | GFAP (pg/mL) | UCH-L1 (pg/mL) | Sensitivity (%) | Specificity (%) | GFAP Alone |
| | | | | | Specificity (% difference) |
| 4-8 hours | 50 | 2000 | 97.5 | 51 | 42 (−9) |
| | 110 | 2000 | 95 | 62 | 50 (−12) |
| | 140 | 2000 | 91.5 | 66 | 61 (−5) |
| | | | | | Sensitivity (% difference) |
| | 500 | 1450 | 76 | 80 | 75 (−1) |
| | 840 | 2000 | 54 | 90 | 51 (−3) |
| | | | | | Specificity (% difference) |
| 8-12 hours | 115 | 110 | 97.5 | 32 | 21 (−11) |
| | 95 | 2000 | 95 | 45 | 37 (−8) |
| | 240 | 300 | 91.5 | 52 | 40 (−12) |
| | | | | | Sensitivity (% difference) |
| | 800 | 900 | 61 | 80 | 57 (−4) |
| | | | | | Specificity (% difference) |
| 12-16 hours | 190 | 90 | 99 | 36 | 5 (−31) |
| | 150 | 190 | 95 | 50 | 34 (−16) |
| | 285 | 190 | 91.5 | 60 | 50 (−10) |
| | 555 | 810 | 72 | 80 | 70 (−2) |
| | 880 | 810 | 66 | 85 | 62 (−4) |
| | 975 | 1580 | 60 | 87 | 58 (−2) |

Figure 7:
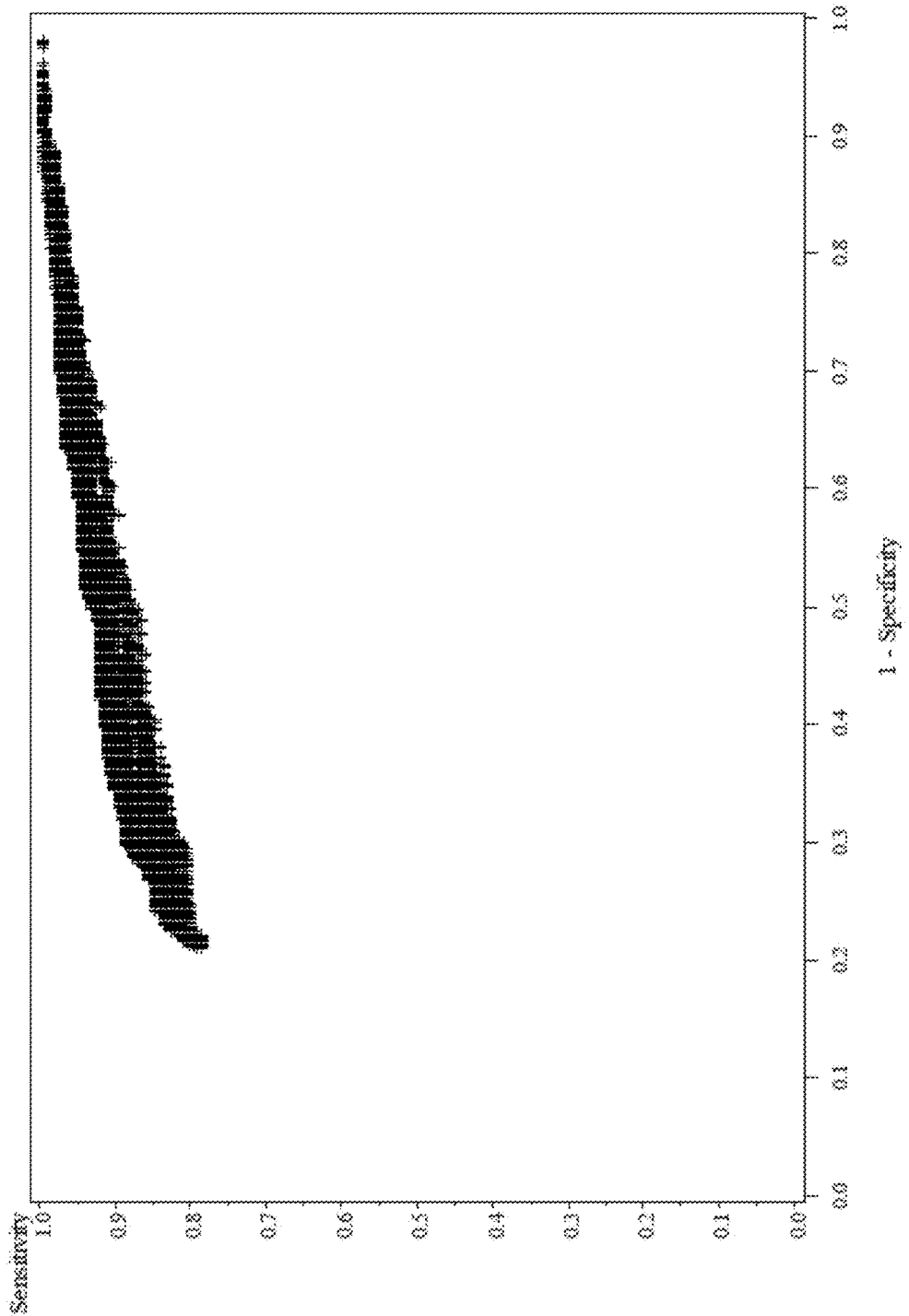
FIG. 7 is a representative graph comparing assay sensitivity and specificity for various GFAP and UCH-L1 levels in subjects assigned a GCS score; subjects assigned a GCS score≤12 were positive (moderate or severe TBI) and subjects assigned a GCS score 12>were negative (mild TBI or healthy controls).

GFAP and UCH-L1 levels in subjects diagnosed as having a TBI based on GCS score. FIG. 7 is a representative graph comparing assay sensitivity and specificity for various GFAP and UCH-L1 levels in subjects assigned a GCS score; subjects assigned a GCS score≤12 were positive (moderate or severe TBI) and subjects assigned a GCS score 12> were negative (mild TBI or healthy controls). Each data point (depicted using a "+" sign) represents the sensitivity and specificity associated with a level of GFAP and a level of UCH-L1 from a subject diagnosed as having a TBI based on an assigned GCS score. As shown in FIG. 7, combinations of reference levels for both GFAP and UCH-L1 can be correlated with one or more clinical outcomes, such as GCS score, to determine whether a subject has sustained a TBI.

For example, in addition to CT scan results discussed above, Table 6 includes a summary of data correlating GFAP and UCH-L1 reference levels with assay sensitivity and specificity ranges at various time points over 48 hours post-injury based on GSC score. For several time points, assay sensitivity and specificity improved using a combination of reference levels for GFAP and UCH-L1, as compared to assay sensitivity and specificity based on a GFAP reference level alone as shown below in Table 10.

TABLE 10

Biomarker Cut-offs (Reference Levels) for GFAP/UCH-L1
Combination Compared to GFAP Alone (based on GCS score)

| | Combined Biomarker Cut-offs | | | | |
|---|---|---|---|---|---|
| | GFAP (pg/mL) | UCH-L1 (pg/mL) | Sensitivity (%) | Specificity (%) | GFAP Alone |
| | | | | | Specificity (% difference) |
| 8-12 hours | 240 | 860 | 97 | 51 | 40 (−11) |
| | 265 | 860 | 93 | 53 | 44 (−9) |
| | 890 | 920 | 90 | 79 | 45 (−34) |
| 12-16 hours | 105 | 840 | 97.5 | 36 | 30 (−6) |
| | 370 | 110 | 95 | 33 | 31 (−2) |
| | 505 | 1580 | 90 | 66 | 63 (−3) |
| | | | | | Sensitivity (% difference) |
| | 695 | 1570 | 88 | 70 | 84 (−4) |
| | 150 | 2000 | 79 | 75 | 77 (−2) |

Figure 8:
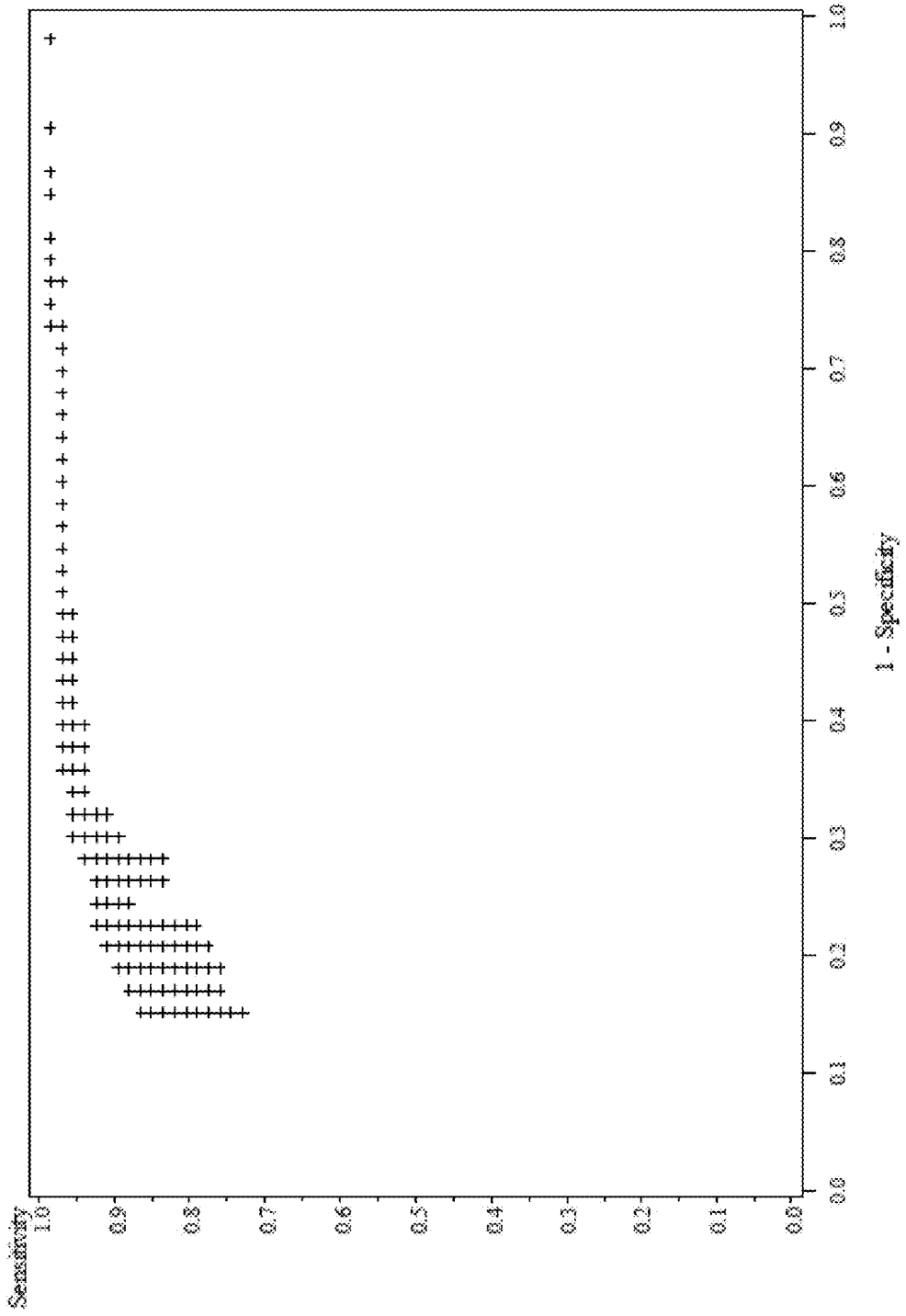
FIG. 8 is a representative graph comparing assay sensitivity and specificity for various GFAP and UCH-L1 levels in subjects diagnosed as having a TBI based on MRI result (positive MRI) and healthy control subjects (negative MRI).

GFAP and UCH-L1 levels in subjects diagnosed as having a TBI based on MRI scan result. FIG. 8 is a representative graph comparing assay sensitivity and specificity for various GFAP and UCH-L1 levels in subjects diagnosed as having a TBI based on MRI result (positive MRI) and healthy control subjects (negative MRI). Each data point (depicted using a "+" sign) represents the sensitivity and specificity associated with a level of GFAP and a level of UCH-L1 from a subject diagnosed as having a TBI based on an MRI scan. As shown in FIG. 8, combinations of reference levels for both GFAP and UCH-L1 can be correlated with one or more clinical outcomes, such as MRI scan result, to determine whether a subject has sustained a TBI.

Figure 9:
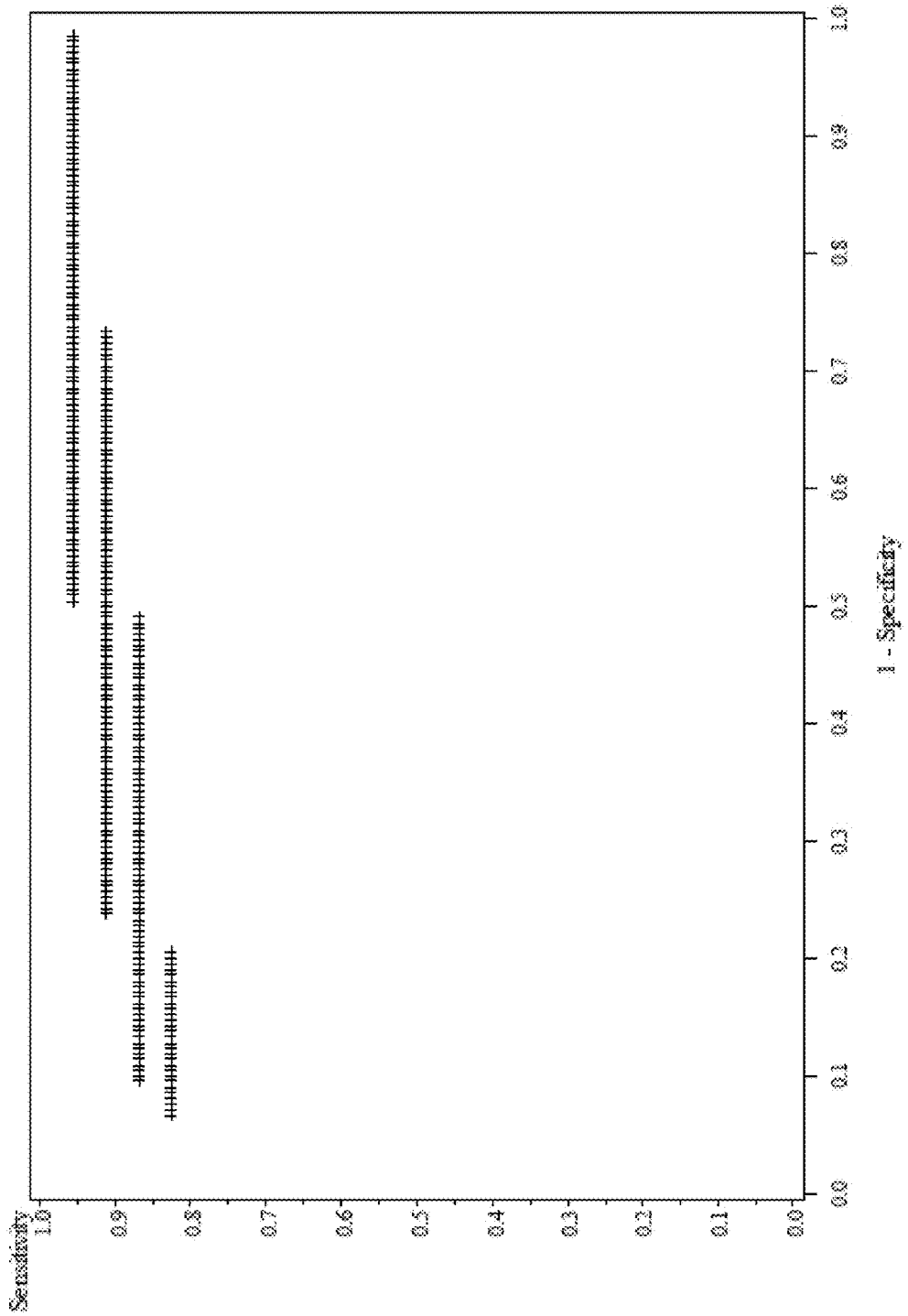
FIG. 9 is a representative graph comparing assay sensitivity and specificity for various GFAP and UCH-L1 levels in subjects diagnosed as having a TBI based on GOSE score (1=TBI/death) and healthy control subjects (8=healthy/recovered).

GFAP and UCH-L1 levels in subjects diagnosed as having a TBI based on GOSE score. FIG. 9 is a representative graph comparing assay sensitivity and specificity for various GFAP and UCH-L1 levels in subjects diagnosed as having a TBI based on GOSE score (1=TBI/death) and healthy control subjects (8=healthy/recovered). Each data point (depicted using a "+" sign) represents the sensitivity and specificity associated with a level of GFAP and a level of UCH-L1 from a subject diagnosed as having a TBI based on a GOSE score of 8. As shown in FIG. 9, combinations of reference levels for both GFAP and UCH-L1 can be correlated with one or more clinical outcomes, such as GOSE scores, to predict recovery in a subject that has sustained a TBI.

GFAP and UCH-L1 levels in subjects presented as having a TBI. Table 11 below shows that at various time points (namely, 4-8 hours, 8-12 hours and 12-16 hours), assay sensitivity and specificity improved using a combination of reference levels for GFAP and UCH-L1, as compared to assay sensitivity and specificity based on a GFAP reference level alone.

TABLE 11

Biomarker Cut-offs (Reference Levels) for GFAP/UCH-L1 Combination Compared to GFAP Alone (suspected TBI)

| | Combined Biomarker Cut-offs | | | | |
|---|---|---|---|---|---|
| | GFAP (pg/mL) | UCH-L1 (pg/mL) | Sensitivity (%) | Specificity (%) | GFAP Alone |
| | | | | | Specificity (% difference) |
| 4-8 hours | 15 | 70 | 97 | 59 | 35 (−24) |
| | 30 | 70 | 95 | 76 | 47 (−29) |
| | 40 | 100 | 90 | 94 | 64 (−30) |

TABLE 11-continued

Biomarker Cut-offs (Reference Levels) for GFAP/UCH-L1 Combination Compared to GFAP Alone (suspected TBI)

| | Combined Biomarker Cut-offs | | | | |
|---|---|---|---|---|---|
| | GFAP (pg/mL) | UCH-L1 (pg/mL) | Sensitivity (%) | Specificity (%) | GFAP Alone |
| | | | | | Sensitivity (% difference) |
| | 30 | 110 | 98 | 100 | 76 (−22) |
| | | | | | Specificity (% difference) |
| 8-12 hours | 15 | 90 | 97 | 71 | 47 (−24) |
| | 15 | 150 | 95 | 82 | 53 (−29) |
| | | | | | Sensitivity (% difference) |
| | 30 | 110 | 92 | 100 | 89 (−3) |
| | | | | | Specificity (% difference) |
| 12-16 hours | 10 | 60 | 97.5 | 35 | 18 (−17) |
| | 20 | 60 | 95 | 65 | 35 (−30) |
| | | | | | Sensitivity (% difference) |
| | 30 | 110 | 90 | 100 | 86 (−4) |

GFAP and UCH-L1 levels in subjects diagnosed as having a TBI vs. ortho controls. In addition to assessing correlations between GFAP and UCH-L1 levels individually with various clinical indicators of TBI using healthy controls, data from the present disclosure also addresses the predictive diagnostic value of a combination of GFAP and UCH-L1 reference levels in determining whether a subject that has sustained an orthopedic injury has also sustained a TBI. Analyses were based on the use of simultaneous reference values, or cut-offs, for both GFAP and UCH-L1.

Table 12 below is a summary of data correlating GFAP and UCH-L1 reference levels with assay sensitivity and specificity ranges at various time points over 48 hours post-injury.

TABLE 12

Biomarker Cut-offs (Reference Levels) for GFAP/UCH-L1 Combination Based on CT Result, GCS Score, and MRI (Ortho Controls)

| Suspected TBI vs Ortho | | Sensitivity Range | Specificity Range | GFAP Range | UCH-L1 Range | NPV Range | PPV Range |
|---|---|---|---|---|---|---|---|
| CT | All | 90.09-96.64 | 30-53.01 | 40-480 | 110-2000 | 84.04-93.98 | 42.54-52.55 |
| | 0-4 hrs | Less than 70% | 90.40-97.60 | 370-1000 | 700-2000 | 96.8-98.32 | 25.00-42.86 |
| | 4-8 hrs | 91.53-98.31 | 30.37-65.97 | 20-1000 | 130-2000 | 95.10-98.98 | 30.00-45.45 |
| | 8-12 hrs | 91.30-98.55 | 30.14-56.85 | 25-350 | 120-2000 | 89.09-97.92 | 39.29-50.00 |
| | 12-16 hrs | 90.52-99.14 | 30.07-58.74 | 20-1000 | 70-2000 | 85.90-97.87 | 52.61-64.02 |
| | 16-20 hrs | 90.65-99.07 | 30.05-56.83 | 25-1000 | 100-2000 | 87.14-98.28 | 43.61-55.11 |
| | 20-24 hrs | 90.32-96.13 | 30.28-59.63 | 25-305 | 100-2000 | 82.14-93.33 | 48.29-61.74 |
| | 24-48 hrs | 70.00-100 | 32.14-91.07 | 25-1000 | 110-2000 | 89.47-100 | 32.73-75.00 |
| GCS | All | 90.05-97.51 | 30.06-66.22 | 65-1000 | 120-2000 | 96.17-98.7 | 17.54-29.77 |
| | 0-4 hrs | Less than 70% | 90.63-97.66 | 395-1000 | 710-2000 | 99.15-99.21 | 14.29-40.00 |
| | 4-8 hrs | 90.00-100.00 | 43.91-86.96 | 200-1000 | 210-2000 | 99.00-100 | 12.84-37.50 |
| | 8-12 hrs | 83.33-96.67 | 30.27-81.62 | 40-1000 | 110-2000 | 96.79-99.06 | 18.35-43.33 |
| | 12-16 hrs | 90.48-97.62 | 30.25-67.65 | 75-1000 | 110-2000 | 95.12-98.99 | 19.02-33.04 |
| | 16-20 hrs | 81.58-97.37 | 30.16-80.16 | 45-1000 | 120-2000 | 96.65-99.31 | 17.37-38.27 |
| | 20-24 hrs | 80.00-98.18 | 30.19-81.13 | 45-1000 | 100-2000 | 95.05-98.99 | 18.38-42.31 |
| | 24-48 hrs | 100 | 60.29 | 320-1000 | 180-220 | 100 | 22.86 |

TABLE 12-continued

Biomarker Cut-offs (Reference Levels) for GFAP/UCH-L1 Combination
Based on CT Result, GCS Score, and MRI (Ortho Controls)

| Suspected TBI vs Ortho | | Sensitivity Range | Specificity Range | GFAP Range | UCH-L1 Range | NPV Range | PPV Range |
|---|---|---|---|---|---|---|---|
| GOSE | All | 82.61-95.65 | 30-93.33 | 80-2000 | 130-2000 | 96.92-99.05 | 12.50-57.58 |
| MRI | All | 80.60-97.01 | 31.08-89.19 | 15-1000 | 80-2000 | 82.43-96.36 | 55.26-87.69 |

Figure 10:
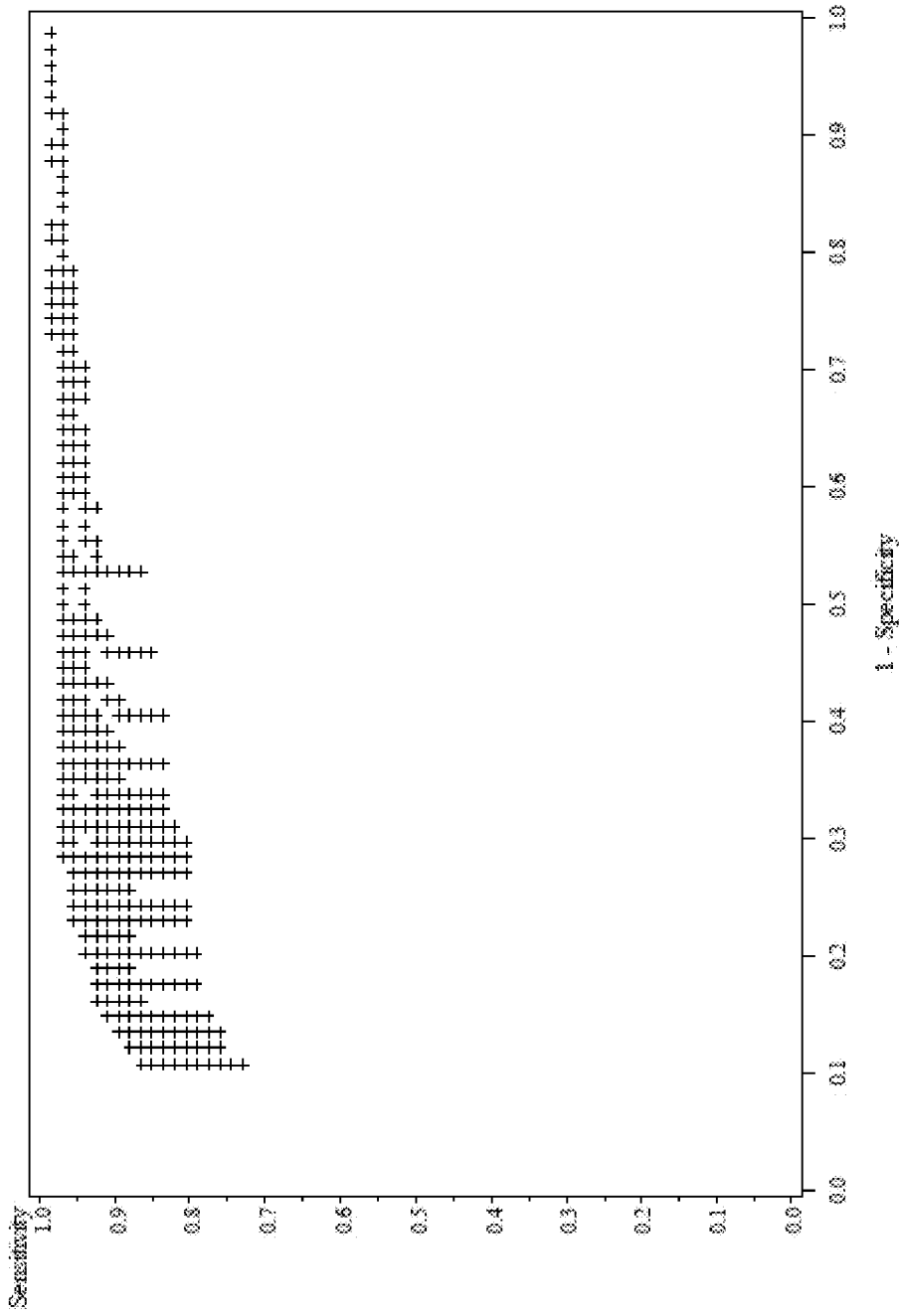
FIG. 10 is a representative graph comparing assay sensitivity and specificity for various GFAP and UCH-L1 levels in subjects diagnosed as having a TBI based on MRI result (positive MRI) and ortho control subjects (negative MRI).

Additionally, Table 12 includes a summary of data correlating GFAP and UCH-L1 reference levels with assay sensitivity and specificity ranges at various time points over 48 hours post-injury based on GCS score. FIG. 10 is a representative graph comparing assay sensitivity and specificity for various GFAP and UCH-L1 levels in subjects diagnosed as having a TBI based on MRI result (positive MRI) and ortho control subjects (negative MRI). Each data point (depicted using a "+" sign) represents the sensitivity and specificity associated with a level of GFAP and a level of UCH-L1 from a subject diagnosed as having a TBI based on an MRI scan. As shown in FIG. 10, combinations of reference levels for both GFAP and UCH-L1 can be correlated with one or more clinical outcomes, such as MRI scan result, to determine whether a subject has sustained a TBI.

Figure 11:
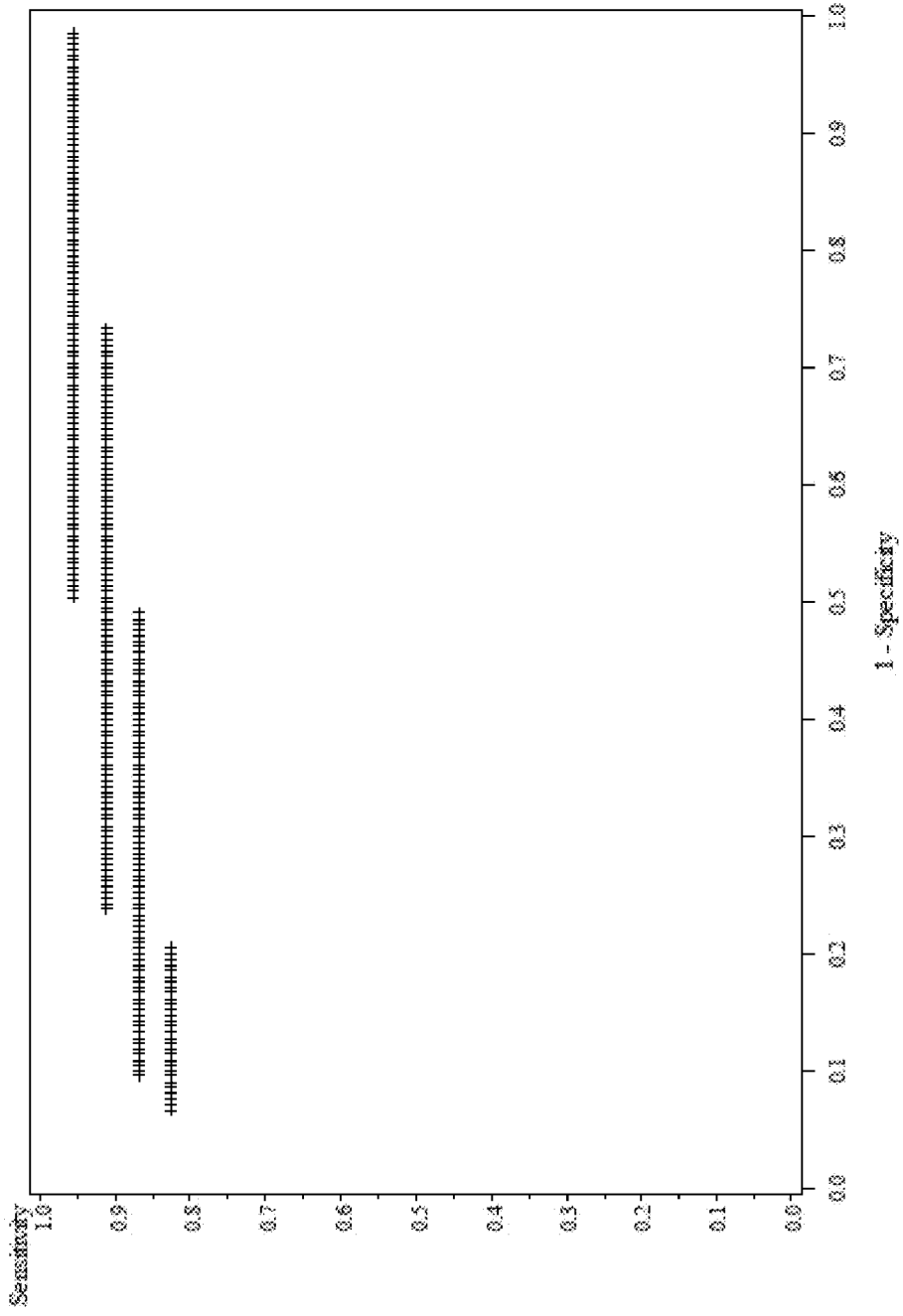
FIG. 11 is a representative graph comparing assay sensitivity and specificity for various GFAP and UCH-L1 levels in subjects diagnosed as having a TBI based on GOSE score (1=TBI/death) and healthy ortho subjects (8=healthy/recovered).

FIG. 11 is a representative graph comparing assay sensitivity and specificity for various GFAP and UCH-L1 levels in subjects diagnosed as having a TBI based on GOSE score (1=TBI/death) and ortho control subjects (8=healthy/recovered). Each data point (depicted using a "+" sign) represents the sensitivity and specificity associated with a level of GFAP and a level of UCH-L1 from a subject diagnosed as having a TBI based on a GOSE score of 8. As shown in FIG. 11, combinations of reference levels for both GFAP and UCH-L1 can be correlated with one or more clinical outcomes, such as GOSE scores, to predict recovery in a subject that has sustained a TBI.

It is understood that the foregoing detailed description and accompanying examples are merely illustrative and are not to be taken as limitations upon the scope, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use, may be made without departing from the spirit and scope thereof.

For reasons of completeness, various aspects are set out in the following numbered clauses:

Clause 1. A method of aiding in the diagnosis of or determining whether a human subject that has sustained or may have sustained an injury to the head has moderate to severe traumatic brain injury (TBI), the method comprising:
performing an assay on a sample obtained from the subject within about 48 hours after the actual or suspected injury to measure or detect a combination of a level of glial fibrillary acidic protein (GFAP) and a level of ubiquitin carboxy-terminal hydrolase L1 (UCH-L1) in the sample; and
(a) determining that the subject has not sustained a moderate, severe, or a moderate to severe TBI when the level of GFAP in the sample is less than a reference level of GFAP of about 105 pg/mL, and the level of UCH-L1 in the sample is less than a reference level of UCH-L1 of about 110 pg/mL; or
(b) determining that the subject has not sustained a moderate, severe, or a moderate to severe TBI when the level of GFAP in the sample is equal to a reference level of GFAP of from about 105 pg/mL to about 890 pg/mL and the level of UCH-L1 in the sample is equal to a reference level of UCH-L1 of from about 110 pg/mL to about 2000 pg/mL; or
(c) determining that the subject more likely than not has sustained a moderate, severe, or a moderate to severe TBI when the level of GFAP in the sample is greater than a reference level of GFAP of about 890 pg/mL, and the level of UCH-L1 in the sample is greater than a reference level of about 2000 pg/mL.

Clause 2. The method of clause 1, wherein the subject has received a Glasgow Coma Scale (GCS) score before or after the assay is performed, and wherein the subject is suspected as having moderate to severe TBI based on the GCS score.

Clause 3. The method of clause 2, wherein the reference level of GFAP and the reference level of UCH-L1 correlate with subjects having moderate to severe TBI based on a GCS score less than or equal to 12.

Clause 4. The method of any of clauses 1-3, wherein the reference level of GFAP and the reference level of UCH-L1 are determined by an assay having a sensitivity equal to or greater than about 79% and a specificity equal to or greater than about 33%.

Clause 5. The method of any of clauses 1-4, wherein the sample is obtained from the subject within about 8 hours to about 16 hours after the actual or suspected injury.

Clause 6. The method of any of clauses 1-5, wherein the assay has at least a 2% higher sensitivity and at least a 3% higher specificity compared to an assay measuring or detecting GFAP or UCH-L1 individually.

Clause 7. The method of any of clauses 1-6, wherein the sample is obtained from the subject within about 8 hours to about 12 hours after the actual or suspected injury; wherein the reference level of GFAP is about 240 pg/mL and the reference level of UCH-L1 is about 860 pg/mL; and wherein the assay has a sensitivity equal to or greater than 97% and a specificity equal to or greater than 51%.

Clause 8. The method of any of clauses 1-6, wherein the sample is obtained from the subject within about 12 hours to about 16 hours after the actual or suspected injury; wherein the reference level of GFAP is about 105 pg/mL and the reference level of UCH-L1 is about 840 pg/mL; and wherein the assay has a sensitivity equal to or greater than 97.5% and a specificity equal to or greater than 36%.

Clause 9. The method of any of clauses 1-6, wherein the sample is obtained from the subject within about 8 hours to about 12 hours after the actual or suspected injury; wherein the reference level of GFAP is about 890 pg/mL and the reference level of UCH-L1 is about 920 pg/mL; and wherein the assay has a sensitivity equal to or greater than 90% and a specificity equal to or greater than 79%.

Clause 10. The method of any of clauses 1-6, wherein the sample is obtained from the subject within about 12 hours to about 16 hours after the actual or suspected injury; wherein the reference level of GFAP is about 505 pg/mL and the reference level of UCH-L1 is about 1580 pg/mL; and wherein the assay has a sensitivity equal to or greater than 90% and a specificity equal to or greater than 66%.

Clause 11. A method of aiding in the determination of or determining whether to perform a head computerized tomography (CT) scan on a human subject that has sustained or may have sustained an injury to the head, the method comprising:

performing an assay on a sample obtained from the subject within about 48 hours after the actual or suspected injury to measure or detect a combination of a level of glial fibrillary acidic protein (GFAP) and a level of ubiquitin carboxy-terminal hydrolase L1 (UCH-L1) in the sample; and (a) determining that the subject does not need a CT scan when the level of GFAP in the sample is less than a reference level of GFAP of about 50 pg/mL, and the level of UCH-L1 in the sample is less than a reference level of UCH-L1 of about 90 pg/mL; or (b) determining that the subject does not need a CT scan when the level of GFAP in the sample is equal to a reference level of GFAP of from about 50 pg/mL to about 975 pg/mL, and the level of UCH-L1 in the sample is equal to a reference level of UCH-L1 of from about 90 pg/mL to about 2000 pg/mL; or (c) determining that the subject more likely than not does need a CT scan when the level of GFAP in the sample is greater than a reference level of GFAP of about 975 pg/mL, and the level of UCH-L1 in the sample is greater than a reference level of UCH-L1 of about 2000 pg/mL.

Clause 12. The method of clause 11, wherein the subject has received a CT scan before or after the assay is performed, and wherein the subject is suspected as having a TBI based on the CT scan result.

Clause 13. The method of clause 12, wherein the reference level of GFAP and the reference level of UCH-L1 correlate with a negative CT scan result.

Clause 14. The method of any of clauses 11-13, wherein the reference level of GFAP and the reference level of UCH-L1 are determined by an assay having a sensitivity equal to or greater than about 54% and a specificity equal to or greater than about 32%.

Clause 15. The method of any of clauses 11-14, wherein the sample is obtained from the subject within about 4 hours to about 16 hours after the actual or suspected injury.

Clause 16. The method of any of clauses 11-15, wherein the assay has at least a 2% higher sensitivity and at least a 4% higher specificity compared to an assay measuring or detecting GFAP or UCH-L1 individually.

Clause 17. The method of any of clauses 11-16, wherein the sample is obtained from the subject within about 4 hours to about 8 hours after the actual or suspected injury; wherein the reference level of GFAP is about 110 pg/mL and the reference level of UCH-L1 is about 2000 pg/mL; and wherein the assay has a sensitivity equal to or greater than 95% and a specificity equal to or greater than 62%.

Clause 18. The method of any of clauses 11-16, wherein the sample is obtained from the subject within about 8 hours to about 12 hours after the actual or suspected injury; wherein the reference level of GFAP is about 240 pg/mL and the reference level of UCH-L1 is about 300 pg/mL; and wherein the assay has a sensitivity equal to or greater than 91.5% and a specificity equal to or greater than 52%.

Clause 19. The method of any of clauses 11-16, wherein the sample is obtained from the subject within about 12 hours to about 16 hours after the actual or suspected injury; wherein the reference level of GFAP is about 190 pg/mL and the reference level of UCH-L1 is about 90 pg/mL; and wherein the assay has a sensitivity equal to or greater than 99% and a specificity equal to or greater than 36%.

Clause 20. A method of aiding in the determination of or determining whether a human subject that has sustained an injury to the head has sustained a traumatic brain injury (TBI), the method comprising:

performing an assay on a sample obtained from the subject within about 48 hours after an injury to measure or detect a combination of a level of glial fibrillary acidic protein (GFAP) and a level of ubiquitin carboxy-terminal hydrolase L1 (UCH-L1) in the sample; and (a) determining that the subject has not sustained a TBI when the level of GFAP in the sample is less than a reference level of GFAP of about 15 pg/mL, and the level of UCH-L1 in the sample is less than a reference level of UCH-L1 of about 70 pg/mL; or (b) determining that the subject more likely than not has sustained a TBI when the level of GFAP in the sample is equal to a reference level of GFAP of from about 15 pg/mL to about 40 pg/mL, and the level of UCH-L1 in the sample is equal to a reference level of UCH-L1 of from about 70 pg/mL to about 150 pg/mL; or (c) determining that the subject more likely than not has sustained a TBI when the level of GFAP in the sample is greater than a reference level of GFAP of about 40 pg/mL, and the level of UCH-L1 in the sample is greater than a reference level of UCH-L1 of about 150 pg/mL.

Clause 21. The method of clause 20, wherein the reference level of GFAP and the reference level of UCH-L1 are determined by an assay having a sensitivity equal to or greater than about 90% and a specificity equal to or greater than about 35%.

Clause 22. The method of clauses 20 or 21, wherein the sample is obtained from the subject within about 4 hours to about 16 hours after the injury.

Clause 23. The method of any of clauses 20-21, wherein the assay has at least a 3% higher sensitivity and at least a 17% higher specificity compared to an assay measuring or detecting GFAP or UCH-L1 individually.

Clause 24. The method of any of clauses 20-23, wherein the sample is obtained from the subject within about 8 hours to about 12 hours after the injury; wherein the reference level of GFAP is about 30 pg/mL and the reference level of UCH-L1 is about 110 pg/mL; and wherein the assay has a sensitivity equal to or greater than 92% and a specificity equal to or greater than 99%.

Clause 25. The method of any of clauses 20-23, wherein the sample is obtained from the subject within about 12 hours to about 16 hours after the injury; wherein the reference level of GFAP is about 30 pg/mL and the reference level of UCH-L1 is about 110 pg/mL; and wherein the assay has a sensitivity equal to or greater than 90% and a specificity equal to or greater than 99%.

Clause 26. The method of any of clauses 20-23, wherein the sample is obtained from the subject within about 4 hours to about 8 hours after the injury; wherein the reference level of GFAP is about 40 pg/mL and the reference level of UCH-L1 is about 100 pg/mL; and wherein the assay has a sensitivity equal to or greater than 90% and a specificity equal to or greater than 94%.

Clause 27. The method of any of clauses 20-23, wherein the sample is obtained from the subject within about 8 hours to about 12 hours after the injury; wherein the reference level of GFAP is about 15 pg/mL and the reference level of UCH-L1 is about 150 pg/mL; and wherein the assay has a sensitivity equal to or greater than 95% and a specificity equal to or greater than 82%.

Clause 28. The method of any of clauses 20-23, wherein the sample is obtained from the subject within about 12 hours to about 16 hours after the injury; wherein the reference level of GFAP is about 20 pg/mL and the reference level of UCH-L1 is about 60 pg/mL; and wherein the assay has a sensitivity equal to or greater than 95% and a specificity equal to or greater than 65%.

Clause 29. A method of aiding in the determination of or determining whether to perform a head magnetic resonance imaging (MRI) procedure on a human subject that has sustained or may have sustained an injury to the head, the method comprising:
  performing an assay on a sample obtained from the subject within about 48 hours after the actual or suspected injury to measure or detect a combination of a level of glial fibrillary acidic protein (GFAP) and a level of ubiquitin carboxy-terminal hydrolase L1 (UCH-L1) in the sample; and
  (a) determining that the subject does not need an MRI procedure when the level of GFAP in the sample is less than a reference level of GFAP of about 15 pg/mL, and the level of UCH-L1 in the sample is less than a reference level of UCH-L1 of about 50 pg/mL; or
  (b) determining that the subject more likely than not does need an MRI procedure when the level of GFAP in the sample is equal to a reference level of GFAP of from about 15 pg/mL to about 1000 pg/mL, and the level of UCH-L1 in the sample is equal to a reference level of UCH-L1 of from about 50 pg/mL to about 2000 pg/mL; or
  (c) determining that the subject more likely than not does need an MRI procedure when the level of GFAP in the sample is greater than a reference level of GFAP of about 1000 pg/mL, and the level of UCH-L1 in the sample is greater than a reference level of UCH-L1 of about 2000 pg/mL.

Clause 30. The method of clause 29, wherein the subject has received an MRI after the assay is performed, and wherein the subject is suspected as having a TBI based on the MRI result.

Clause 31. The method of clause 30, wherein the reference level of GFAP and the reference level of UCH-L1 correlate with a negative MRI result.

Clause 32. The method of any of clauses 29-31, wherein the reference level of GFAP and the reference level of UCH-L1 are determined by an assay having a sensitivity of about 80% to about 98% and a specificity of about 30% to about 85%.

Clause 33. The method of any of clauses 29-32, wherein the subject had received a negative CT scan result before the assay is performed.

Clause 34. A method of aiding in the determination of or determining whether to perform a head magnetic resonance imaging (MRI) procedure on a human subject that has sustained or may have sustained an injury to the head, the method comprising:
  performing an assay on a sample obtained from the subject within about 48 hours after the actual or suspected injury to measure or detect a combination of a level of glial fibrillary acidic protein (GFAP) or a level of ubiquitin carboxy-terminal hydrolase L1 (UCH-L1) in the sample; and
  (a) determining that the subject does not need an MRI procedure when the level of GFAP in the sample is equal to a reference level of GFAP of from about 0 pg/mL to about 68 pg/mL, or the level of UCH-L1 in the sample is equal to a reference level of UCH-L1 of from about 0 pg/mL to about 99 pg/mL; or
  (b) determining that the subject more likely than not does need an MRI procedure when the level of GFAP in the sample is greater than a reference level of GFAP of about 68 pg/mL, and the level of UCH-L1 in the sample is greater than a reference level of UCH-L1 of about 99 pg/mL Clause 35. The method of clause 34, wherein the subject has received an MRI after the assay is performed, and wherein the subject is suspected as having a TBI based on the MRI result.

Clause 36. The method of clause 34, wherein the reference level of GFAP or the reference level of UCH-L1 correlate with a negative MRI result.

Clause 37. The method of any of clauses 34-36, wherein the reference level of GFAP is determined by an assay having a sensitivity of about 90% to about 95% and a specificity of about 31% to about 46%.

Clause 38. The method of any of clauses 34-36, wherein the reference level of UCH-L1 is determined by an assay having a sensitivity of about 81% to about 84% and a specificity of about 31% to about 34%.

Clause 39. The method of any of clauses 34-36, wherein the subject had received a negative CT scan result before the assay is performed.

Clause 40. A method for aiding in predicting or predicting the outcome of a human subject that has sustained or may have sustained a head injury, the method comprising:
  performing an assay on a sample obtained from the subject within about 48 hours after the actual or suspected injury to measure or detect a combination of a level of glial fibrillary acidic protein (GFAP) and a level of ubiquitin carboxy-terminal hydrolase L1 (UCH-L1) in the sample; and
  (a) predicting for the subject a favorable outcome when the level of GFAP in the sample is less than a reference level of GFAP of about 80 pg/mL, and the level of UCH-L1 in the sample is less than a reference level of UCH-L1 of about 130 pg/mL; or
  (b) predicting for the subject more likely than not an unfavorable outcome when the level of GFAP in the sample is equal to a reference level of GFAP of from about 80 pg/mL to about 2000 pg/mL, and the level of UCH-L1 in the sample is equal to a reference level of UCH-L1 of from about 130 pg/mL to about 2000 pg/mL; or
  (c) predicting for the subject more likely than not an unfavorable outcome when the level of GFAP in the sample is greater than a reference level of GFAP of about 2000 pg/mL, and the level of UCH-L1 in the sample is greater than a reference level of UCH-L1 of about 2000 pg/mL.

Clause 41. The method of clause 40, wherein the subject has received an Extended Glasgow Outcome Scale (GOSE) score after the assay is performed, and wherein the subject is suspected as having a poor outcome based on the GOSE score.

Clause 42. The method of clause 41, wherein the reference level of GFAP and the reference level of UCH-L1 correlate with subjects having a poor outcome based on a GOSE score of 1.

Clause 43. The method of any of clauses 40-42, wherein the reference level of GFAP and the reference level of UCH-L1 are determined by an assay having a sensitivity of about 80% to about 97% and a specificity of about 30% to about 95%.

Clause 44. The method of any one of clauses 1-43, wherein measuring the levels of GFAP and UCH-L1 are measured or detected using an immunoassay or clinical chemistry assay.

Clause 45. The method of any one of clauses 1-43, wherein measuring the levels of GFAP and UCH-L1 are measured or detected using a single molecule detection assay.

Clause 46. The method of any one of clauses 1-43, wherein measuring the level of GFAP comprises:
  (a) contacting the sample, either simultaneously or sequentially, in any order with:
    (1) at least one GFAP-capture antibody, which binds to an epitope on GFAP or GFAP fragment to form an at least one GFAP-capture antibody-GFAP antigen complex, and
    (2) at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and
  (b) measuring the amount or concentration of GFAP in the sample based on the signal generated by the detectable label in the at least one GFAP-capture antibody-GFAP antigen—at least one GFAP-detection antibody complex.

Clause 47. The method of any one of clauses 1-43 and 46, wherein measuring the level of UCH-L1 comprises:
  (a) contacting the sample, either simultaneously or sequentially, in any order with:
    (1) at least one UCH-L1-capture antibody, which binds to an epitope on UCH-L1 or UCH-L1 fragment to form an at least one UCH-L1-capture antibody-UCH-L1 antigen complex, and
    (2) at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and
  (b) measuring the amount or concentration of UCH-L1 in the sample based on the signal generated by the detectable label in the at least one UCH-L1-capture antibody-UCH-L1 antigen—at least one UCH-L1-detection antibody complex.

Clause 48. The method of any one of clauses 1-47, wherein the sample is selected from the group consisting of a whole blood sample, a serum sample, a cerebrospinal fluid sample, and a plasma sample.

Clause 49. The method of any one of clauses 1-48, wherein the sample is obtained after the subject sustained an injury to the head caused by physical shaking, blunt impact by an external mechanical or other force that results in a closed or open head trauma, one or more falls, explosions or blasts or other types of blunt force trauma.

Clause 50. The method of any one of clauses 1-48, wherein the sample is obtained after the subject has ingested or been exposed to a chemical, toxin or combination of a chemical and toxin.

Clause 51. The method of any one of clauses 1-48, wherein the sample is obtained from a subject that suffers from an autoimmune disease, a metabolic disorder, a brain tumor, hypoxia, a virus, meningitis, hydrocephalus or combinations thereof.

Clause 52. The method of any one of clauses 1-51, wherein said method can be carried out on any subject without regard to factors selected from the group consisting of the subject's clinical condition, the subject's laboratory values, the subject's classification as suffering from mild, moderate or severe traumatic brain injury, the subject's exhibition of low or high levels of UCH-L1, and the timing of any event wherein said subject may have sustained an injury to the head.

Clause 53. The method of any one of clauses 1-52, further comprising treating the subject with a traumatic brain injury treatment.

Clause 54. The method of any one of clauses 1-53, further comprising monitoring the subject.

Clause 55. The method of any one of clauses 1-52, wherein the sample is obtained after the subject has sustained an orthopedic injury.

Clause 57. The method of any one of clauses 1-52, wherein the sample is a whole blood sample.

Clause 58. The method of any one of clauses 1-46, wherein the sample is a serum sample.

Clause 59. The method of any one of clauses 1-46, wherein the sample is a plasma sample.

Clause 60. The method of any one of clauses 57-59, wherein the assay is an immunoassay.

Clause 61. The method of any one of clauses 57-59, wherein the assay is a clinical chemistry assay.

Clause 62. The method of any one of clauses 57-59, wherein the assay is a single molecule detection assay.

Clause 63. A method of aiding in the diagnosis of or determining whether a human subject that has sustained or may have sustained an injury to the head has moderate to severe traumatic brain injury (TBI), the method comprising:
  performing an assay on a sample obtained from the subject within about 48 hours after an actual or suspected injury to measure a combination of a level of glial fibrillary acidic protein (GFAP) and a level of ubiquitin carboxy-terminal hydrolase L1 (UCH-L1) in the sample; and determining that the subject has not sustained a moderate, severe, or a moderate to severe TBI when the level of GFAP in the sample is equal to a reference level of GFAP of from about 105 pg/mL to about 890 pg/mL and the level of UCH-L1 in the sample is equal to a reference level of UCH-L1 of from about 110 pg/mL to about 2000 pg/mL.

Clause 64. The method of clause 63, wherein the subject has received a Glasgow Coma Scale (GCS) score before or after the assay is performed, and wherein the subject is suspected as having a moderate, severe, or a moderate to severe TBI based on the GCS score.

Clause 65. The method of clause 64, wherein the reference level of GFAP and the reference level of UCH-L1 correlate with subjects having moderate to severe TBI based on a GCS score of 3-12.

Clause 66. The method of any of clauses 63-65, wherein the sample is obtained from a subject: within about 0 to about 4 hours after the actual or suspected injury, within about 4 hours to about 8 hours of an actual or suspected injury, within about 8 hours to about 12 hours after the actual or suspected injury, within about 12 hours to about 16 hours after the actual or suspected injury, within about 16 hours to about 20 hours after the actual or suspected injury, within about 20 hours to about 24 hours after the actual or suspected injury, within about 24 hours to about 28 hours after the actual or suspected injury, within about 24 hours to about 48 hours after the actual or suspected injury, within about 28 hours to about 32 hours after the actual or suspected injury, within about 32 hours to about 36 hours after the actual or suspected injury, within about 36 hours to about 40 hours after the actual or suspected injury, with about 40 hours to about 44 hours after the actual or suspected injury, or within 44 to about 48 hours after the actual or suspected injury.

Clause 67. The method of any of clauses 63-66, wherein: (a) the reference level of GFAP is about 105 pg/mL and the reference level of UCH-L1 is about 840 pg/mL; (b) the reference level of GFAP is about 150 pg/mL and the reference level of UCH-L1 is about 2000 pg/mL; (c) the reference level of GFAP is about 240 pg/mL and the reference level of UCH-L1 is about 860 pg/mL; (d) the reference level of GFAP is about 265 pg/mL and the reference level of UCH-L1 is about 860 pg/mL; (e) the reference level of GFAP is about 370 pg/mL and the reference level of UCH-L1 is about 110 pg/mL; (f) the reference level of GFAP is about 505 pg/mL and the reference level of UCH-L1 is about 1580 pg/mL; (g) the reference level of GFAP is about 695 pg/mL and the reference level of UCH-L1 is about 1570 pg/mL; or (h) the reference level of GFAP is about 890 pg/mL and the reference level of UCH-L1 is about 920 pg/mL.

Clause 68. The method of any of clauses 63-66, wherein the sample is obtained from the subject within: (a) about 8 hours to about 12 hours after the actual or suspected injury and the level of GFAP is about 240 pg/mL and the level of UCH-L1 is about 860 pg/mL; (b) about 8 hours to about 12 hours after the actual or suspected injury and the level of GFAP is about 265 pg/mL and the level of UCH-L1 is about 860 pg/mL; (c) about 8 hours to about 12 hours after the actual or suspected injury and the level of GFAP is about 890 pg/mL and the level of UCH-L1 is about 920 pg/mL; (d) about 12 hours to about 16 hours after the actual or suspected injury and the level of GFAP is about 105 pg/mL and the level of UCH-L1 is about 840 pg/mL; (e) about 12 hours to about 16 hours after the actual or suspected injury and the level of GFAP is about 370 pg/mL and the level of UCH-L1 is about 110 pg/mL; (f) about 12 hours to about 16 hours after the actual or suspected injury and the level of GFAP is about 370 pg/mL and the level of UCH-L1 is about 110 pg/mL; (g) about 12 hours to about 16 hours after the actual or suspected injury and the level of GFAP is about 505 pg/mL and the level of UCH-L1 is about 1590 pg/mL; (h) about 12 hours to about 16 hours after the actual or suspected injury and the level of GFAP is about 695 pg/mL and the level of UCH-L1 is about 1570 pg/mL; or (i) about 12 hours to about 16 hours after the actual or suspected injury and the level of GFAP is about 150 pg/mL and the level of UCH-L1 is about 2000 pg/mL.

Clause 69. The method of any of clauses 63-68, wherein the reference level of GFAP and the reference level of UCH-L1 are determined by an assay having a sensitivity equal to or greater than about 79% and a specificity equal to or greater than about 33%.

Clause 70. The method of any of clauses 63-69, wherein the sample is obtained from the subject within about 8 hours to about 16 hours after the actual or suspected injury.

Clause 71. The method of any of clauses 63-70, wherein the assay has at least a 2% higher sensitivity and at least a 3% higher specificity compared to an assay measuring or detecting GFAP or UCH-L1 individually.

Clause 72. The method of any of clauses 63-71, wherein the sample is obtained from the subject within:
(a) about 8 hours to about 12 hours after the actual or suspected injury; wherein the reference level of GFAP is about 240 pg/mL and the reference level of UCH-L1 is about 860 pg/mL; and wherein the assay has a sensitivity equal to or greater than 97% and a specificity equal to or greater than 51%;
(b) about 12 hours to about 16 hours after the actual or suspected injury; wherein the reference level of GFAP is about 105 pg/mL and the reference level of UCH-L1 is about 840 pg/mL; and wherein the assay has a sensitivity equal to or greater than 97.5% and a specificity equal to or greater than 36%;
(c) about 8 hours to about 12 hours after the actual or suspected injury; wherein the reference level of GFAP is about 890 pg/mL and the reference level of UCH-L1 is about 920 pg/mL; and wherein the assay has a sensitivity equal to or greater than 90% and a specificity equal to or greater than 79%; or
(d) about 12 hours to about 16 hours after the actual or suspected injury; wherein the reference level of GFAP is about 505 pg/mL and the reference level of UCH-L1 is about 1580 pg/mL; and wherein the assay has a sensitivity equal to or greater than 90% and a specificity equal to or greater than 66%.

Clause 73. A method of aiding in the determination of or determining whether to perform a head computerized tomography (CT) scan on a human subject that has sustained or may have sustained an injury to the head, the method comprising:
performing an assay on a sample obtained from the subject within about 48 hours after an actual or suspected injury to measure a combination of a level of glial fibrillary acidic protein (GFAP) and a level of ubiquitin carboxy-terminal hydrolase L1 (UCH-L1) in the sample; and
determining that the subject does not need a CT scan when the level of GFAP in the sample is equal to a reference level of GFAP of from about 50 pg/mL to about 975 pg/mL, and the level of UCH-L1 in the sample is equal to a reference level of UCH-L1 of from about 90 pg/mL to about 2000 pg/mL.

Clause 74. The method of clause 73, wherein the subject has received a CT scan before or after the assay is performed, and wherein the subject is suspected as having a TBI based on the CT scan result.

Clause 75. The method of clause 74, wherein the reference level of GFAP and the reference level of UCH-L1 correlate with a negative CT scan result.

Clause 76. The method of any of clauses 73-75, wherein the sample is obtained from a subject: within about 0 to about 4 hours after the actual or suspected injury, within about 4 hours to about 8 hours after the actual or suspected injury, within about 8 hours to about 12 hours after the actual or suspected injury, within about 12 hours to about 16 hours after the actual or suspected injury, within about 16 hours to about 20 hours after the actual or suspected injury, within about 20 hours to about 24 hours after the actual or suspected injury, within about 24 hours to about 28 hours after the actual or suspected injury, within about 24 hours to about 48 hours after the actual or suspected injury, within about 28 hours to about 32 hours after the actual or suspected injury, within about 32 hours to about 36 hours after the actual or suspected injury, within about 36 hours to about 40 hours after the actual or suspected injury, with about 40 hours to about 44 hours after the actual or suspected injury, or within 44 to about 48 hours after the actual or suspected injury.

Clause 77. The method of any of clauses 73-76, wherein the (a) reference level of GFAP is about 50 pg/mL and the reference level of UCH-L1 is about 2000 pg/mL; (b) the reference level of GFAP is about 95 pg/mL and the reference level of UCH-L1 is about 2000 pg/mL; (c) the reference level of GFAP is about 110 pg/mL and the reference level of UCH-L1 is about 2000 pg/mL; (d) the reference level of GFAP is about 115 pg/mL and the reference level of UCH-L1 is about 110 pg/mL; (e) the reference level of GFAP is about 140 pg/mL and the reference level of UCH-L1 is about 2000 pg/mL; (f) the reference level of GFAP is about 150 pg/mL and the reference level of UCH-L1 is about 190 pg/mL; (g) the reference level of GFAP is about 190 pg/mL and the reference level of UCH-L1 is about 90 pg/mL; (h) the reference level of GFAP is about 240 pg/mL and the reference level of UCH-L1 is about 300 pg/mL; (i) the reference level of GFAP is about 285 pg/mL and the reference level of UCH-L1 is about 190 pg/mL; (j) the reference level of GFAP is about 500 pg/mL and the reference level of UCH-L1 is about 1450 pg/mL; (k) the reference level of GFAP is about 555 pg/mL and the reference level of UCH-L1 is about 810 pg/mL; (1) the reference level of GFAP is about 800 pg/mL and the reference level of UCH-L1 is about 900 pg/mL; (m) the reference level of GFAP is about 840 pg/mL and the reference level of UCH-L1 is about 2000 pg/mL; (n) the reference level of GFAP is about 880 pg/mL and the reference level of UCH-L1 is about 810 pg/mL; or (0) the reference level of GFAP is about 975 pg/mL and the reference level of UCH-L1 is about 1580 pg/mL.

Clause 78. The method of any of clauses 73-76, wherein the sample is obtained from the subject within: (a) about 4 hours to about 8 hours after the actual or suspected injury and the level of GFAP is about 50 pg/mL and the level of UCH-L1 is about 2000 pg/mL; (b) about 4 hours to about 8 hours after the actual or suspected injury and the level of GFAP is about 110 pg/ml, and the level of UCH-L1 is about 2000 pg/mL; (c) about 4 hours to about 8 hours after the actual or suspected injury and the level of GFAP is about 140 pg/mL and the level of UCH-L1 is about 2000 pg/mL; (d) about 4 hours to about 8 hours after the actual or suspected injury and the level of GFAP is about 500 pg/mL and the level of UCH-L1 is about 1450 pg/mL; (e) about 4 hours to about 8 hours after the actual or suspected injury and the level of GFAP is about 890 pg/mL and the level of UCH-L1 is about 920 pg/mL; (f) about 12 hours to about 16 hours after the actual or suspected injury and the level of GFAP is about 105 pg/mL and the level of UCH-L1 is about 840 pg/mL; (g) about 12 hours to about 16 hours after the actual or suspected injury and the level of GFAP is about 370 pg/mL and the level of UCH-L1 is about 110 pg/mL;
(h) about 12 hours to about 16 hours after the actual or suspected injury and the level of GFAP is about 505 pg/mL and the level of UCH-L1 is about 1580 pg/mL; (i) about 12 hours to about 16 hours after the actual or suspected injury and the level of GFAP is about 695 pg/mL and the level of UCH-L1 is about 1570 pg/mL; or (j) about 12 hours to about 16 hours after the actual or suspected injury and the level of GFAP is about 150 pg/mL and the level of UCH-L1 is about 2000 pg/mL..

Clause 79. The method of any of clauses 73-78, wherein the reference level of GFAP and the reference level of UCH-L1 are determined by an assay having a sensitivity equal to or greater than about 54% and a specificity equal to or greater than about 32%.

Clause 80. The method of any of clauses 73-79, wherein the sample is obtained from the subject within about 4 hours to about 16 hours after the actual or suspected injury.

Clause 81. The method of any of clauses 73-80, wherein the assay has at least a 2% higher sensitivity and at least a 4% higher specificity compared to an assay measuring or detecting GFAP or UCH-L1 individually.

Clause 82. The method of any of clauses 73-81, wherein the sample is obtained from the subject within:
(a) about 4 hours to about 8 hours after the actual or suspected injury; wherein the reference level of GFAP is about 110 pg/mL and the reference level of UCH-L1 is about 2000 pg/mL; and wherein the assay has a sensitivity equal to or greater than 95% and a specificity equal to or greater than 62%;
(b) about 8 hours to about 12 hours after the actual or suspected injury; wherein the reference level of GFAP is about 240 pg/mL and the reference level of UCH-L1 is about 300 pg/mL; and wherein the assay has a sensitivity equal to or greater than 91.5% and a specificity equal to or greater than 52%; or
(c) about 12 hours to about 16 hours after the actual or suspected injury; wherein the reference level of GFAP is about 190 pg/mL and the reference level of UCH-L1 is about 90 pg/mL; and wherein the assay has a sensitivity equal to or greater than 99% and a specificity equal to or greater than 36%.

Clause 83. A method of aiding in the determination of or determining whether a human subject that has sustained an injury to the head has sustained a traumatic brain injury (TBI), the method comprising:
performing an assay on a sample obtained from the subject within about 48 hours after an actual or suspected injury to measure a combination of a level of glial fibrillary acidic protein (GFAP) and a level of ubiquitin carboxy-terminal hydrolase L1 (UCH-L1) in the sample; and
determining that the subject more likely than not has sustained a TBI when the level of GFAP in the sample is equal to a reference level of GFAP of from about 15 pg/mL to about 40 pg/mL, and the level of UCH-L1 in the sample is equal to a reference level of UCH-L1 of from about 70 pg/mL to about 150 pg/mL.

Clause 84. The method of any of clause 83, wherein the sample is obtained from a subject: within about 0 to about 4 hours after the injury, within about 4 hours to about 8 hours after the injury, within about 8 hours to about 12 hours after the injury, within about 12 hours to about 16 hours after the injury, within about 16 hours to about 20 hours after the injury, within about 20 hours to about 24 hours after the injury, within about 24 hours to about 28 hours after injury, within about 24 hours to about 48 hours after the injury, within about 28 hours to about 32 hours after injury, within about 32 hours to about 36 hours after injury, within about 36 hours to about 40 hours after injury, with about 40 hours to about 44 hours after injury, or within 44 to about 48 hours after injury.

Clause 85. The method of clauses 83 or 84, wherein (a) the reference level of GFAP is about 10 pg/mL and the reference level of UCH-L1 is about 60 pg/mL; (b) the reference level of GFAP is about 15 pg/mL and the reference level of UCH-L1 is about 70 pg/mL; (c) the reference level of GFAP is about 15 pg/mL and the reference level of UCH-L1 is about 90 pg/mL; (d) the reference level of GFAP is about 15 pg/mL and the reference level of UCH-L1 is about 150 pg/mL; (e) the reference level of GFAP is about 20 pg/mL and the reference level of UCH-L1 is about 60 pg/mL; (f) the reference level of GFAP is about 30 pg/mL and the reference level of UCH-L1 is about 70 pg/mL; or (g) the reference level of GFAP is about 30 pg/mL and the reference level of UCH-L1 is about 110 pg/mL.

Clause 86. The method of clauses 83 or 84, wherein the sample is obtained from the subject within: (a) about 4 hours to about 8 hours after the actual or suspected injury and the level of GFAP is about 15 pg/mL and the level of UCH-L1 is about 70 pg/mL; (b) about 4 hours to about 8 hours after the actual or suspected injury and the level of GFAP is about 30 pg/mL and the level of UCH-L1 is about 70 pg/mL; (c) about 4 hours to about 8 hours after the actual or suspected injury and the level of GFAP is about 40 pg/mL and the level of UCH-L1 is about 100 pg/mL; (d) about 8 hours to about 12 hours after the actual or suspected injury and the level of GFAP is about 15 pg/mL and the level of UCH-L1 is about 90 pg/mL; (e) about 8 hours to about 12 hours after the actual or suspected injury and the level of GFAP is about 15 pg/mL and the level of UCH-L1 is about 150 pg/mL; (f) about 8 hours to about 12 hours after the actual or suspected injury and the level of GFAP is about 30 pg/mL and the level of UCH-L1 is about 110 pg/mL; (g) about 12 hours to about 16 hours after the actual or suspected injury and the level of GFAP is about 10 pg/mL and the level of UCH-L1 is about 60 pg/mL; (h) about 12 hours to about 16 hours after the actual or suspected injury and the level of GFAP is about 20 pg/mL and the level of UCH-L1 is about 60 pg/mL; or (i) about 12 hours to about 16 hours after the actual or suspected injury and the level of GFAP is about 30 pg/mL, and the level of UCH-L1 is about 110 pg/mL.

Clause 87. The method of clauses 83-86, wherein the reference level of GFAP and the reference level of UCH-L1 are determined by an assay having a sensitivity equal to or greater than about 90% and a specificity equal to or greater than about 35%.

Clause 88. The method of any one of clauses 83-87, wherein the sample is obtained from the subject within about 4 hours to about 16 hours after the injury.

Clause 89. The method of any of clauses 83-88, wherein the assay has at least a 3% higher sensitivity and at least a 17% higher specificity compared to an assay measuring or detecting GFAP or UCH-L1 individually.

Clause 90. The method of any of clauses 83-89, wherein the sample is obtained from the subject within:
(a) about 8 hours to about 12 hours after the injury; wherein the reference level of GFAP is about 30 pg/mL and the reference level of UCH-L1 is about 110 pg/mL; and wherein the assay has a sensitivity equal to or greater than 92% and a specificity equal to or greater than 99%;
(b) about 12 hours to about 16 hours after the injury; wherein the reference level of GFAP is about 30 pg/mL and the reference level of UCH-L1 is about 110 pg/mL; and wherein the assay has a sensitivity equal to or greater than 90% and a specificity equal to or greater than 99%;
(c) about 4 hours to about 8 hours after the injury; wherein the reference level of GFAP is about 40 pg/mL and the reference level of UCH-L1 is about 100 pg/mL; and wherein the assay has a sensitivity equal to or greater than 90% and a specificity equal to or greater than 94%;
(d) about 8 hours to about 12 hours after the injury; wherein the reference level of GFAP is about 15 pg/mL and the reference level of UCH-L1 is about 150 pg/mL; and wherein the assay has a sensitivity equal to or greater than 95% and a specificity equal to or greater than 82%; or
(e) about 12 hours to about 16 hours after the injury; wherein the reference level of GFAP is about 20 pg/mL and the reference level of UCH-L1 is about 60 pg/mL; and wherein the assay has a sensitivity equal to or greater than 95% and a specificity equal to or greater than 65%.

Clause 91. A method of aiding in the determination of or determining whether to perform a head magnetic resonance imaging (MRI) procedure on a human subject that has sustained or may have sustained an injury to the head, the method comprising:
performing an assay on a sample obtained from the subject within about 48 hours after an actual or suspected injury, to measure a combination of a level of glial fibrillary acidic protein (GFAP) and a level of ubiquitin carboxy-terminal hydrolase L1 (UCH-L1) in the sample; and
(a) determining that the subject does not need an MRI procedure when the level of GFAP in the sample is less than a reference level of GFAP of about 15 pg/mL, and the level of UCH-L1 in the sample is less than a reference level of UCH-L1 of about 50 pg/mL; or
(b) determining that the subject more likely than not does need an MRI procedure when the level of GFAP in the sample is equal to a reference level of GFAP of from about 15 pg/mL to about 1000 pg/mL, and the level of UCH-L1 in the sample is equal to a reference level of UCH-L1 of from about 50 pg/mL to about 2000 pg/mL; or
(c) determining that the subject more likely than not does need an MRI procedure when the level of GFAP in the sample is greater than a reference level of GFAP of about 1000 pg/mL, and the level of UCH-L1 in the sample is greater than a reference level of UCH-L1 of about 2000 pg/mL.

Clause 92. The method of clause 91, wherein the subject has received an MRI after the assay is performed, and wherein the subject is suspected as having a TBI based on the MRI result.

Clause 93. The method of clause 91, wherein the reference level of GFAP and the reference level of UCH-L1 correlate with a negative MRI result.

Clause 94. The method of any of clauses 91-93, wherein the sample is obtained from a subject: within about 0 to about 4 hours after the actual or suspected injury, within about 4 hours to about 8 hours after the actual or suspected injury, within about 8 hours to about 12 hours after the actual or suspected injury, within about 12 hours to about 16 hours after the actual or suspected injury, within about 16 hours to about 20 hours after the actual or suspected injury, within about 20 hours to about 24 hours after the actual or suspected injury, within about 24 hours to about 28 hours after the actual or suspected injury, within about 24 hours to about 48 hours after the actual or suspected injury, within about 28 hours to about 32 hours after the actual or suspected injury, within about 32 hours to about 36 hours after the actual or suspected injury, within about 36 hours to about 40 hours after the actual or suspected injury, with about 40 hours to about 44 hours after the actual or suspected injury, or within 44 to about 48 hours after the actual or suspected injury.

Clause 95. The method of any of clauses 91-94, wherein the reference level of GFAP and the reference level of UCH-L1 are determined by an assay having a sensitivity of about 80% to about 98% and a specificity of about 30% to about 85%.

Clause 96. The method of any of clauses 91-95, wherein the subject had received a negative CT scan result before the assay is performed.

Clause 97. A method for aiding in predicting or predicting the outcome of a human subject that has sustained or may have sustained a head injury, the method comprising:
performing an assay on a sample obtained from the subject within about 48 hours after an actual or suspected injury on a sample obtained from the subject to measure or detect a combination of a level of glial fibrillary acidic protein (GFAP) and a level of ubiquitin carboxy-terminal hydrolase L1 (UCH-L1) in the sample; and
predicting for the subject more likely than not an unfavorable outcome when the level of GFAP in the sample is equal to a reference level of GFAP of from about 80 pg/mL to about 2000 pg/mL, and the level of UCH-L1 in the sample is equal to a reference level of UCH-L1 of from about 130 pg/mL to about 2000 pg/mL.

Clause 98. The method of clause 97, wherein the subject has received an Extended Glasgow Outcome Scale (GOSE) score after the assay is performed, and wherein the subject is suspected as having a poor outcome based on the GOSE score.

Clause 99. The method of clause 97, wherein the reference level of GFAP and the reference level of UCH-L1 correlate with subjects having a poor outcome based on a GOSE score of 1.

Clause 100. The method of any of clauses 97-99, wherein the sample is obtained from a subject: within about 0 to about 4 hours after the actual or suspected injury, within about 4 hours to about 8 hours after the actual or suspected injury, within about 8 hours to about 12 hours after the actual or suspected injury, within about 12 hours to about 16 hours after the actual or suspected injury, within about 16 hours to about 20 hours after the actual or suspected injury, within about 20 hours to about 24 hours after the actual or suspected injury, within about 24 hours to about 28 hours after the actual or suspected injury, within about 24 hours to about 48 hours after the actual or suspected injury, within about 28 hours to about 32 hours after the actual or suspected injury, within about 32 hours to about 36 hours after the actual or suspected injury, within about 36 hours to about 40 hours after the actual or suspected injury, with about 40 hours to about 44 hours after the actual or suspected injury, or within 44 to about 48 hours after the actual or suspected injury.

Clause 101. The method of any of clauses 97-100, wherein the reference level of GFAP and the reference level of UCH-L1 are determined by an assay having a sensitivity of about 80% to about 97% and a specificity of about 30% to about 95%.

Clause 102. The method of any one of clauses 63-101, wherein measuring the level of GFAP comprises:
(a) contacting the sample, either simultaneously or sequentially, in any order with:
(1) at least one GFAP-capture antibody, which binds to an epitope on GFAP or GFAP fragment to form an at least one GFAP-capture antibody-GFAP antigen complex, and
(2) at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and
(b) measuring the amount or concentration of GFAP in the sample based on the signal generated by the detectable label in the at least one GFAP-capture antibody-GFAP antigen—at least one GFAP-detection antibody complex.

Clause 103. The method of any one of clauses 63-102, wherein measuring the level of UCH-L1 comprises:
(a) contacting the sample, either simultaneously or sequentially, in any order with:
(1) at least one UCH-L1-capture antibody, which binds to an epitope on UCH-L1 or UCH-L1 fragment to form an at least one UCH-L1-capture antibody-UCH-L1 antigen complex, and
(2) at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and
(b) measuring the amount or concentration of UCH-L1 in the sample based on the signal generated by the detectable label in the at least one UCH-L1-capture antibody-UCH-L1 antigen—at least one UCH-L1-detection antibody complex.

Clause 104. The method of any one of clauses 63-103, wherein the sample is selected from the group consisting of a whole blood sample, a serum sample, a cerebrospinal fluid sample, and a plasma sample.

Clause 105. The method of any one of clauses 63-104, wherein the sample is obtained:
(a) after the subject sustained an injury to the head caused by physical shaking, blunt impact by an external mechanical or other force that results in a closed or open head trauma, one or more falls, explosions or blasts or other types of blunt force trauma;
(b) after the subject has ingested or been exposed to a chemical, toxin or combination of a chemical and toxin; or
(c) from a subject that suffers from an autoimmune disease, a metabolic disorder, a brain tumor, hypoxia, a virus, meningitis, hydrocephalus or combinations thereof.

Clause 106. The method of any one of clauses 63-105, wherein said method can be carried out on any subject without regard to factors selected from the group consisting of the subject's clinical condition, the subject's laboratory values, the subject's classification as suffering from mild, moderate or severe traumatic brain injury, the subject's exhibition of low or high levels of UCH-L1, and the timing of any event wherein said subject may have sustained an injury to the head.

Clause 107. The method of any one of clauses 63-106, further comprising treating the subject with a traumatic brain injury treatment.

Clause 108. The method of any one of clauses 63-107, further comprising monitoring the subject.

Clause 109. The method of any one of clauses 63-107, wherein the sample is obtained after the subject has sustained an orthopedic injury.

Clause 110. The method of any one of clauses 63-109, wherein the sample is: (a) a whole blood sample; (b) a serum sample; or (c) a plasma sample.

Clause 111. The method of any one of clauses 63-110, wherein the assay is: (a) an immunoassay; (b) a clinical chemistry assay; or (c) a single molecule detection assay.

What is claimed is:

1. A method comprising:
   (a) performing at least one assay for ubiquitin carboxy-terminal hydrolase L1 (UCH-L1) and glial fibrillary acidic protein (GFAP) in at least one sample that is whole blood, serum, plasma, or cerebrospinal fluid obtained from a human subject within about 48 hours after the subject has sustained an actual or suspected injury to the head; and
   (b) treating the subject for a mild traumatic brain injury (TBI) when the level of GFAP in the sample is equal to a reference level of GFAP of from about 105 pg/mL to about 890 pg/mL and the level of UCH-L1 in the sample is equal to a reference level of UCH-L1 of from about 110 pg/mL to about 2000 pg/mL; wherein treatment comprises treatment (i) with rest; (ii) by abstaining from physical activities; (iii) by avoiding light; (iv) by wearing protective eyewear when in light; (v) with one or more therapeutic agents selected from the group consisting of a medication for relief of a headache or migraine, and an anti-nausea medication, or combinations thereof; or (vi) with any combination of (i)-(v).

2. The method of claim 1, wherein the assay is an immunoassay or a clinical chemistry assay.

3. The method of claim 1, wherein the assay is performed using single molecule detection, a lateral flow assay, or a point-of-care device.

4. The method of claim 1, wherein the subject received a Glasgow Coma Scale (GCS) score before or after the assay is performed, and wherein the subject is suspected as having a mild TBI based on the GCS score.

5. The method of claim 1, wherein:
   (a) the reference level of GFAP is about 105 pg/mL and the reference level of UCH-Li is about 840 pg/mL;
   (b) the reference level of GFAP is about 150 pg/mL and the reference level of UCH-L1 is about 2000 pg/mL;
   (c) the reference level of GFAP is about 240 pg/mL and the reference level of UCH-L1 is about 860 pg/mL;
   (d) the reference level of GFAP is about 265 pg/mL and the reference level of UCH-L1 is about 860 pg/mL;
   (e) the reference level of GFAP is about 370 pg/mL and the reference level of UCH-L1 is about 110 pg/mL;
   (f) the reference level of GFAP is about 505 pg/mL and the reference level of UCH-L1 is about 1580 pg/mL;
   (g) the reference level of GFAP is about 695 pg/mL and the reference level of UCH-L1 is about 1570 pg/mL;
   (h) the reference level of GFAP is about 890 pg/mL and the reference level of UCH-L1 is about 920 pg/mL; or
   (i) the reference level of GFAP and the reference level of UCH-L1 are determined by an assay having a sensitivity equal to or greater than about 79% and a specificity equal to or greater than about 33%.

6. The method of claim 1, wherein the sample is obtained from the subject within:
   (a) about 8 hours to about 12 hours after the actual or suspected injury; wherein the reference level of GFAP is about 240 pg/mL and the reference level of UCH-L1 is about 860 pg/mL; and
   wherein the assay has a sensitivity equal to or greater than 97% and a specificity equal to or greater than 51%;
   (b) about 12 hours to about 16 hours after the actual or suspected injury; wherein the reference level of GFAP is about 105 pg/mL and the reference level of UCH-L1 is about 840 pg/mL; and wherein the assay has a sensitivity equal to or greater than 97.5% and a specificity equal to or greater than 36%;
   (c) about 8 hours to about 12 hours after the actual or suspected injury; wherein the reference level of GFAP is about 890 pg/mL and the reference level of UCH-L1 is about 920 pg/mL; and wherein the assay has a sensitivity equal to or greater than 90% and a specificity equal to or greater than 79%; or
   (d) about 12 hours to about 16 hours after the actual or suspected injury; wherein the reference level of GFAP is about 505 pg/mL and the reference level of UCH-L1 is about 1580 pg/mL; and wherein the assay has a sensitivity equal to or greater than 90% and a specificity equal to or greater than 66%.

7. The method of claim 1, wherein
   (a) measuring the level of GFAP comprises: (i) contacting the sample, either simultaneously or sequentially, in any order with: (a') at least one GFAP-capture antibody, which binds to an epitope on GFAP to form an at least one GFAP-capture antibody-GFAP antigen complex, and (b') at least one GFAP-detection antibody which includes a detectable label and binds to an epitope on GFAP that is not bound by the GFAP-capture antibody, to form a GFAP antigen—at least one GFAP-detection antibody complex, such that an at least one GFAP-capture antibody-GFAP antigen—at least one GFAP-detection antibody complex is formed; and (ii) measuring the amount or concentration of GFAP in the sample based on the signal generated by the detectable label in the at least one GFAP-capture antibody-GFAP antigen—at least one GFAP-detection antibody complex; or (b) measuring the level of UCH-L1 comprises: (i) contacting the sample, either simultaneously or sequentially, in any order with: (a') at least one UCH-L1-capture antibody, which binds to an epitope on UCH-L1 to form an at least one UCH-L1-capture antibody-UCH-L1 antigen complex, and (b') at least one UCH-L1-detection antibody which includes a detectable label and binds to an epitope on UCH-L1 that is not bound by the at least one UCH-L1-capture antibody, to form a UCH-L1 antigen—at least one UCH-L1-detection antibody complex, such that an at least one UCH-L1-capture antibody-UCH-L1 antigen—at least one UCH-L1-detection antibody complex is formed; and (ii) measuring the amount or concentration of UCH-L1 in the sample based on the signal generated by the detectable label in the at least one UCH-L1-capture antibody-UCH-L1 antigen—at least one UCH-L1-detection antibody complex.

8. The method of claim 1, wherein the sample is obtained:
(a) after the subject sustained an injury to the head caused by physical shaking, blunt impact by an external mechanical or other force that results in a closed or open head trauma, one or more falls, explosions or blasts;
(b) after the subject has ingested or been exposed to a chemical, toxin or combination of a chemical and toxin;
(c) from a subject that suffers from an autoimmune disease, a metabolic disorder, a brain tumor, hypoxia, a virus, meningitis, hydrocephalus or combination thereof; or
(d) after the subject sustained an orthopedic injury.

9. The method of claim 1, wherein said method is carried out on any subject without regard to factors selected from the group consisting of the subject's clinical condition, the subject's laboratory values, the subject's classification as suffering from mild, moderate or severe traumatic brain injury, the subject's exhibition of low or high levels of UCH-L1, and the timing of any event wherein said subject may have sustained an injury to the head.

10. The method of claim 1, further comprising monitoring the subject.

11. A method comprising:
(a) performing at least one assay for ubiquitin carboxy-terminal hydrolase L1 (UCH-L1) and glial fibrillary acidic protein (GFAP) in at least one sample that is whole blood, serum, plasma, or cerebrospinal fluid obtained from a human subject within about 48 hours after the subject has sustained an actual or suspected injury to the head; and
(b) not performing a head computerized tomography (CT) scan; and
(c) treating the subject for a mild traumatic brain injury when the level of GFAP in the sample is equal to a reference level of GFAP of from about 50 pg/mL to about 975 pg/mL, and the level of UCH-L1 in the sample is equal to a reference level of UCH-L1 of from about 90 pg/mL to about 2000 pg/mL; wherein treatment comprises treatment (i) with rest; (ii) by abstaining from physical activities; (iii) by avoiding light; (iv) by wearing protective eyewear when in light; (v) with one or more therapeutic agents selected from the group consisting of a medication for relief of a headache or migraine, and an anti-nausea medication, or combinations thereof; or (vi) with any combination of (i)-(v).

12. The method of claim 11, wherein the assay an immunoassay or a clinical chemistry assay.

13. The method of claim 11, wherein the assay is performed using single molecule detection, a lateral flow assay, or a point-of-care device.

14. The method of claim 11, wherein
(a) the reference level of GFAP is about 95 pg/mL and the reference level of UCH-L1 is about 2000 pg/mL;
(b) the reference level of GFAP is about 110 pg/mL and the reference level of UCH-L1 is about 2000 pg/mL;
(c) the reference level of GFAP is about 115 pg/mL and the reference level of UCH-L1 is about 110 pg/mL;
(d) the reference level of GFAP is about 140 pg/mL and the reference level of UCH-L1 is about 2000 pg/mL;
(e) the reference level of GFAP is about 150 pg/mL and the reference level of UCH-L1 is about 190 pg/mL;
(f) the reference level of GFAP is about 190 pg/mL and the reference level of UCH-L1 is about 90 pg/mL;
(g) the reference level of GFAP is about 240 pg/mL and the reference level of UCH-L1 is about 300 pg/mL;
(h) the reference level of GFAP is about 285 pg/mL and the reference level of UCH-L1 is about 190 pg/mL;
(i) the reference level of GFAP is about 500 pg/mL and the reference level of UCH-L1 is about 1450 pg/mL;
(j) the reference level of GFAP is about 555 pg/mL and the reference level of UCH-L1 is about 810 pg/mL;
(k) the reference level of GFAP is about 800 pg/mL and the reference level of UCH-L1 is about 900 pg/mL;
(l) the reference level of GFAP is about 840 pg/mL and the reference level of UCH-L1 is about 2000 pg/mL;
(m) the reference level of GFAP is about 880 pg/mL and the reference level of UCH-L1 is about 810 pg/mL;
(n) the reference level of GFAP is about 975 pg/mL and the reference level of UCH-L1 is about 1580 pg/mL; or
(o) the reference level of GFAP and the reference level of UCH-L1 are determined by an assay having a sensitivity equal to or greater than about 54% and a specificity equal to or greater than about 32%.

15. The method of claim 11, wherein the sample is obtained from the subject within:
(a) about 4 hours to about 8 hours after the actual or suspected injury; wherein the reference level of GFAP is about 110 pg/mL and the reference level of UCH-L1 is about 2000 pg/mL;
and wherein the assay has a sensitivity equal to or greater than 95% and a specificity equal to or greater than 62%;
(b) about 8 hours to about 12 hours after the actual or suspected injury; wherein the reference level of GFAP is about 240 pg/mL and the reference level of UCH-L1 is about 300 pg/mL;
and wherein the assay has a sensitivity equal to or greater than 91.5% and a specificity equal to or greater than 52%; or
(c) about 12 hours to about 16 hours after the actual or suspected injury; wherein the reference level of GFAP is about 190 pg/mL and the reference level of UCH-L1 is about 90 pg/mL; and wherein the assay has a sensitivity equal to or greater than 99% and a specificity equal to or greater than 36%.

16. The method of claim 11, further comprising monitoring the subject.

17. The method of claim 11, wherein the sample is obtained after the subject sustained an orthopedic injury.

18. A method comprising:
(a) performing at least one assay for ubiquitin carboxy-terminal hydrolase L1 (UCH-L1) and glial fibrillary acidic protein (GFAP) in at least one sample that is whole blood, serum, plasma, or cerebrospinal fluid obtained from a human subject within about 48 hours after the subject has sustained an actual or suspected injury to the head;
(b) determining that the subject has sustained a traumatic brain injury (TBI) when a level of GFAP in the sample is equal to a reference level of GFAP of from about 15 pg/mL to about 40 pg/mL, and a level of UCH-L1 in the sample is equal to a reference level of UCH-L1 of from about 70 pg/mL to about 150 pg/mL; and
(c) treating the subject determined to have sustained a TBI, wherein the TBI may be a mild TBI or a moderate, severe, or moderate to severe TBI and where the treatment for a mild TBI comprises treatment (i) with rest; (ii) by abstaining from physical activities; (iii) by avoiding light; (iv) by wearing protective eyewear when in light; (v) with one or more therapeutic agents selected from the group consisting of a medication for relief of a headache or migraine, an anti-nausea medication, or combinations thereof; or (vi) with any combination of (i)-(v) or where the treatment for a moderate, severe, or moderate to severe TBI comprises treatment (i') with one or more therapeutic agents selected from the group consisting of a diuretic, an anti-convulsant medication, a medication to sedate and put an individual in a drug-induced coma, or any combination thereof; (ii') with one or more surgical procedures selected from the group consisting of removal of a hematoma, repairing a skull fracture, and a decompressive craniectomy, or any combination thereof; (iii') with one or more therapies selected from the group consisting of rehabilitation for TBI, cognitive behavioral therapy, anger management, and counseling psychology, or any combinations thereof; or (iv') with any combination of (i')-(iii').

19. The method of claim 18, wherein the assay is an immunoassay or a clinical chemistry assay.

20. The method of claim 18, wherein the assay is performed using single molecule detection, a lateral flow assay, or a point-of-care device.

21. The method of claim 18, wherein
(a) the reference level of GFAP is about 10 pg/mL and the reference level of UCH-L1 is about 60 pg/mL;
(b) the reference level of GFAP is about 15 pg/mL and the reference level of UCH-L1 is about 70 pg/mL;
(c) the reference level of GFAP is about 15 pg/mL and the reference level of UCH-L1 is about 90 pg/mL;
(d) the reference level of GFAP is about 15 pg/mL and the reference level of UCH-L1 is about 150 pg/mL;
(e) the reference level of GFAP is about 20 pg/mL and the reference level of UCH-L1 is about 60 pg/mL;
(f) the reference level of GFAP is about 30 pg/mL and the reference level of UCH-L1 is about 70 pg/mL;
(g) the reference level of GFAP is about 30 pg/mL and the reference level of UCH-L1 is about 110 pg/mL; or
(h) reference level of GFAP and the reference level of UCH-L1 are determined by an assay having a sensitivity equal to or greater than about 90% and a specificity equal to or greater than about 35%.

22. The method of claim 18, wherein the sample is obtained from the subject within:
(a) about 8 hours to about 12 hours after the injury; wherein the reference level of GFAP is about 30 pg/mL and the reference level of UCH-L1 is about 110 pg/mL; and wherein the assay has a sensitivity equal to or greater than 92% and a specificity equal to or greater than 99%;
(b) about 12 hours to about 16 hours after the injury; wherein the reference level of GFAP is about 30 pg/mL and the reference level of UCH-L1 is about 110 pg/mL; and wherein the assay has a sensitivity equal to or greater than 90% and a specificity equal to or greater than 99%;
(c) about 4 hours to about 8 hours after the injury; wherein the reference level of GFAP is about 40 pg/mL and the reference level of UCH-L1 is about 100 pg/mL; and wherein the assay has a sensitivity equal to or greater than 90% and a specificity equal to or greater than 94%;
(d) about 8 hours to about 12 hours after the injury; wherein the reference level of GFAP is about 15 pg/mL and the reference level of UCH-L1 is about 150 pg/mL; and wherein the assay has a sensitivity equal to or greater than 95% and a specificity equal to or greater than 82%; or
(e) about 12 hours to about 16 hours after the injury; wherein the reference level of GFAP is about 20 pg/mL and the reference level of UCH-L1 is about 60 pg/mL; and wherein the assay has a sensitivity equal to or greater than 95% and a specificity equal to or greater than 65%.

23. The method of claim 18, further comprising monitoring the subject.

24. A method comprising:
(a) performing at least one assay for ubiquitin carboxy-terminal hydrolase L1 (UCH-L1) and glial fibrillary acidic protein (GFAP) in at least one sample that is whole blood, serum, plasma, or cerebrospinal fluid obtained from a human subject within about 48 hours after the subject has sustained an actual or suspected injury to the head; and
(b) performing a magnetic resonance imaging (MRI) procedure when the:
(i) level of GFAP in the sample is equal to a reference level of GFAP of from about 15 pg/mL to about 1000 pg/mL, and the level of UCH-L1 in the sample is equal to a reference level of UCH-L1 of from about 50 pg/mL to about 2000 pg/mL; or
(ii) level of GFAP in the sample is greater than a reference level of GFAP of about 1000 pg/mL, and the level of UCH-L1 in the sample is greater than a reference level of UCH-L1 of about 2000 pg/mL or not performing a MRI procedure when the level of GFAP in the sample is less than a reference level of GFAP of about 15 pg/mL and the level of UCH-L1 in the sample is less than a reference level of UCH-L1 of about 50 pg/mL; and
(c) treating the subject determined to have sustained a traumatic brain injury (TBI) based on the MRI procedure, wherein the TBI may be a mild TBI or a moderate, severe, or moderate to severe TBI and where the treatment for a mild TBI comprises treatment (i) with rest; (ii) by abstaining from physical activities; (iii) by avoiding light; (iv) by wearing protective eyewear when in light; (v) with one or more therapeutic agents selected from the group consisting of a medication for relief of a headache or migraine, and an anti-nausea medication, or combinations thereof; or (vi) with any combination of (i)-(v); or where the treatment for a moderate, severe, or moderate to severe TBI comprises treatment (i') with one or more therapeutic agents selected from the group consisting of a diuretic, an anti-convulsant medication, and a medication to sedate and put an individual in a drug-induced coma, or any combination thereof; (ii') with one or more surgical procedures selected from the group consisting of removal of a hematoma, repairing a skull fracture, and a decompressive craniectomy, or any combination thereof;

(iii') with one or more therapies selected from the group consisting of rehabilitation for TBI, cognitive behavioral therapy, anger management, and counseling psychology, or any combinations thereof; or (iv') with any combination of (i')-(iii'); or (iv) with any combination of (i) (iii).

25. The method of claim 24, wherein the assay is an immunoassay or a clinical chemistry assay.

26. The method of claim 24, wherein the assay is performed using single molecule detection, a lateral flow assay, or a point-of-care device.

27. The method of claim 24, wherein the reference level of GFAP and the reference level of UCH-L1 are determined by an assay having a sensitivity of from about 80% to about 98% and a specificity of from about 30% to about 85%.

28. The method of claim 24, further comprising monitoring the subject.

29. The method of claim 24, wherein the sample is obtained after the subject sustained an orthopedic injury.

30. The method of claim 24, wherein the sample is taken from the subject within about within about 4 hours to about 8 hours, within about 8 hours to about 12 hours, within about 12 hours to about 16 hours, within about 16 hours to about 20 hours, within about 20 hours to about 24 hours, and within about 24 hours to about 48 hours.

31. A method comprising:
(a) performing at least one assay for ubiquitin carboxy-terminal hydrolase L1 (UCH-L1) and glial fibrillary acidic protein (GFAP) in at least one sample that is whole blood, serum, plasma, or cerebrospinal fluid, a tissue sample or a bodily fluid obtained from a human subject within about 48 hours after the subject has sustained an actual or suspected injury to the head; and
(b) determining that the subject has sustained a traumatic brain injury (TBI) when the level of GFAP in the sample is equal to a reference level of GFAP of from about 80 pg/mL to about 2000 pg/mL, and the level of UCH-L1 in the sample is equal to a reference level of UCH-L1 of from about 130 pg/mL to about 2000 pg/mL predicting a more likely than not an unfavorable for the subject; and (c) treating the subject determined to have sustained a TBI, wherein the TBI may be a mild TBI or a moderate, severe, or moderate to severe TBI and where the treatment for a mild TBI comprises treatment (i) with rest; (ii) by abstaining from physical activities; (iii) by avoiding light; (iv) by wearing protective eyewear when in light; (v) with one or more therapeutic agents selected from the group consisting of a medication for relief of a headache or migraine, and an anti-nausea medication, or combinations thereof; or (vi) with any combination of (i)-(v); or where the treatment for a moderate, severe, or moderate to severe TBI comprises treatment (i') with one or more therapeutic agents selected from the group consisting of a diuretic, an anti-convulsant medication, and a medication to sedate and put an individual in a drug-induced coma, or any combination thereof; (ii') with one or more surgical procedures selected from the group consisting of removal of a hematoma, repairing a skull fracture, and a decompressive craniectomy, or any combination thereof; (iii') with one or more therapies selected from the group consisting of rehabilitation for TBI, cognitive behavioral therapy, anger management, and counseling psychology, or any combinations thereof; or (iv') with any combination of (i')-(iii').

32. The method of claim 31, wherein the assay is an immunoassay or a clinical chemistry assay.

33. The method of claim 31, wherein the assay is performed using single molecule detection, a lateral flow assay, or a point-of-care device.

34. The method of claim 31, wherein the subject received an Extended Glasgow Outcome Scale (GOSE) score after the assay is performed, and wherein the subject is suspected as having a poor outcome based on the GOSE score.

35. The method of claim 31, wherein the reference level of GFAP and the reference level of UCH-L1 are determined by an assay having a sensitivity of from about 80% to about 97% and a specificity of from about 30% to about 95%.

36. The method of claim 31, further comprising monitoring the subject.

37. The method of claim 31, wherein the sample is obtained after the subject sustained an orthopedic injury.

38. The method of claim 31, wherein the sample is taken from the subject within about within about 4 hours to about 8 hours, within about 8 hours to about 12 hours, within about 12 hours to about 16 hours, within about 16 hours to about 20 hours, within about 20 hours to about 24 hours, and within about 24 hours to about 48 hours.

\* \* \* \* \*

SEQUENCE LISTING

<160> NUMBER OF SEQ ID NOS: 5

<210> SEQ ID NO 1
<211> LENGTH: 223
<212> TYPE: PRT
<213> ORGANISM: Homo sapiens

<400> SEQUENCE: 1

Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
        35                  40                  45

Leu Leu Leu Leu Phe Pro Leu Thr Ala Gln His Glu Asn Phe Arg Lys
    50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
            100                 105                 110

Val Leu Lys Gln Phe Leu Ser Glu Thr Glu Lys Met Ser Pro Glu Asp
        115                 120                 125

Arg Ala Lys Cys Phe Glu Lys Asn Glu Ala Ile Gln Ala Ala His Asp
    130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
            180                 185                 190

Leu Leu Lys Asp Ala Ala Lys Val Cys Arg Glu Phe Thr Glu Arg Glu
        195                 200                 205

Gln Gly Glu Val Arg Phe Ser Ala Val Ala Leu Cys Lys Ala Ala
    210                 215                 220

<210> SEQ ID NO 2
<211> LENGTH: 432
<212> TYPE: PRT
<213> ORGANISM: Homo sapiens

<400> SEQUENCE: 2

Met Glu Arg Arg Arg Ile Thr Ser Ala Ala Arg Ser Tyr Val Ser
1               5                   10                  15

Ser Gly Glu Met Met Val Gly Gly Leu Ala Pro Gly Arg Arg Leu Gly
            20                  25                  30

Pro Gly Thr Arg Leu Ser Leu Ala Arg Met Pro Pro Pro Leu Pro Thr
        35                  40                  45

Arg Val Asp Phe Ser Leu Ala Gly Ala Leu Asn Ala Gly Phe Lys Glu
    50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu

```
            100                 105                 110
Ala Asp Val Tyr Gln Ala Glu Leu Arg Glu Leu Arg Leu Asp
        115                 120                 125

Gln Leu Thr Ala Asn Ser Ala Arg Leu Glu Val Glu Arg Asp Asn Leu
130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
        195                 200                 205

Arg Glu Leu Gln Glu Gln Leu Ala Arg Gln Gln Val His Val Glu Leu
    210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
        275                 280                 285

Leu Gln Ser Leu Thr Cys Asp Leu Glu Ser Leu Arg Gly Thr Asn Glu
    290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                325                 330                 335

Ser Leu Lys Asp Glu Met Ala Arg His Leu Gln Glu Tyr Gln Asp Leu
            340                 345                 350

Leu Asn Val Lys Leu Ala Leu Asp Ile Glu Ile Ala Thr Tyr Arg Lys
        355                 360                 365

Leu Leu Glu Gly Glu Glu Asn Arg Ile Thr Ile Pro Val Gln Thr Phe
    370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
                405                 410                 415

Asp Gly Glu Val Ile Lys Glu Ser Lys Gln Glu His Lys Asp Val Met
            420                 425                 430

<210> SEQ ID NO 3
<211> LENGTH: 6
<212> TYPE: PRT
<213> ORGANISM: Artificial sequence
<220> FEATURE:
<223> OTHER INFORMATION: Synthetic

<400> SEQUENCE: 3

His His His His His His
1               5

<210> SEQ ID NO 4
<211> LENGTH: 5
<212> TYPE: PRT
```

```
<213> ORGANISM: Artificial sequence
<220> FEATURE:
<223> OTHER INFORMATION: Synthetic

<400> SEQUENCE: 4

Asp Asp Asp Asp Lys
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic

<400> SEQUENCE: 5

Ala Asp Asp Asp Asp Lys
1               5
```